United States Patent
Linge et al.

(10) Patent No.: US 12,052,919 B2
(45) Date of Patent: Jul. 30, 2024

(54) MATERIALS FOR ORGANIC ELECTROLUMINESCENT DEVICES

(71) Applicant: Merck Patent GmbH, Darmstadt (DE)

(72) Inventors: Rouven Linge, Darmstadt (DE); Amir Hossain Parham, Darmstadt (DE); Sebastian Meyer, Darmstadt (DE); Anna Hayer, Darmstadt (DE); Nils Koenen, Darmstadt (DE)

(73) Assignee: Merck Patent GmbH, Damstadt (DE)

( * ) Notice: Subject to any disclaimer, the term of this patent is extended or adjusted under 35 U.S.C. 154(b) by 119 days.

(21) Appl. No.: 17/785,417

(22) PCT Filed: Dec. 15, 2020

(86) PCT No.: PCT/EP2020/086130
§ 371 (c)(1),
(2) Date: Jun. 15, 2022

(87) PCT Pub. No.: WO2021/122535
PCT Pub. Date: Jun. 24, 2021

(65) Prior Publication Data
US 2023/0067309 A1    Mar. 2, 2023

(30) Foreign Application Priority Data

Dec. 17, 2019 (EP) .................................. 19216933

(51) Int. Cl.

| C07D 405/14 | (2006.01) |
|---|---|
| C07D 409/14 | (2006.01) |
| C09K 11/06 | (2006.01) |
| H10K 85/60 | (2023.01) |
| H10K 50/11 | (2023.01) |
| H10K 101/00 | (2023.01) |

(52) U.S. Cl.
CPC ....... H10K 85/6572 (2023.02); C07D 405/14 (2013.01); C07D 409/14 (2013.01); C09K 11/06 (2013.01); H10K 85/626 (2023.02); H10K 85/654 (2023.02); H10K 85/6574 (2023.02); H10K 85/6576 (2023.02); C09K 2211/1018 (2013.01); H10K 50/11 (2023.02); H10K 2101/90 (2023.02)

(58) Field of Classification Search
CPC ............. H10K 85/6572; H10K 85/626; H10K 85/654; H10K 85/6574; H10K 85/6576; H10K 50/11; H10K 2101/90; H10K 50/16; H10K 2101/10; H10K 2101/20; H10K 85/624; C07D 405/14; C07D 409/14; C09K 11/06; C09K 2211/1018
See application file for complete search history.

(56) References Cited

U.S. PATENT DOCUMENTS

| 2009/0134784 A1 | 5/2009 | Lin et al. |
|---|---|---|
| 2018/0006237 A1 | 1/2018 | Anémain et al. |
| 2018/0037546 A1 | 2/2018 | Sugino et al. |
| 2019/0185411 A1 | 6/2019 | Lee et al. |
| 2019/0198780 A1 * | 6/2019 | Kim ..................... H10K 85/653 |
| 2022/0336757 A1 | 10/2022 | Jung et al. |

FOREIGN PATENT DOCUMENTS

| CN | 101939296 A | 1/2011 |
|---|---|---|
| CN | 106459018 A | 2/2017 |
| CN | 107108578 A | 8/2017 |
| CN | 107250132 A | 10/2017 |
| CN | 108368078 A | 8/2018 |
| CN | 109970724 A | 7/2019 |
| KR | 10-2018-0076357 A | 7/2018 |
| WO | 2015/169412 A1 | 11/2015 |

OTHER PUBLICATIONS

International Search Report and Written Opinion received for PCT Patent Application No. PCT/EP2020/086130, mailed on Feb. 26, 2021, 14 pages (6 pages of English Translation and 8 pages of Original Document).
International Preliminary Report on Patentability received for PCT Patent Application No. PCT/EP2020/086130, mailed on Jun. 30, 2022, 12 pages (6 pages of English Translation and 6 pages of Original Document).

* cited by examiner

Primary Examiner — Mark Kopec
Assistant Examiner — Jaison P Thomas
(74) Attorney, Agent, or Firm — Faegre Drinker Biddle & Reath LLP

(57) ABSTRACT

The present invention describes dibenzofuran derivatives substituted by electron-deficient heteroaryl groups, and electronic devices, especially organic electroluminescent devices, comprising these compounds as triplet matrix materials.

15 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2020/086130, filed Dec. 15, 2020, which claims benefit of European Application No. 19216933.2, filed Dec. 17, 2019, both of which are incorporated herein by reference in their entirety.

The present invention describes dibenzofuran and dibenzothiophene derivatives substituted by electron-deficient heteroaromatic systems, and electronic devices comprising these compounds, especially organic electroluminescent devices comprising these compounds as triplet matrix materials.

Phosphorescent organometallic complexes are frequently used in organic electroluminescent devices (OLEDs). There is generally still a need for improvement in OLEDs. The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, carbazole derivatives and dibenzofuran derivatives, especially those substituted by electron-deficient heteroaromatic systems such as triazine, are among the matrix materials used for phosphorescent emitters, as disclosed, for example, in WO 2015/169412. In general, there is still a need for improvement with regard to solubility and lifetime in these material classes, especially when they are to be processed from solution. It is therefore an object of the present invention to provide compounds which have good processability from solution and lead to an improvement in lifetime as matrix material in phosphorescent OLEDs that are produced from solution.

It has been found that, surprisingly, organic electroluminescent devices containing compounds of the formula (1) below have high solubility and a high glass transition temperature, have very good processability from solution as a result, and have improved lifetime compared to the prior art when used as matrix material for phosphorescent dopants.

The invention therefore provides a compound of the following formula (1):

where the symbols and indices used are as follows:

$Y^1$ is the same or different at each instance and is O or S;

$Y^2$ is the same or different at each instance and is $NAr^2$, O, S or $CR_2$;

Z is the same or different at each instance and is CR or N, with the proviso that at least two Z are N;

$Ar^1$, $Ar^2$ is the same or different at each instance and is an aromatic or heteroaromatic ring system which has 5 to 40 aromatic ring atoms and may be substituted by one or more R radicals;

R is the same or different at each instance and is H, D, F, Cl, Br, I, $N(Ar')_2$, $N(R^1)_2$, OAr, SAr, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, $C=O$, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;

Ar' is the same or different at each instance and is an aromatic or heteroaromatic ring system which has 5 to 40 aromatic ring atoms and may be substituted by one or more $R^1$ radicals; at the same time, two Ar' radicals bonded to the same nitrogen atom may also be bridged to one another by a single bond or a bridge selected from $N(R^1)$, $C(R^1)_2$, O and S;

$R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more nonadjacent $CH_2$ groups may be replaced by $Si(R^2)_2$, $C=O$, $NR^2$, O, S or $CONR^2$ and where one or more hydrogen atoms in the alkyl, alkenyl or alkynyl group may be replaced by D, F, Cl, Br, I or CN, or an aromatic

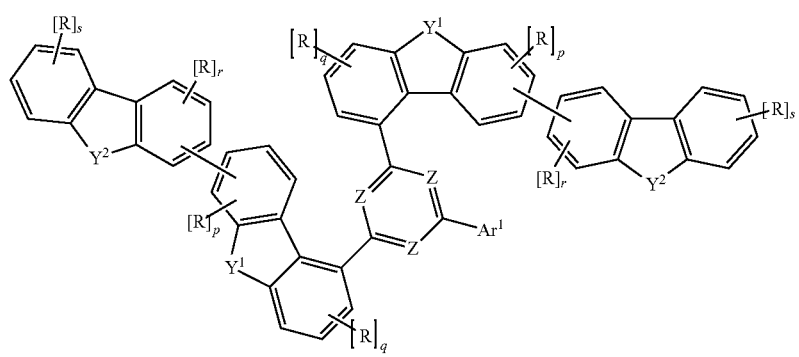

Formula (1)

or heteroaromatic ring system which has 5 to 40 aromatic ring atoms and may be substituted in each case by one or more $R^2$ radicals; at the same time, two or more $R^1$ radicals together may form an aliphatic ring system;

$R^2$ is the same or different at each instance and is H, D, F, CN or an aliphatic, aromatic or heteroaromatic organic radical, especially a hydrocarbyl radical, having 1 to 20 carbon atoms, in which one or more hydrogen atoms may also be replaced by F;

p, q, r is the same or different at each instance and is 0, 1, 2 or 3;

s is the same or different at each instance and is 0, 1, 2, 3 or 4.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least S. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 40 carbon atoms in the ring system. A heteroaromatic ring system in the context of this invention contains 2 to 39 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. These shall likewise be understood to mean systems in which two or more aryl or heteroaryl groups are joined directly to one another, for example biphenyl, terphenyl, bipyridine or phenylpyridine. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group. Preferred aromatic or heteroaromatic ring systems are simple aryl or heteroaryl groups and groups in which two or more aryl or heteroaryl groups are joined directly to one another, for example biphenyl or bipyridine, and also fluorene or spirobifluorene.

In the context of the present invention, the term "alkyl group" is used as an umbrella term for linear, branched or cyclic alkyl groups. Analogously, the terms "alkenyl group" and "alkynyl group" are used as umbrella terms both for linear and for branched and cyclic alkenyl and alkynyl groups respectively.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups is preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group $OR^1$ having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group $SR^1$ having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups, in addition, it is also possible for one or more hydrogen atoms to be replaced by D, F, Cl, Br, I, CN or $NO_2$, preferably F, Cl or CN, more preferably F or CN.

An aromatic or heteroaromatic ring system which has 5-40 aromatic ring atoms and may also be substituted in each case by the abovementioned $R^2$ radicals or a hydrocarbyl radical and which may be joined to the aromatic or heteroaromatic system via any desired positions is understood to mean especially groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

The wording that two or more radicals together may form a ring system is understood to mean the formation of an aliphatic, heteroaliphatic, aromatic or heteroaromatic ring system, and, in the context of the present description, should be understood to mean, inter alia, that the two radicals are joined to one another by a chemical bond with formal elimination of two hydrogen atoms. This is illustrated by the following scheme:

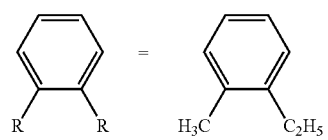

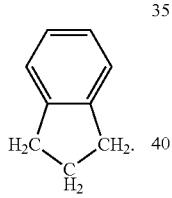

In addition, however, the abovementioned wording shall also be understood to mean that, if one of the two radicals is hydrogen, the second radical binds to the position to which the hydrogen atom was bonded, forming a ring. This shall be illustrated by the following scheme:

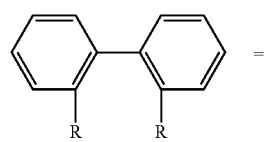

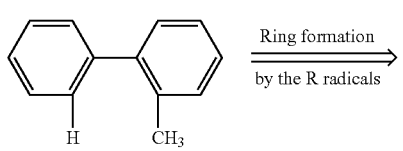

-continued

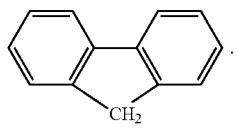

In a preferred embodiment of the invention, the group

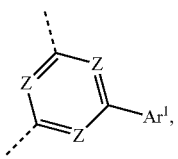

incorporated in formula (1) is selected from the following groups (HetAr-1), (HetAr-2) and (HetAr-3):

(HetAr - 1)

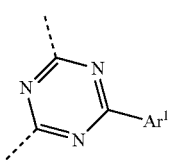

(HetAr - 2)

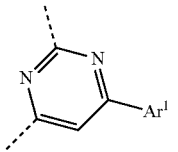

(HetAr - 3)

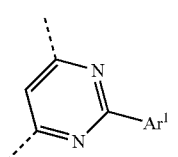

where $Ar^1$ has the definitions given above and the dotted bond indicates the linkage of this group within the compound of the formula (1).

In a preferred embodiment of the invention, all three Z groups are N, and so the compound is preferably one of the following formula (2):

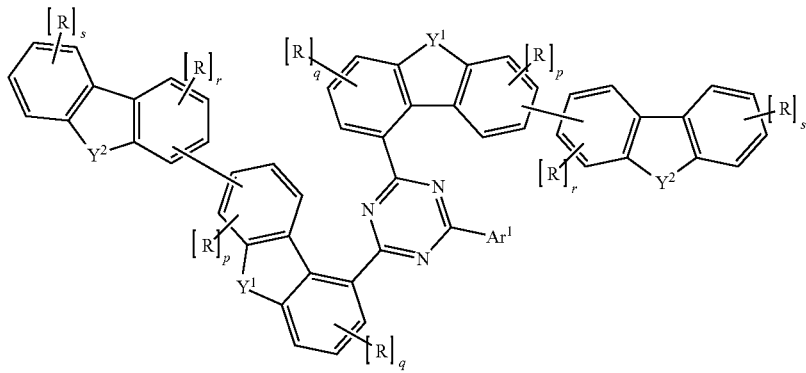

Formula (2)

where the symbols and indices used have the definitions given above.

In a further preferred embodiment of the invention, $Y^1$ is O, and so the compound is one of the following formula (3):

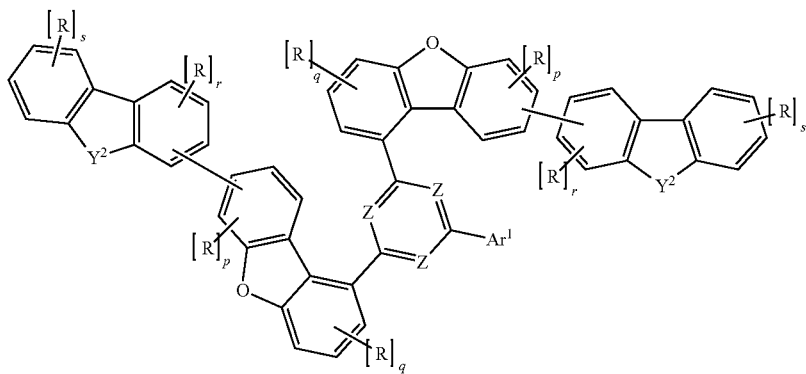

Formula (3)

where the symbols and indices used have the definitions given above.

In a further preferred embodiment of the invention, $Y^2$ is $NAr^2$, and so the compound is one of the following formula (4):

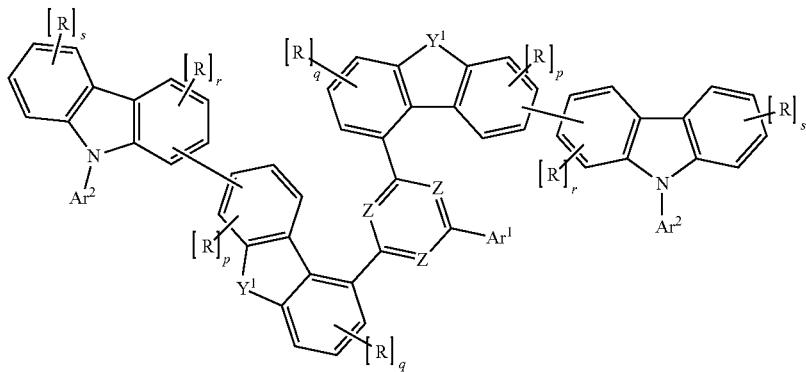

Formula (4)

where the symbols and indices used have the definitions given above.

When $Y^2$ is $NAr^2$ and the carbazole group has at least two adjacent R radicals that form a ring system with one another, preferred carbazole groups are selected from the groups of the following formulae (CARB-1) to (CARB-6):

(CARB-1)

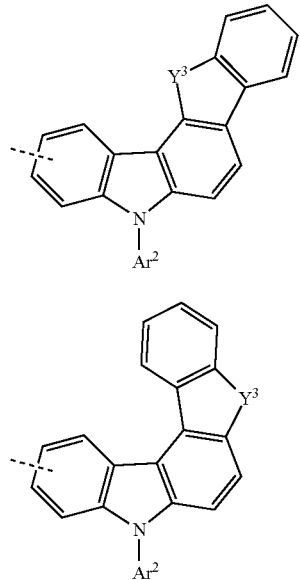

(CARB-2)

(CARB-3)

(CARB-4)

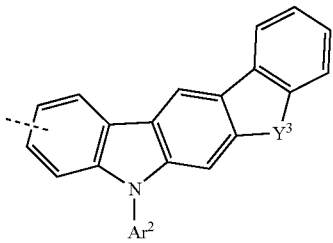

(CARB-5)

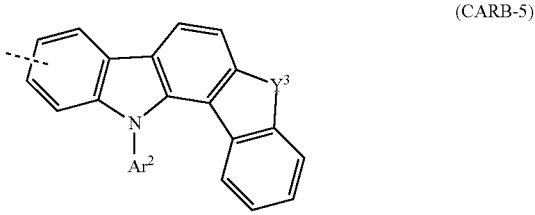

(CARB-6)

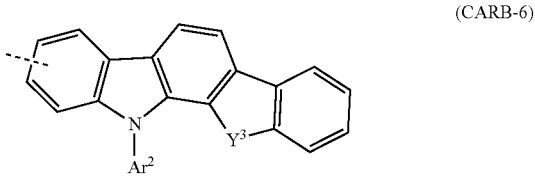

where the structures may each be substituted by one or more R radicals on the carbazole and by one or more $R^1$ radicals on the fused-on structure, but are preferably unsubstituted, $Y^3$ is $C(R^1)_2$, $NR^1$, O or S, preferably $C(R^1)_2$ or $NR^1$ and more preferably $C(R^1)_2$, and the structures are joined to the dibenzofuran or dibenzothiophene via the dotted bond.

In a further preferred embodiment of the invention, all Z are N, and at the same time all $Y^1$ are O. In yet a further preferred embodiment of the invention, all Z are N, and at the same time all $Y^2$ are $NAr^2$. In yet a further preferred embodiment of the invention, all $Y^1$ are O, and at the same time all $Y^2$ are $NAr^2$. In a particularly preferred embodiment of the invention, all Z are N, and at the same time all $Y^1$ are O, and at the same time all $Y^2$ are $NAr^2$, such that the compound is one of the following formula (5):

Formula (5)

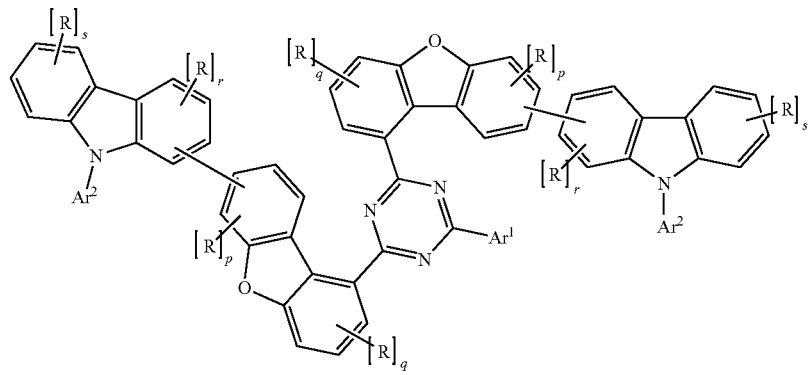

where the symbols and indices used have the definitions given above.

The linkage of the group containing $Y^1$, i.e. the dibenzofuran or dibenzothiophene, is preferably via the 8 position, i.e. the position para to $Y^1$. In addition, the linkage of the group containing $Y^2$ is preferably via the 3 position when $Y^2=NAr^2$ and via the 2 position when $Y^2=O$ or S, i.e. in each case via the position para to $Y^2$ and via the 2 position when $Y^2=CR_2$.

The numbering of the dibenzofuran and of the carbazole is shown in the scheme below, the numbering of the dibenzothiophene being analogous to the dibenzofuran and the numbering of the fluorene analogous to the carbazole:

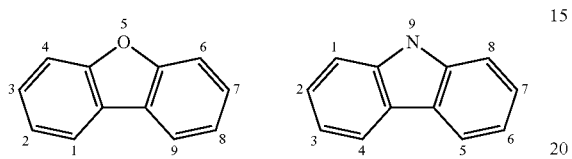

Preferred embodiments of the compounds of the formulae (1) to (5) are thus the compounds of the following formulae (1a) to (5a):

Formula (1a)


Formula (2a)


Formula (3a)

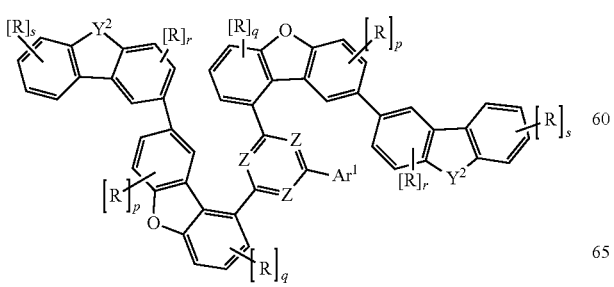

Formula (4a)

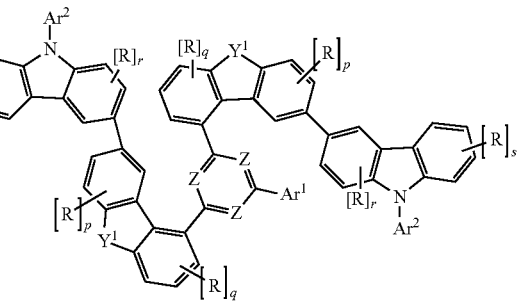

Formula (5a)

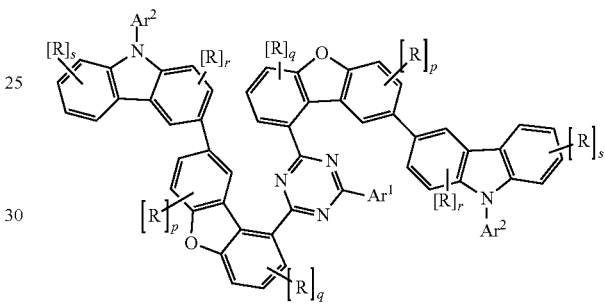

where the symbols and indices used have the definitions given above.

In a further preferred embodiment of the compounds of formulae (1), (2), (3), (4), (5), (1a), (2a), (3a), (4a) and (5a), p, q and r are the same or different at each instance and are 0 or 1, and more preferably 0. In yet a further preferred embodiment of the compounds of formulae (1), (2), (3), (4), (5), (1a), (2a), (3a), (4a) and (5a), s is the same or different at each instance and is 0, 1 or 2, more preferably 0 or 1, and most preferably 0. Particular preference is thus given to a compound of the following formula (6):

Formula (6)

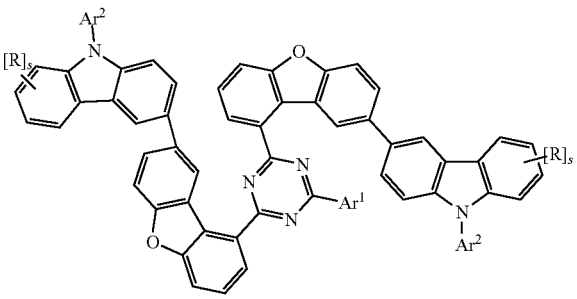

where the symbols used have the definitions given above and s is the same or different at each instance and is 0 or 1.

A particularly preferred embodiment is the compound of the following formula (6a):

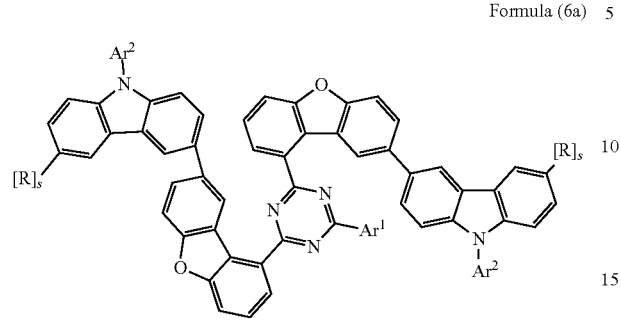

Formula (6a)

where the symbols used have the definitions given above and s is the same or different at each instance and is 0 or 1, preferably 0.

In a further preferred embodiment of the invention, $Ar^1$, i.e. the substituent on the triazine or pyrimidine, is the same or different at each instance and is an aromatic or heteroaromatic ring system which has 6 to 30 aromatic ring atoms and may be substituted by one or more R radicals. More preferably, $Ar^1$ is the same or different at each instance and is an aromatic or heteroaromatic ring system, especially an aromatic ring system, which has 6 to 24 aromatic ring atoms, especially 6 to 13 aromatic ring atoms, and may be substituted by one or more, preferably nonaromatic, R radicals. When $Ar^1$ is a heteroaryl group, especially triazine, pyrimidine, quinazoline or carbazole, preference may also be given to aromatic or heteroaromatic substituents R on this heteroaryl group.

Suitable aromatic or heteroaromatic ring systems $Ar^1$ are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, phenanthrene, triphenylene or a combination of two or three of these groups, each of which may be substituted by one or more R radicals, preferably nonaromatic R radicals. When $Ar^1$ is a heteroaryl group, especially triazine, pyrimidine, quinazoline or carbazole, preference may also be given to aromatic or heteroaromatic R radicals on this heteroaryl group.

$Ar^1$ here is preferably the same or different at each instance and is selected from the groups of the following formulae Ar-1 to Ar-81:

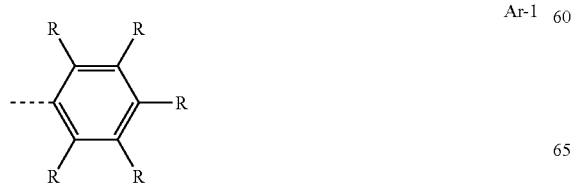

Ar-1

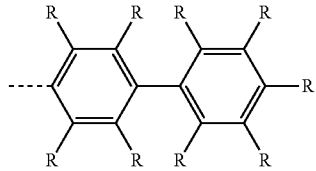

Ar-2

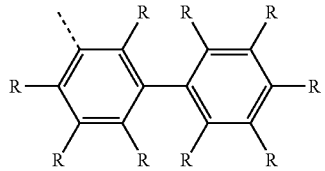

Ar-3

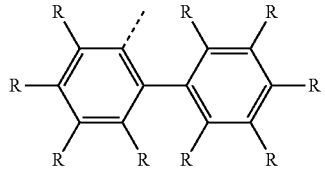

Ar-4

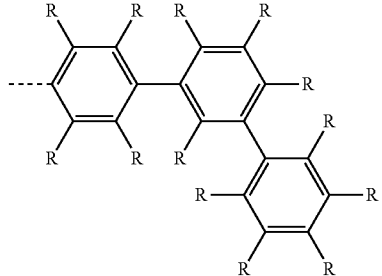

Ar-5

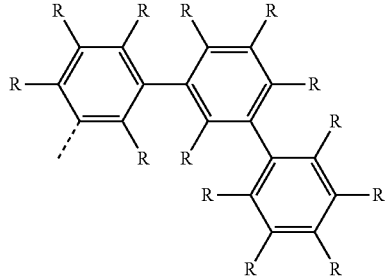

Ar-6

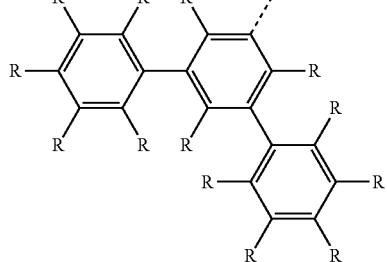

Ar-7

-continued
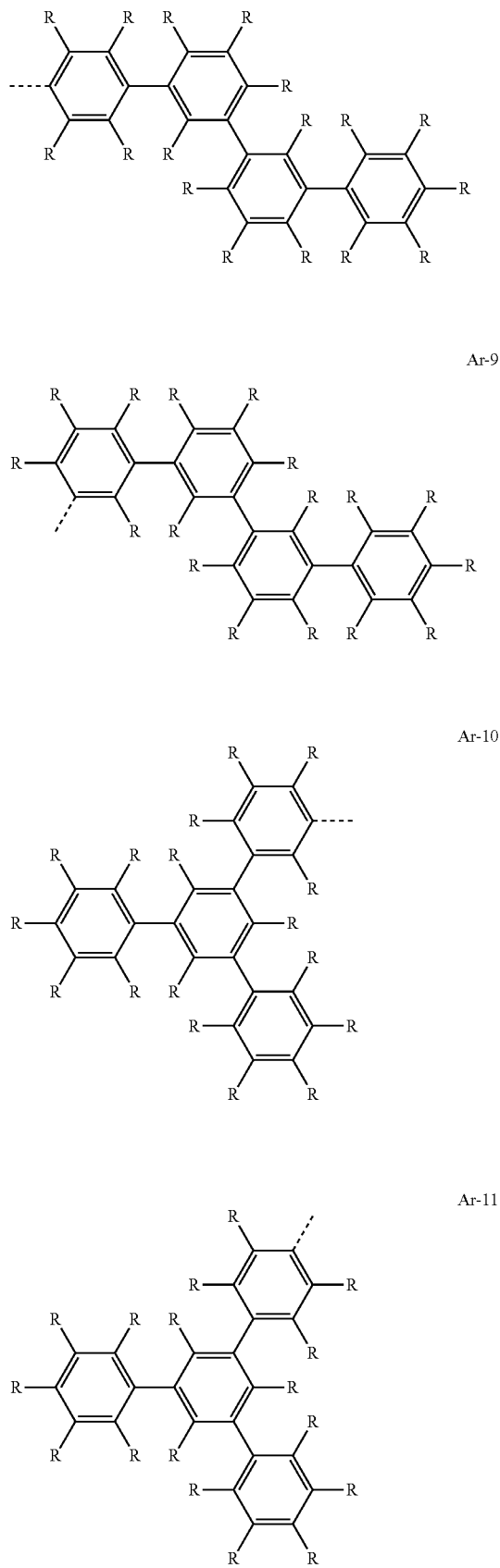
Ar-8
Ar-9
Ar-10
Ar-11
-continued
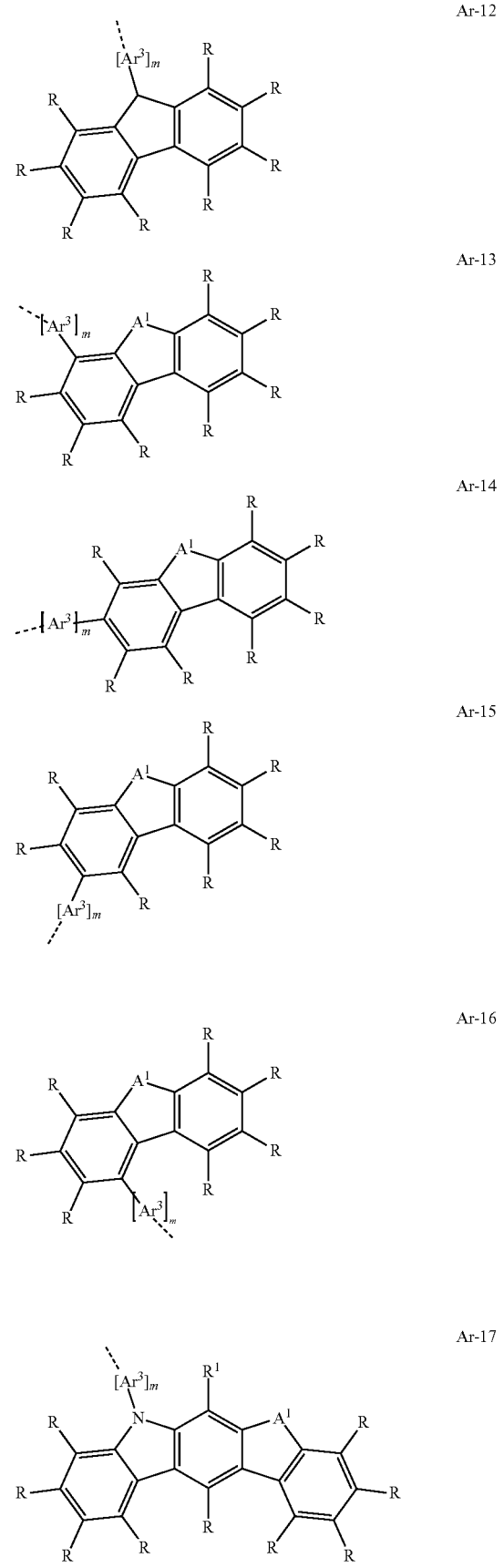
Ar-12
Ar-13
Ar-14
Ar-15
Ar-16
Ar-17

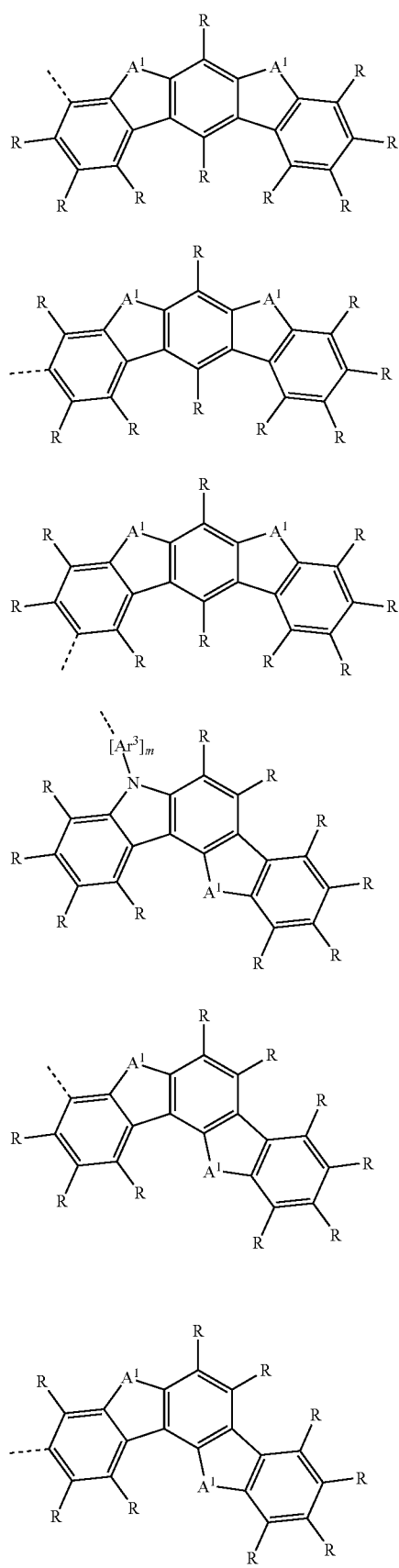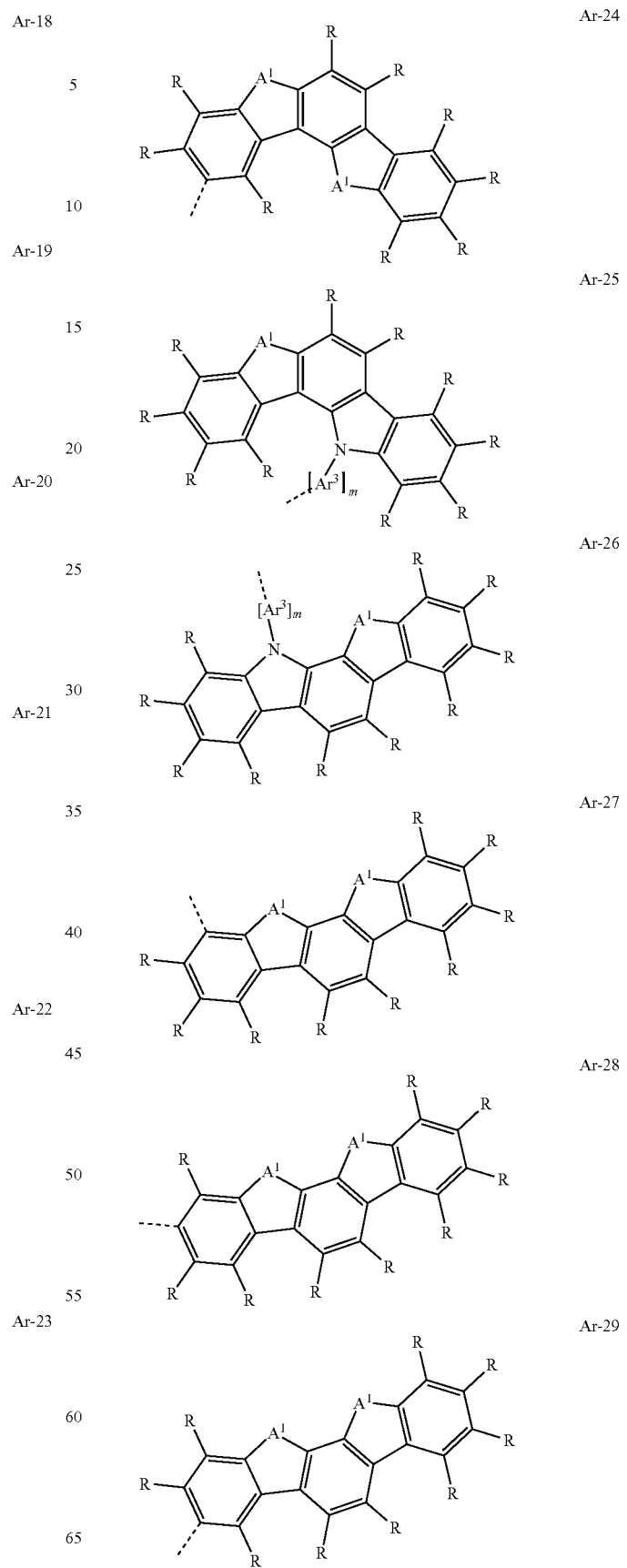

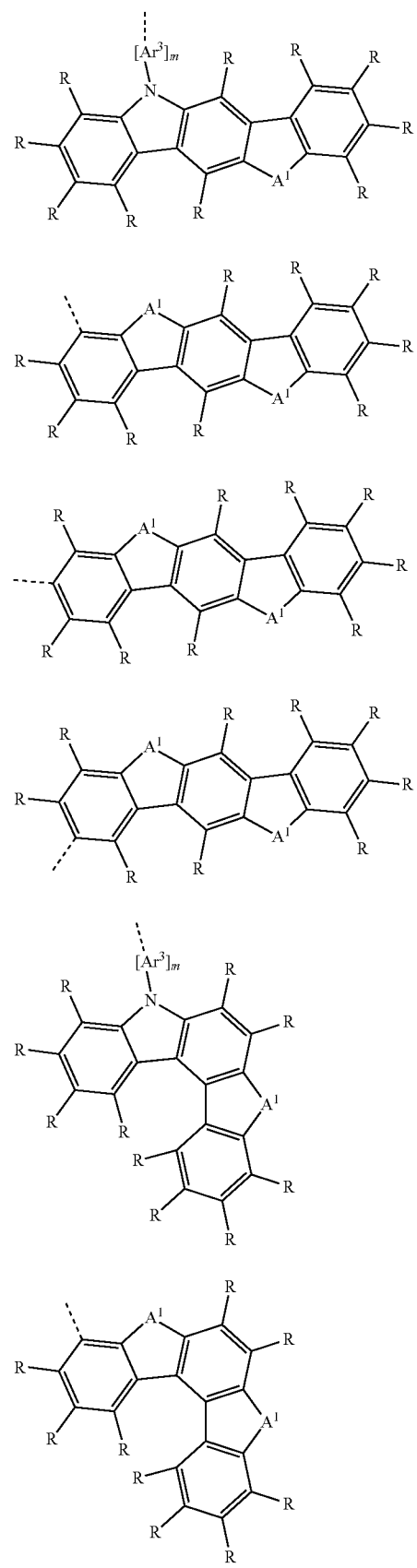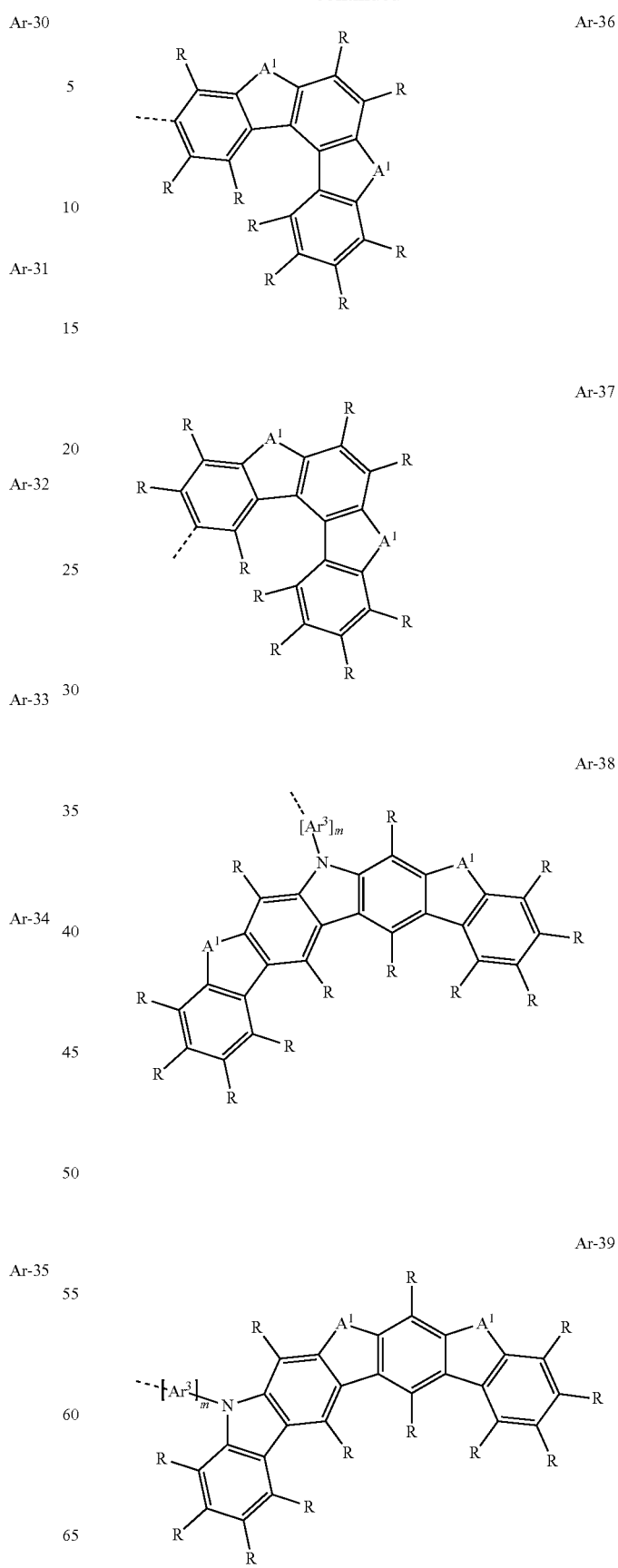

-continued
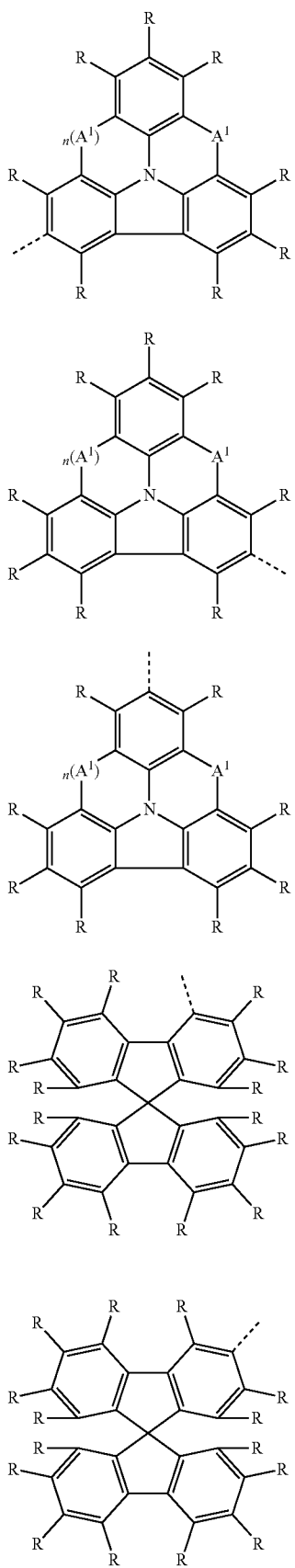
Ar-40
Ar-41
Ar-42
Ar-43
Ar-44
-continued
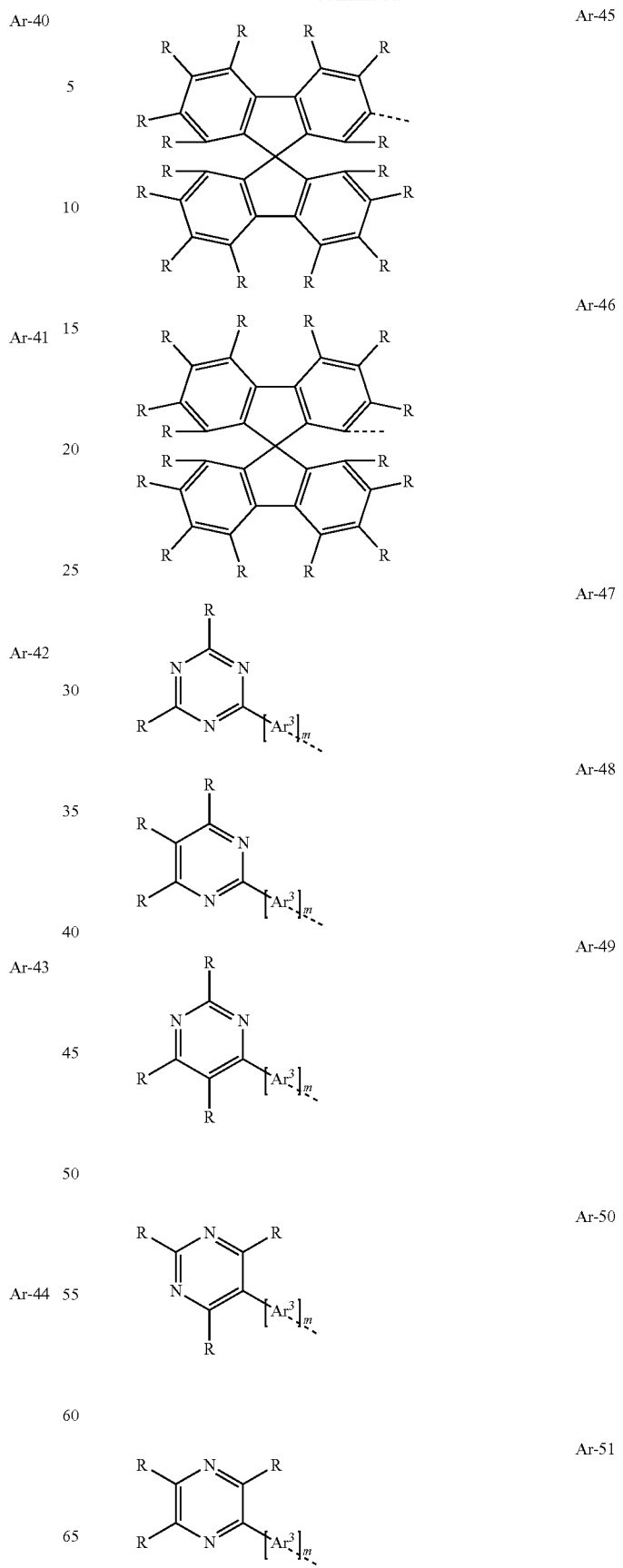
Ar-45
Ar-46
Ar-47
Ar-48
Ar-49
Ar-50
Ar-51

Ar-52 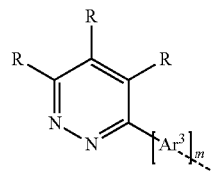
Ar-53 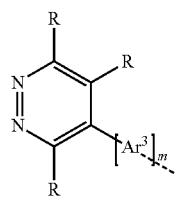
Ar-54 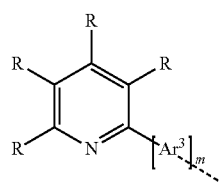
Ar-55 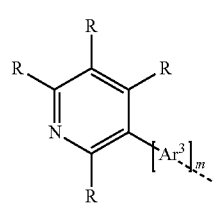
Ar-56 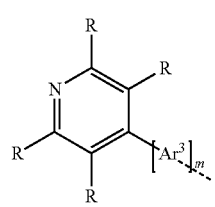
Ar-57 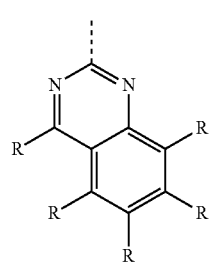
Ar-58 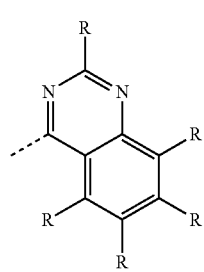
Ar-59 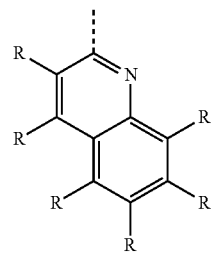
Ar-60 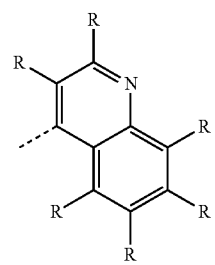
Ar-61 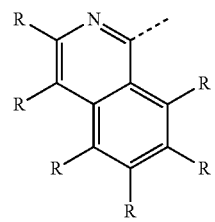
Ar-62 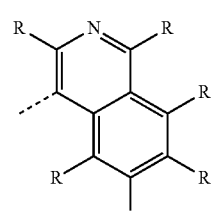
Ar-63 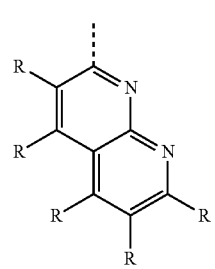
Ar-64 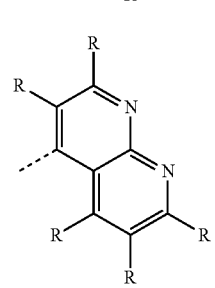

Ar-65 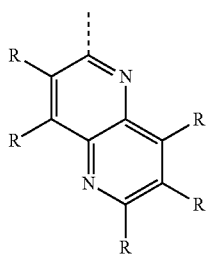
Ar-66 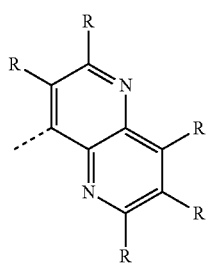
Ar-67 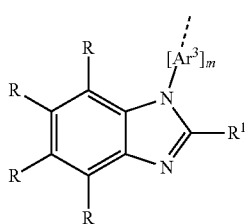
Ar-68 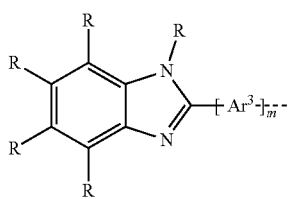
Ar-69 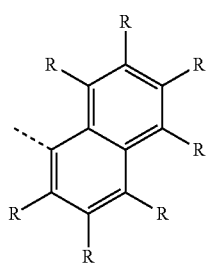
Ar-70 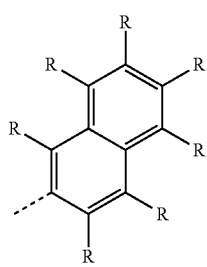
Ar-71 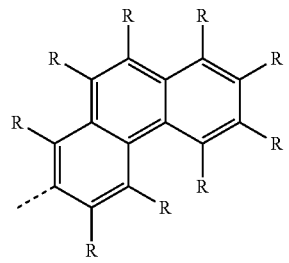
Ar-72 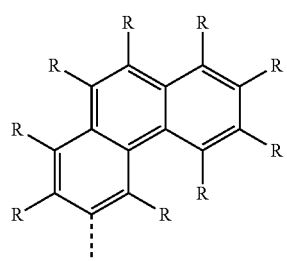
Ar-73 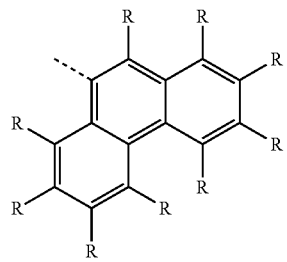
Ar-74 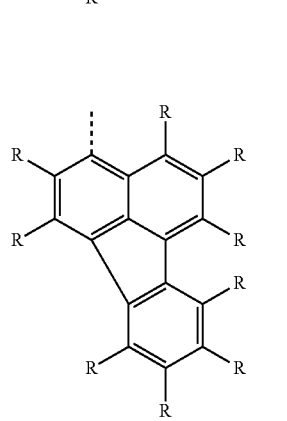
Ar-75 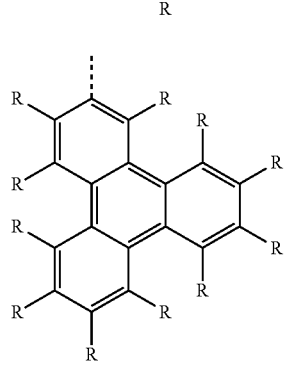

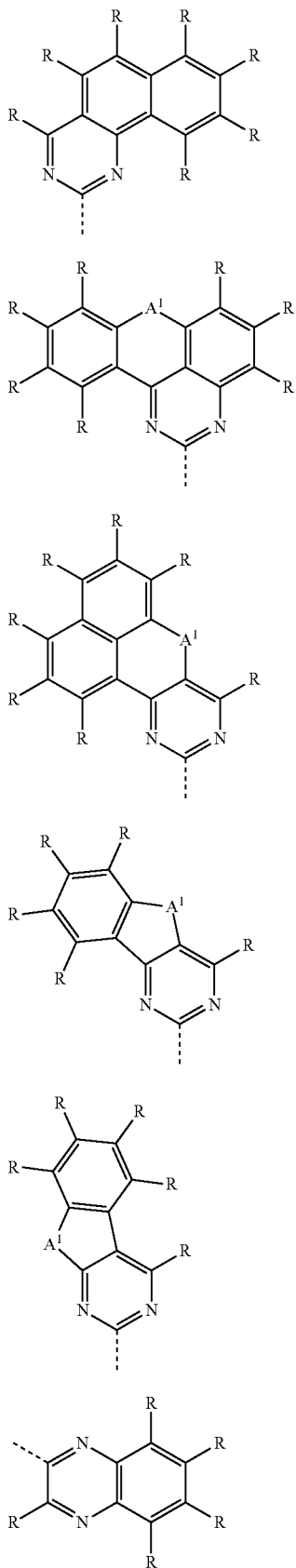

where R is as defined above, the dotted bond represents the bond to the heteroaryl group and, in addition:

$A^1$ is the same or different at each instance and is $CR_2$, NR, O or S;

$Ar^3$ is the same or different at each instance and is a bivalent aromatic or heteroaromatic ring system which has 6 to 18 aromatic ring atoms and may be substituted in each case by one or more R radicals;

n is 0 or 1, where n=0 means that no $A^1$ group is bonded at this position and R radicals are bonded to the corresponding carbon atoms instead;

m is 0 or 1, where m=0 means that the $Ar^3$ group is absent and that the corresponding aromatic or heteroaromatic group is bonded directly to the triazine or pyrimidine group in formula (1).

Particularly preferred $Ar^1$ groups are selected from the group consisting of 1-dibenzofuranyl, i.e. a group of the formula Ar-16 with $A^1$=O and m=0, phenyl-1-dibenzofuranyl, i.e. a group of the formula Ar-16 with $A^1$=O, m=1 and $Ar^3$=para-phenylene, phenyl, ortho-biphenyl, meta-biphenyl, para-biphenyl, quaterphenyl, para-tert-butylphenyl, naphthyl, fluorenyl, especially 9,9-dimethyl-2-fluorenyl, and 1-dibenzothienyl.

In a further preferred embodiment of the invention, $Ar^2$, i.e. the substituent on the carbazole when $Y^2$=$NAr^2$, is the same or different at each instance and is an aromatic or heteroaromatic ring system which has 6 to 30 aromatic ring atoms and may be substituted by one or more R radicals. More preferably, $Ar^2$ is the same or different at each instance and is an aromatic or heteroaromatic ring system, especially an aromatic ring system, which has 6 to 24 aromatic ring atoms, especially 6 to 13 aromatic ring atoms, and may be substituted by one or more, preferably nonaromatic, R radicals. When $Ar^2$ is a heteroaryl group, especially triazine, pyrimidine, quinazoline or carbazole, preference may also be given to aromatic or heteroaromatic substituents R on this heteroaryl group.

Suitable aromatic or heteroaromatic ring systems $Ar^2$ are the same or different at each instance and are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, phenanthrene, triphenylene or a combination of two or three of these groups, each of which may be substituted by one or more R radicals, preferably nonaromatic R radicals. When $Ar^2$ is a heteroaryl group, especially triazine, pyrimidine, quinazoline or carbazole, preference may also be given to aromatic or heteroaromatic R radicals on this heteroaryl group.

$Ar^2$ here is preferably the same or different at each instance and is selected from the above-detailed groups of the formulae Ar-1 to Ar-81.

Particularly preferred $Ar^2$ groups are selected from the group consisting of 1-dibenzofuranyl, i.e. a group of the formula Ar-16 with $A^1$=O and m=0, phenyl-1-dibenzofuranyl, i.e. a group of the formula Ar-16 with $A^1$=O, m=1 and $Ar^3$=para-phenylene, phenyl, ortho-biphenyl, meta-biphenyl, para-biphenyl, ortho-para-terphenyl, quaterphenyl, para-tert-butylphenyl, triphenylene and N-phenyl-3-carbazolyl.

In a preferred embodiment of the invention, R is the same or different at each instance and is selected from the group consisting of H, D, F, N(Ar')$_2$, CN, OR$^1$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may each be substituted by one or more R$^1$ radicals, but is preferably unsubstituted, and where one or more nonadjacent CH$_2$ groups may be replaced by O, or an aromatic or heteroaromatic ring system which has 6 to 30 aromatic ring atoms and may be substituted in each case by one or more R$^1$ radicals; at the same time, two R radicals together may also form an aliphatic, aromatic or heteroaromatic ring system. More preferably, R is the same or different at each instance and is selected from the group consisting of H, N(Ar')$_2$, a straight-chain alkyl group having 1 to 6 carbon atoms, especially having 1, 2, 3 or 4 carbon atoms, or a branched or cyclic alkyl group having 3 to 6 carbon atoms, where the alkyl group in each case may be substituted by one or more R$^1$ radicals, but is preferably unsubstituted, or an aromatic or heteroaromatic ring system which has 6 to 24 aromatic ring atoms and may be substituted in each case by one or more R$^1$ radicals, preferably nonaromatic R$^1$ radicals. Most preferably, R is the same or different at each instance and is selected from the group consisting of H or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more R$^1$ radicals, preferably nonaromatic R$^1$ radicals.

In a further preferred embodiment of the invention, Ar' is an aromatic or heteroaromatic ring system which has 6 to 30 aromatic ring atoms and may be substituted by one or more R$^1$ radicals. In a particularly preferred embodiment of the invention, Ar' is an aromatic or heteroaromatic ring system which has 6 to 24 aromatic ring atoms, even more preferably 6 to 18 aromatic ring atoms, especially 6 to 13 aromatic ring atoms, and may be substituted by one or more, preferably nonaromatic, R$^1$ radicals.

Suitable aromatic or heteroaromatic ring systems R or Ar' are selected from phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorene which may be joined via the 1, 2, 3 or 4 position, spirobifluorene which may be joined via the 1, 2, 3 or 4 position, naphthalene which may be joined via the 1 or 2 position, indole, benzofuran, benzothiophene, carbazole which may be joined via the 1, 2, 3 or 4 position, dibenzofuran which may be joined via the 1, 2, 3 or 4 position, dibenzothiophene which may be joined via the 1, 2, 3 or 4 position, indenocarbazole, indolocarbazole, pyridine, pyrimidine, pyrazine, pyridazine, triazine, quinoline, quinazoline, benzimidazole, phenanthrene, triphenylene or a combination of two or three of these groups, each of which may be substituted by one or more nonaromatic R$^1$ radicals. When R or Ar' is a heteroaryl group, especially triazine, pyrimidine or quinazoline, preference may also be given to aromatic or heteroaromatic R$^1$ radicals on this heteroaryl group.

The R groups here, when they are an aromatic or heteroaromatic ring system, or Ar' are preferably selected from the groups of the following formulae R-1 to R-81:

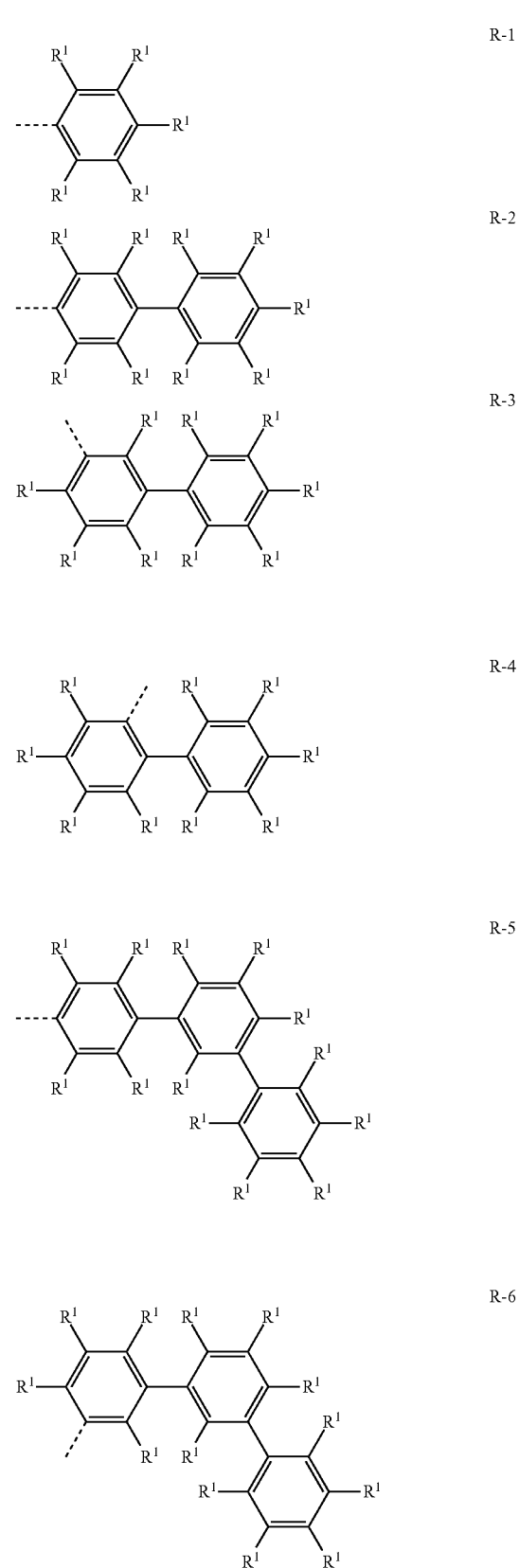

-continued
R-7
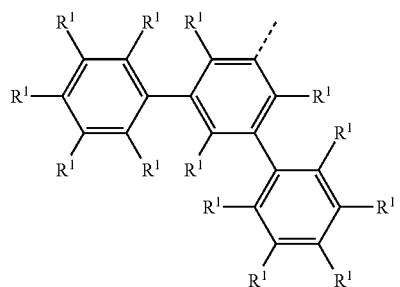
R-8
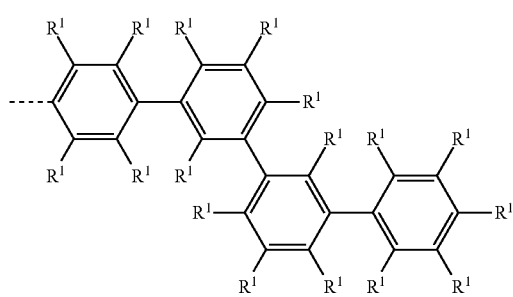
R-9
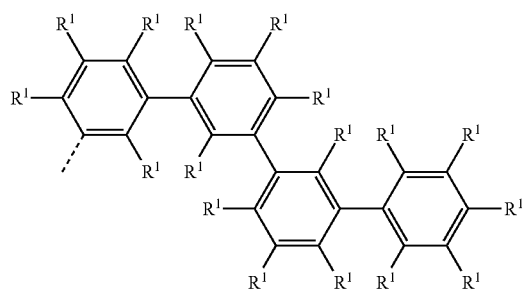
R-10
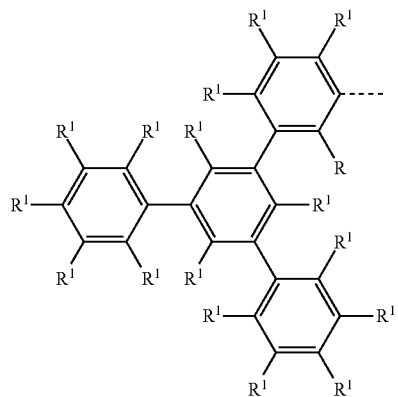
-continued
R-11
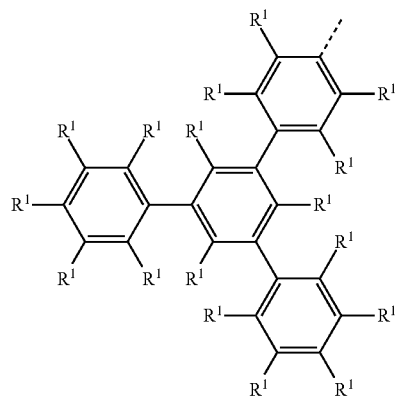
R-12
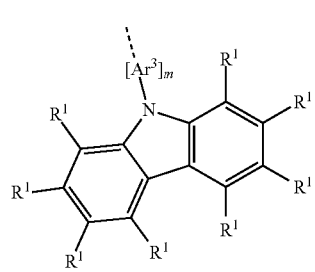
R-13
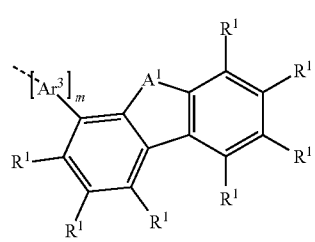
R-14
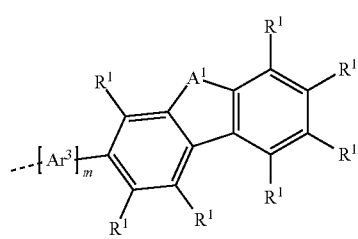
R-15
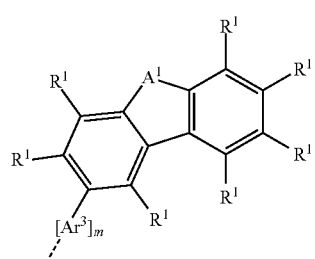
R-16
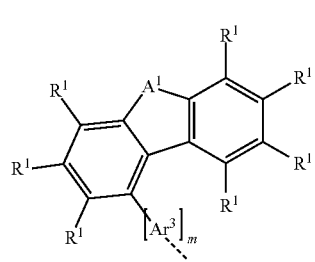

R-17
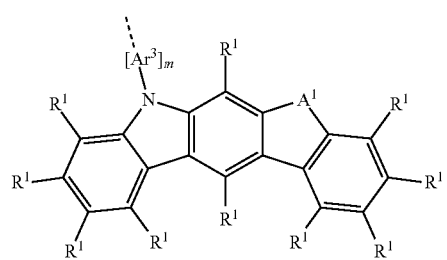
R-18
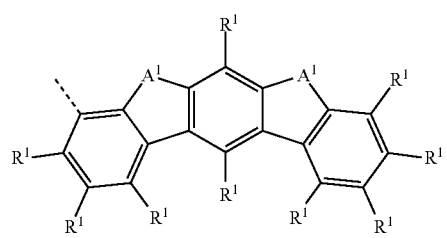
R-19
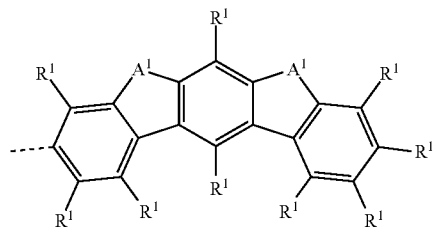
R-20
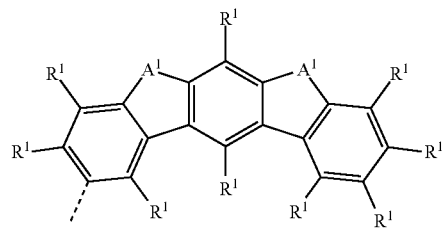
R-21
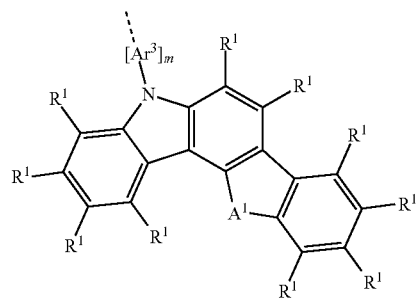
R-22
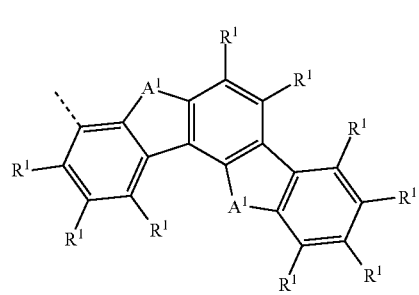
R-23
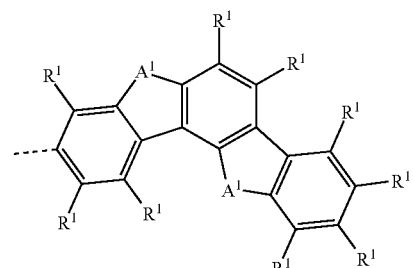
R-24
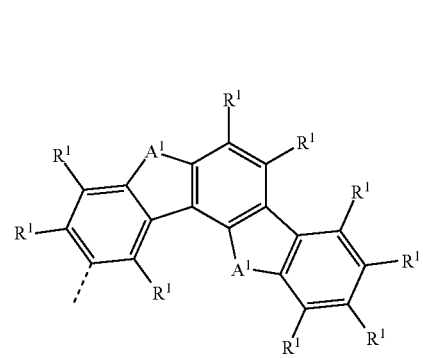
R-25
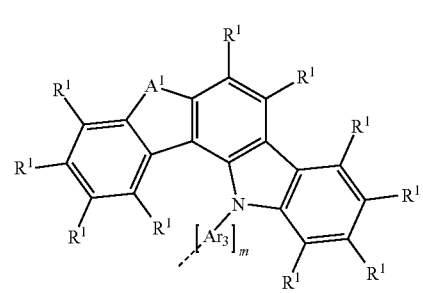
R-26
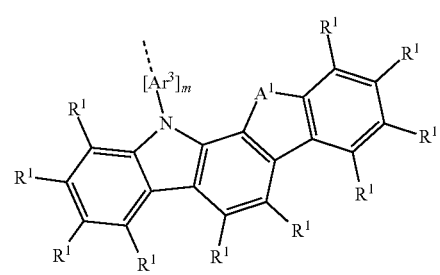
R-27
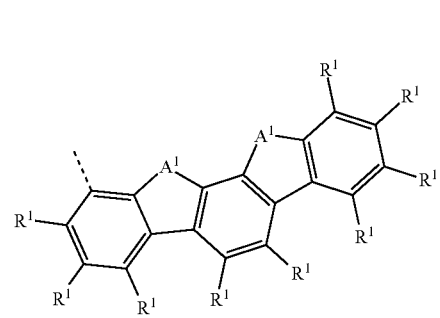

R-28
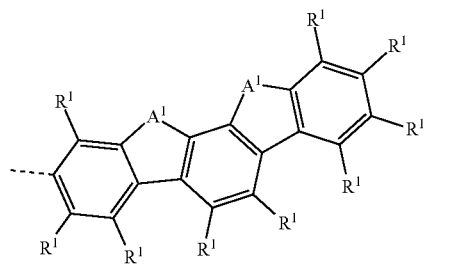
R-29
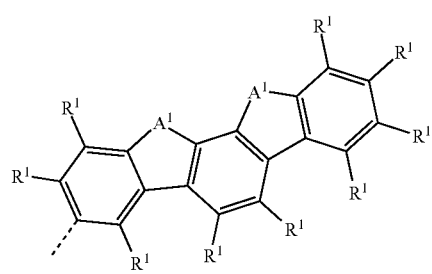
R-30
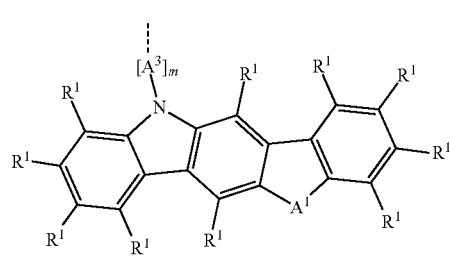
R-31
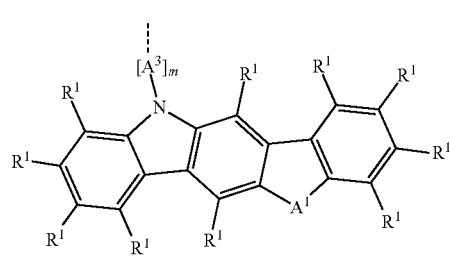
R-32
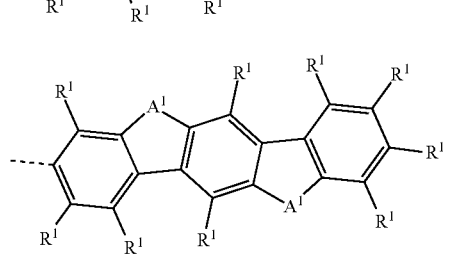
R-33
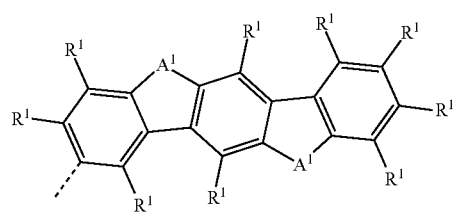
R-34
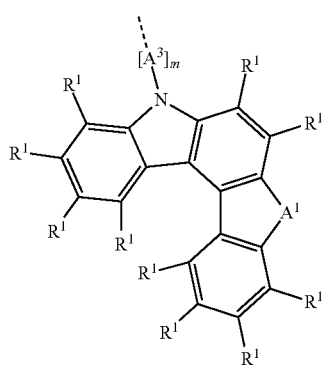
R-35
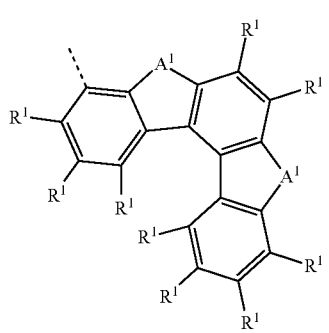
R-36
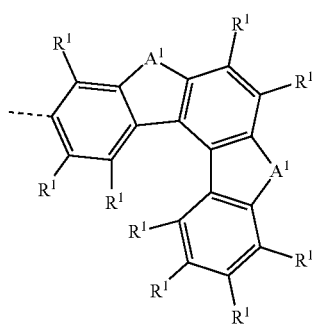
R-37
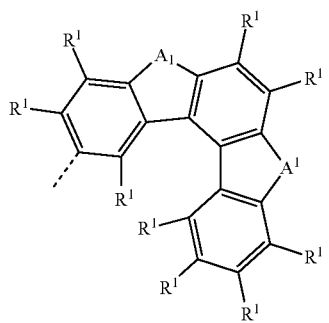

-continued
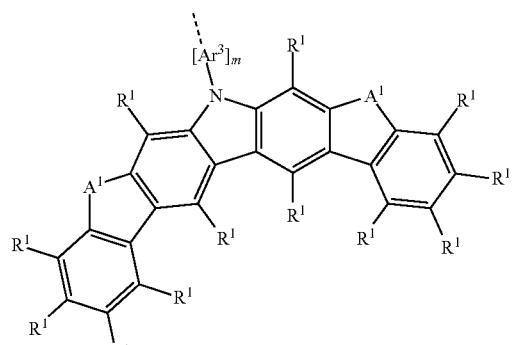
R-38
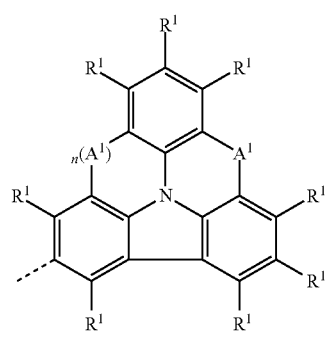
R-39
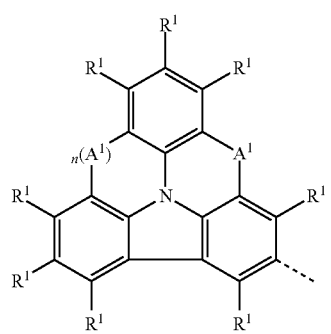
R-40
R-41
-continued
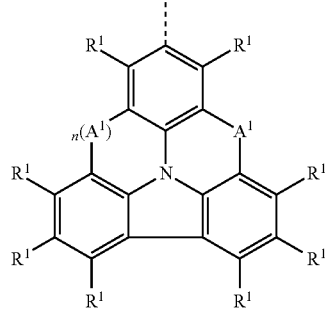
R-42
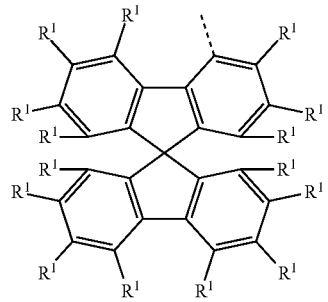
R-43
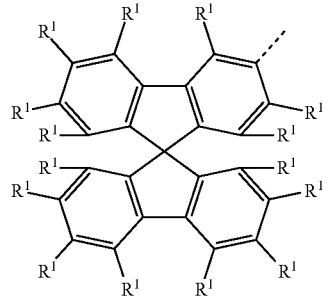
R-44
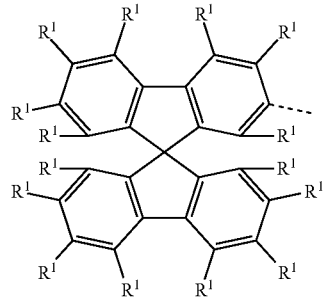
R-45
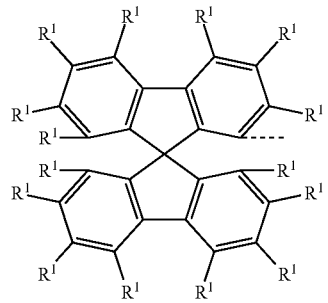
R-46

R-47 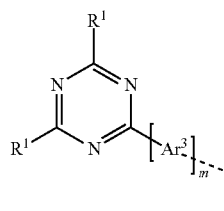
R-48 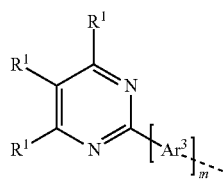
R-49 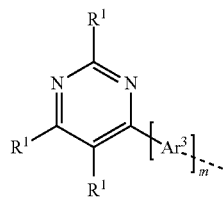
R-50 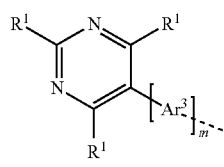
R-51 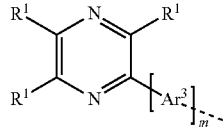
R-52 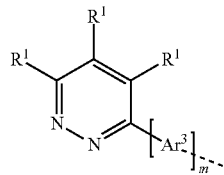
R-53 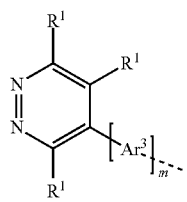
R-54 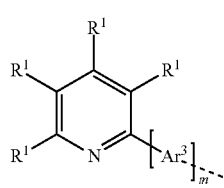
R-55 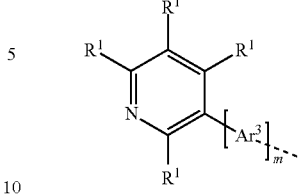
R-56 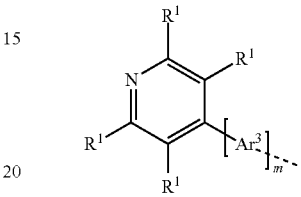
R-57 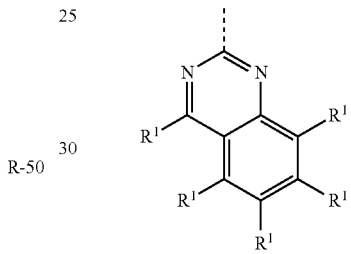
R-58 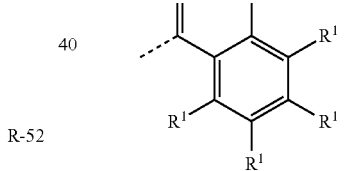
R-59 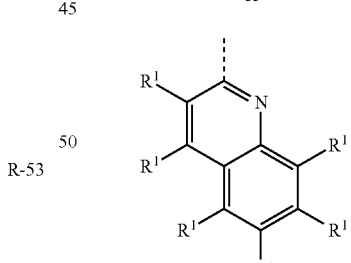
R-60 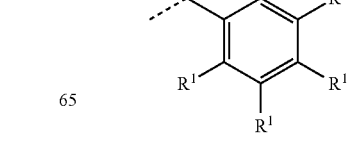

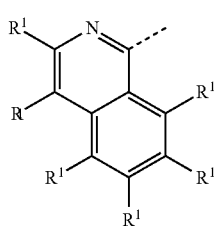 R-61
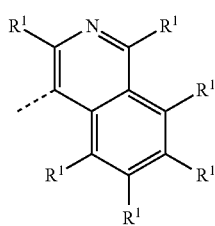 R-62
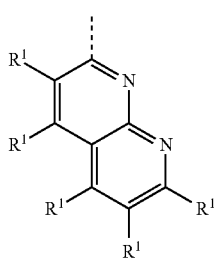 R-63
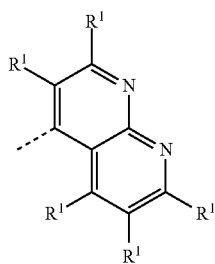 R-64
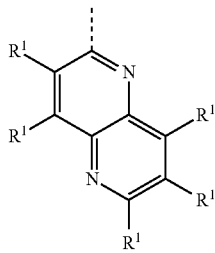 R-65
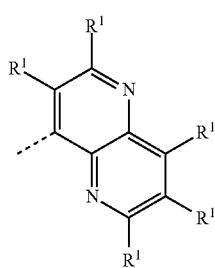 R-66
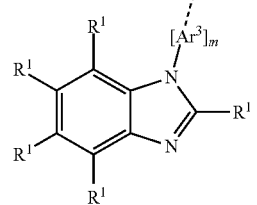 R-67
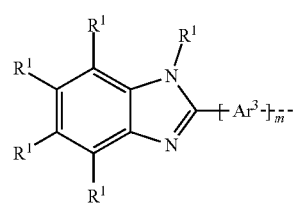 R-68
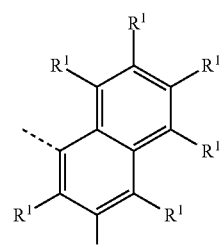 R-69
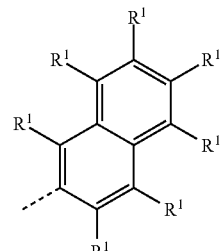 R-70
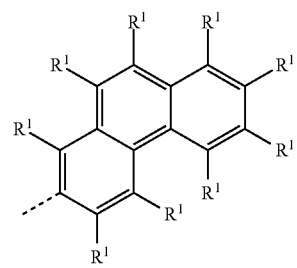 R-71
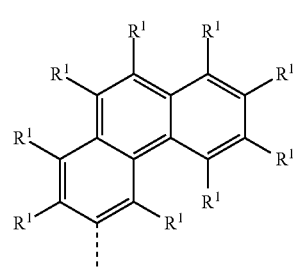 R-72

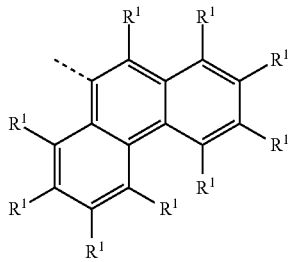
R-73

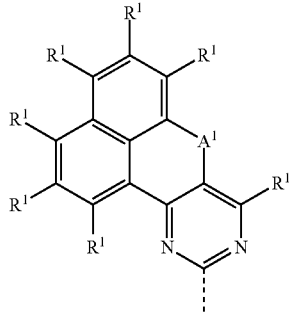
R-78

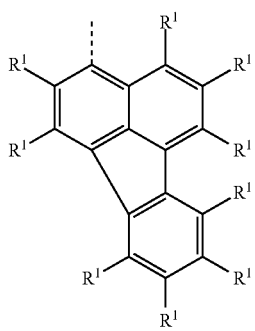
R-74

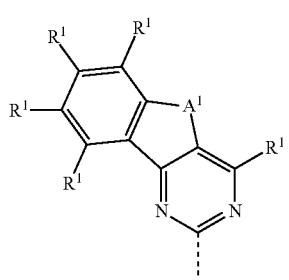
R-79

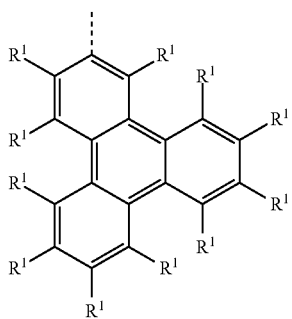
R-75

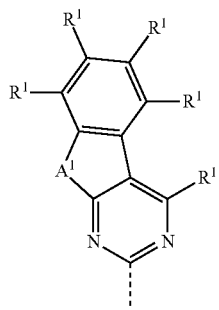
R-80

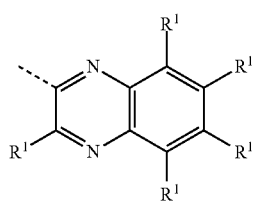
R-81

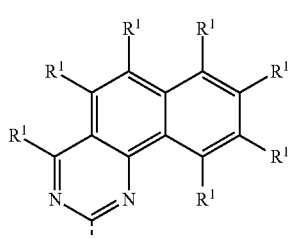
R-76

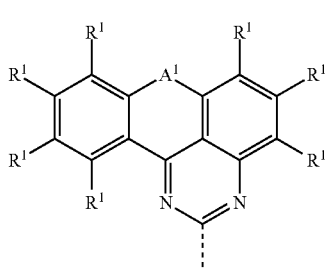
R-77 where $R^1$ has the definitions given above, the dotted bond represents the bond to the base skeleton in formula (1) or the bond to $Ar^1$ or $Ar^2$ or to the nitrogen atom in the $N(Ar')_2$ group and, in addition:

$A^1$ is the same or different at each instance and is $C(R^1)_2$, $NR^1$, O or S;

$Ar^3$ is the same or different at each instance and is a bivalent aromatic or heteroaromatic ring system which has 6 to 18 aromatic ring atoms and may be substituted in each case by one or more $R^1$ radicals;

n is 0 or 1, where n=0 means that no $A^1$ group is bonded at this position and $R^1$ radicals are bonded to the corresponding carbon atoms instead;

m is 0 or 1, where m=0 means that the $Ar^3$ group is absent and that the corresponding aromatic or heteroaromatic group is bonded directly to the base skeleton in formula (1) or in the preferred embodiments, or to the nitrogen atom in the $N(Ar')_2$ group; with the proviso that m=1 for the structures (R-12), (R-17), (R-21), (R-25), (R-26), (R-30), (R-34), (R-38) and (R-39) when these groups are embodiments of Ar.

When the abovementioned Ar-1 to Ar-81 groups for $Ar^1$ or $Ar^2$ or R-1 to R-81 groups for R or Ar' have two or more $A^1$ groups, possible options for these include all combinations from the definition of $A^1$. Preferred embodiments in that case are those in which one $A^1$ group is NR or $NR^1$ and the other $A^1$ group is $C(R)_2$ or $C(R^1)_2$ or in which both $A^1$ groups are NR or $NR^1$ or in which both $A^1$ groups are O. In a particularly preferred embodiment of the invention, in $Ar^1$, $Ar^2$, R or Ar' groups having two or more $A^1$ groups, at least one $A^1$ group is $C(R)_2$ or $C(R^1)_2$ or is NR or $NR^1$.

When $A^1$ is NR or $NR^1$, the substituent R or $R^1$ bonded to the nitrogen atom is preferably an aromatic or heteroaromatic ring system which has 5 to 24 aromatic ring atoms and may also be substituted by one or more $R^1$ or $R^2$ radicals. In a particularly preferred embodiment, this R or $R^1$ substituent is the same or different at each instance and is an aromatic or heteroaromatic ring system which has 6 to 24 aromatic ring atoms, preferably 6 to 12 aromatic ring atoms, and which does not have any fused aryl groups or heteroaryl groups in which two or more aromatic or heteroaromatic 6-membered ring groups are fused directly to one another, and which may also be substituted in each case by one or more $R^1$ or $R^2$ radicals. Particular preference is given to phenyl, biphenyl, terphenyl and quaterphenyl having bonding patterns as listed above for Ar-1 to Ar-11 or R-1 to R-11, where these structures may be substituted by one or more $R^1$ or $R^2$ radicals, but are preferably unsubstituted.

When $A^1$ is $C(R)_2$ or $C(R^1)_2$, the substituents R or $R^1$ bonded to this carbon atom are preferably the same or different at each instance and are a linear alkyl group having 1 to 10 carbon atoms or a branched or cyclic alkyl group having 3 to 10 carbon atoms or an aromatic or heteroaromatic ring system which has 5 to 24 aromatic ring atoms and may also be substituted by one or more $R^1$ or $R^2$ radicals. Most preferably, R or $R^1$ is a methyl group or a phenyl group. In this case, the R or $R^1$ radicals together may also form a ring system, which leads to a spiro system.

In a further preferred embodiment of the invention, $R^1$ is the same or different at each instance and is selected from the group consisting of H, D, F, CN, $OR^2$, a straight-chain alkyl group having 1 to 10 carbon atoms or an alkenyl group having 2 to 10 carbon atoms or a branched or cyclic alkyl group having 3 to 10 carbon atoms, where the alkyl or alkenyl group may in each case be substituted by one or more $R^2$ radicals, and where one or more nonadjacent $CH_2$ groups may be replaced by O, or an aromatic or heteroaromatic ring system which has 6 to 30 aromatic ring atoms and may be substituted in each case by one or more $R^2$ radicals; at the same time, two or more $R^1$ radicals together may form an aliphatic ring system. In a particularly preferred embodiment of the invention, $R^1$ is the same or different at each instance and is selected from the group consisting of H, a straight-chain alkyl group having 1 to 6 carbon atoms, especially having 1, 2, 3 or 4 carbon atoms, or a branched or cyclic alkyl group having 3 to 6 carbon atoms, where the alkyl group may be substituted by one or more $R^2$ radicals, but is preferably unsubstituted, or an aromatic or heteroaromatic ring system which has 6 to 24 aromatic ring atoms, preferably 6 to 18 aromatic ring atoms, more preferably 6 to 13 aromatic ring atoms, and may be substituted in each case by one or more $R^2$ radicals, but is preferably unsubstituted.

In a further preferred embodiment of the invention, $R^2$ is the same or different at each instance and is H, F, an alkyl group having 1 to 4 carbon atoms or an aryl group having 6 to 10 carbon atoms, which may be substituted by an alkyl group having 1 to 4 carbon atoms, but is preferably unsubstituted.

The abovementioned preferences can occur individually or together. It is preferable when the abovementioned preferences occur together.

Examples of suitable compounds of the invention are the structures depicted below:

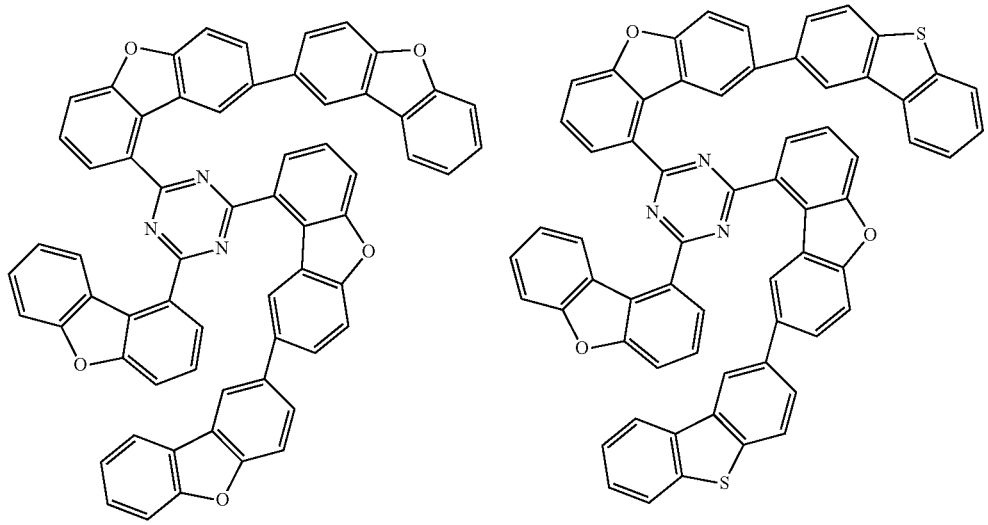

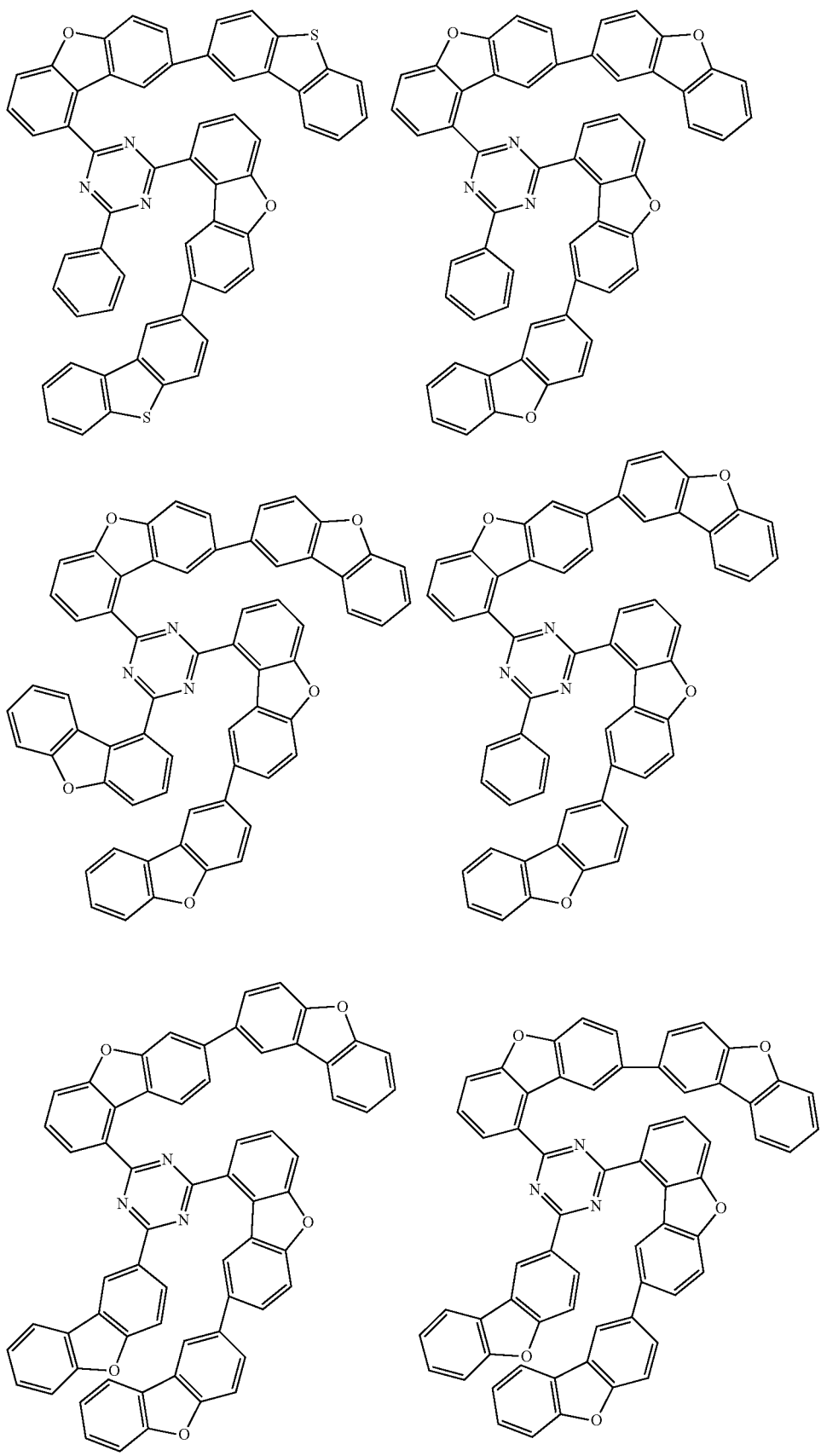

-continued
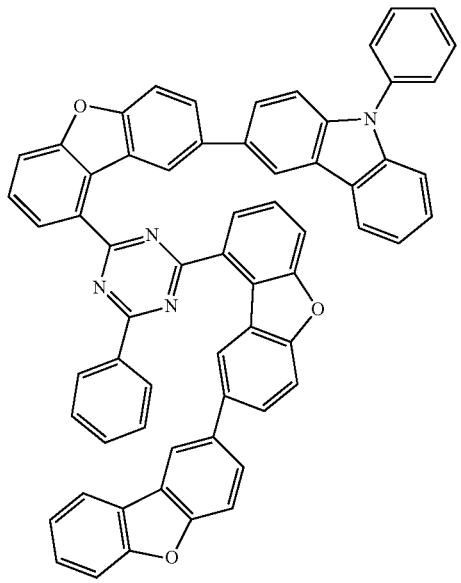
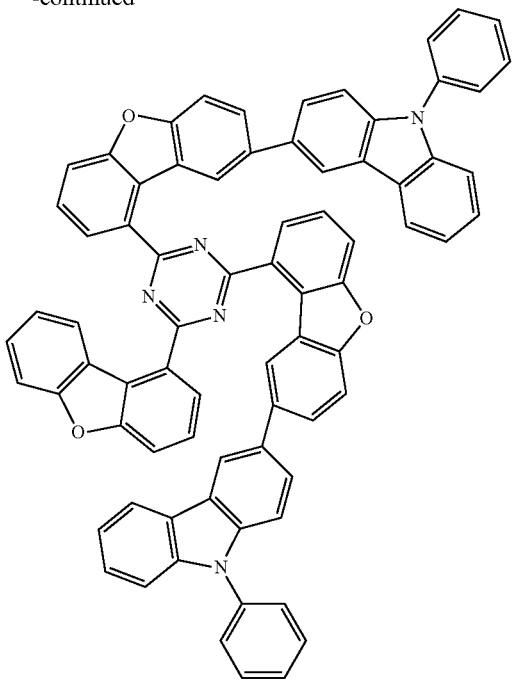
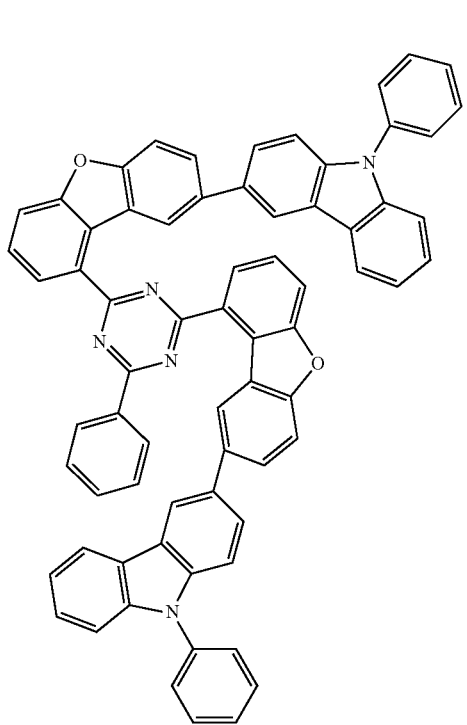
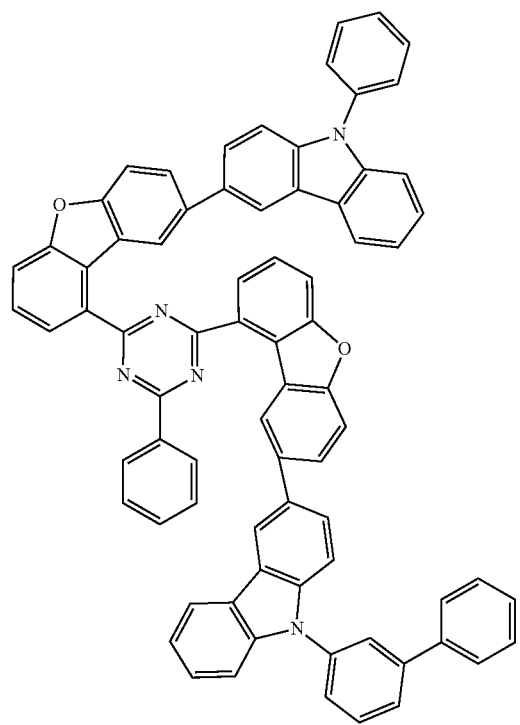

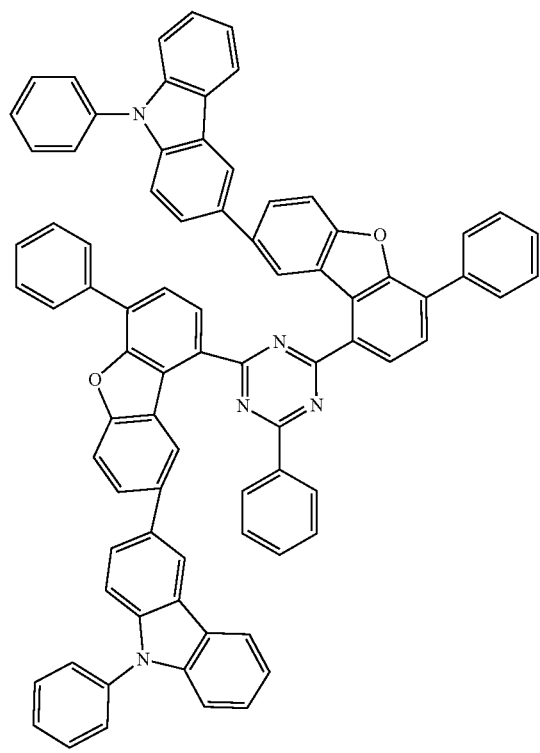
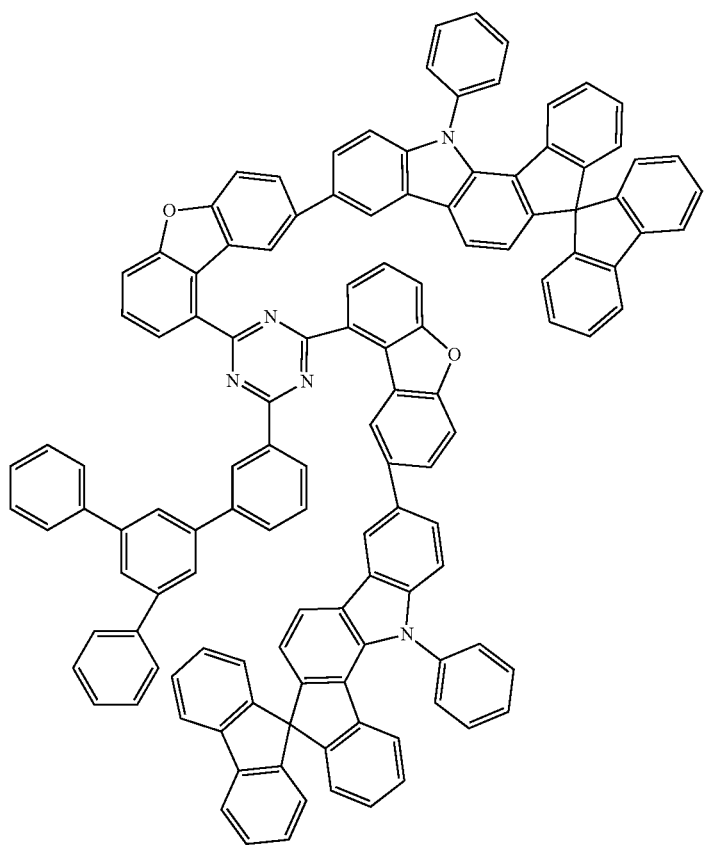

-continued
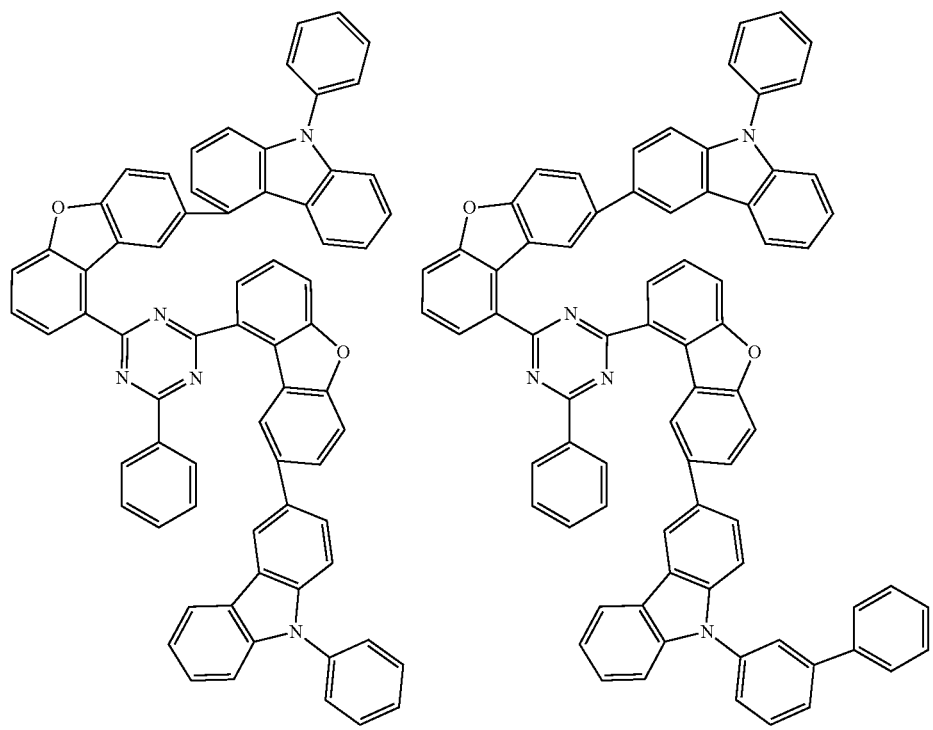 [SMILES: c1ccc(-c2nc(-c3cccc4oc5ccc(-c6ccc7c(c6)c6ccccc6n7-c6ccccc6)cc5c34)nc(-c3cccc4oc5ccc(-c6cccc7c6c6ccccc6n7-c6ccccc6)cc5c34)n2)cc1 ; c1ccc(-c2cccc(-n3c4ccccc4c4cc(-c5ccc6oc7cccc(-c8nc(-c9ccccc9)nc(-c9cccc%10oc%11ccc(-c%12ccc%13c(c%12)c%12ccccc%12n%13-c%12ccccc%12)cc%11c9%10)n8)c7c6c5)ccc43)c2)cc1]
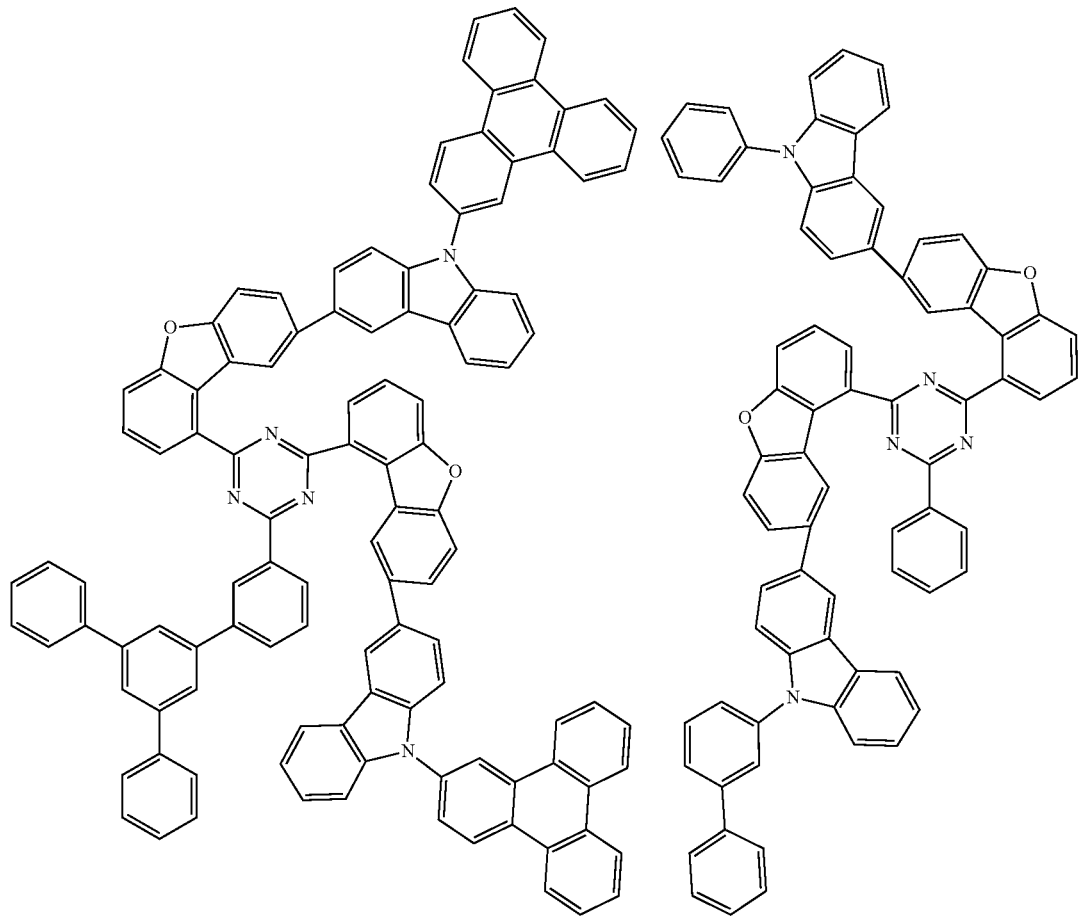

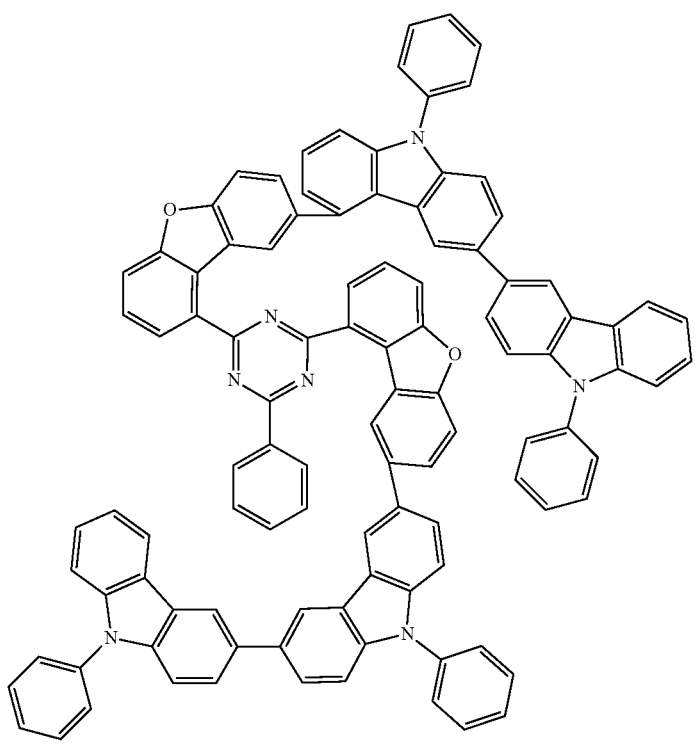
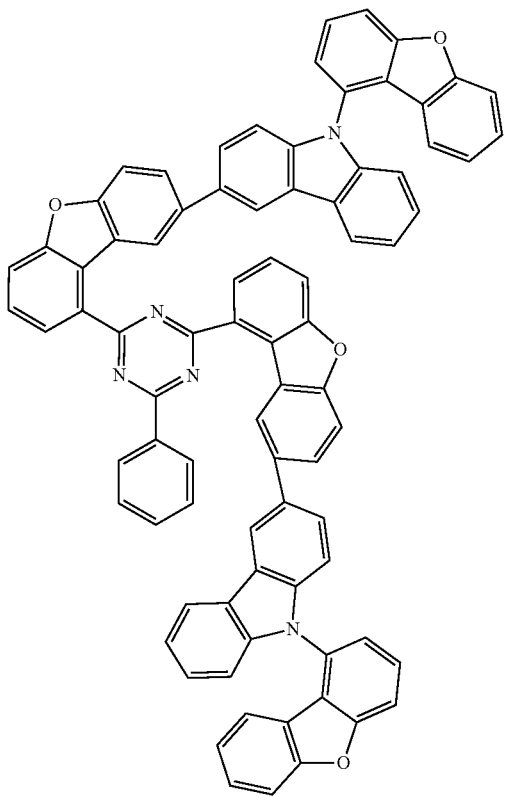

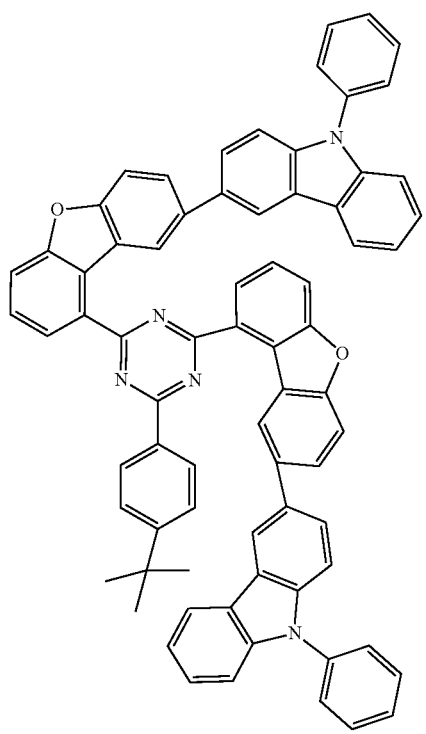
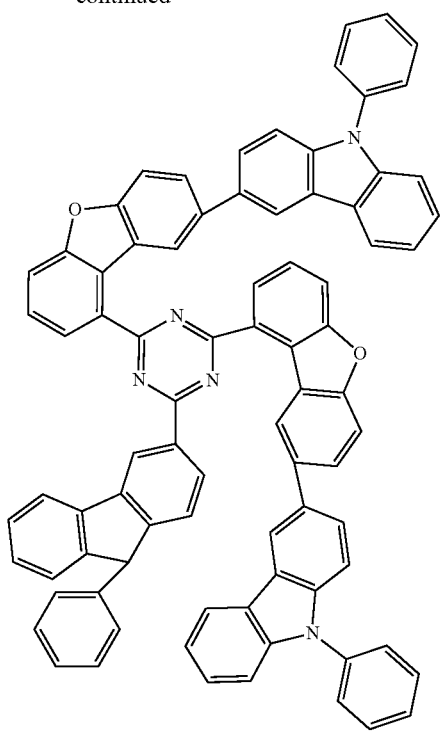
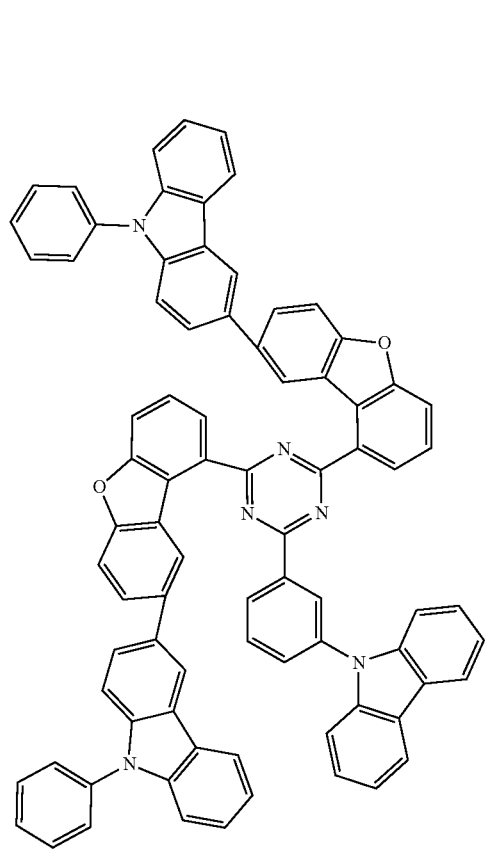
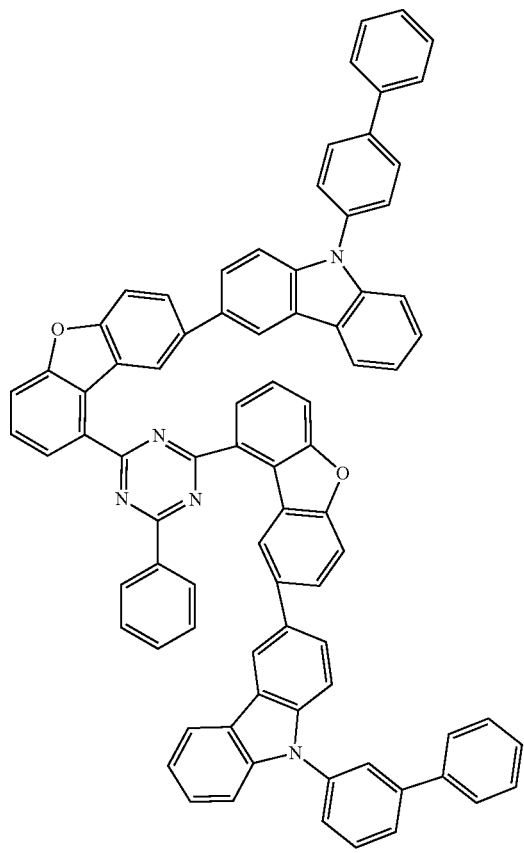

-continued
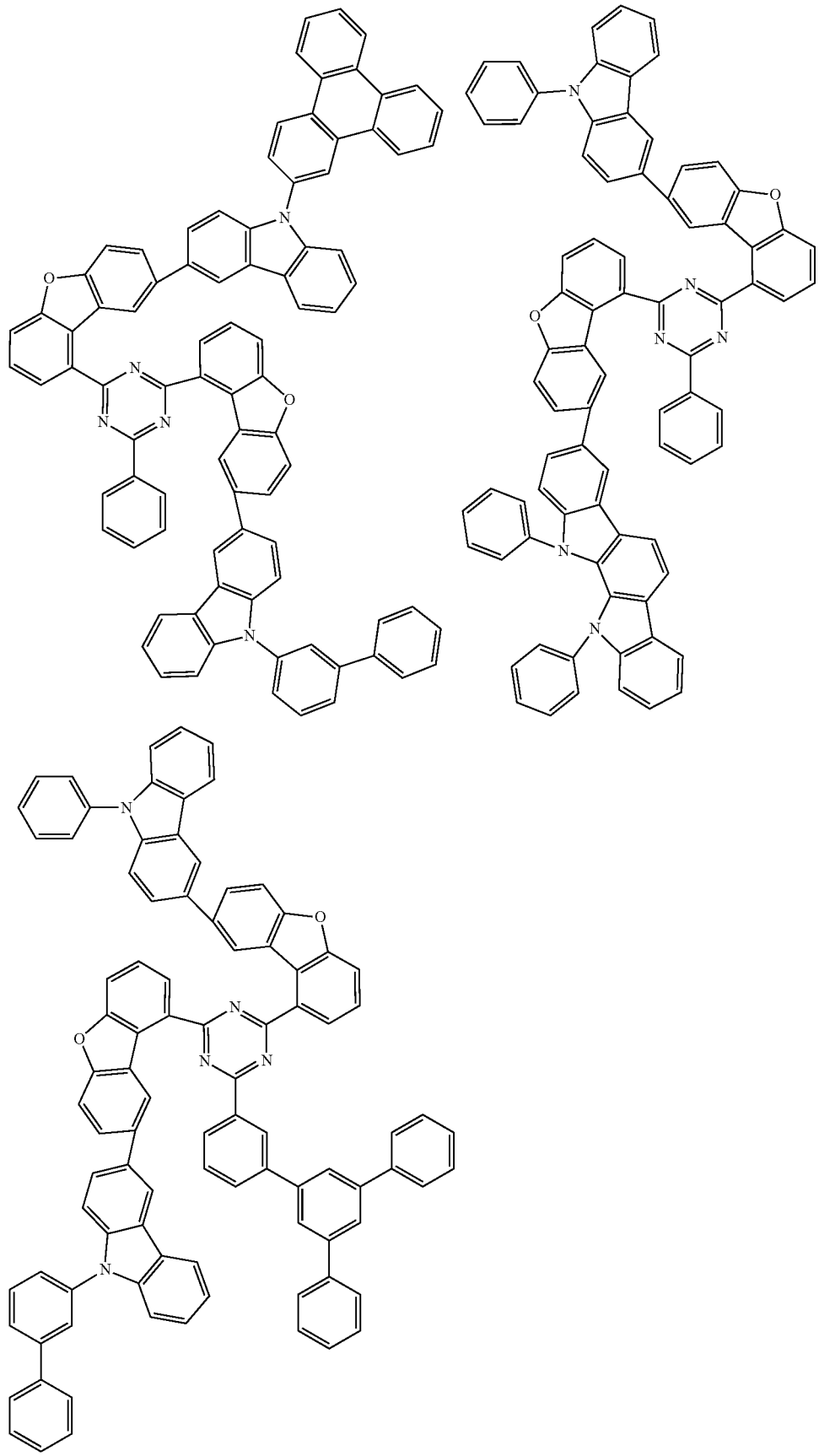

-continued
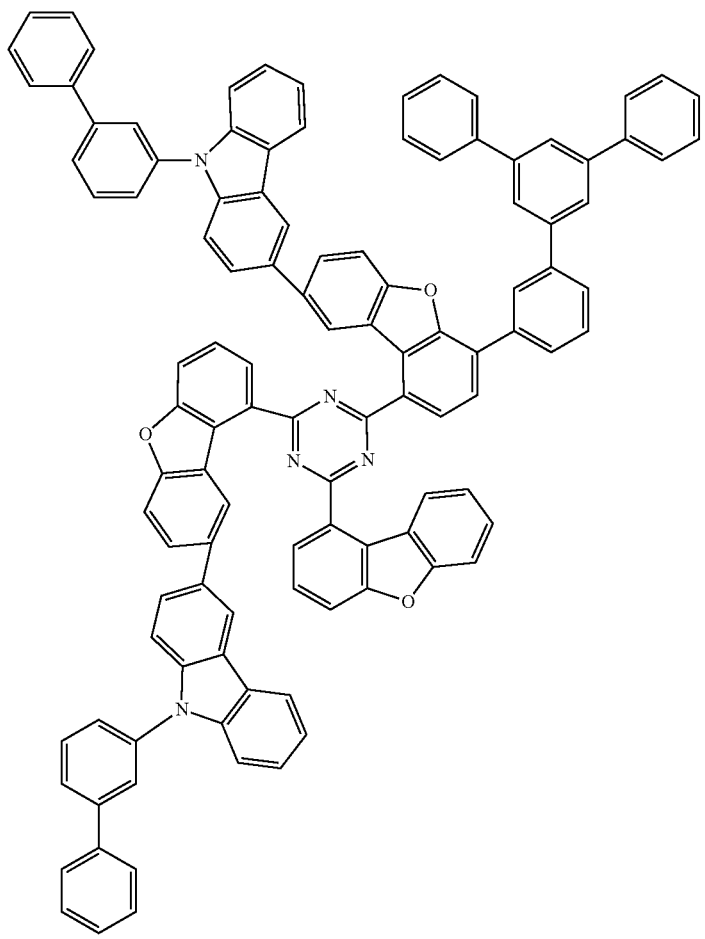

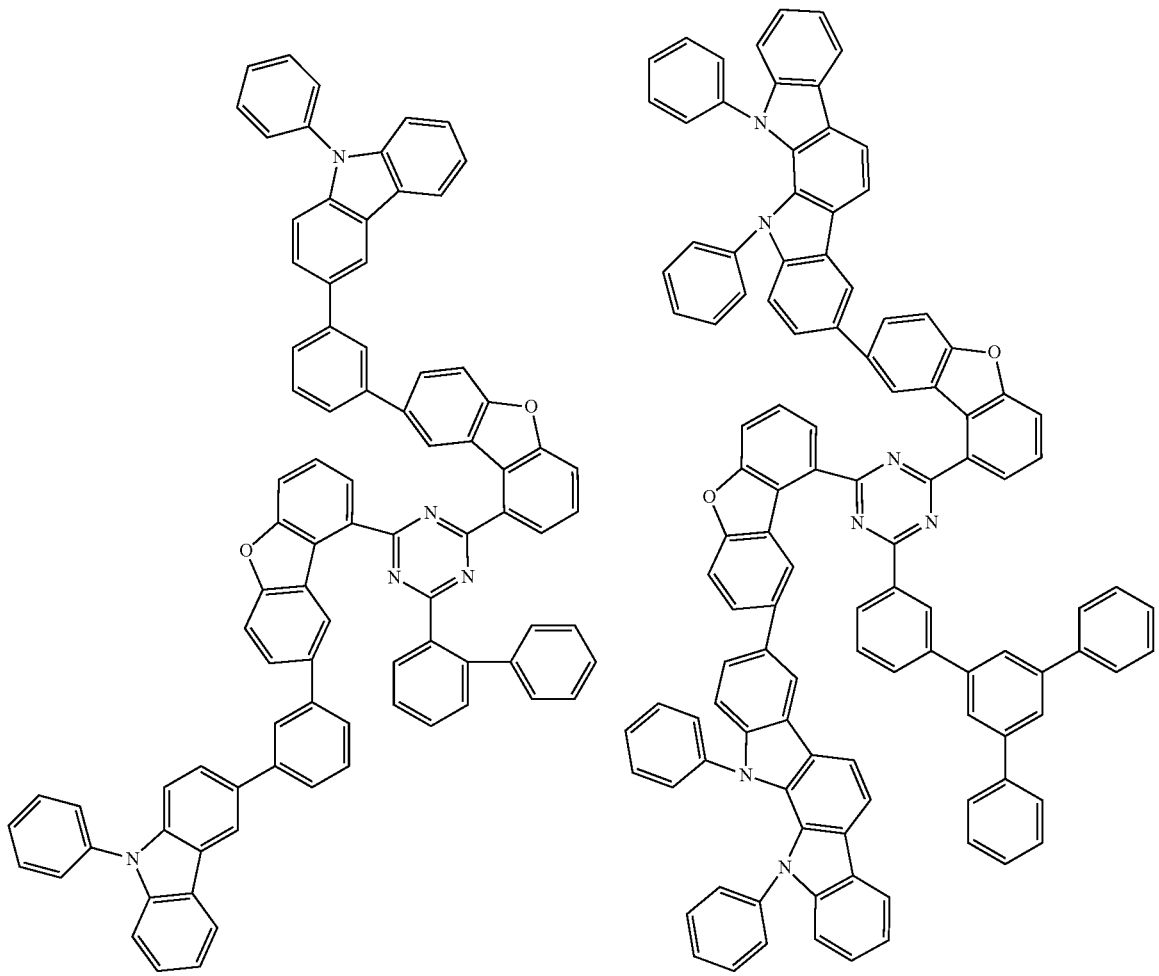 [SMILES: c1ccc(-c2ccccc2-c2nc(-c3cccc4oc5ccc(-c6cccc(-c7ccc8c(c7)c7ccccc7n8-c7ccccc7)c6)cc5c34)nc(-c3cccc4oc5ccc(-c6cccc(-c7ccc8c(c7)c7ccccc7n8-c7ccccc7)c6)cc5c34)n2)cc1 ; c1ccc(-c2cc(-c3ccccc3)cc(-c3cccc(-c4nc(-c5cccc6oc7ccc(-c8ccc9c(c8)c8ccc%10c%11ccccc%11n(-c%11ccccc%11)c%10c8n9-c8ccccc8)cc7c56)nc(-c5cccc6oc7ccc(-c8ccc9c(c8)c8ccc%10c%11ccccc%11n(-c%11ccccc%11)c%10c8n9-c8ccccc8)cc7c56)n4)c3)c2)cc1]

-continued
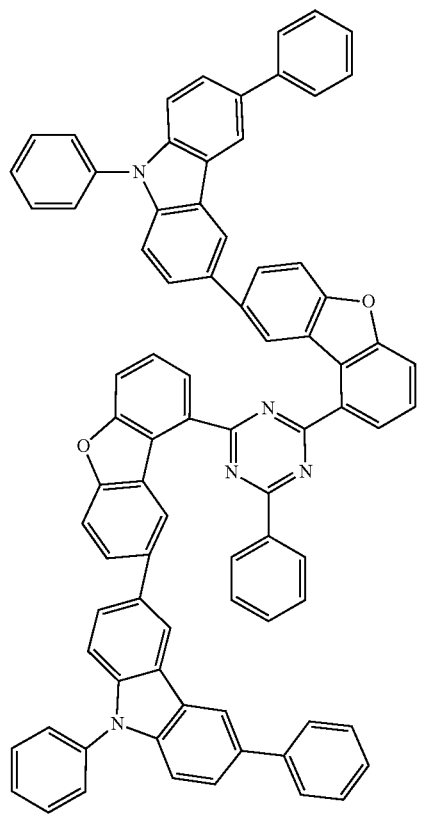
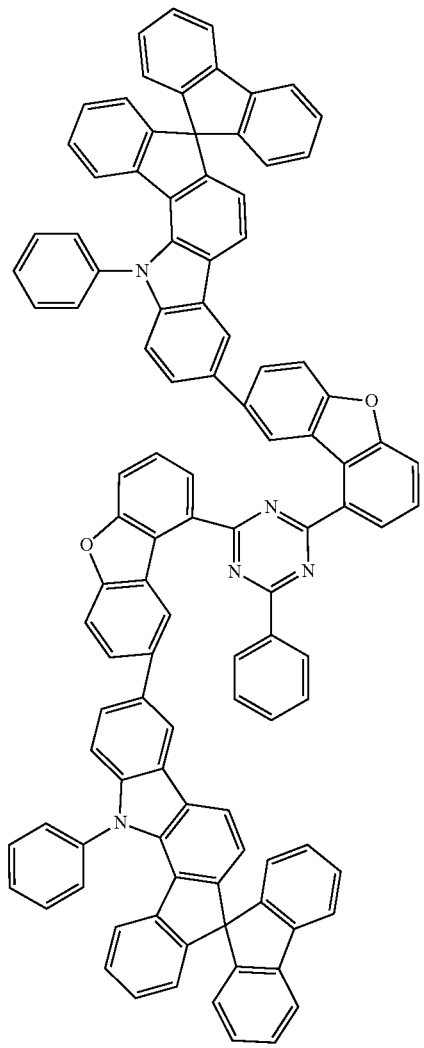

-continued
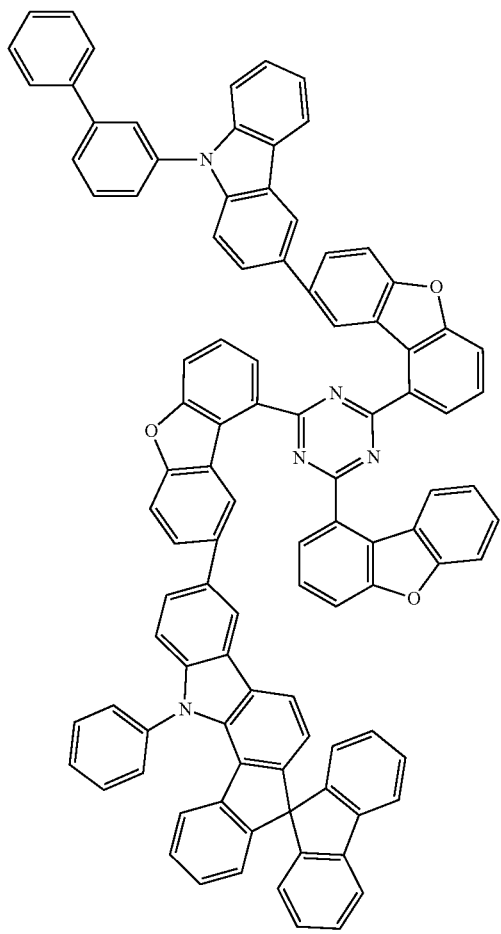 [SMILES: c1ccc(-c2cccc(-n3c4ccccc4c4cc(-c5ccc6oc7cccc(-c8nc(-c9cccc%10oc%11ccccc%11c9%10)nc(-c9cccc%10oc%11ccc(-c%12ccc%13c(c%12)c%12ccc%14c(c%12n%13-c%12ccccc%12)-c%12ccccc%12C%14%12c%13ccccc%13-c%13ccccc%13%12)cc%11c9%10)n8)c7c6c5)ccc43)c2)cc1]

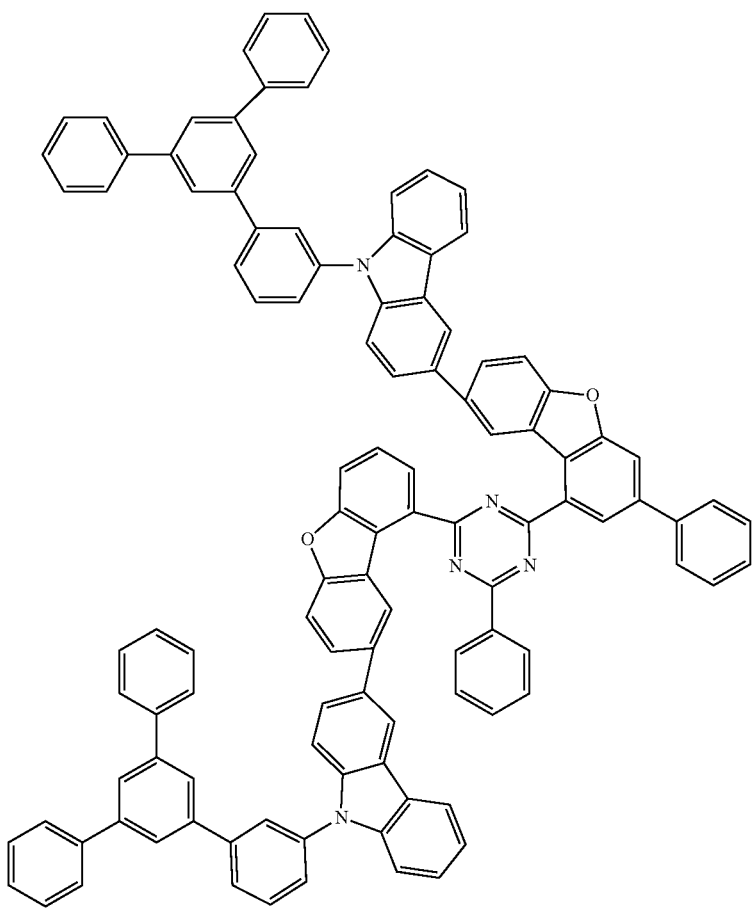
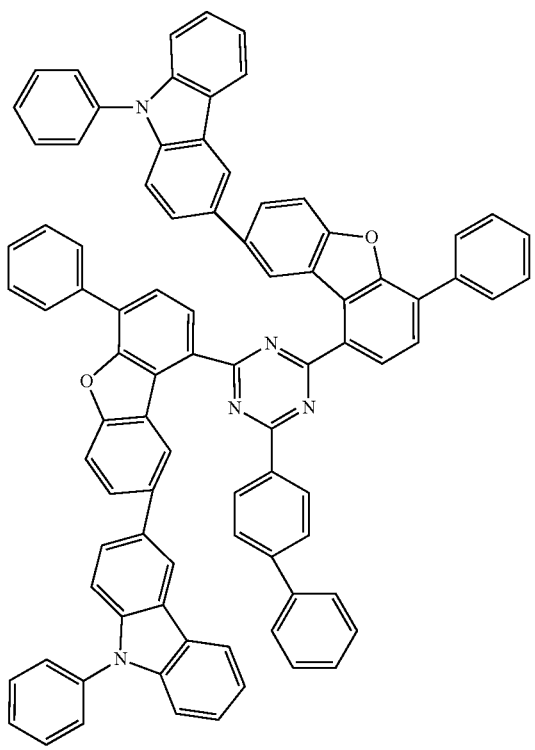

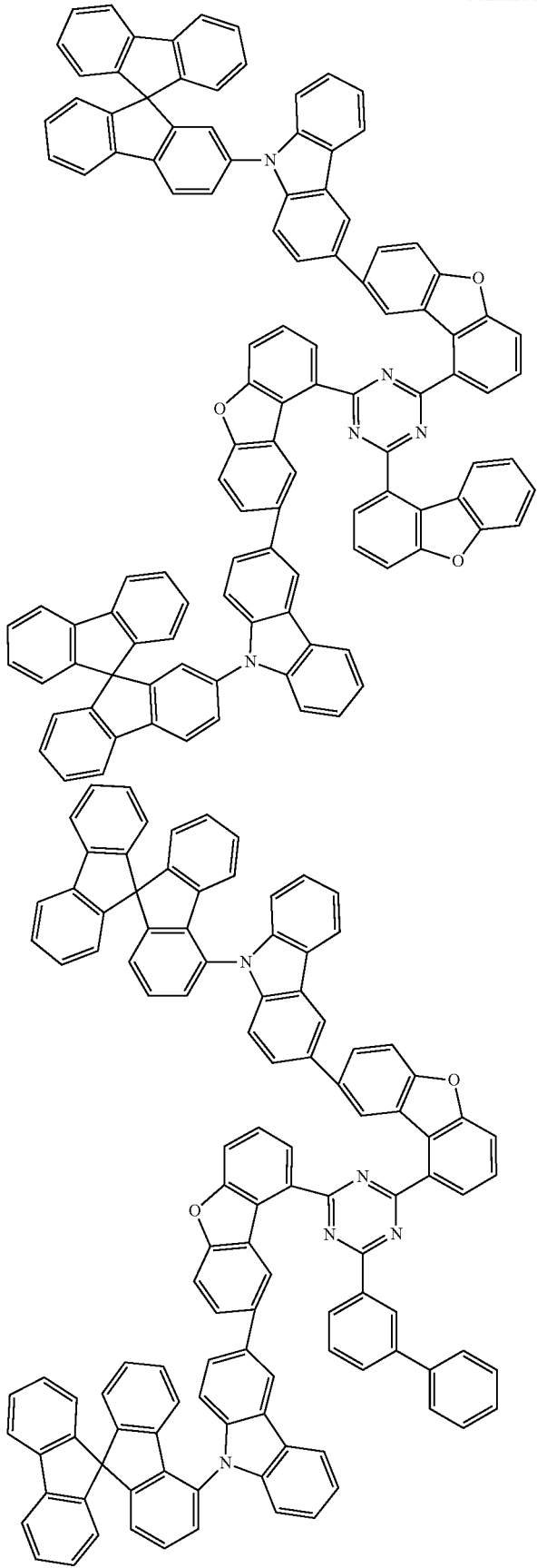

-continued
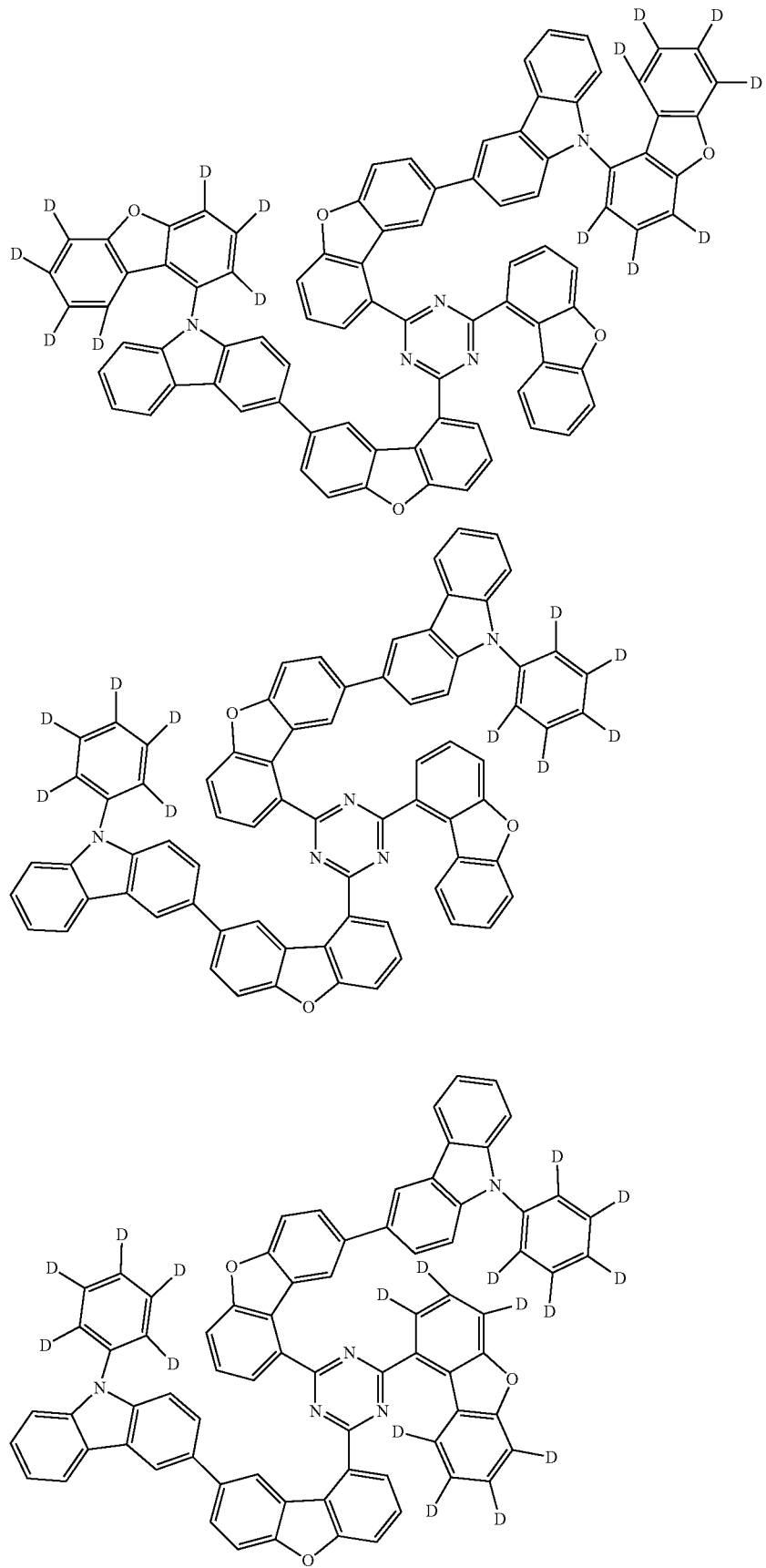

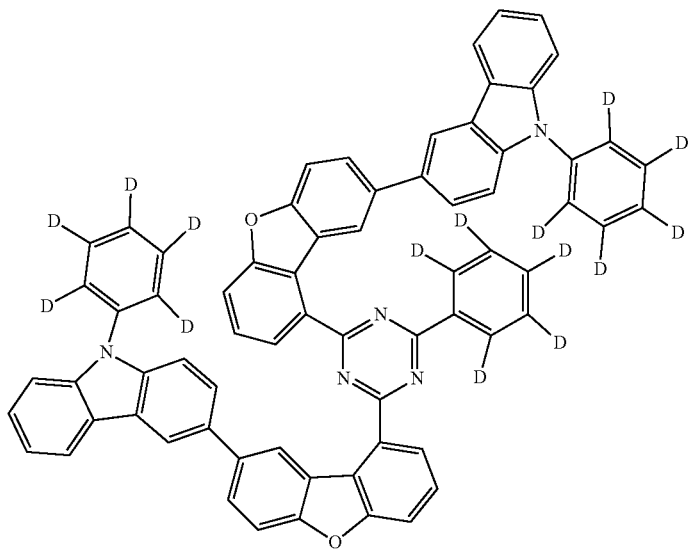 [SMILES: [2H]c1c([2H])c([2H])c(-c2nc(-c3cccc4oc5ccc(-c6ccc7c(c6)c6ccccc6n7-c6c([2H])c([2H])c([2H])c([2H])c6[2H])cc5c34)nc(-c3cccc4oc5ccc(-c6ccc7c(c6)c6ccccc6n7-c6c([2H])c([2H])c([2H])c([2H])c6[2H])cc5c34)n2)c([2H])c1[2H]]
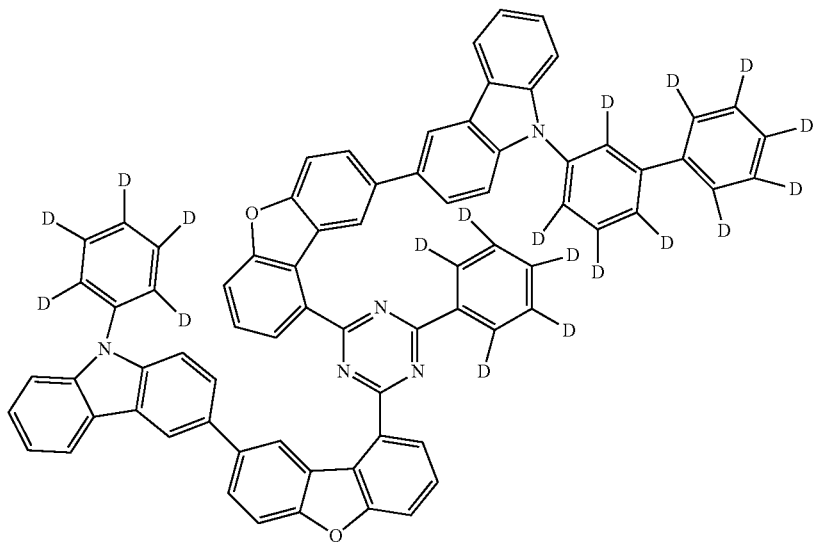
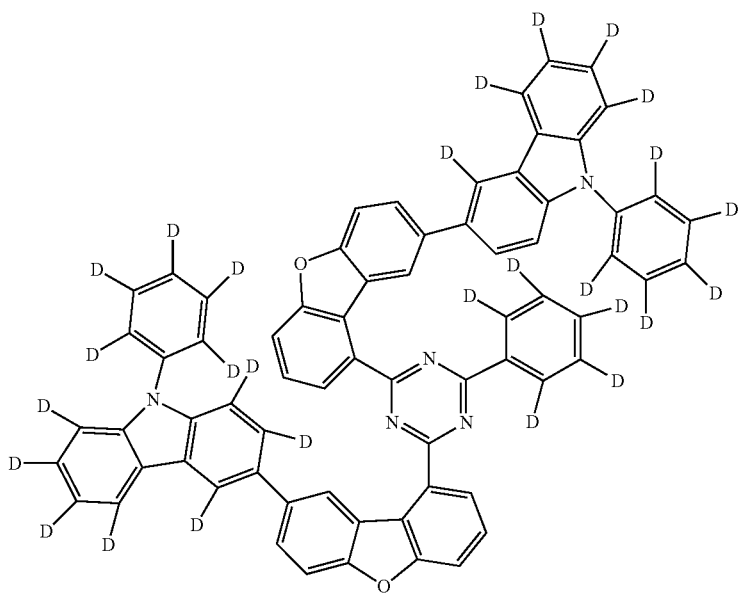

77
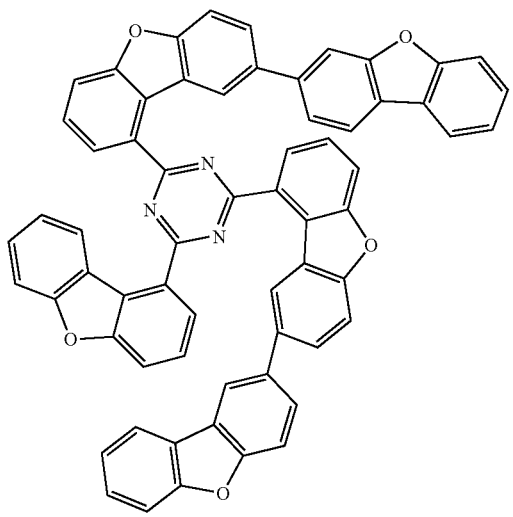
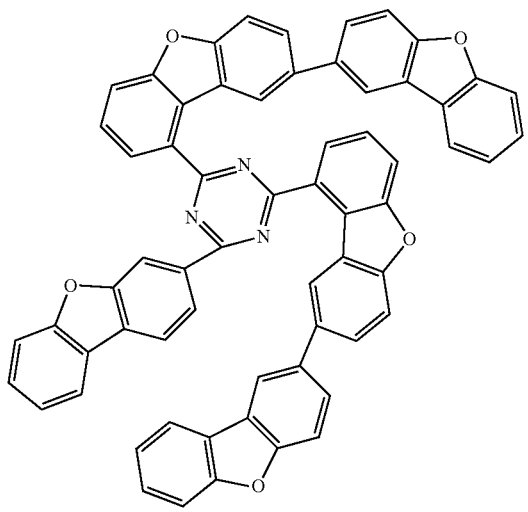
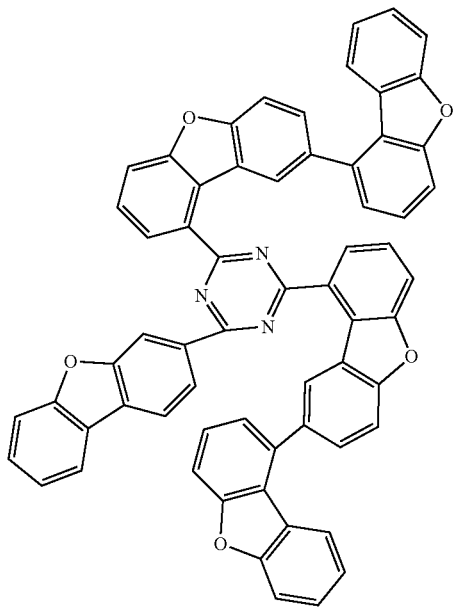
78
-continued
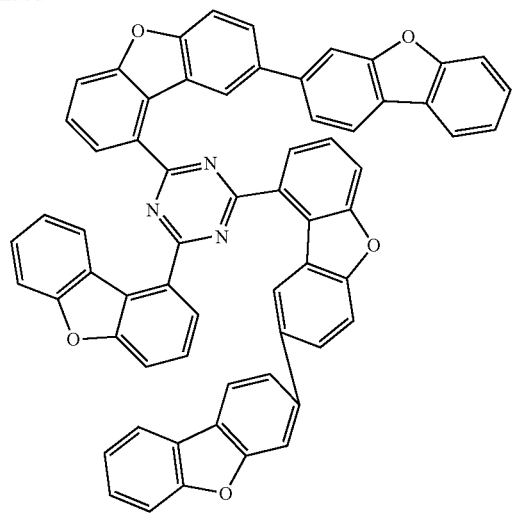
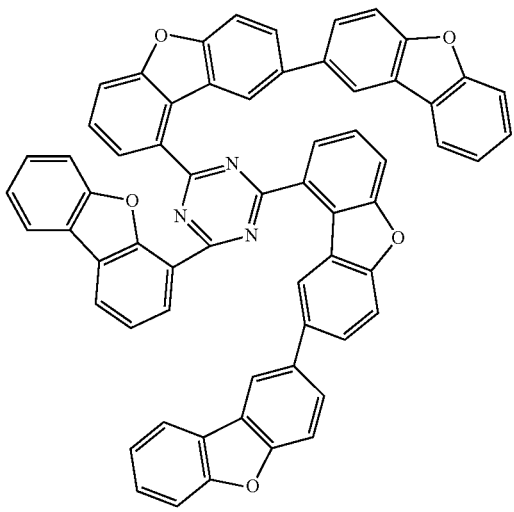

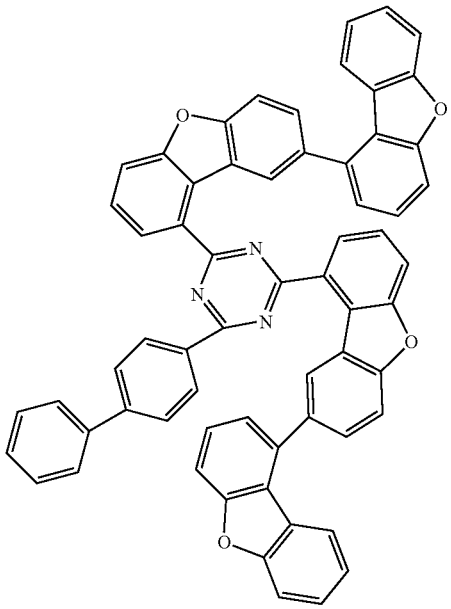
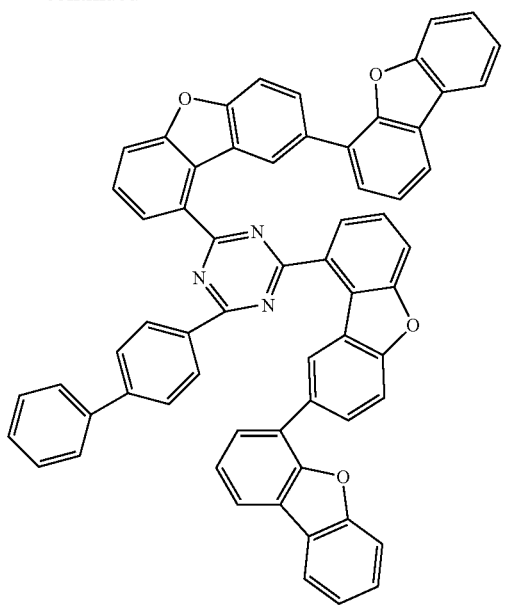
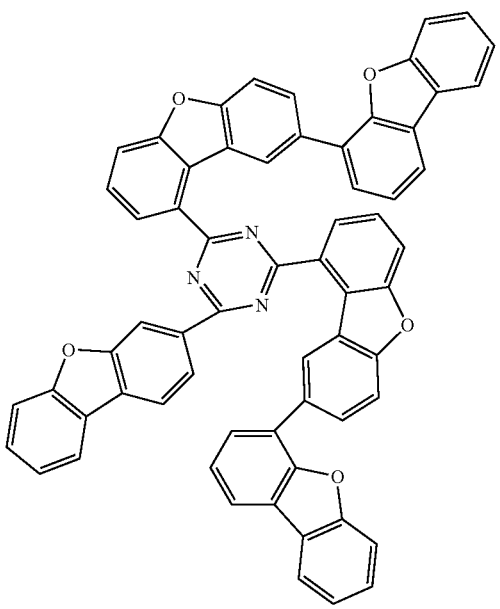
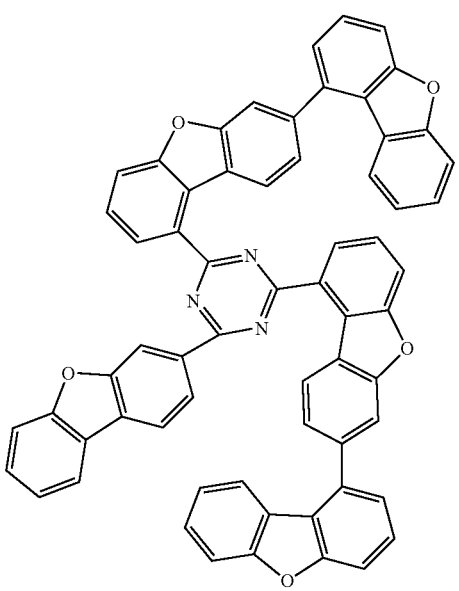

The compounds of the invention can be prepared by synthesis steps known to those skilled in the art, for example bromination, Suzuki coupling, Ullmann coupling, Hartwig-Buchwald coupling, etc. A suitable synthesis method is shown in general terms in Scheme 1 below, where the symbols and indices used have the definitions given above. The compounds of the invention may be prepared here proceeding from an $Ar^1$-functionalized dichloropyrimidine or -triazine by reaction with a 1-dibenzofuranboronic acid or ester thereof in a Suzuki coupling. The reaction may be performed in two steps as shown in Scheme 1, or else in one step when identically substituted 1-dibenzofuranboronic acids or -boronic esters are used. The Suzuki coupling may be performed in aprotic solvents (e.g. toluene, dioxane, DHF, DMF, DMSO) or with addition of protic solvents (e.g. alcohols, water). Catalysts used are typically Pd catalysts or Pd compounds (palladium acetate, Pd-dba, etc.) and phosphines (triphenylphosphine, tri-o-tolylphosphine, S-Phos, X-Phos, BINAP, DPPF, Xanth-Phos, etc.). Bases used for the coupling reaction include inorganic salts (sodium carbonate, potassium carbonate or caesium carbonate, sodium phosphate, potassium phosphate or caesium phosphate, sodium fluoride, potassium fluoride or caesium fluoride, sodium borate, potassium borate or caesium borate) and hydrates thereof.

Scheme 1

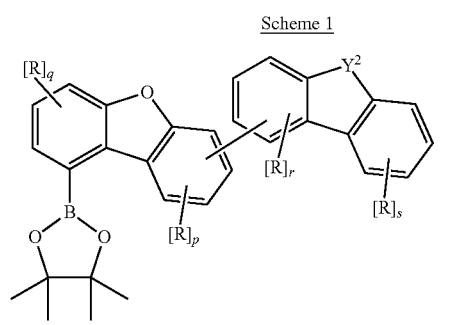

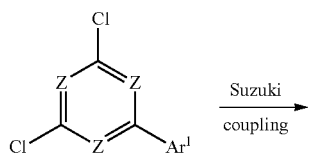

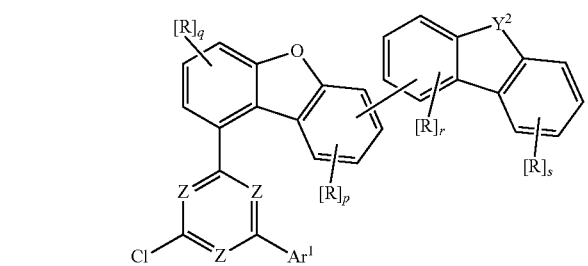

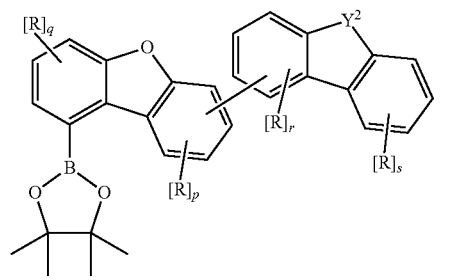

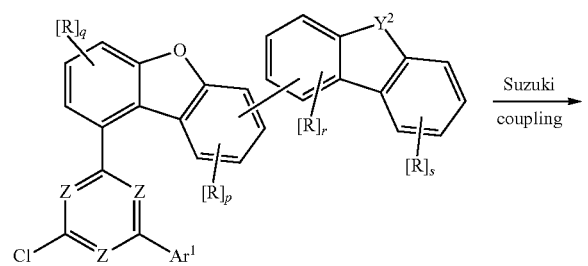

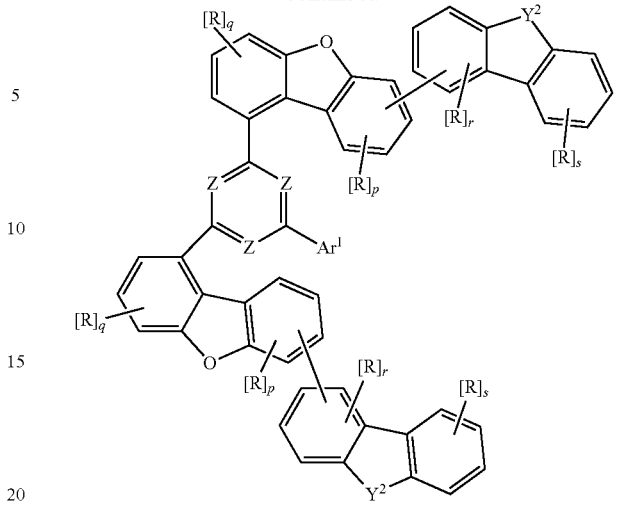

-continued

Even though the compounds of the invention can also be processed by vapour deposition under reduced pressure, the primary object of the present invention is that of providing compounds for processing from the liquid phase, for example by spin-coating or by printing methods. For this purpose, formulations of the compounds of the invention are required. These formulations may, for example, be solutions, dispersions or emulsions, preferably solutions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate, alkoxy-substituted ethyl benzoates, especially 2-methoxyethyl benzoate and 4-methoxyethyl benzoate, alkyl-substituted ethyl benzoates, especially 2-methylethyl benzoate and 4-methylethyl benzoate, propylene carbonate, ethylene carbonate, isopropylbiphenyls, especially 2-isopropylbiphenyl, 3-isopropylbiphenyl and 2,2'-diisopropylbiphenyl, amyl benzoate, isoamyl benzoate, 1-isopropylnaphthalene, 2-isopropylnaphthalene, 1-isopropylnaphthalene, diisopropylnaphthalene, benzyl benzoate or mixtures of these solvents.

The present invention therefore further provides a formulation comprising at least one compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device. The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials. The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (0-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. The organic electroluminescent device of the invention may also be a tandem OLED, especially for white-emitting OLEDs.

The compound of the invention according to the above-detailed embodiments may be used in different layers. Preference is given to an organic electroluminescent device comprising a compound of formula (1) or the above-recited preferred embodiments in an emitting layer as matrix material for phosphorescent emitters or for emitters that exhibit TADF (thermally activated delayed fluorescence), especially for phosphorescent emitters. In this case, the organic electroluminescent device may contain an emitting layer, or it may contain a plurality of emitting layers, where at least one emitting layer contains at least one compound of the invention as matrix material. In addition, the compound of the invention may also be used in an electron transport layer and/or in a hole blocker layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

Examples of the emitters described above can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, WO 2019/020538, WO 2018/178001, WO 2019/115423 or WO 2019/158453. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of phosphorescent dopants are adduced below.

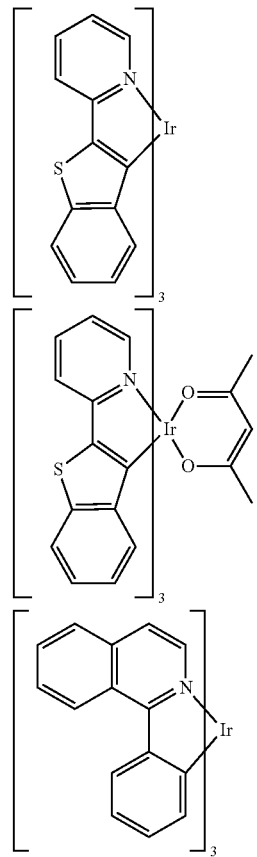

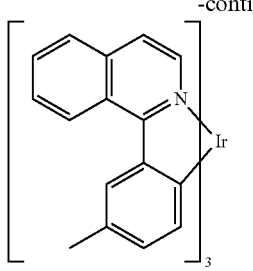
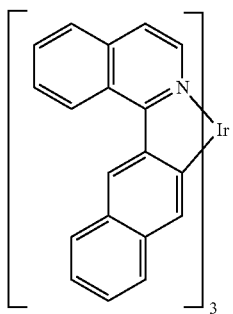
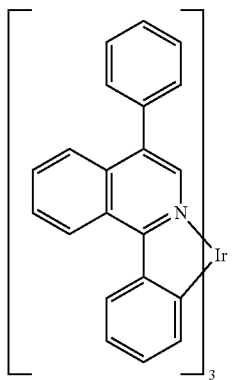
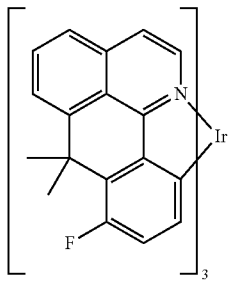
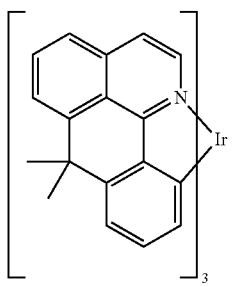
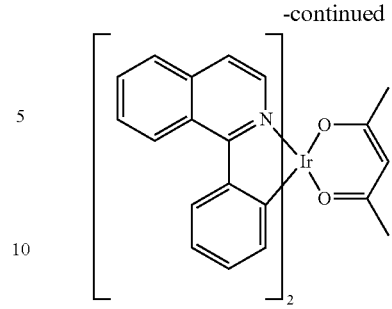
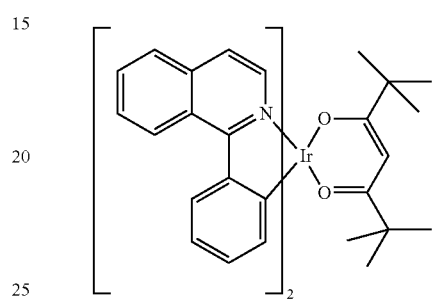
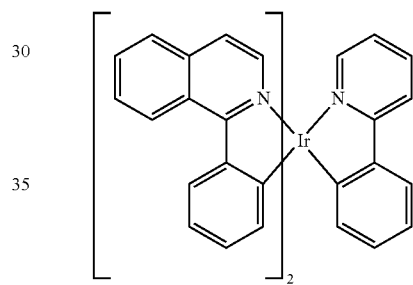
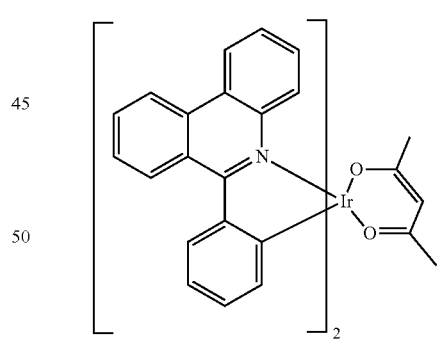
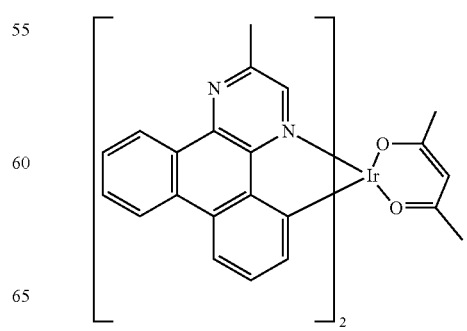

87
-continued
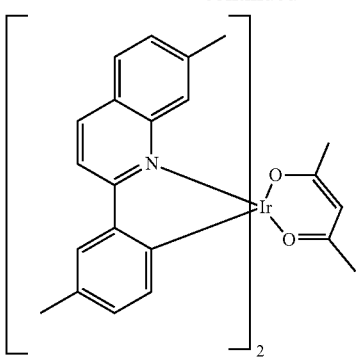
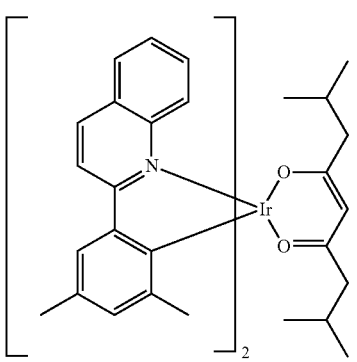
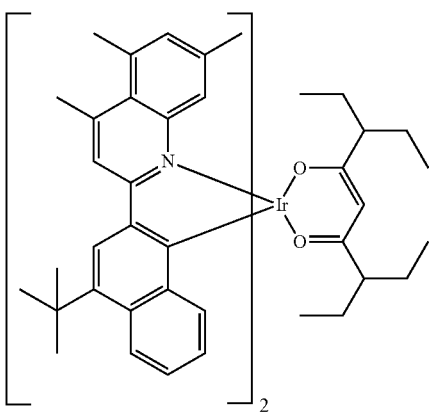
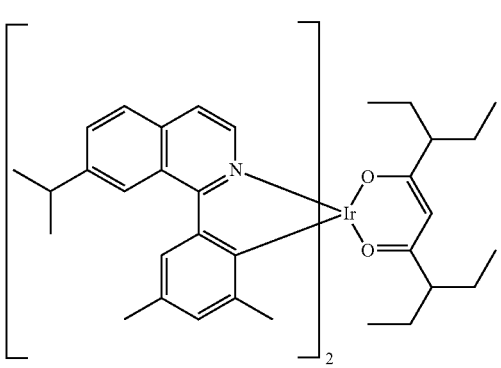
88
-continued
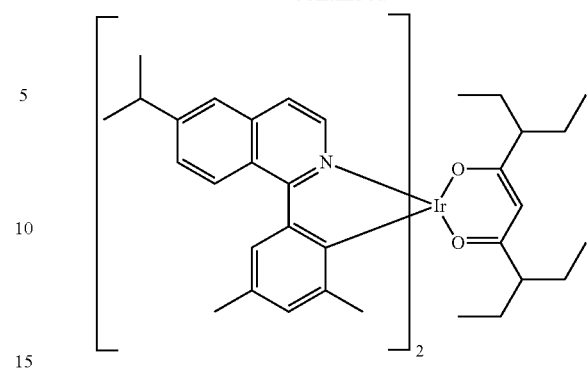
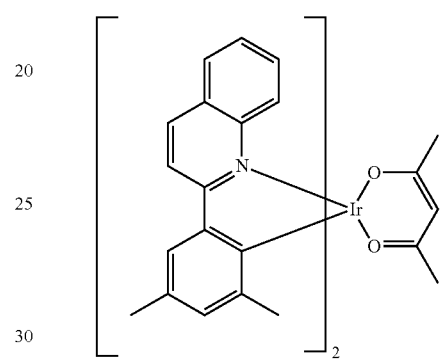
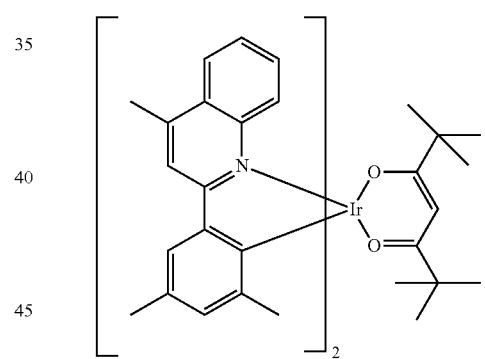
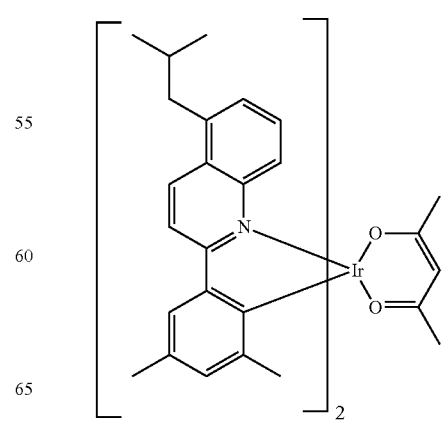

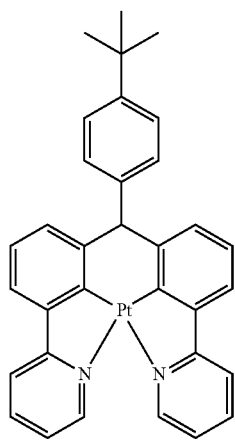
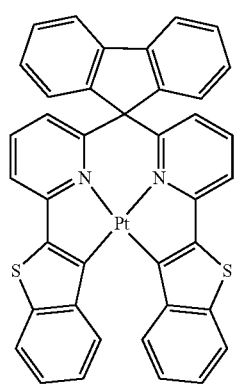
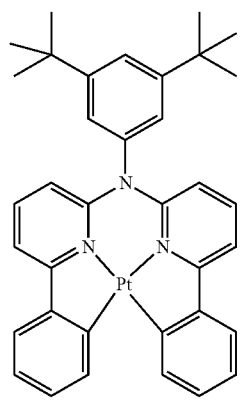
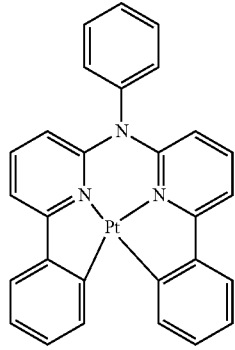
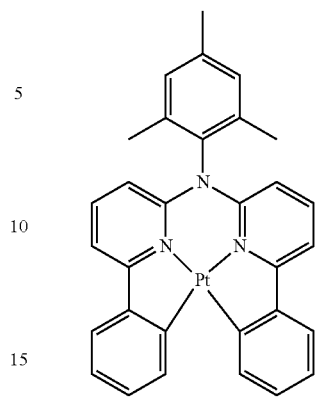
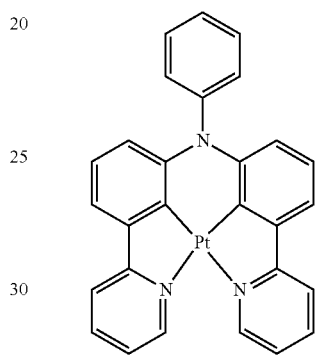
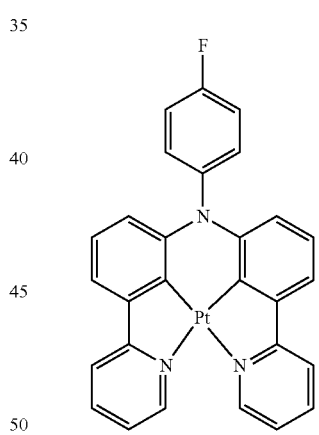
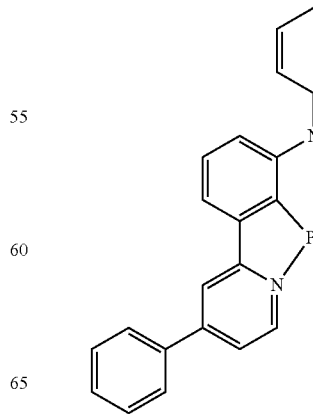

91
-continued
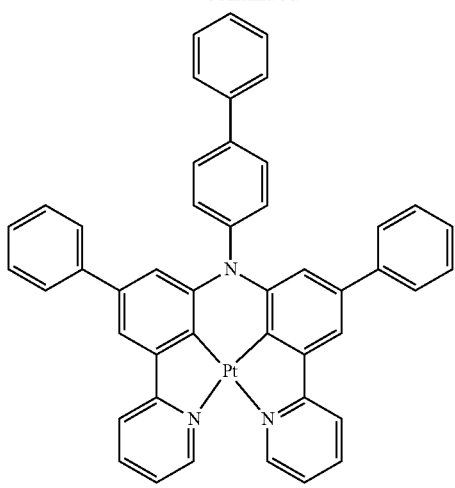
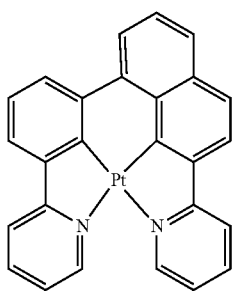
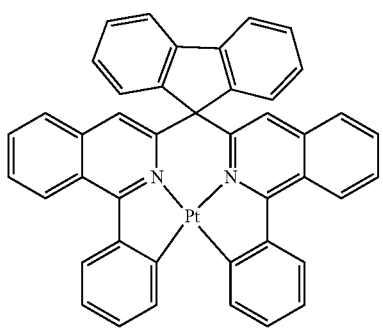
92
-continued
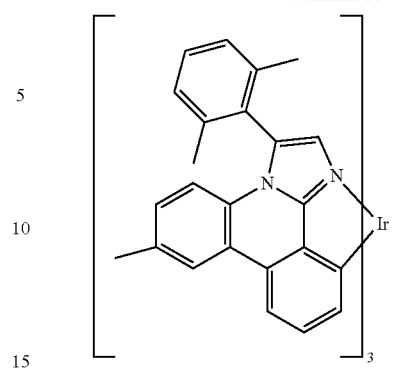
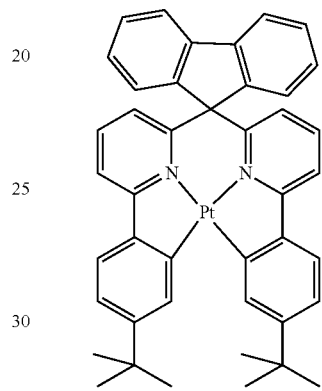
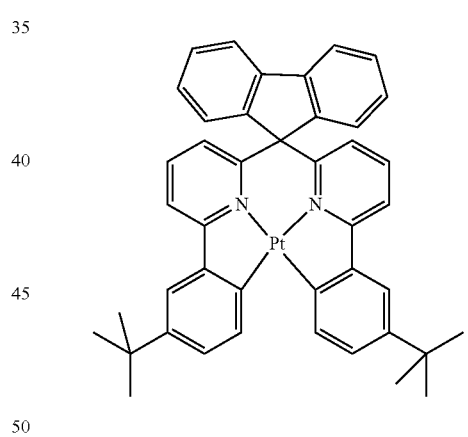
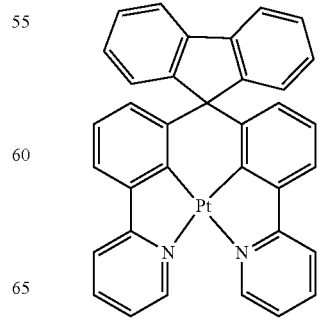

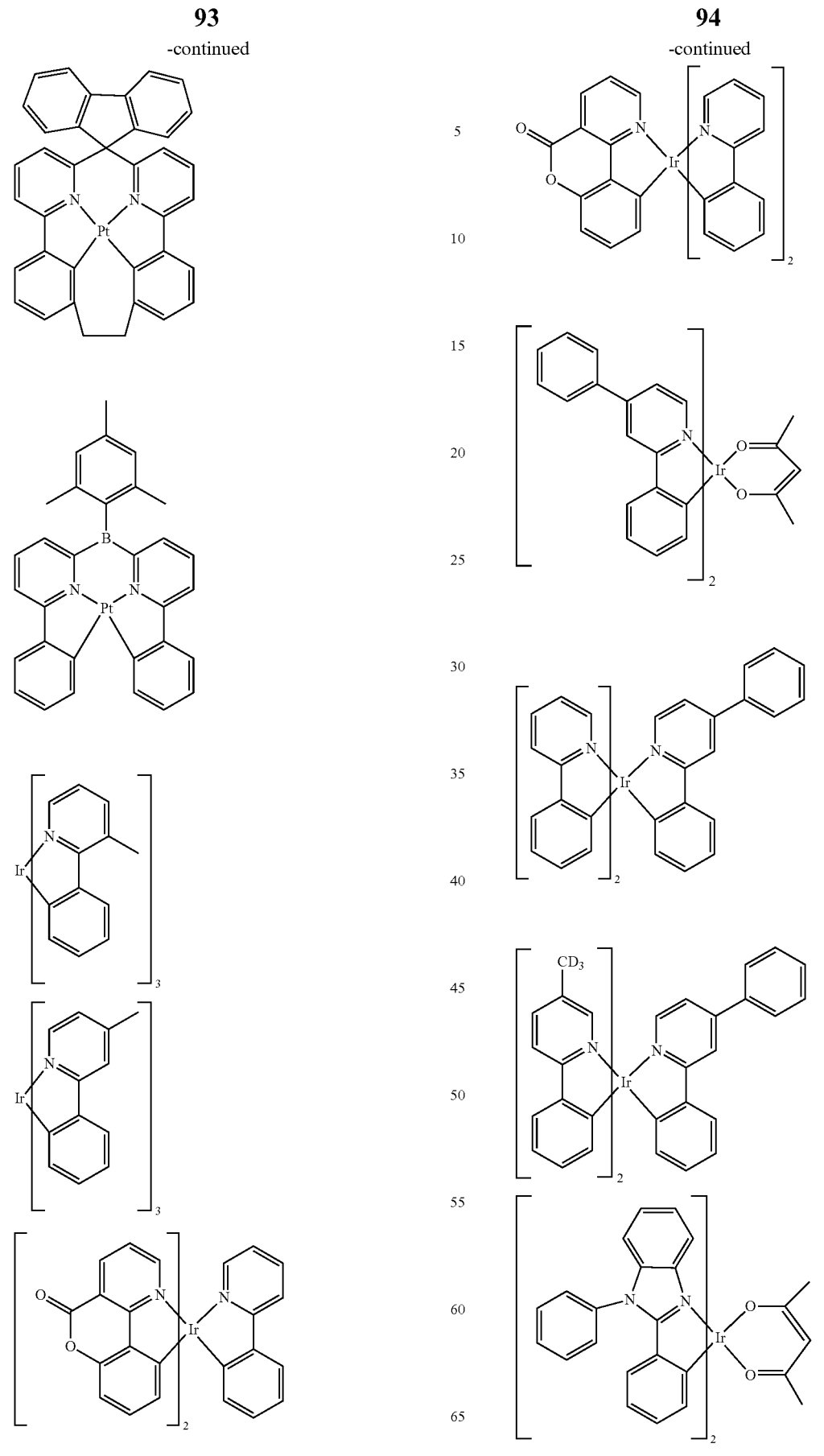

93
-continued

94
-continued

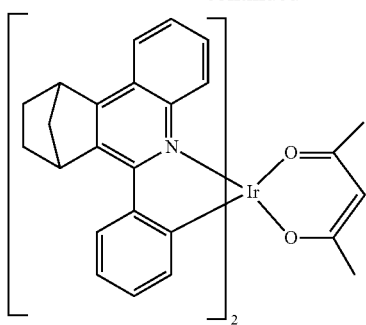
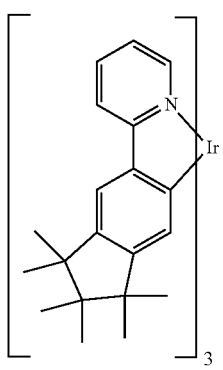
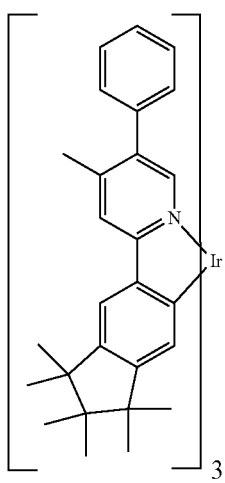
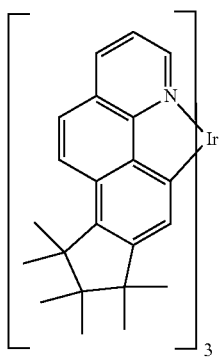
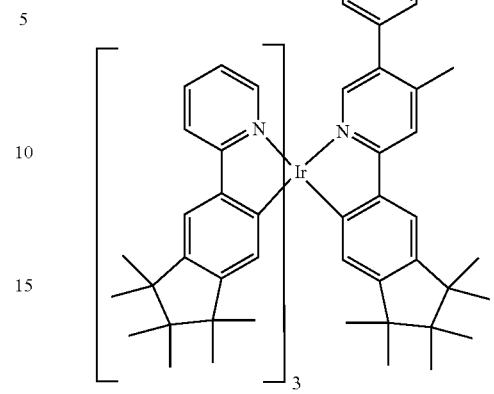
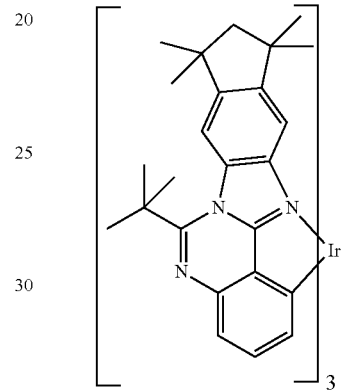
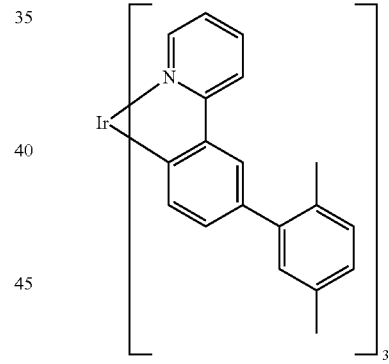
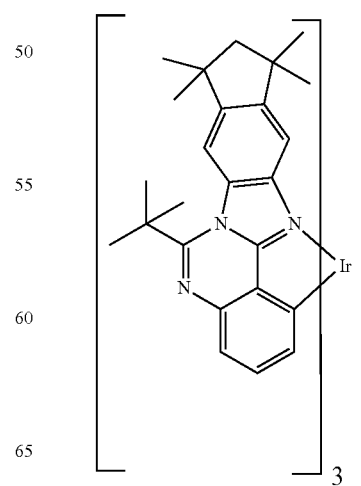

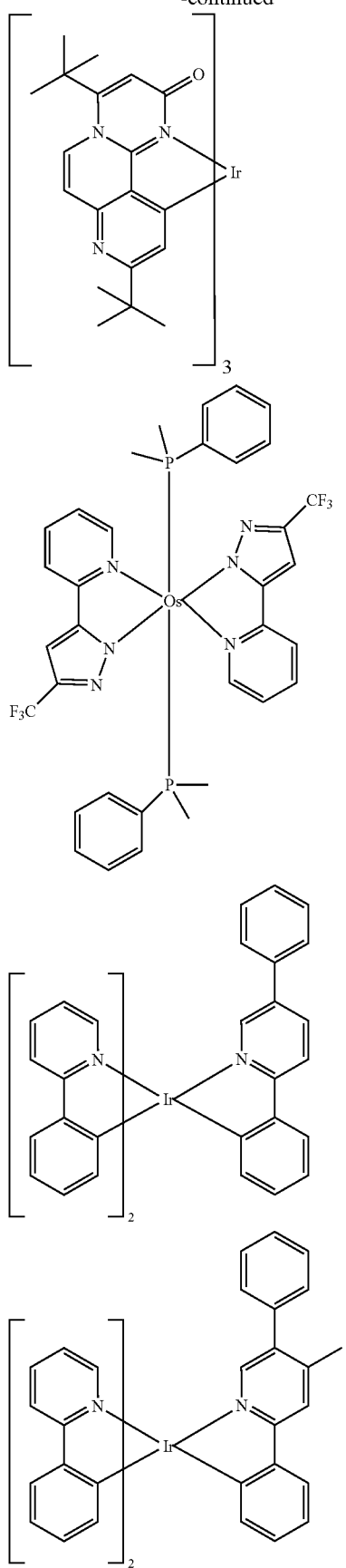
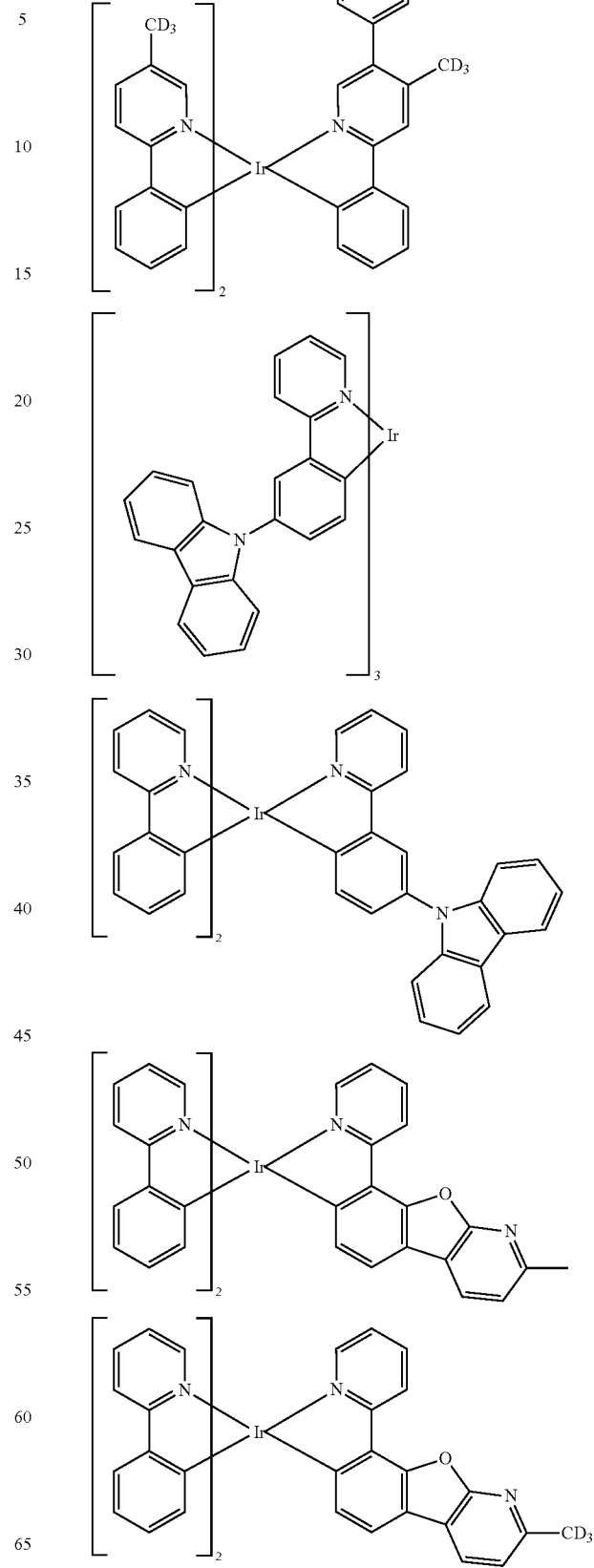

99
-continued
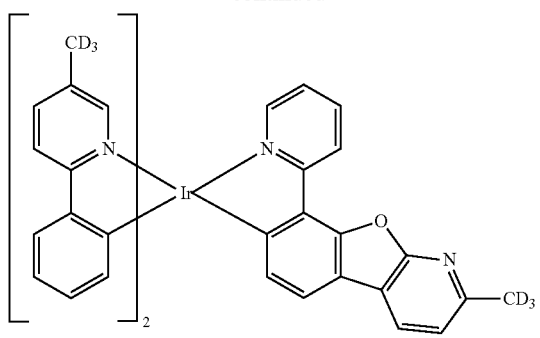
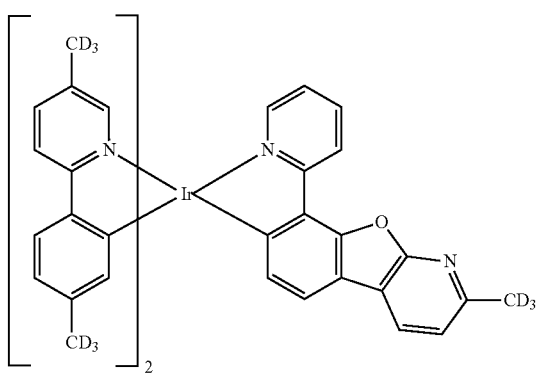
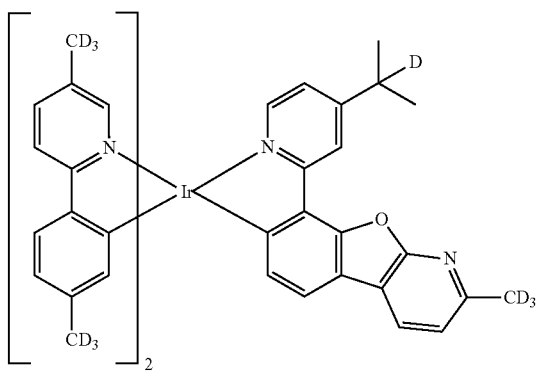
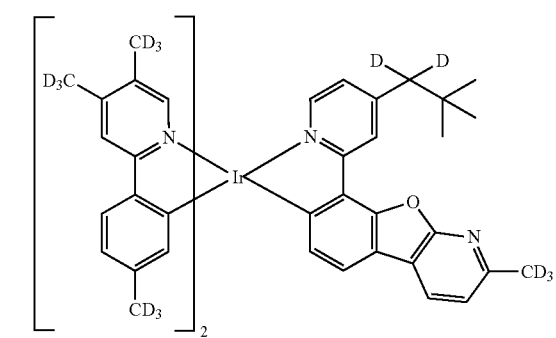
100
-continued
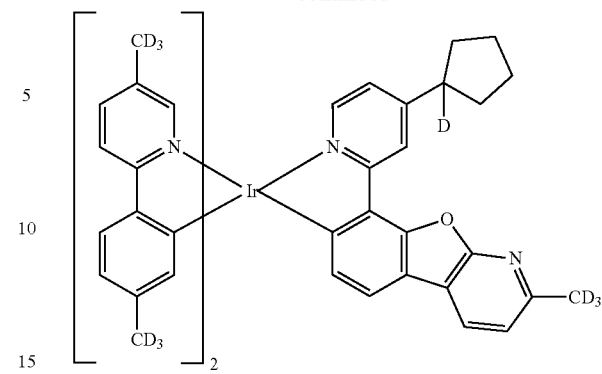
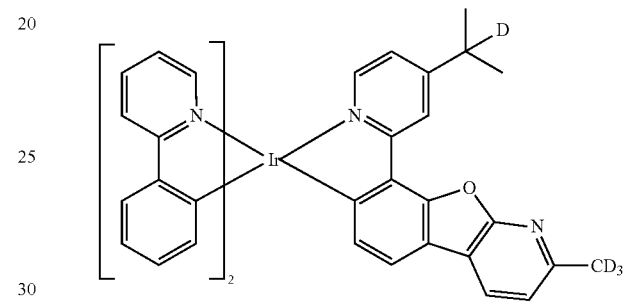
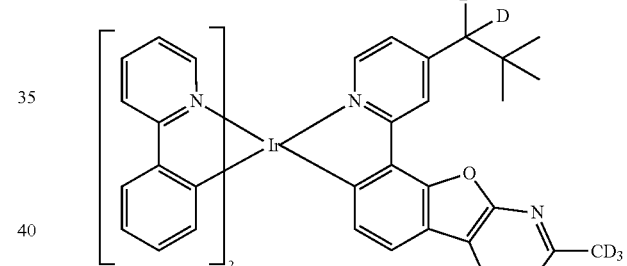
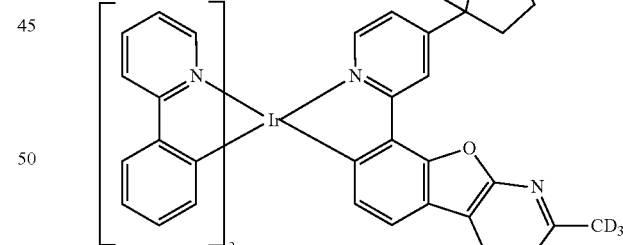
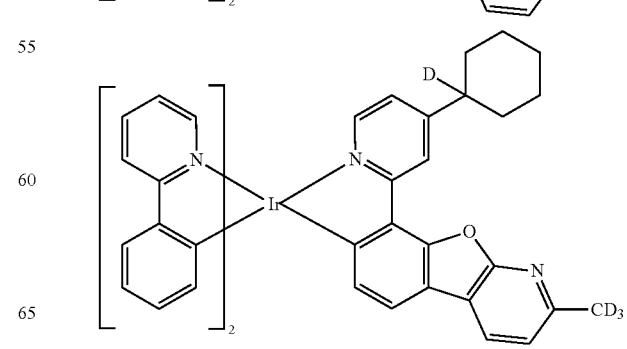

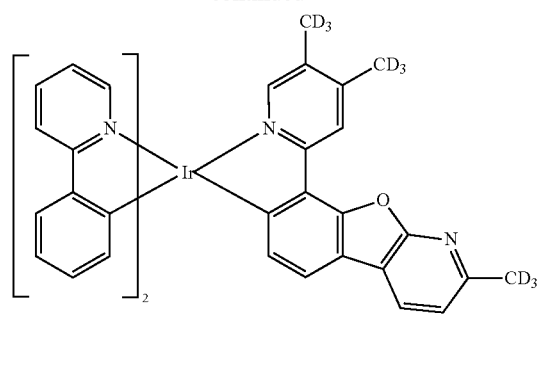
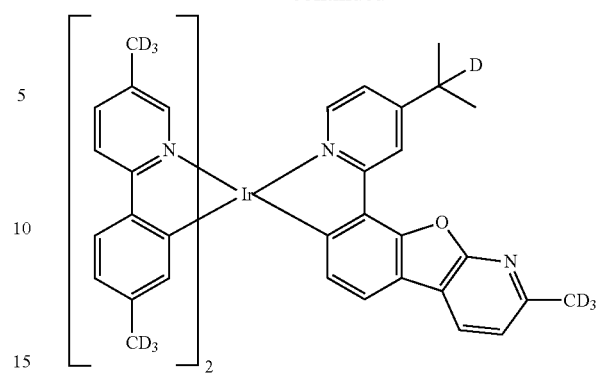
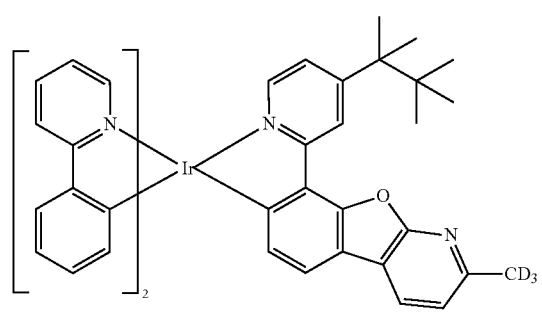
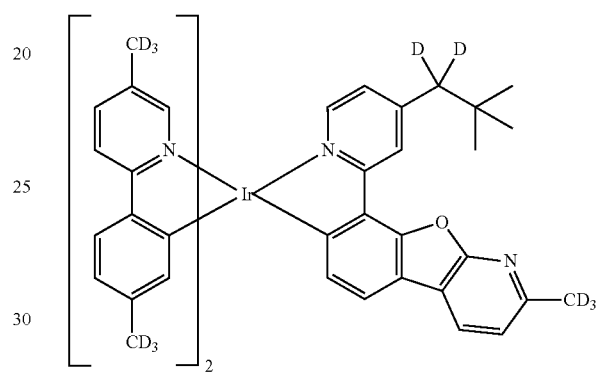
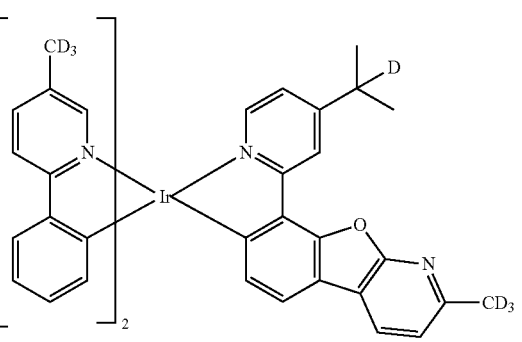
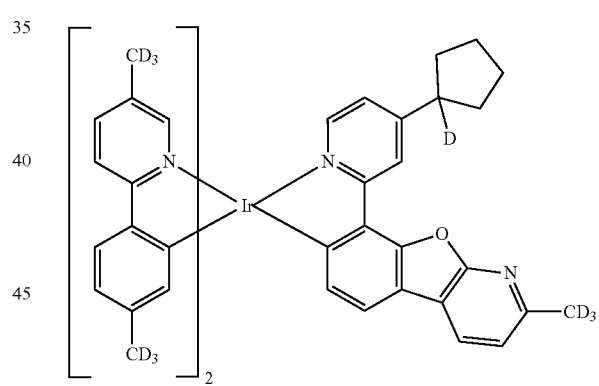
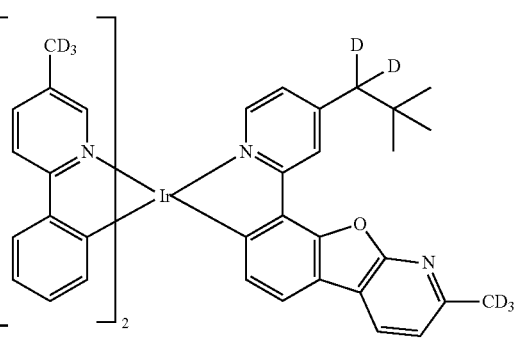
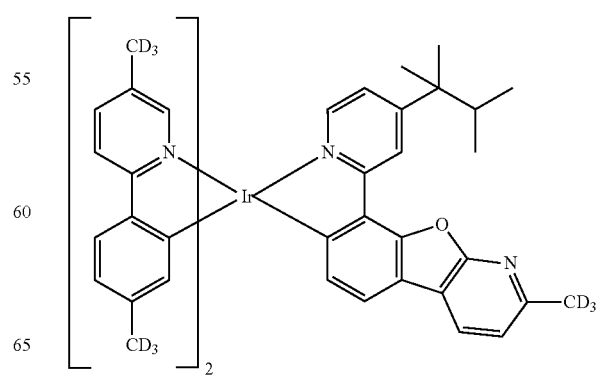
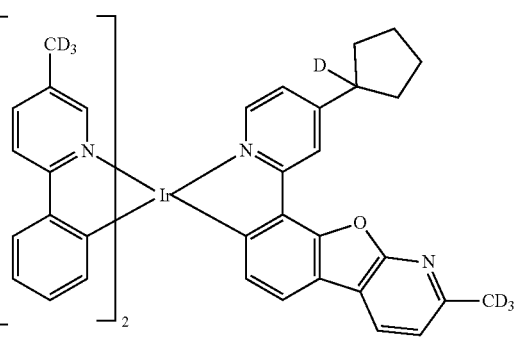
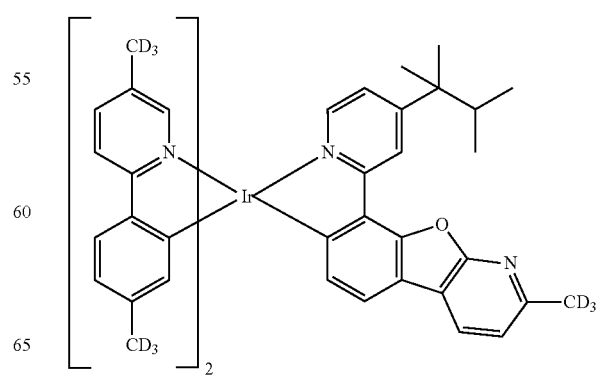

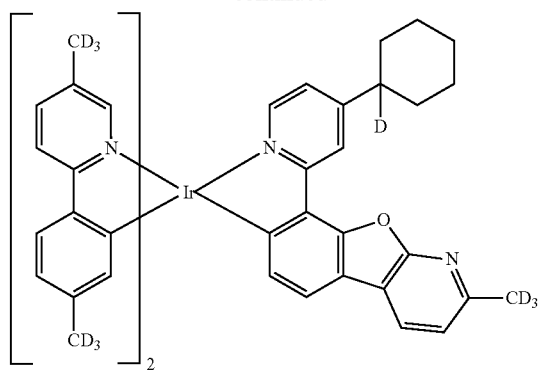
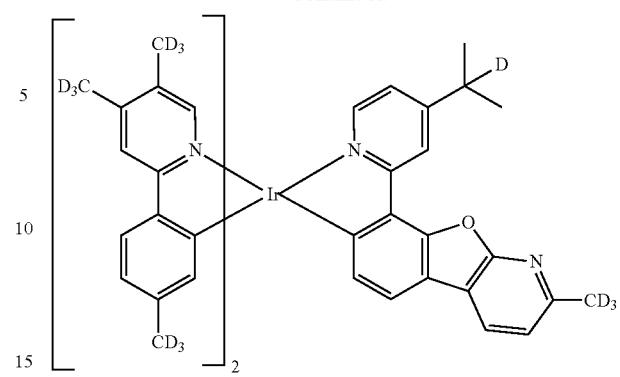
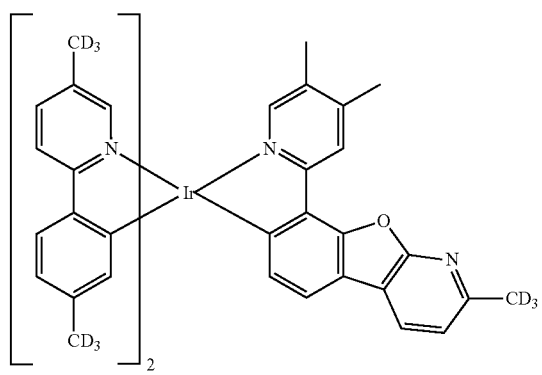
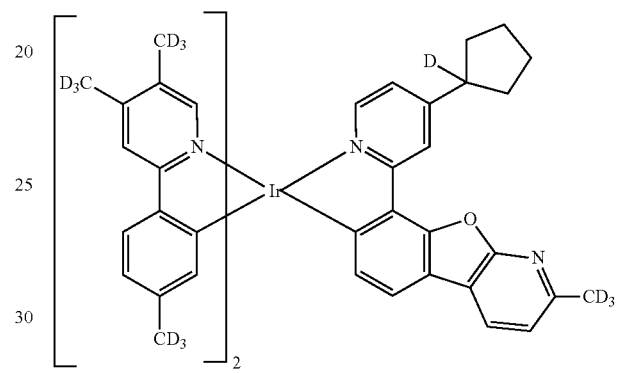
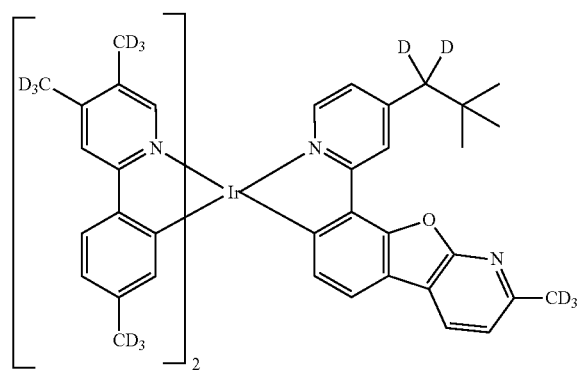
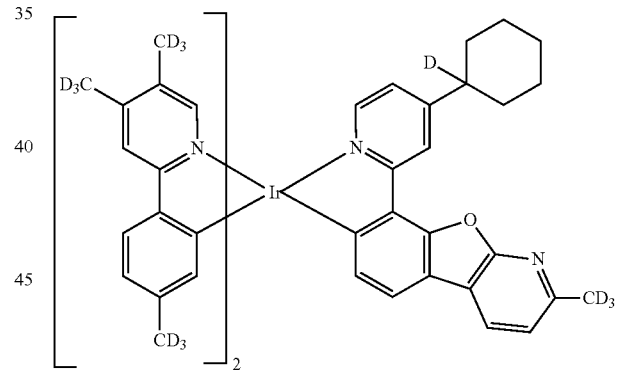
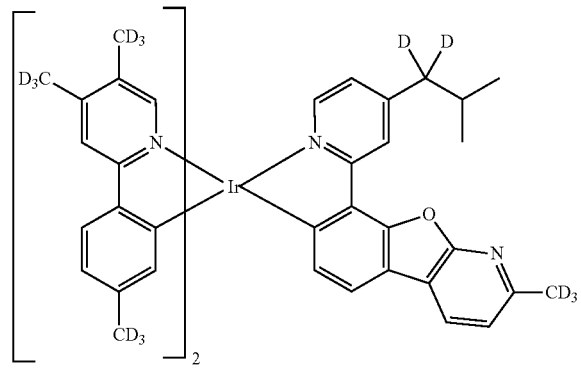
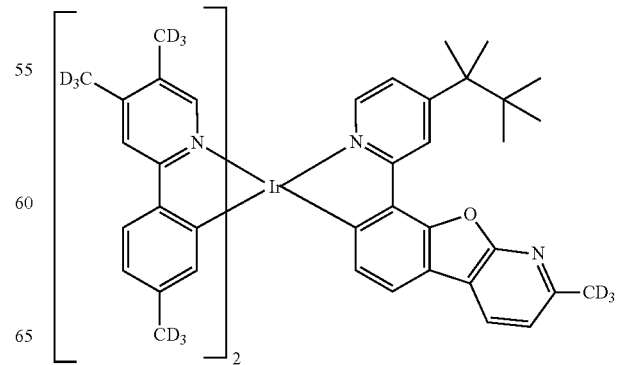

105
-continued
106
-continued
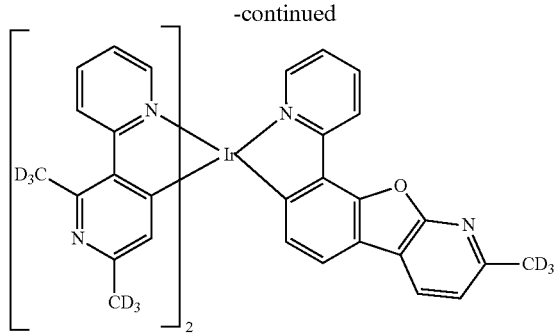
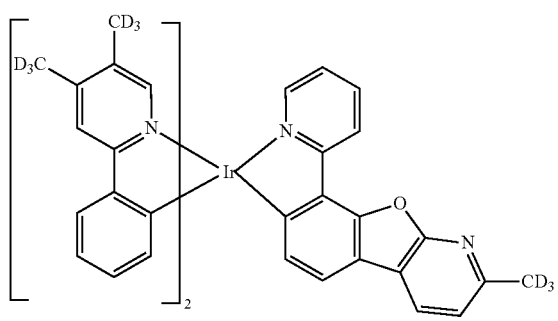
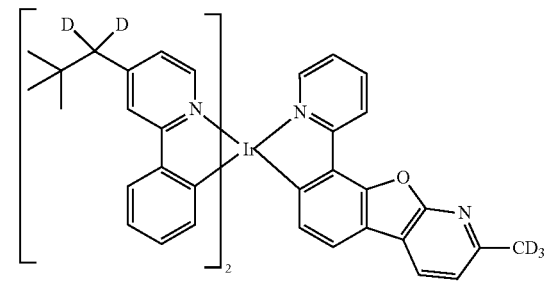
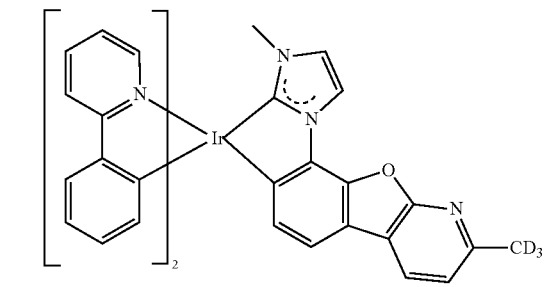
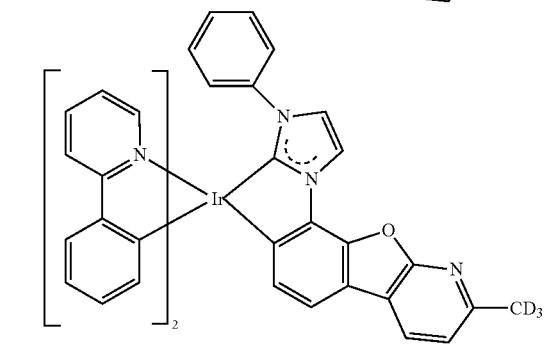

107
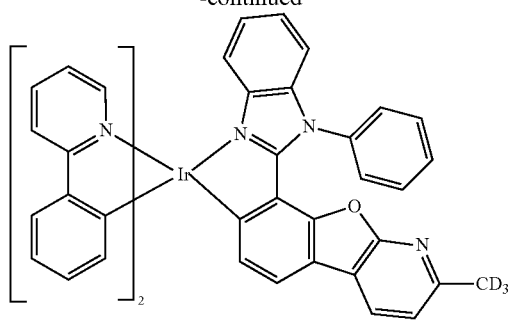
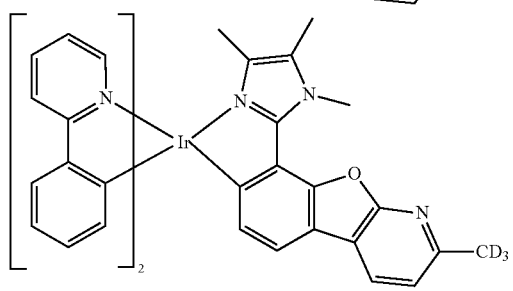
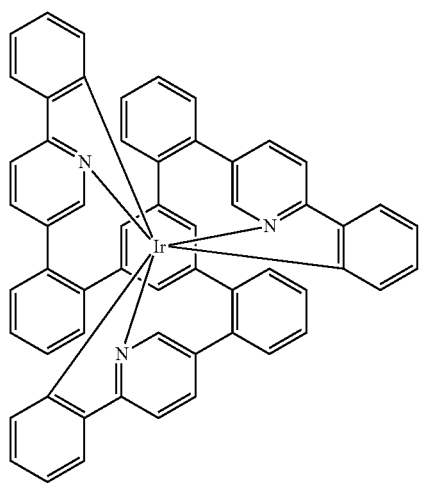
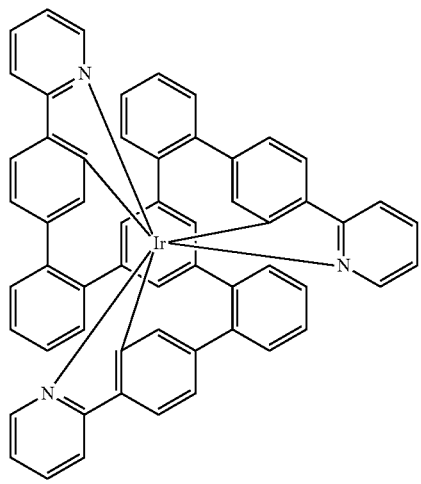
108
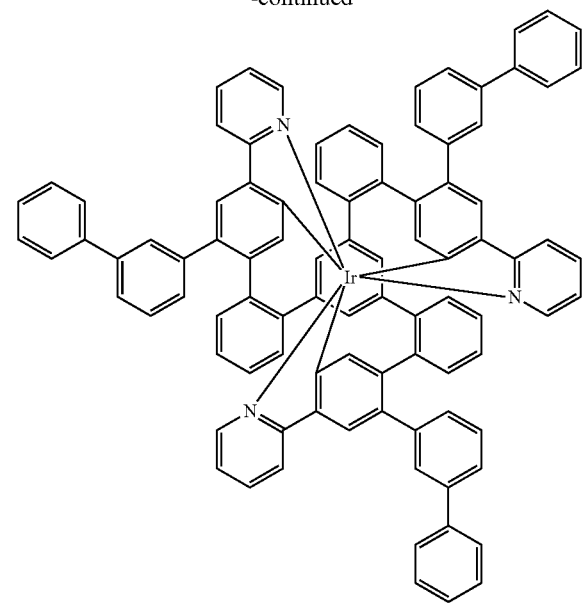

109
-continued
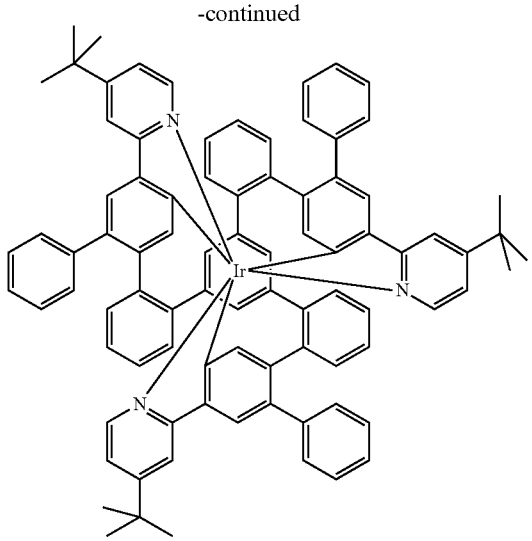
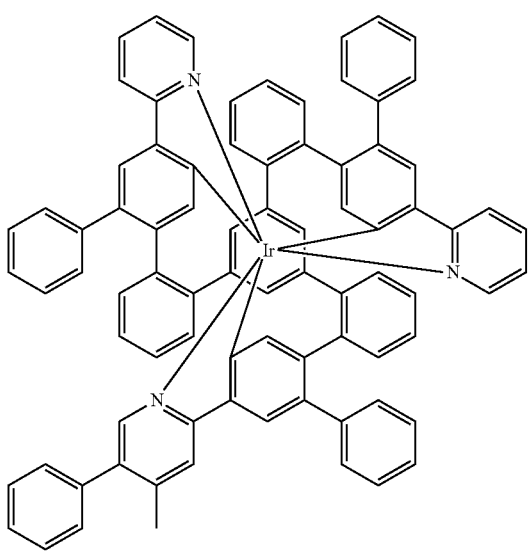
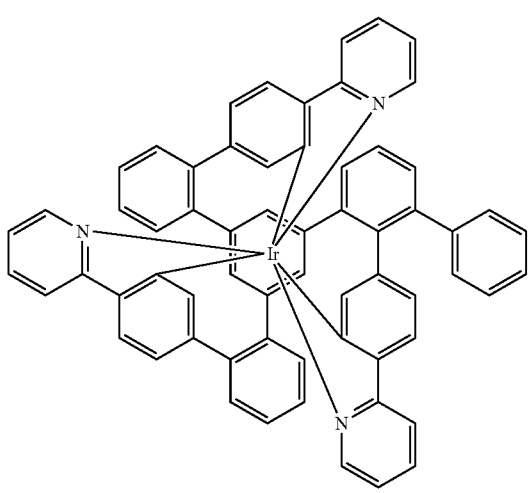
110
-continued
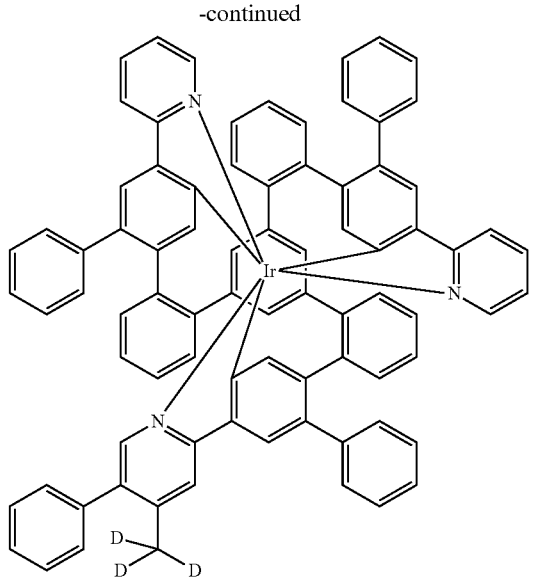
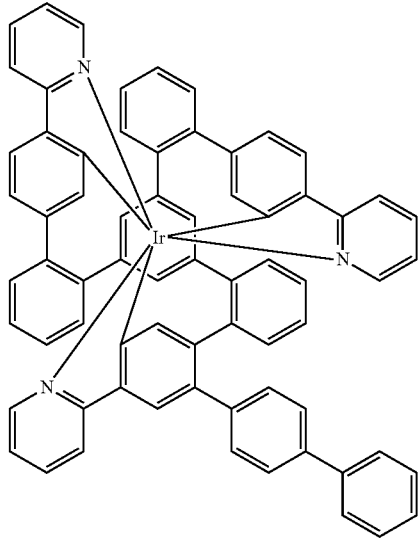
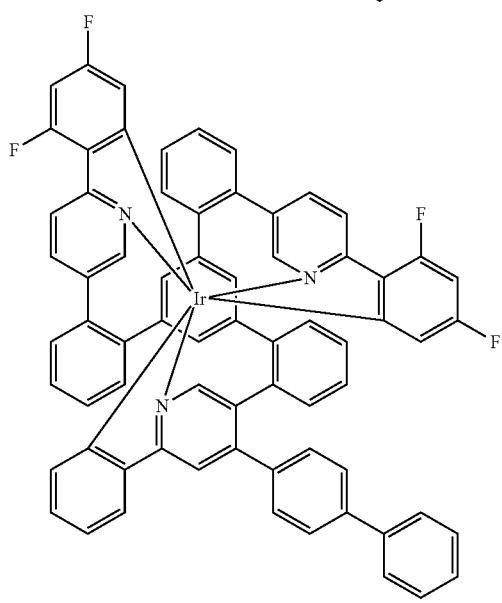

-continued
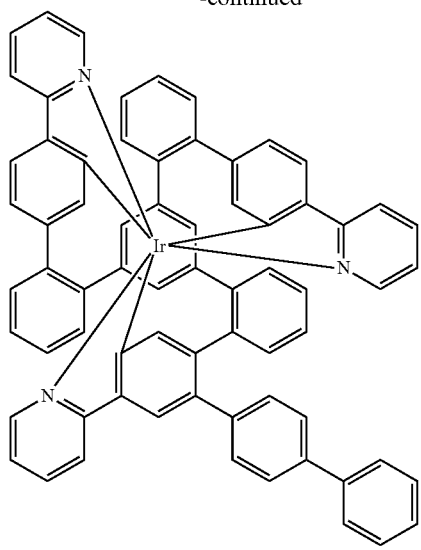
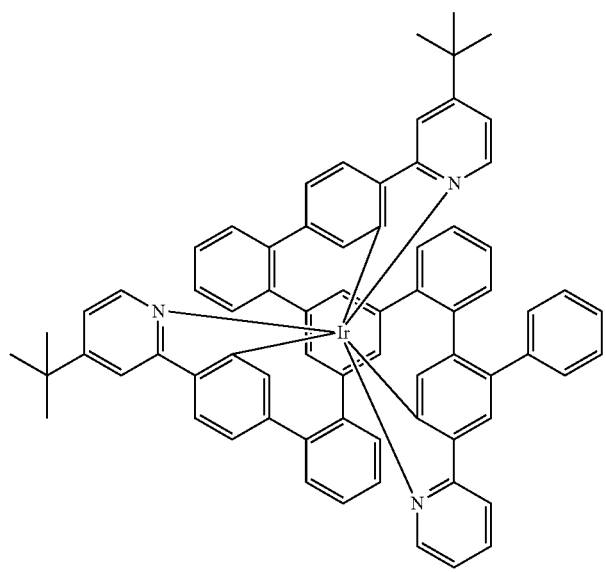

-continued
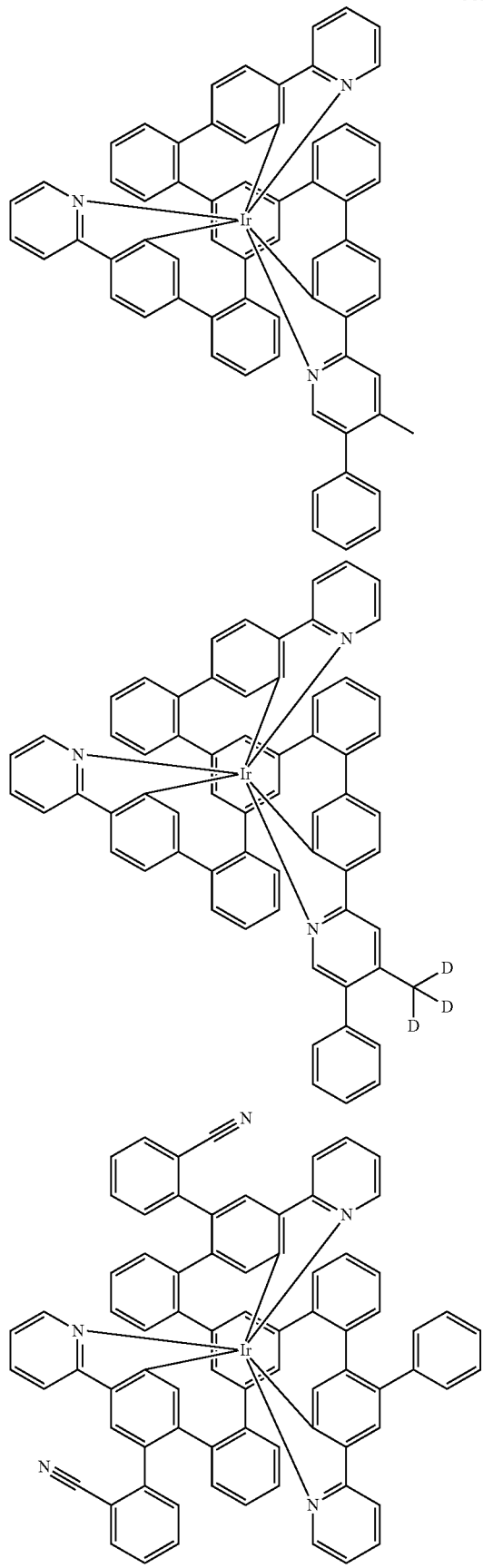

-continued
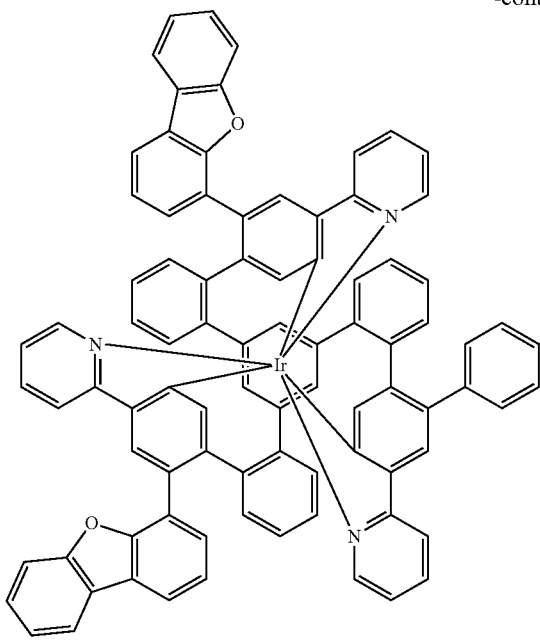
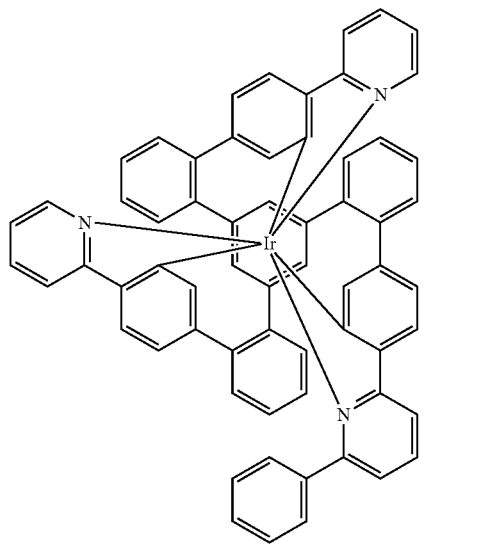
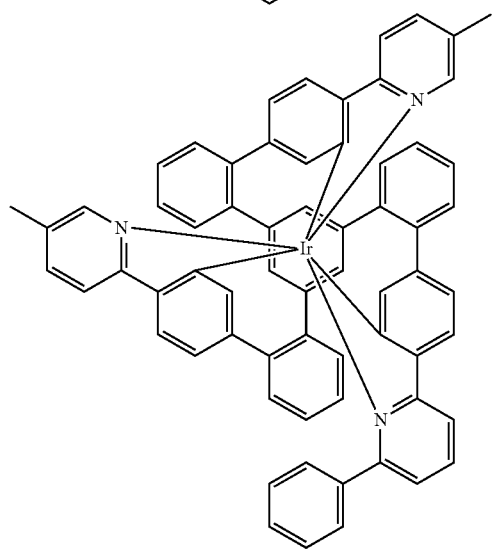

-continued
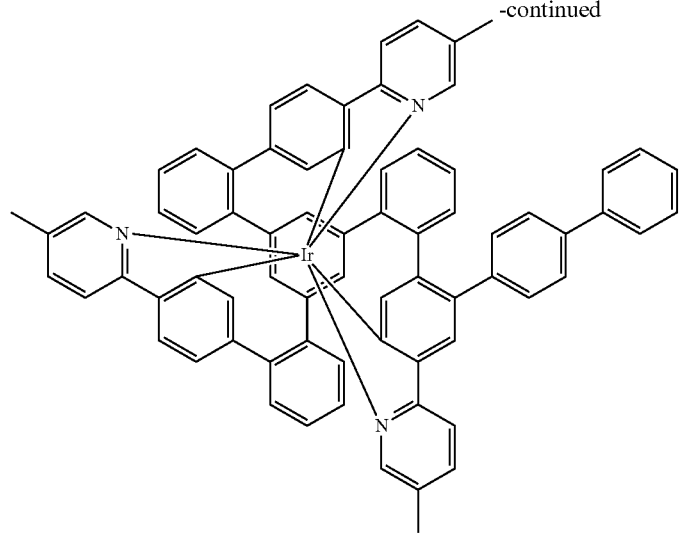
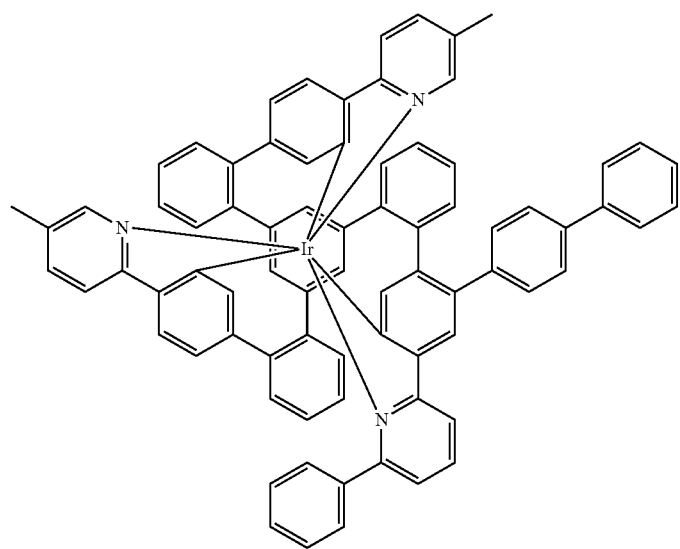
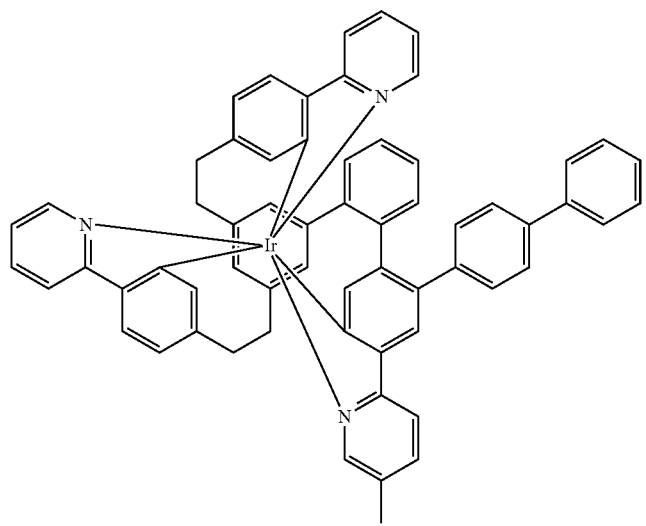

-continued
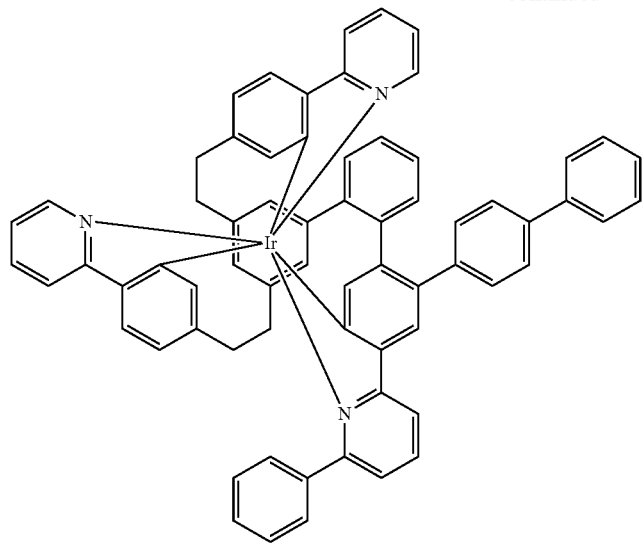
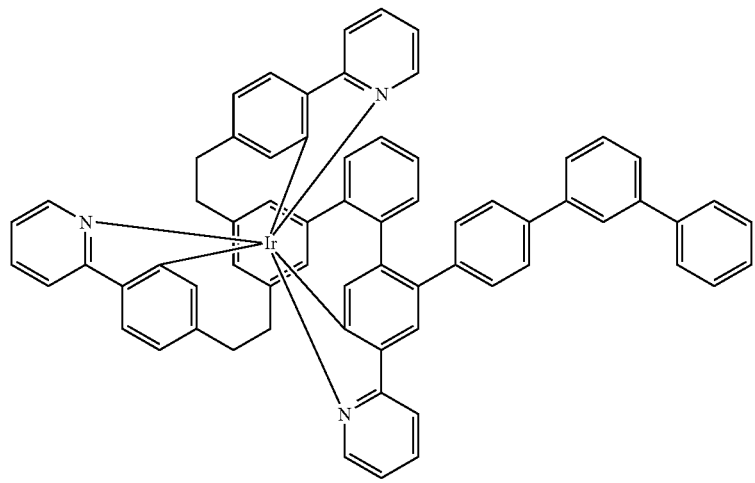
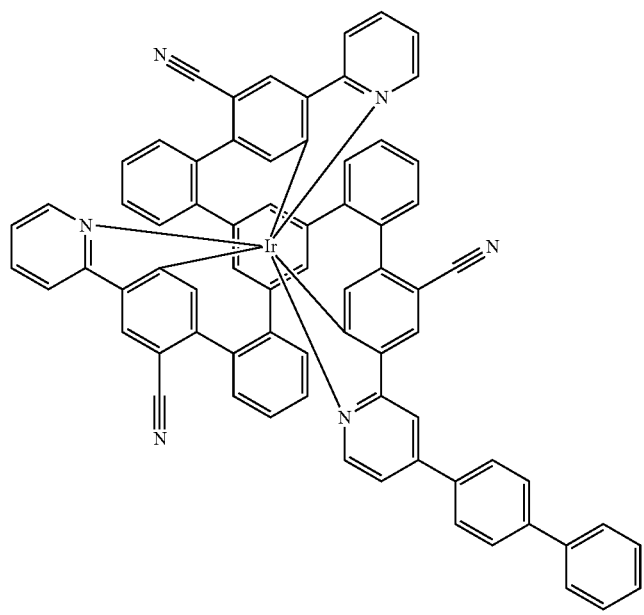

-continued
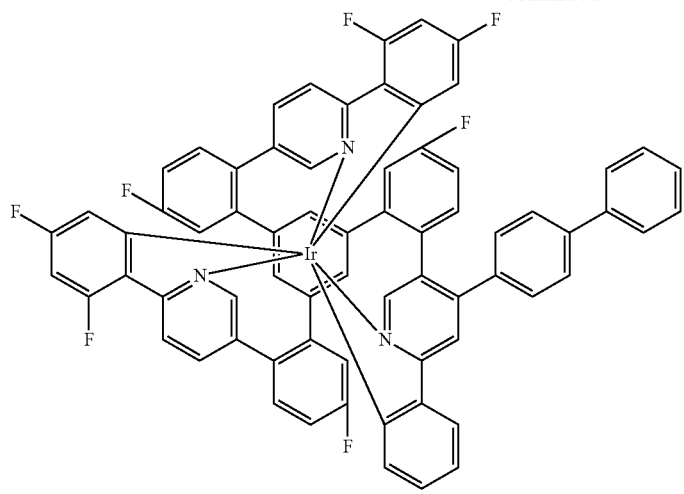
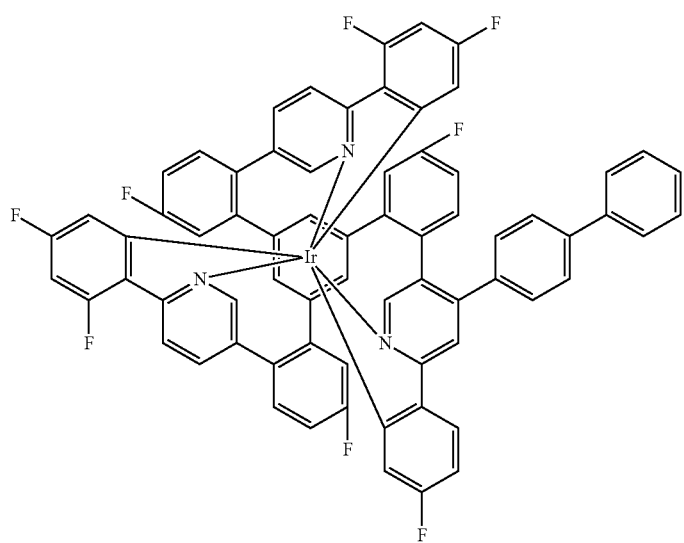
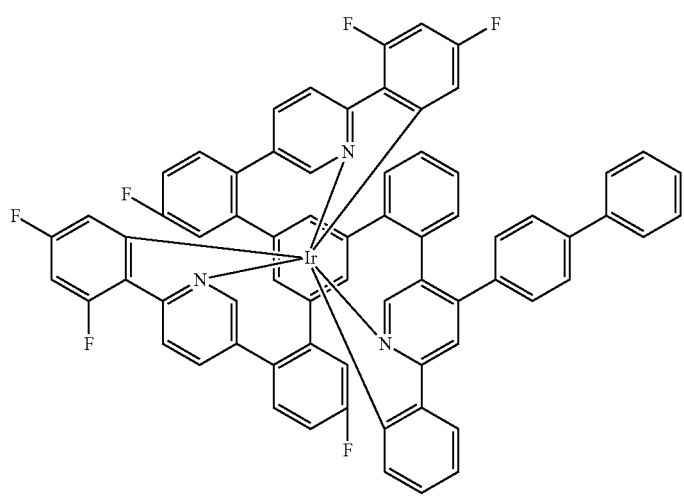

-continued
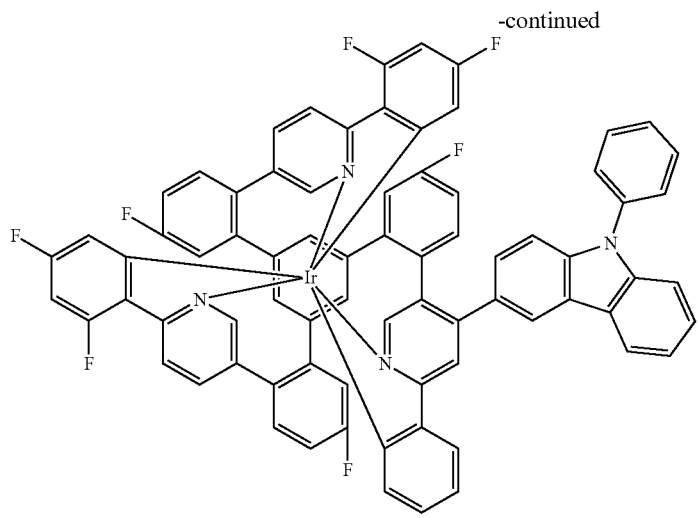
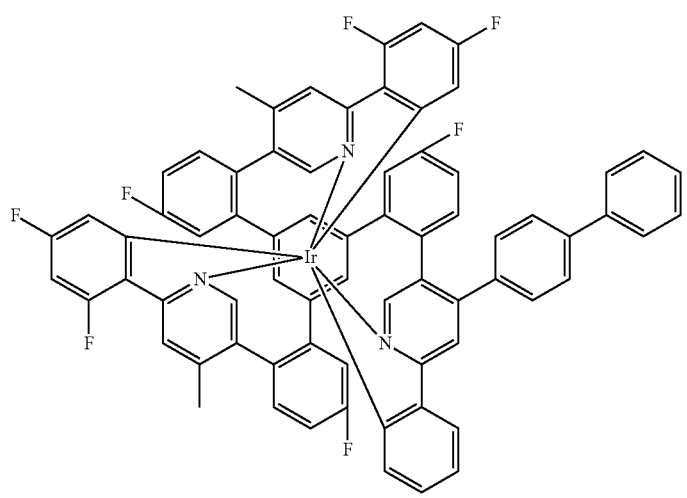
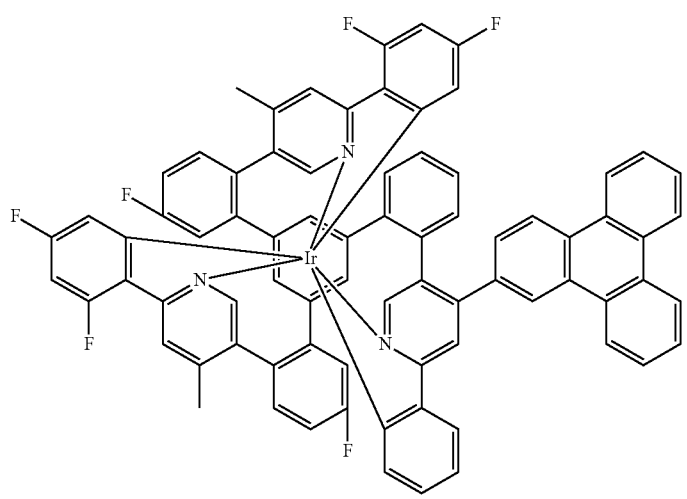

-continued
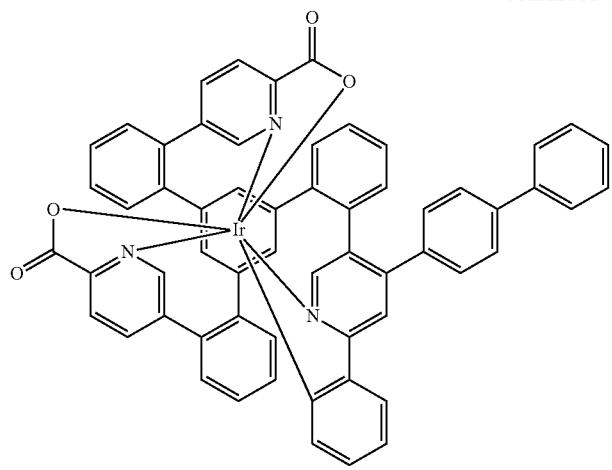
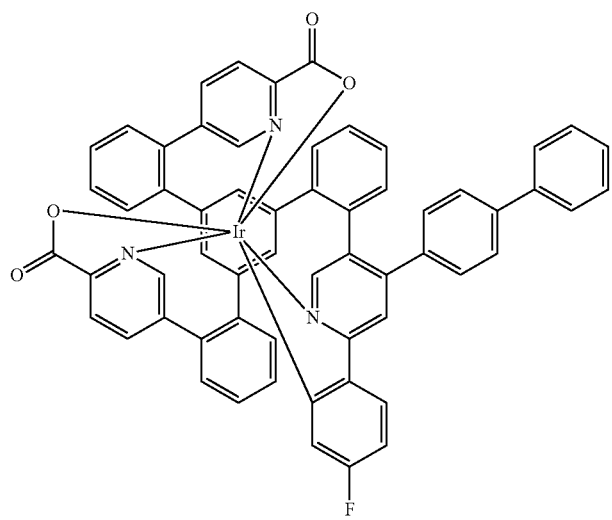
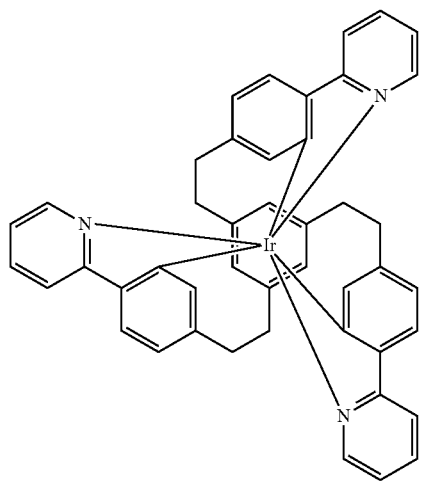

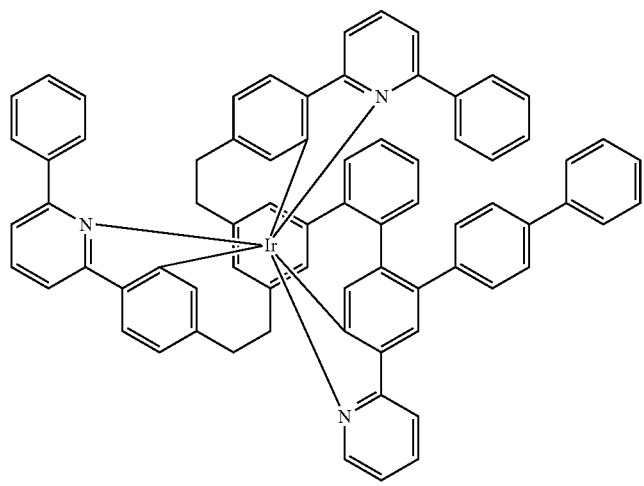
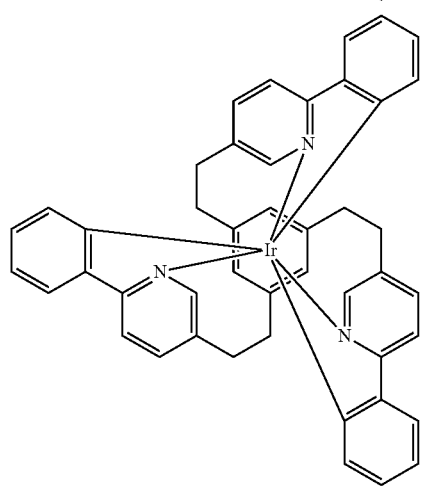
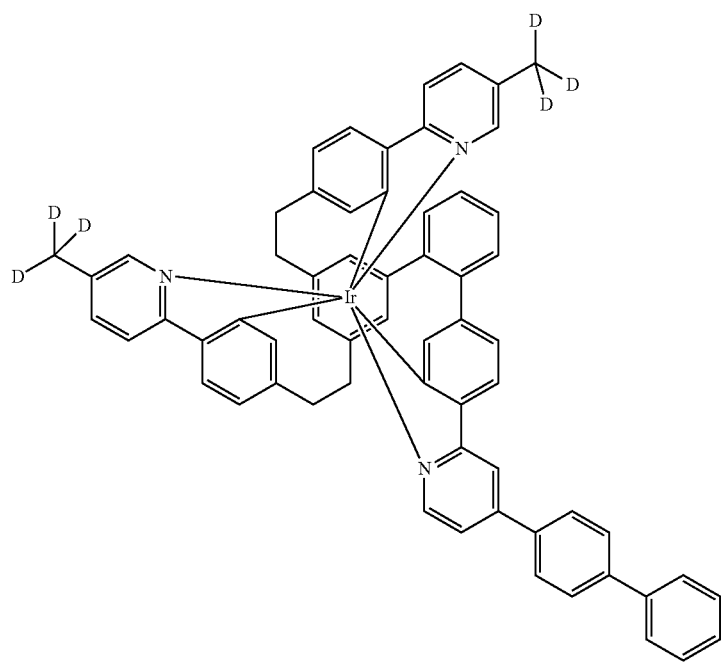

-continued
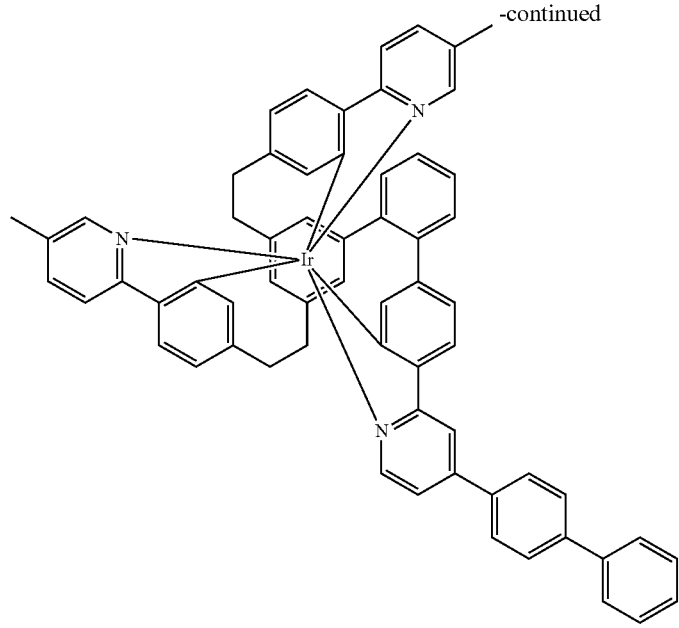
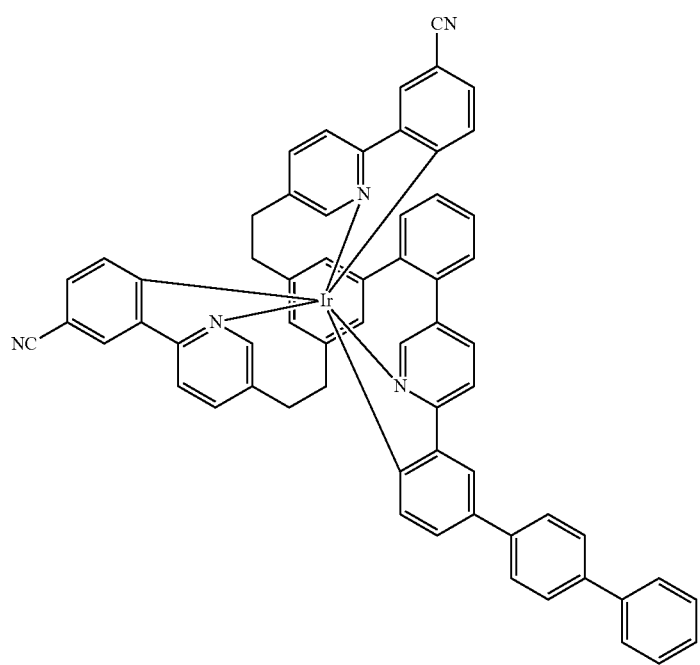

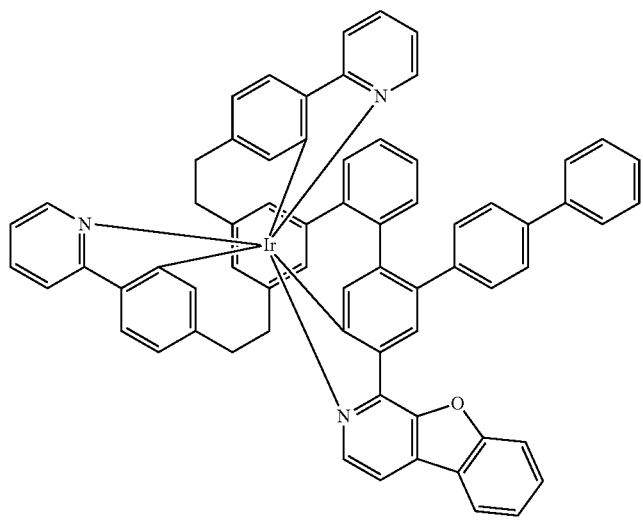
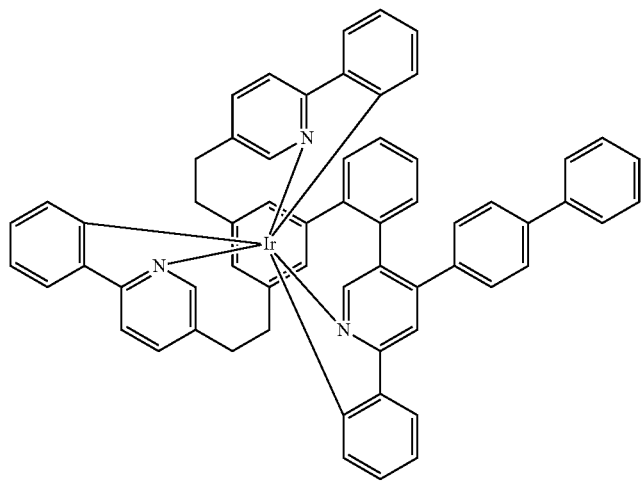
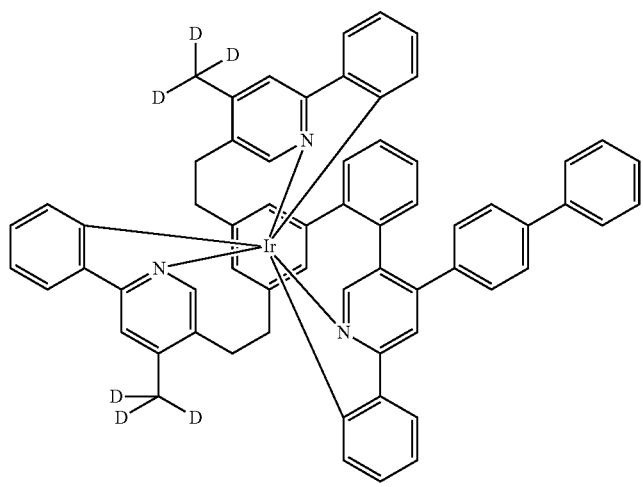

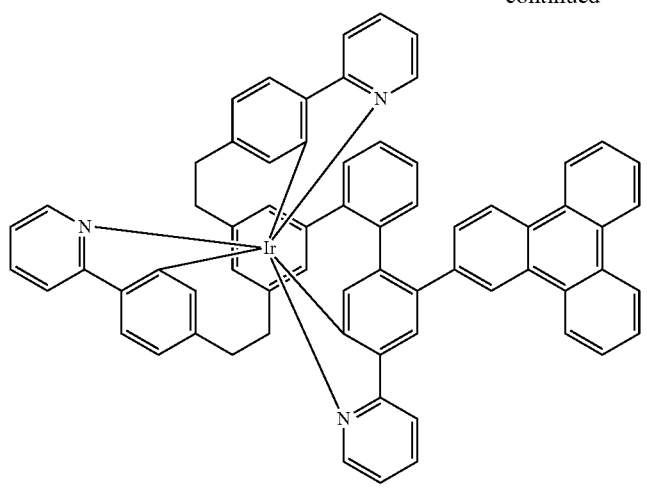
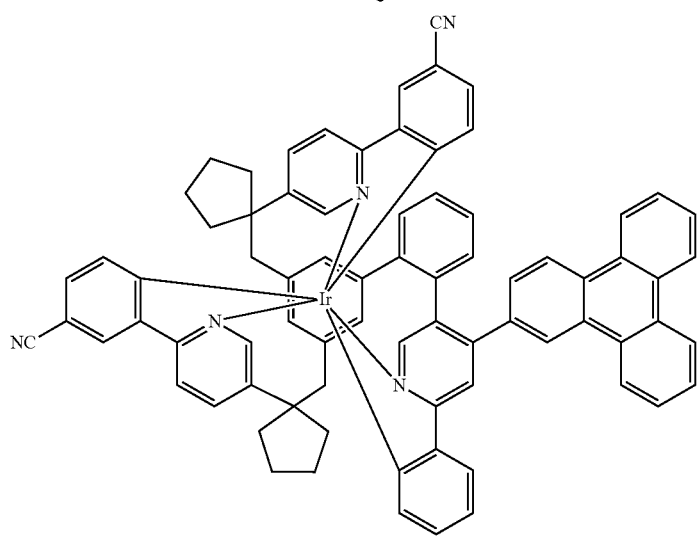
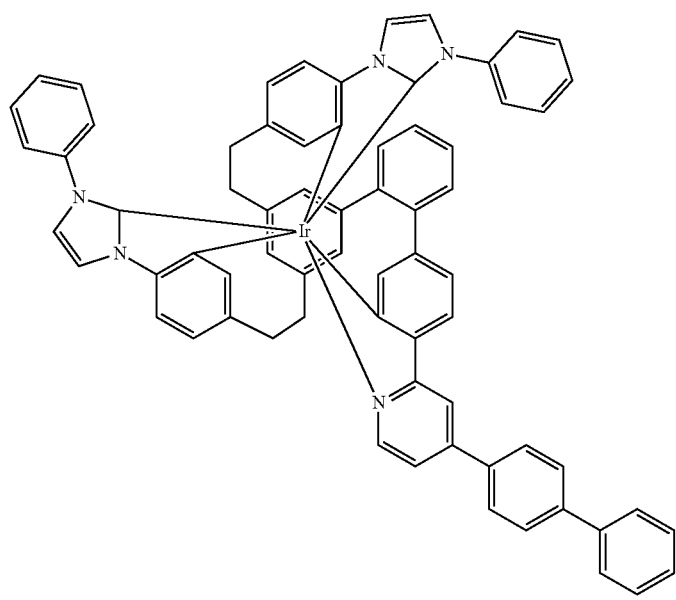

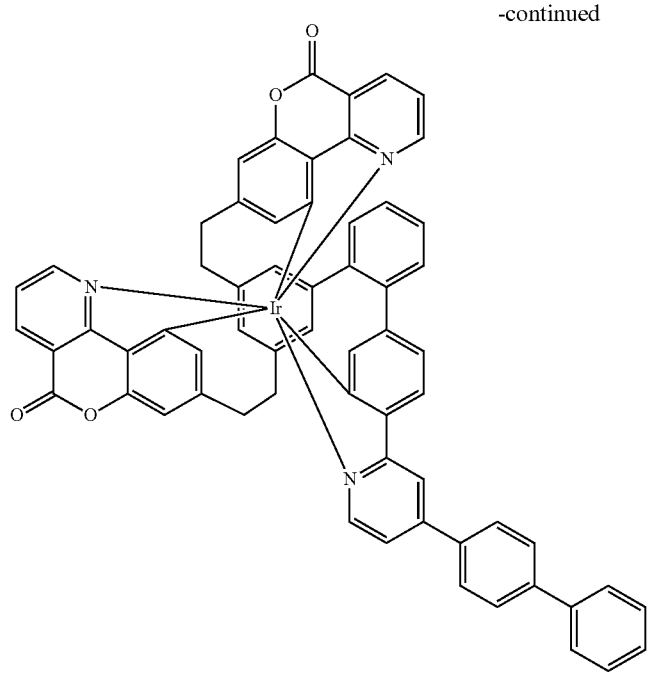
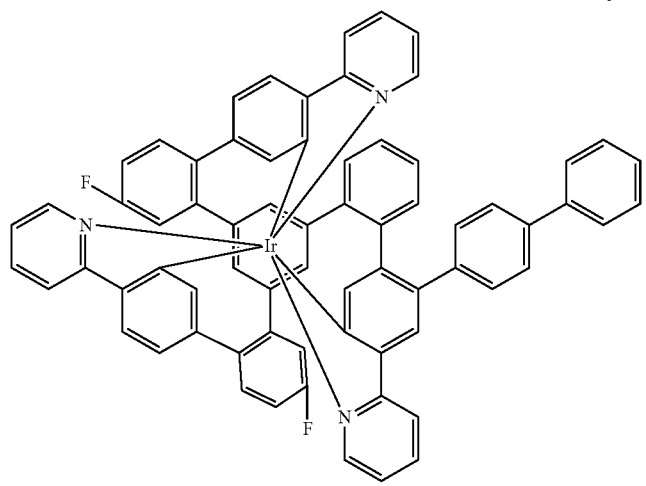
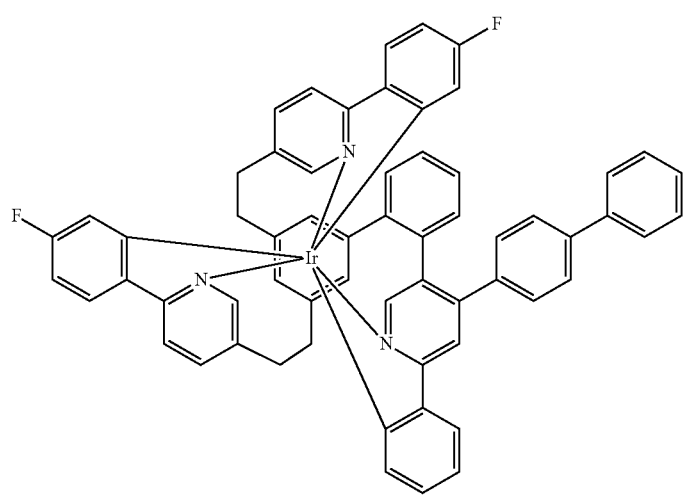

-continued
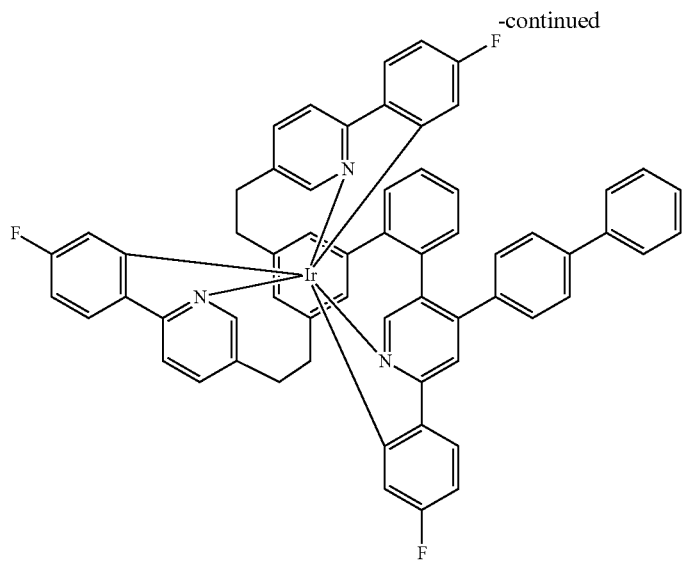
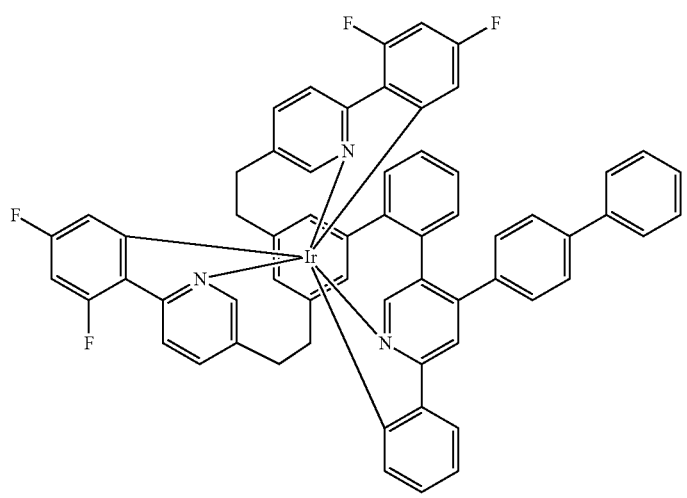
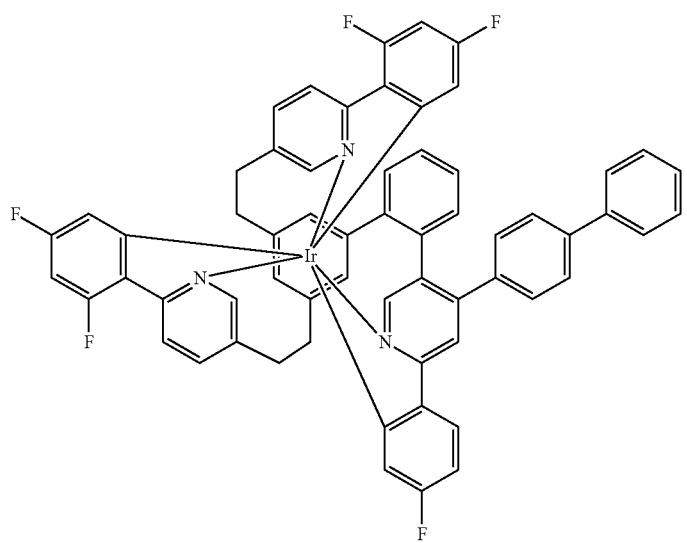

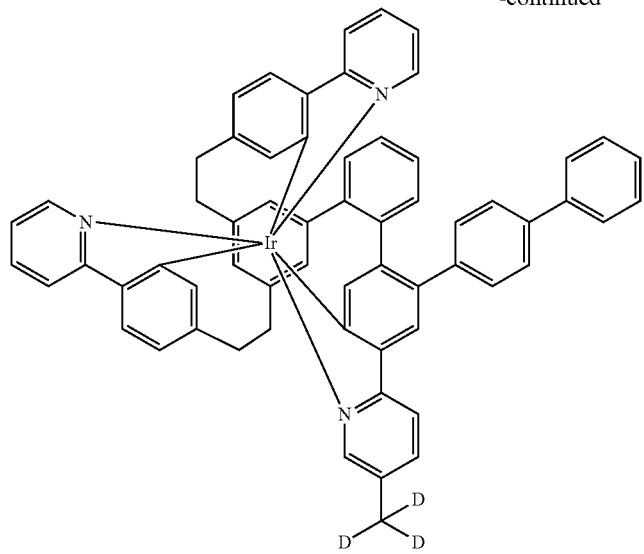
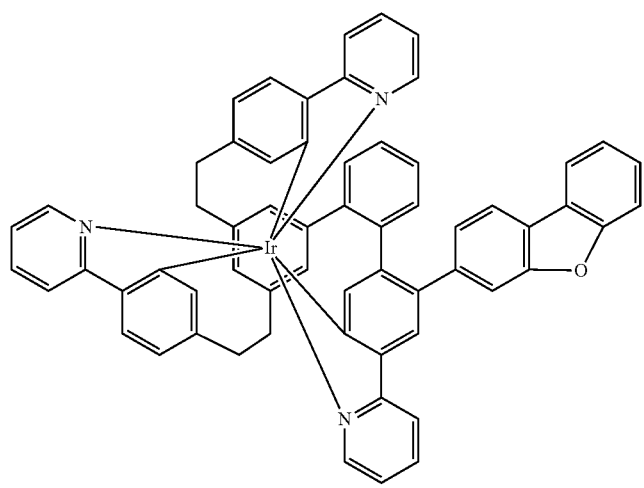
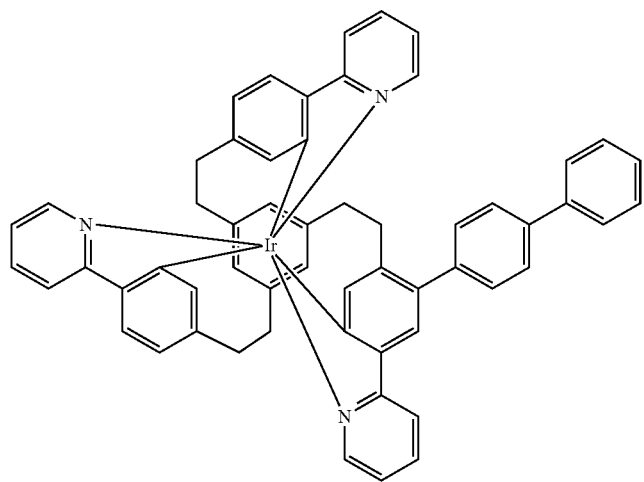

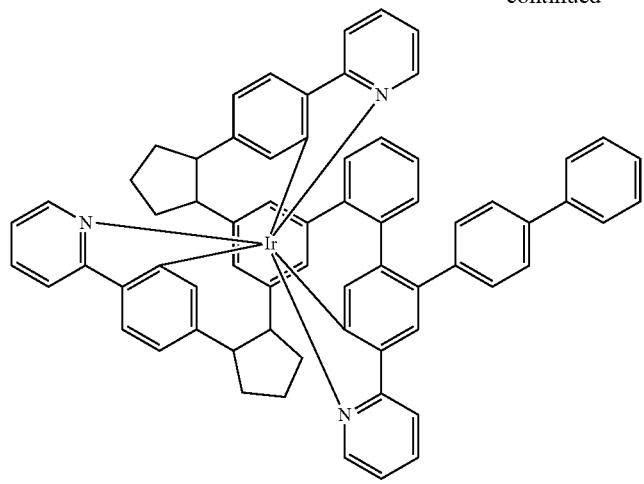
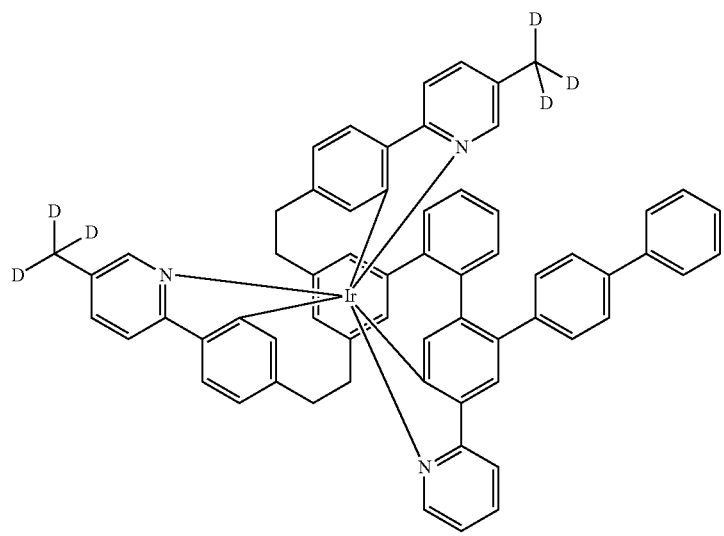
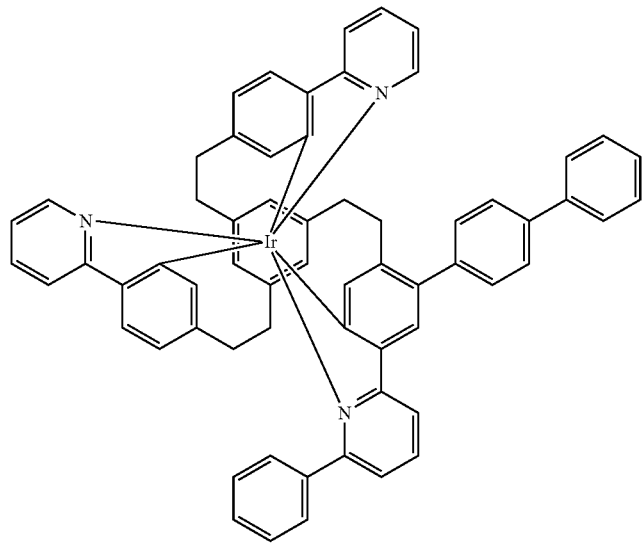

-continued
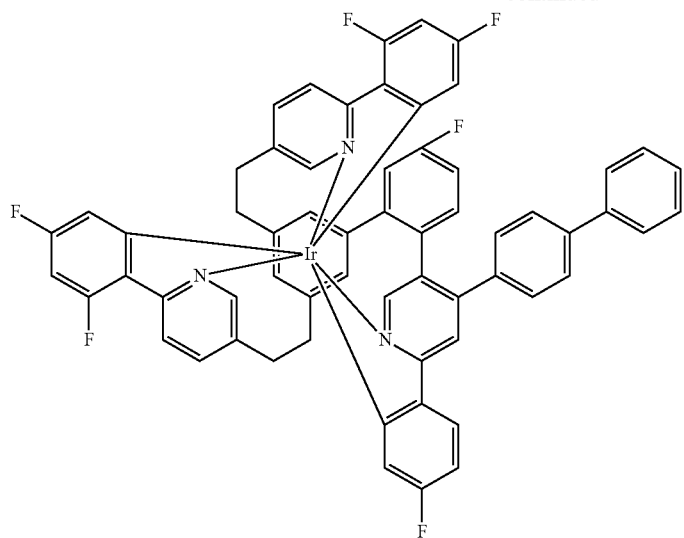
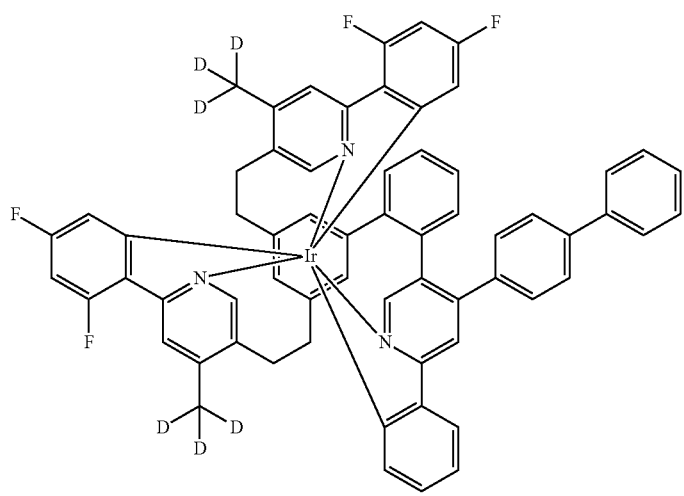
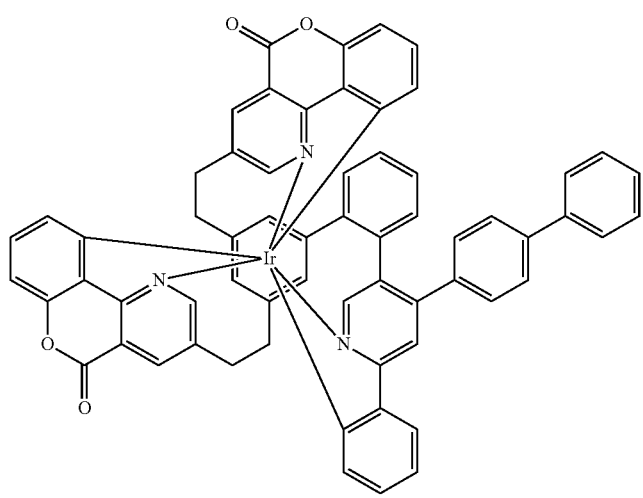

-continued
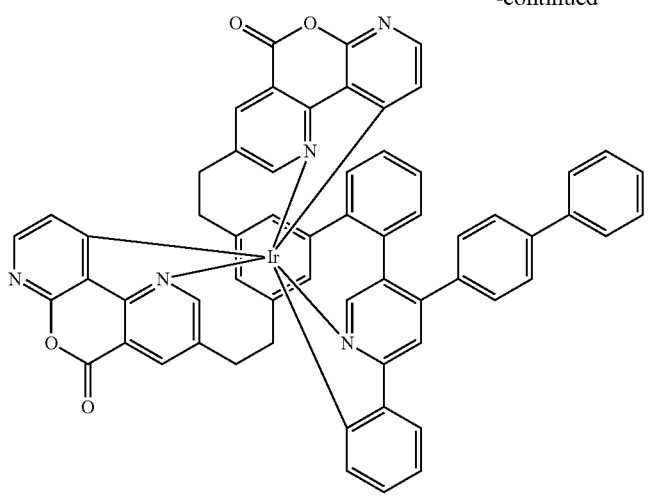
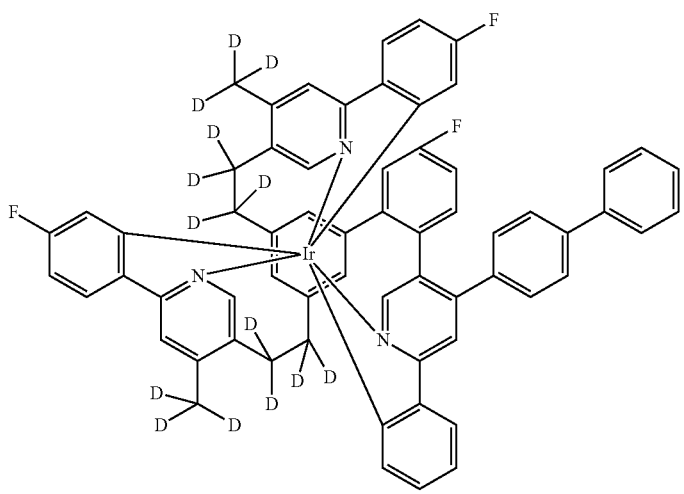
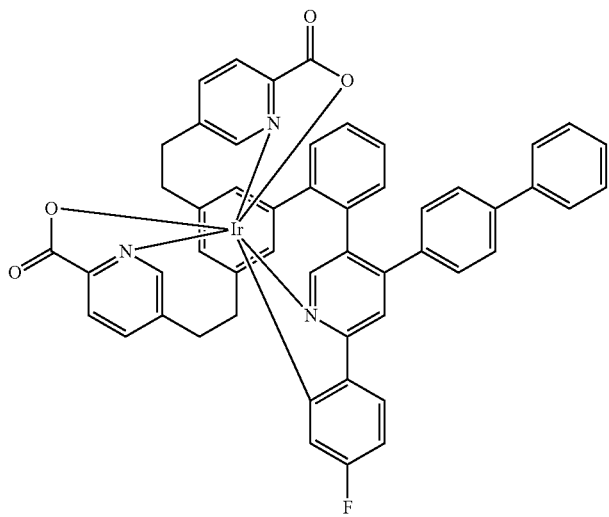

-continued
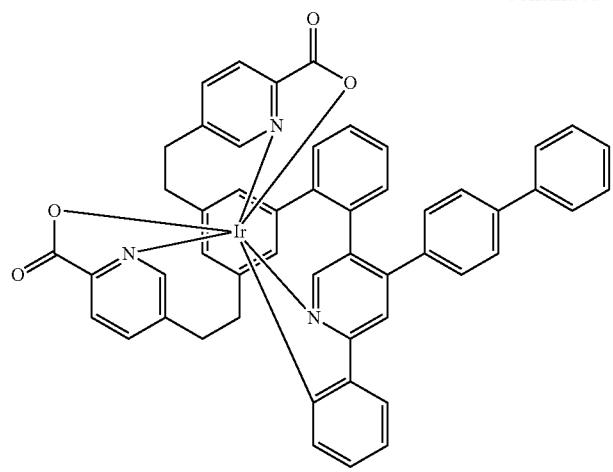
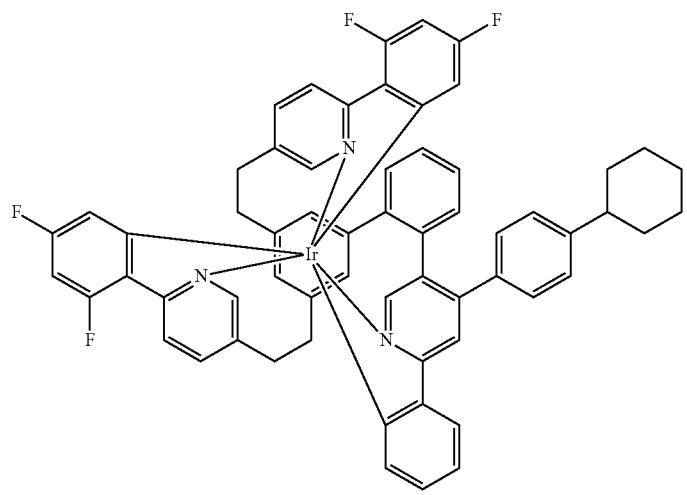
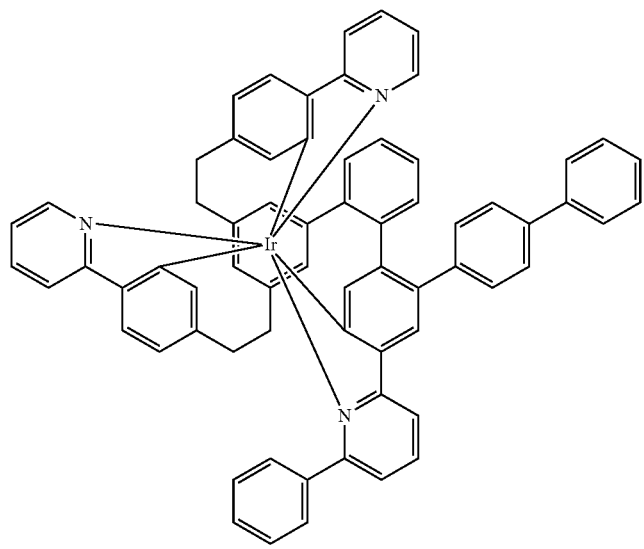

-continued
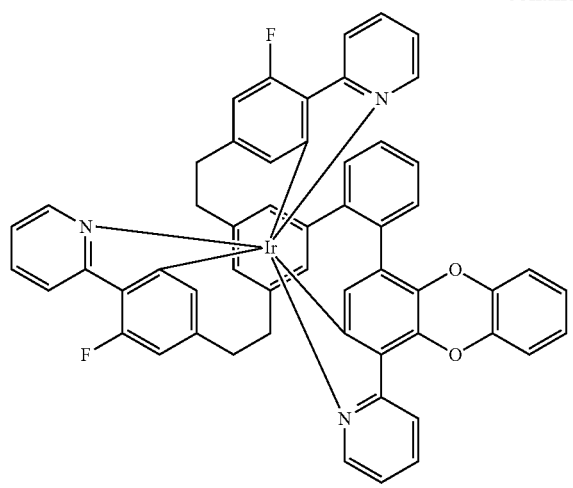
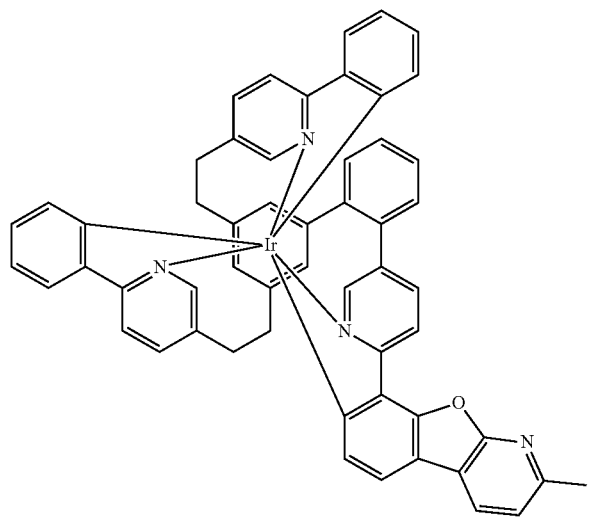
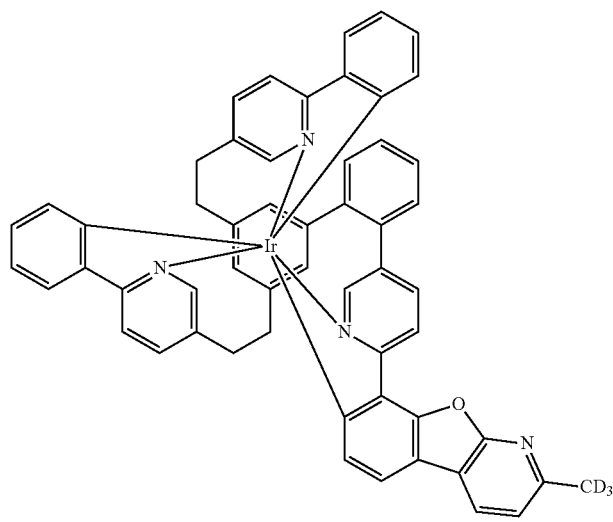

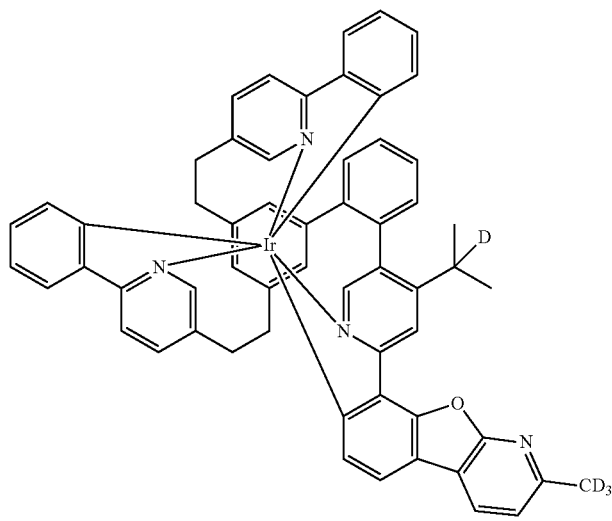
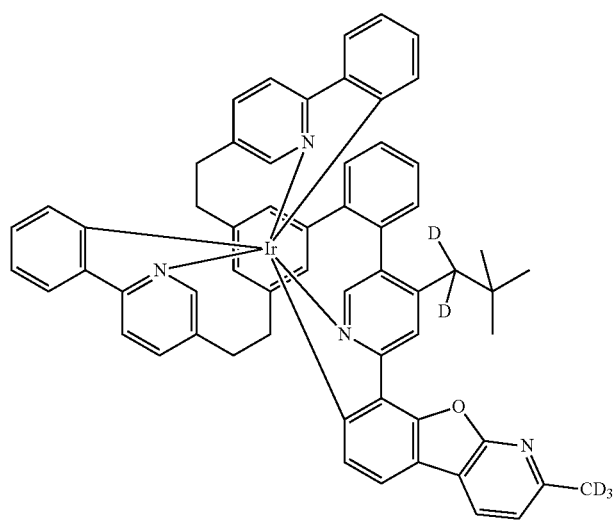
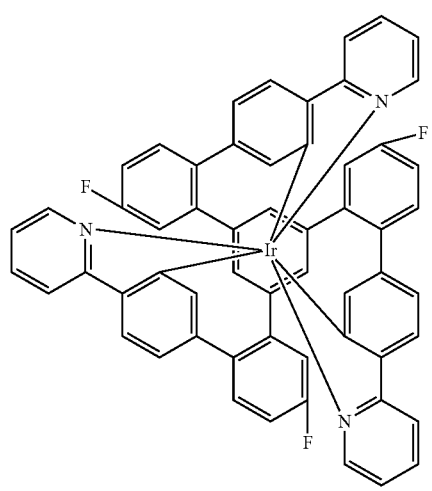

-continued
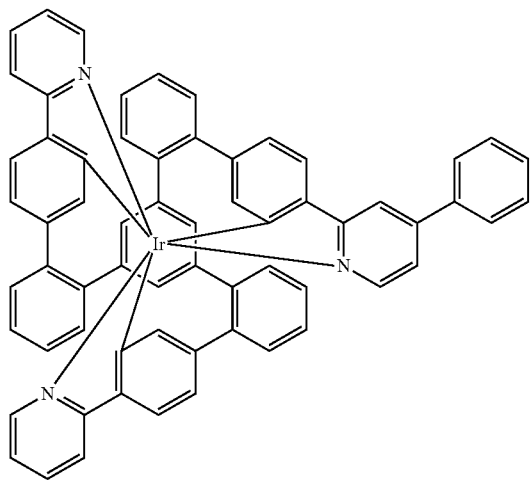
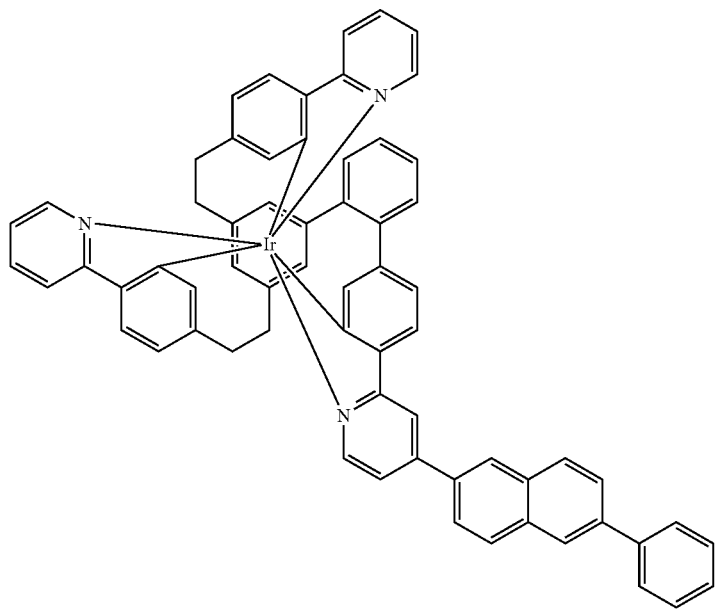
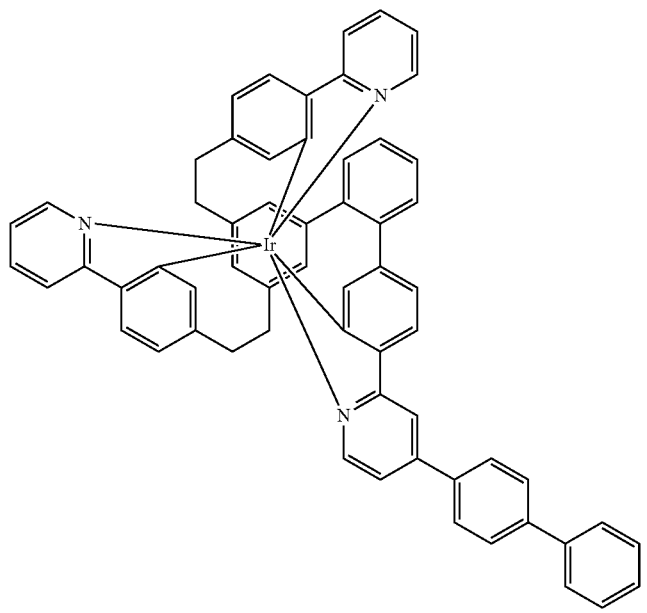

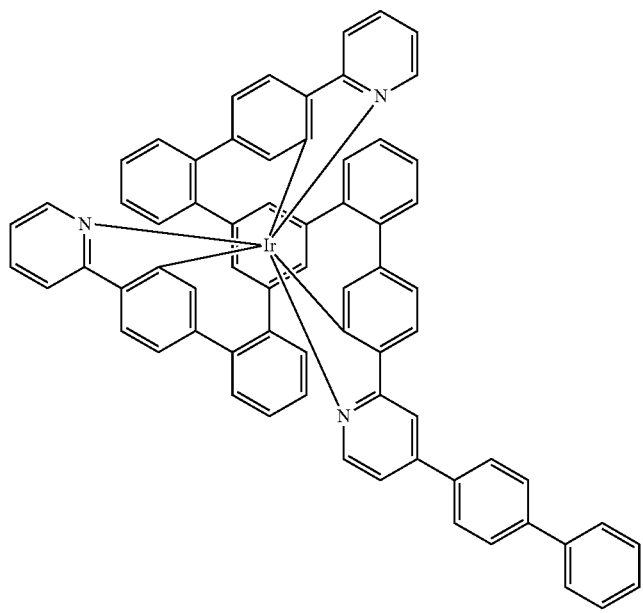
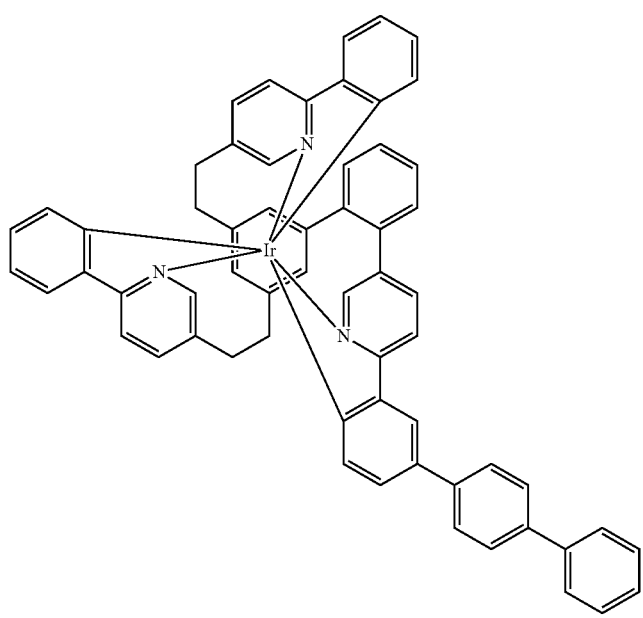
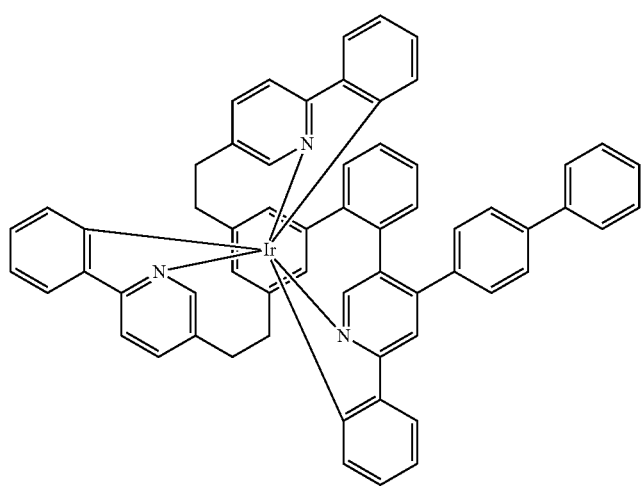

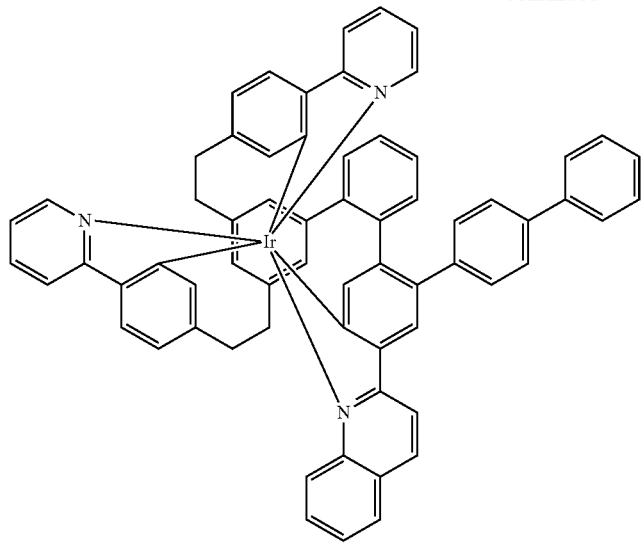
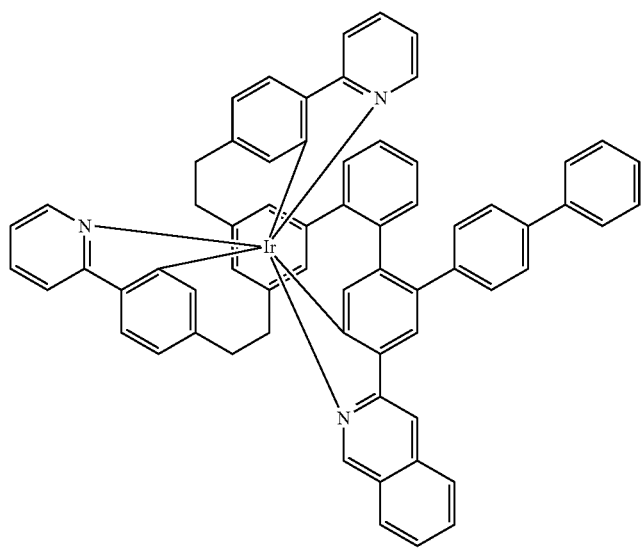
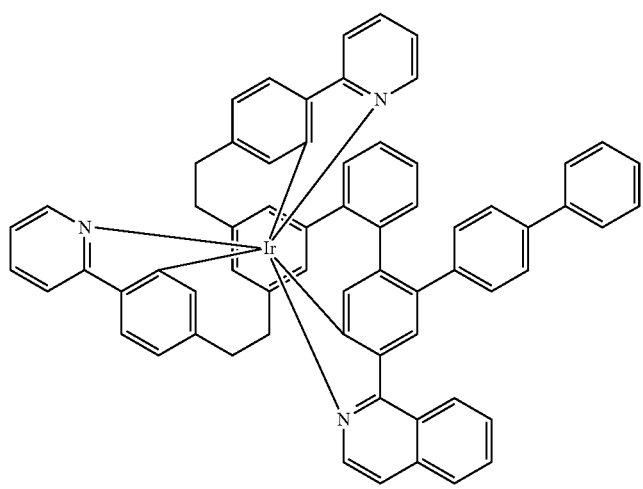

-continued
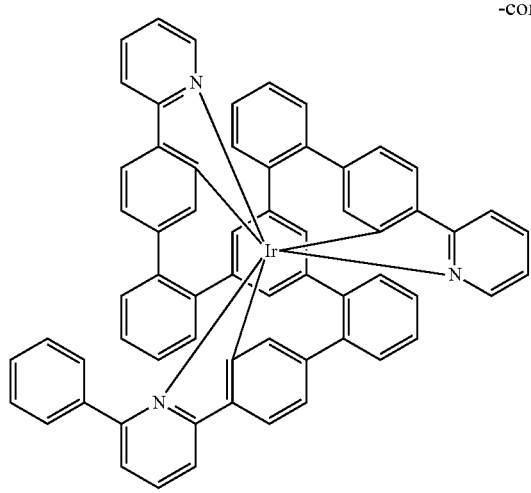
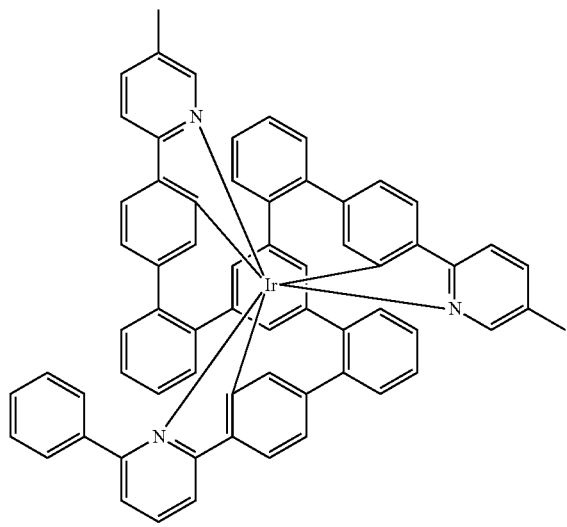
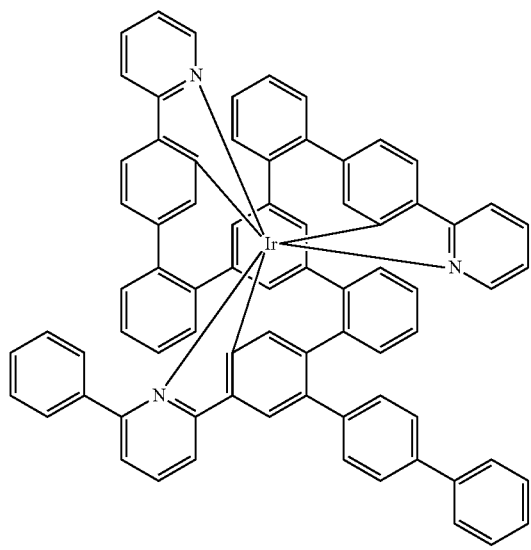

-continued
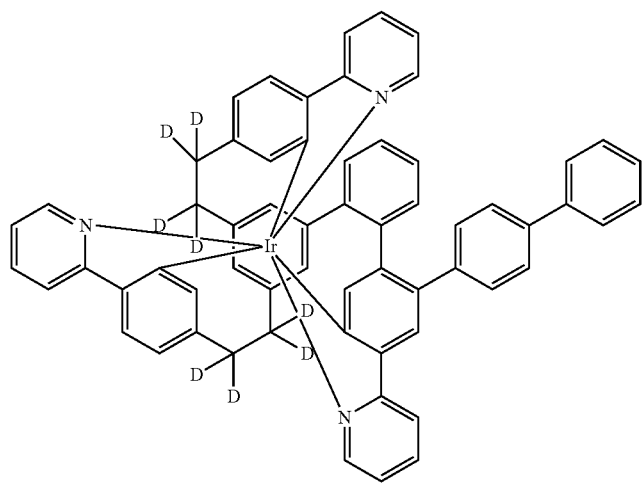
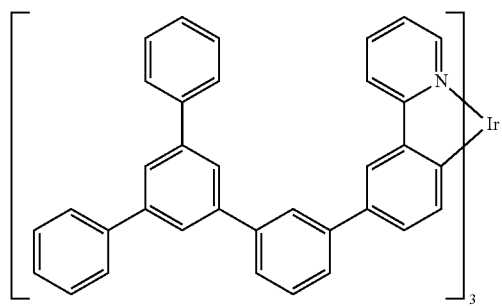
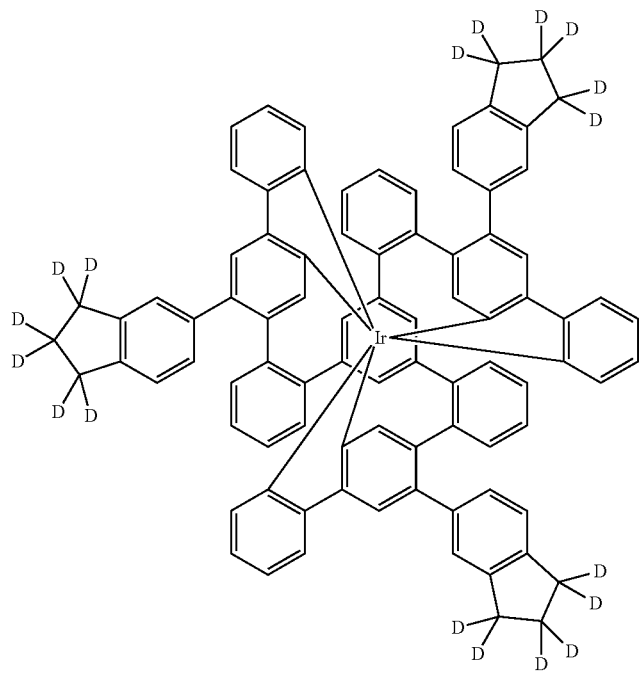

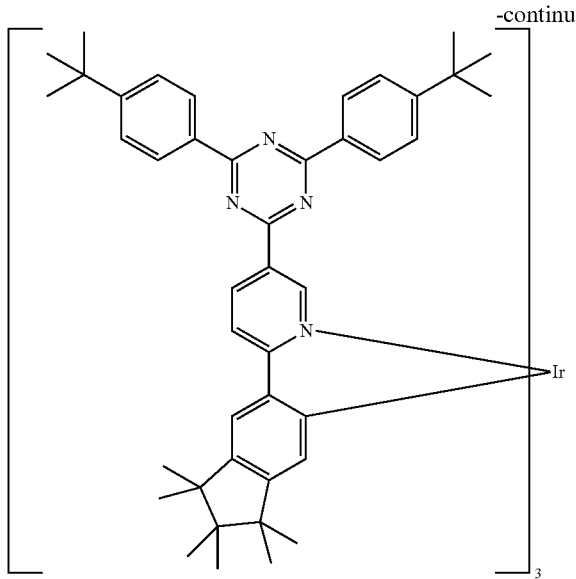
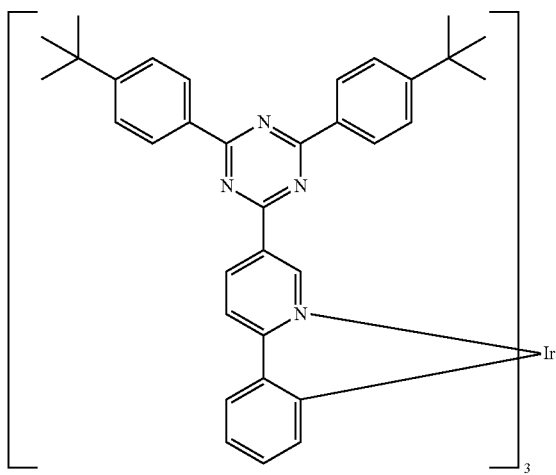
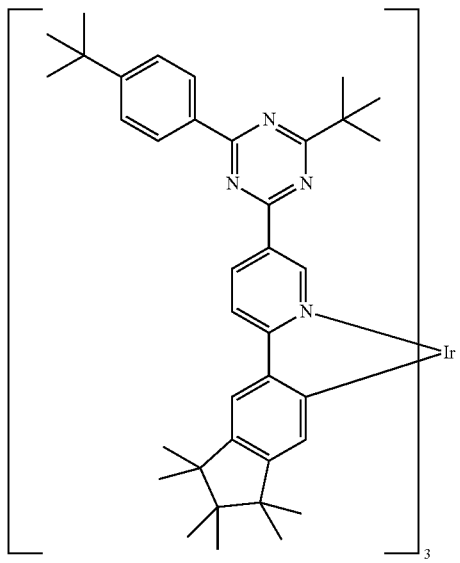

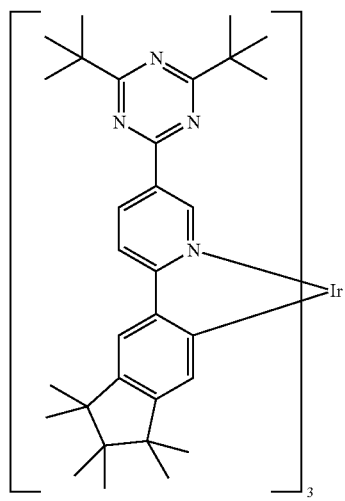
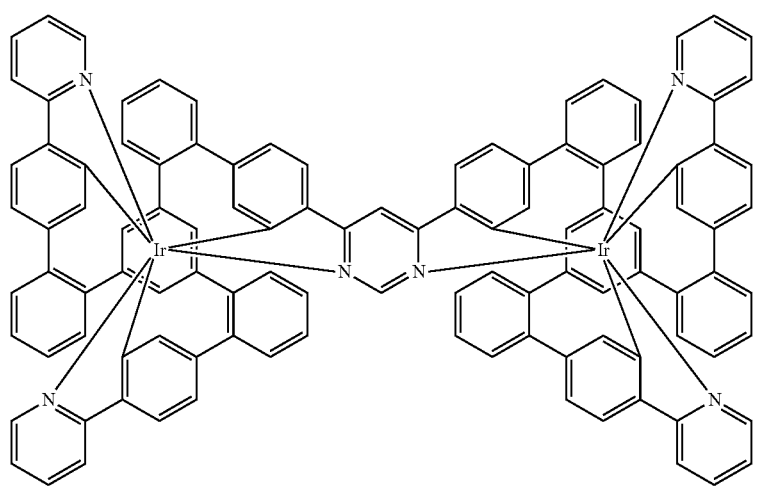

167 168
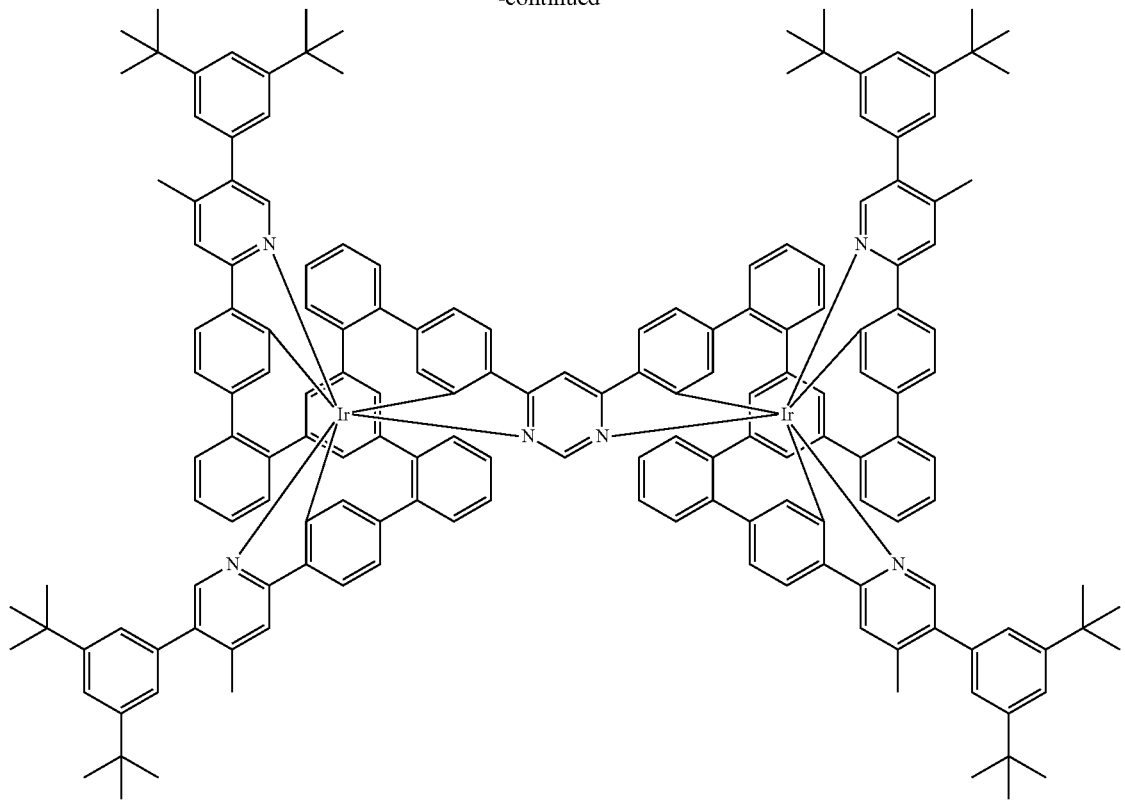
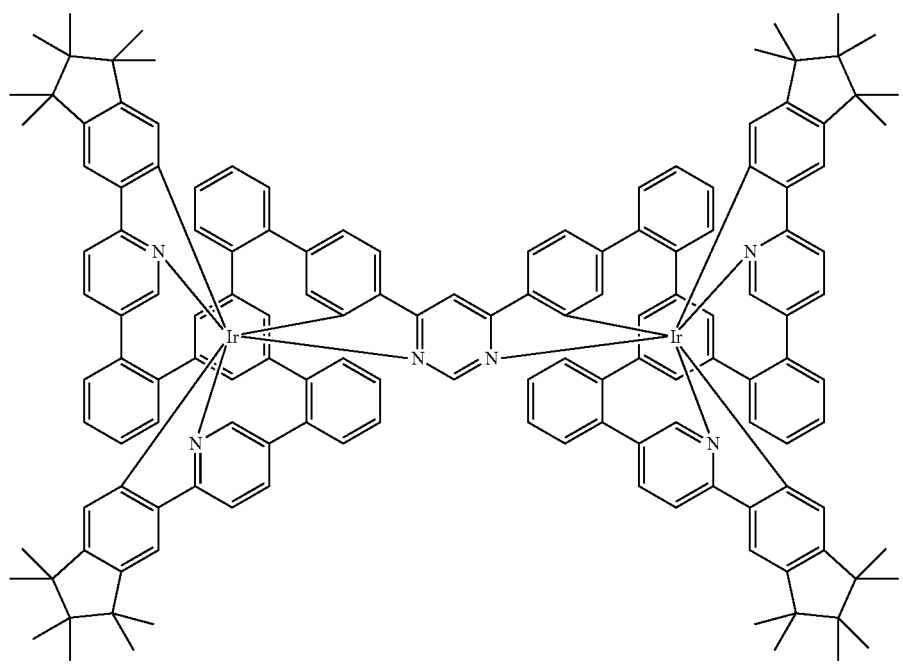

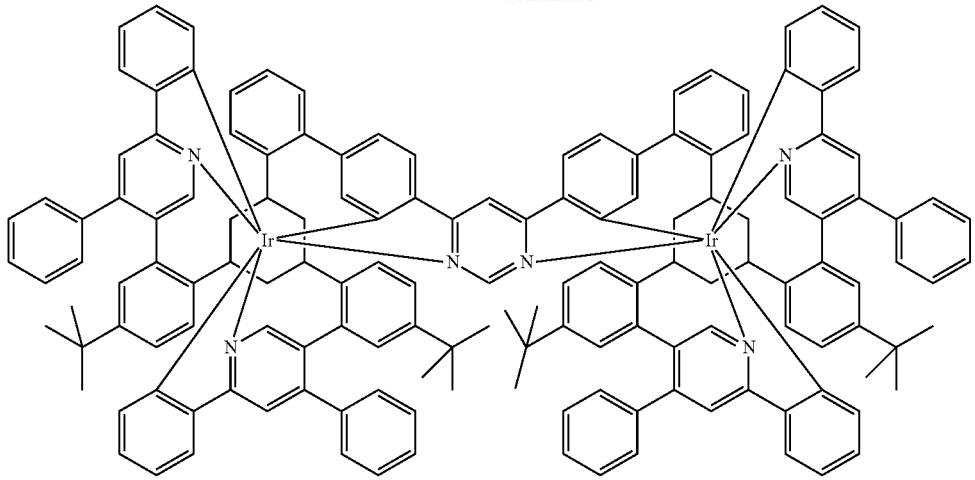

When the organic electroluminescent device is produced from solution, the mixture of the host overall, containing the compound of the invention, and the emitting compound contains between 99% and 1% by weight, preferably between 97% and 50% by weight, more preferably between 96% and 60% by weight and especially preferably between 95% and 75% by weight of the host containing the compound of the invention. Correspondingly, the mixture contains between 1% and 99% by weight, preferably between 3% and 50% by weight, more preferably between 5% and 40% by weight and especially between 5% and 25% by weight of the emitter, based on the overall mixture of emitter and all matrix materials.

The host material, as set out in more detail hereinafter, may also be a mixture of two or more materials, at least one of which is a compound of the invention. The proportion of the host material of the invention, i.e. of the compound of formula (1) or of the preferred embodiments, here is between 99% and 1% by weight, preferably between 95% and 10% by weight, more preferably between 80% and 20% by weight and most preferably between 70% and 25% by weight, based on all components of the emitting layer.

When the organic electroluminescent device is produced by vapour deposition, the mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of the invention as matrix material for a phosphorescent emitter in combination with a further matrix material. Suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, triphenylene derivatives, for example according to WO 2012/048781, dibenzofuran derivatives, for example according to WO 2015/169412, WO 2016/015810, WO 2016/023608, WO 2017/148564 or WO 2017/148565, or dibenzothiophene derivatives.

It is likewise possible for a further phosphorescent emitter which emits at a shorter wavelength than the actual emitter to be present as co-host in the mixture. For example, it is possible, when a red-emitting OLED is to be built, to use a green-phosphorescing emitter in addition to the red-phosphorescing emitter.

In addition, it is possible for a compound that takes no significant part in charge transport, if any, to be used as an additional "wide bandgap" matrix material, as described, for example, in WO 2010/108579, WO 2016/184540 or the as yet unpublished application EP 19152285.3. In a preferred embodiment of the invention, the wide bandgap material is a hydrocarbon, i.e. contains no heteroatoms.

A wide bandgap matrix material in the context of the present invention is a material which, in the emitting layer mixture used, features a HOMO at least 0.2 eV lower than the highest HOMO of all other materials represented in the mixture (emitters and host materials), and a LUMO at least 0.2 eV higher than the lowest LUMO of all other materials represented in the mixture (emitters and host materials).

The energy values reported relate to isolated compounds and are ascertained as set out hereinafter.

The HOMO (highest occupied molecular orbital) and LUMO (lowest unoccupied molecular orbital) energies and the triplet level of the materials are determined via quantum-chemical calculations. For this purpose, in the present case, the "Gaussian09, Revision D.01" software package (Gaussian Inc.) is used. It is alternatively possible to use other software packages provided that the same methods have been implemented therein. For calculation of organic substances without metals, a geometry optimization is first conducted by the semi-empirical method AM1 (Gaussian input line "#AM1 opt") with charge 0 and multiplicity 1. Subsequently, on the basis of the optimized geometry, a (single-point) energy calculation is effected for electronic ground state and triplet level. This is done using the TDDFT (Time Dependent Density Functional Theory) method B3PW91 with the 6-31G(d) basis set (Gaussian input line "#B3PW91/6-31G(d) td=(50-50,nstates=4)") (charge 0, multiplicity 1). For organometallic compounds, the geometry is optimized by the Hartree-Fock method and the LanL2 MB basis set (Gaussian input line "#HF/LanL2 MB opt") (charge 0, multiplicity 1). The energy calculation is effected analogously to the organic substances, as described above, except that the "LanL2DZ" basis set is used for the metal atom and the "6-31G(d)" basis set for the ligands (Gaussian input line "#B3PW91/gen pseudo=lanl2 td=(50-50, nstates=4)"). From the energy calculation, the HOMO is obtained as the last orbital occupied by two electrons (alpha occ. eigenvalues) and LUMO as the first unoccupied orbital (alpha virt. eigenvalues) in Hartree units (HEh and LEh). This is used to determine the HOMO and LUMO value in electron volts, calibrated by cyclic voltammetry measurements, as follows:

$$\text{LUMO (eV)} = (1.0658 * LEh * 27.212) - 0.5049$$

$$\text{HOMO (eV)} = (0.8308 * HEh * 27.212) - 1.1180$$

These values are to be regarded as HOMO and as LUMO of the materials in the context of this application.

Examples of suitable wide bandgap materials are the structures shown in the following table:

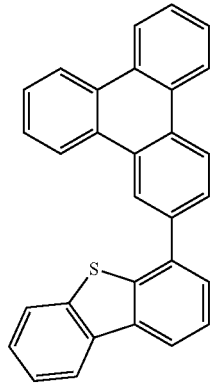 [SMILES: c1ccc2c(c1)sc1c(-c3ccc4c5ccccc5c5ccccc5c4c3)cccc12]

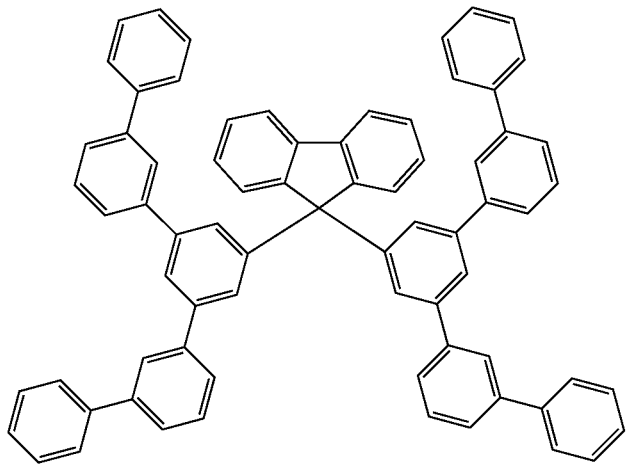 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1]

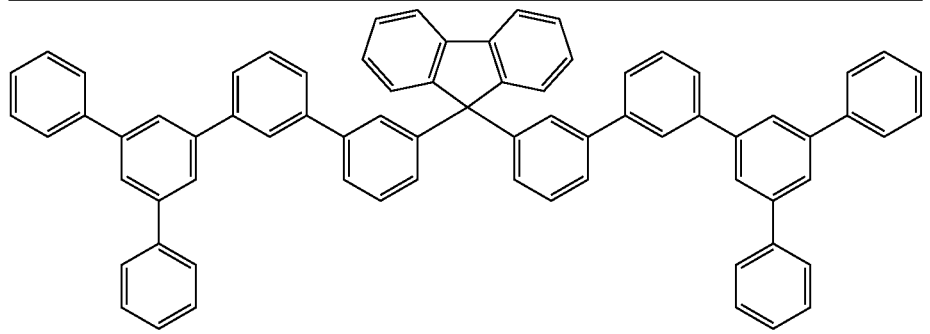
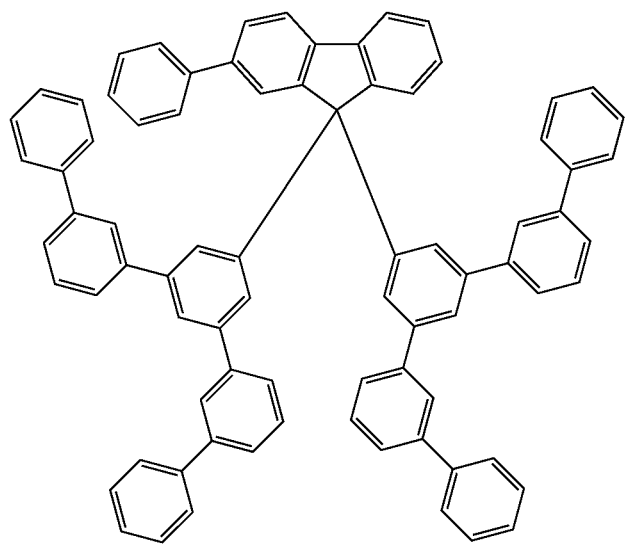 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccc(-c6ccccc6)cc54)c3)c2)cc1]
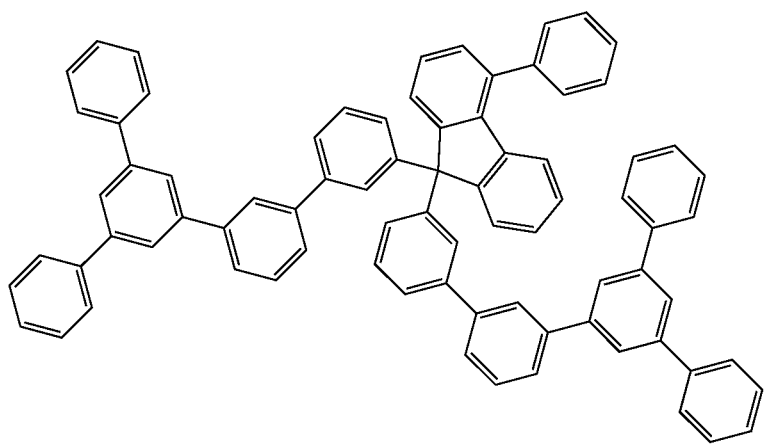 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6c(-c7ccccc7)cccc65)c4)c3)c2)cc1]
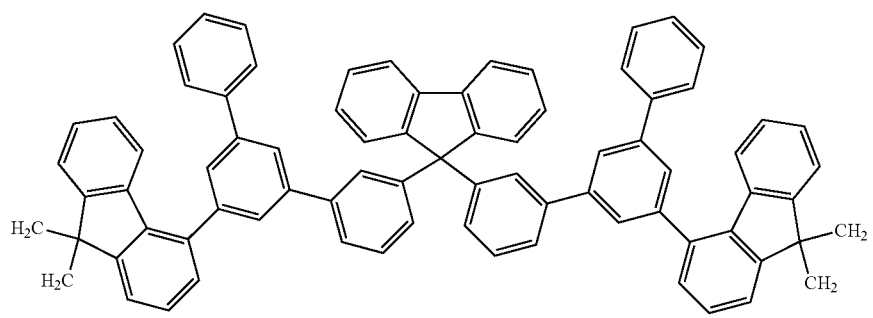

-continued
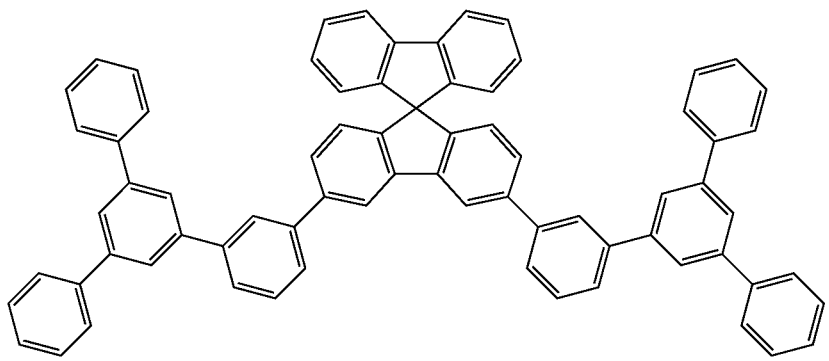 [SMILES: c1ccc(-c2cc(-c3ccccc3)cc(-c3cccc(-c4ccc5c(c4)-c4cc(-c6cccc(-c7cc(-c8ccccc8)cc(-c8ccccc8)c7)c6)ccc4C54c5ccccc5-c5ccccc54)c3)c2)cc1]
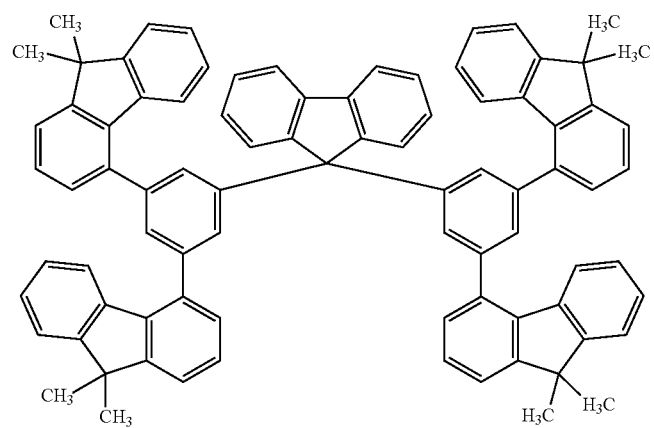 [SMILES: CC1(C)c2ccccc2-c2c(-c3cc(-c4cccc5c4-c4ccccc4C5(C)C)cc(C4(c5cc(-c6cccc7c6-c6ccccc6C7(C)C)cc(-c6cccc7c6-c6ccccc6C7(C)C)c5)c5ccccc5-c5ccccc54)c3)cccc21]
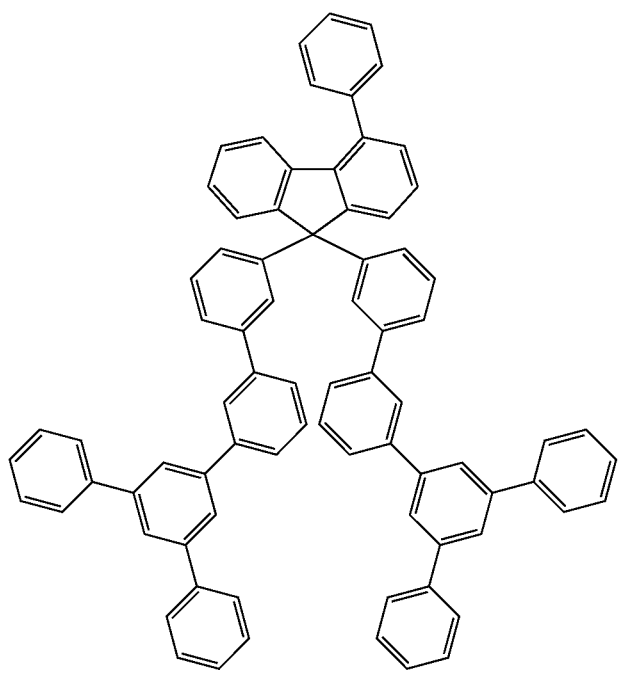 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6c(-c7ccccc7)cccc65)c4)c3)c2)cc1]

-continued
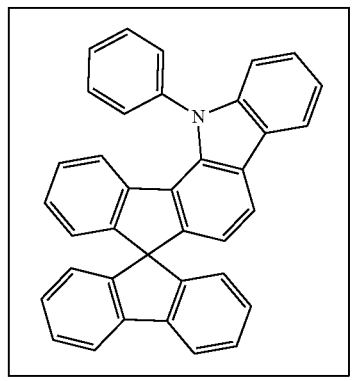 [SMILES: c1ccc(-n2c3ccccc3c3ccc4c(c32)-c2ccccc2C42c3ccccc3-c3ccccc32)cc1]
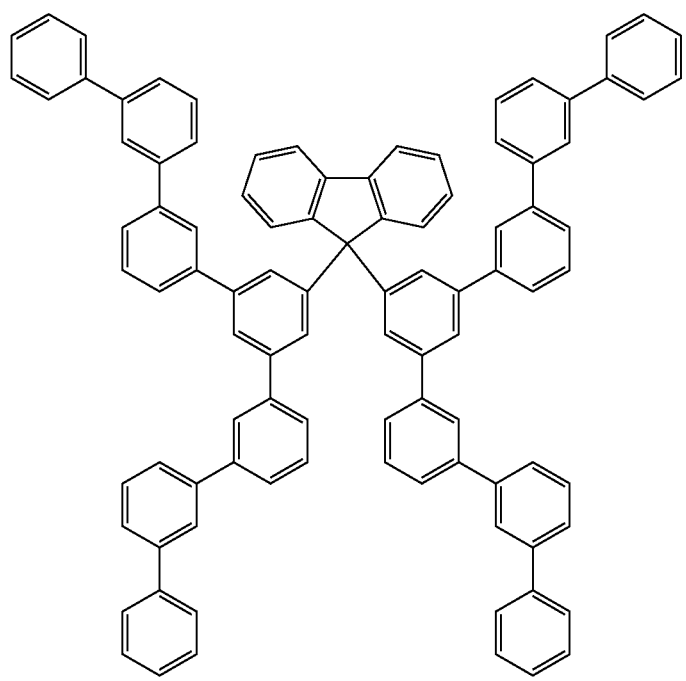 [SMILES: c1ccc(-c2cccc(-c3cccc(-c4cc(-c5cccc(-c6cccc(-c7ccccc7)c6)c5)cc(C5(c6cc(-c7cccc(-c8cccc(-c9ccccc9)c8)c7)cc(-c7cccc(-c8cccc(-c9ccccc9)c8)c7)c6)c6ccccc6-c6ccccc65)c4)c3)c2)cc1]
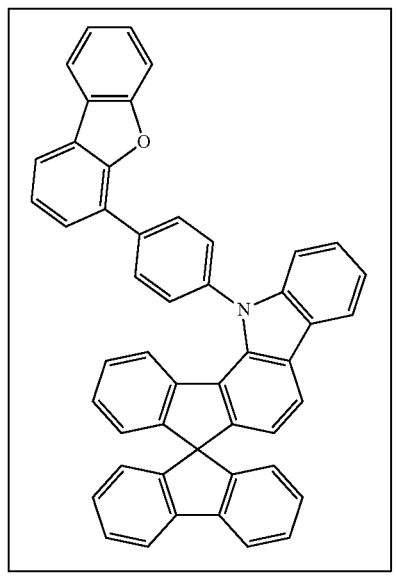 [SMILES: c1ccc2c(c1)-c1ccccc1C21c2ccccc2-c2c1ccc1c3ccccc3n(-c3ccc(-c4cccc5c4oc4ccccc45)cc3)c21]

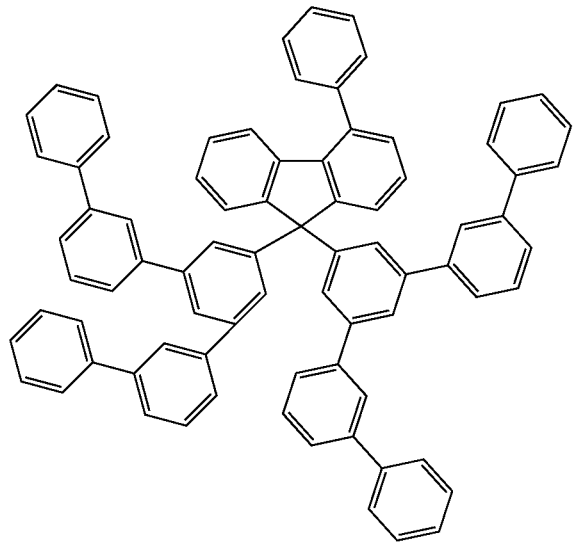 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5c(-c6ccccc6)cccc54)c3)c2)cc1]
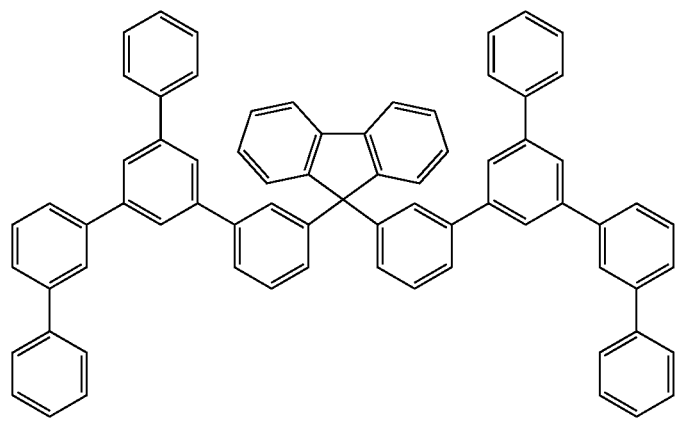 [SMILES: c1ccc(-c2cccc(-c3cc(-c4ccccc4)cc(-c4cccc(C5(c6cccc(-c7cc(-c8ccccc8)cc(-c8cccc(-c9ccccc9)c8)c7)c6)c6ccccc6-c6ccccc65)c4)c3)c2)cc1]
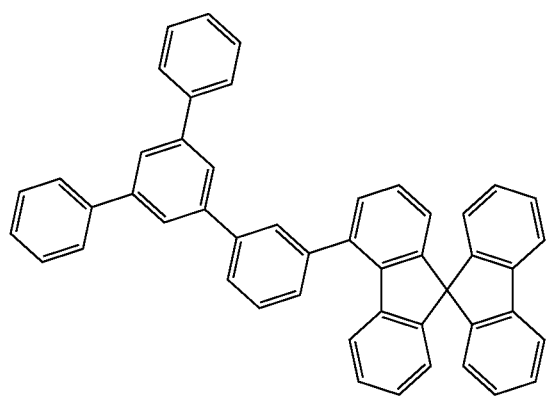 [SMILES: c1ccc(-c2cc(-c3ccccc3)cc(-c3cccc(-c4cccc5c4-c4ccccc4C54c5ccccc5-c5ccccc54)c3)c2)cc1]

In addition, it is possible to use the compounds of the invention in a hole blocker and/or electron transport layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are applied by a sublimation process. In this case, the materials are applied by vapour deposition in vacuum sublimation systems at an initial pressure of less than $10^{-5}$ mbar, preferably less than $10^{-6}$ mbar. It is also possible, however, that the initial pressure is even lower or higher, for example less than $10^{-7}$ mbar.

Preference is likewise given to an organic electroluminescent device, characterized in that one or more layers are applied by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. It has been found that the compounds of the invention are particularly suitable specifically for processing from solution.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied by those skilled in the art without exercising inventive skill to organic electroluminescent devices comprising the compounds of the invention.

The compounds of the invention are of very good suitability for processing from solution. At the same time, they have very good solubility in standard organic solvents and a high glass transition temperature. The use of the compounds of the invention as matrix material for phosphorescent emitters in organic electroluminescent devices produced from solution leads to a significant improvement in the lifetime of the organic electroluminescent devices compared to prior art compounds, especially compared to compounds containing only one dibenzofuran-carbazole unit on the triazine or to compounds in which the triazine is substituted by two or more 1-dibenzofuran groups but only one dibenzofuran group is substituted by one carbazole group. At the same time, the further properties of the organic electroluminescent device, especially the efficiency and voltage, are comparable or better.

The invention is now illustrated in detail by the examples which follow, without any intention of restricting it thereby.

EXAMPLES

The syntheses which follow, unless stated otherwise, are conducted under a protective gas atmosphere in dried solvents. The solvents and reagents can be purchased, for example, from Sigma-ALDRICH or ABCR. The respective figures in square brackets or the numbers quoted for individual compounds relate to the CAS numbers of the compounds known from the literature.

Stage 1: BB-1a

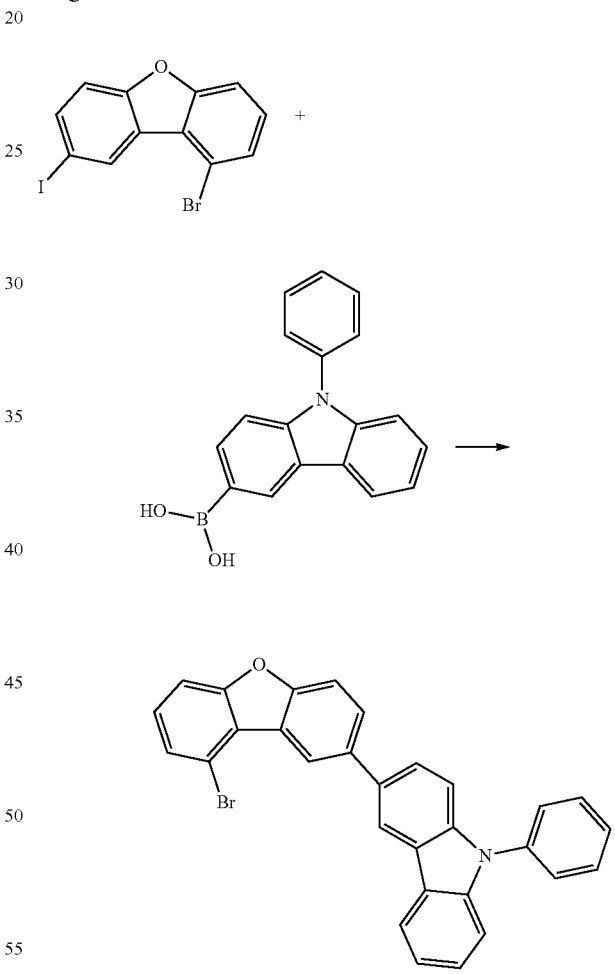

100 g (26 mmol) of 1-bromo-8-iododibenzofuran (CAS: 1822311-11-4), 92.4 g (32 mmol) of (9-phenyl-9H-carbazol-3-yl)boronic acid, 85.2 g (61 mmol) of potassium carbonate and 15.5 g (13 mmol) of tetrakis(triphenylphosphine)palladium(0) are mixed in 1 l of ethylene glycol dimethyl ether/water (3:1) and heated under reflux overnight. The mixture is allowed to come to room temperature, and the precipitate is filtered off and washed with water and ethanol. Yield: 86 g (176 mmol; 66%).

The following compounds can be synthesized analogously:
| Ex. | Reactant 1 | Reactant 2 |
|---|---|---|
| BB-1b | 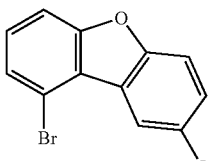<br>CAS 1822311-11-4 | 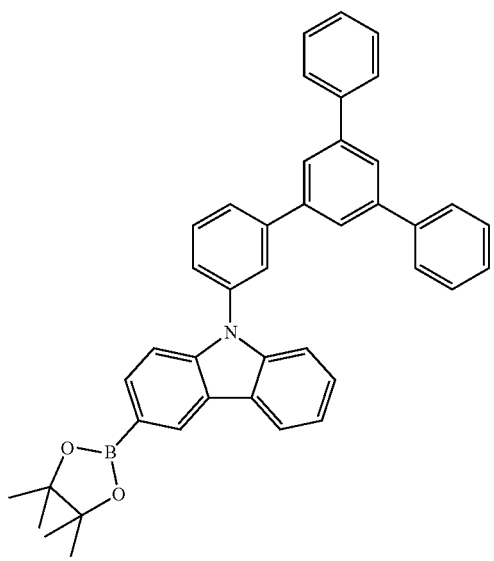<br>CAS 1846559-20-3 |
| BB-1c | 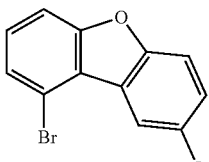<br>CAS 1822311-11-4 | 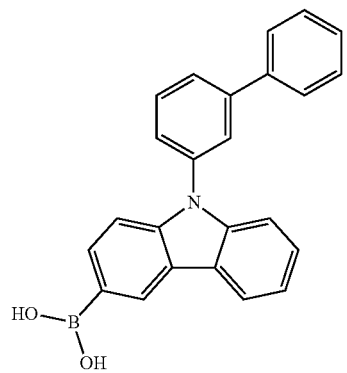<br>CAS 1416814-68-0 |
| BB-1d | 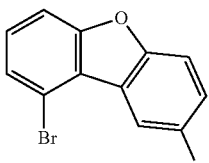<br>CAS 1822311-11-4 | 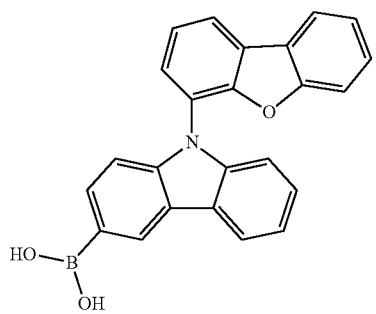<br>CAS 1547397-15-8 |

| | | |
|---|---|---|
| BB-1e | 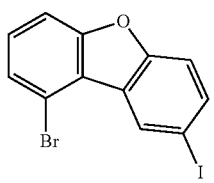 CAS 1822311-11-4 | 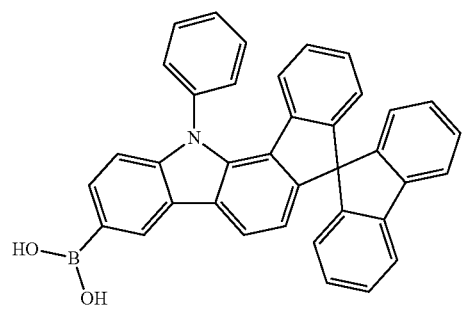 [SMILES: OB(O)c1ccc2c(c1)c1ccc3c(c1n2-c1ccccc1)-c1ccccc1C31c2ccccc2-c2ccccc21] |
| BB-1f | 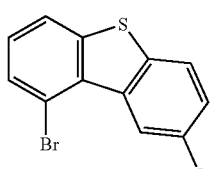 CAS 1822311-12-5 | 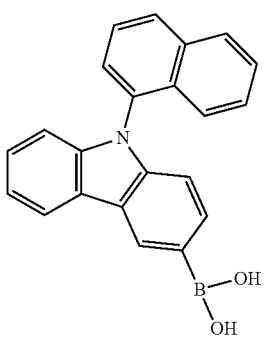 CAS 113057-97-2 |
| BB-1g | 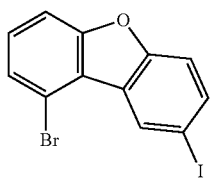 CAS 1822311-11-4 | 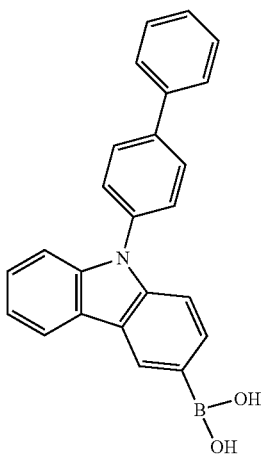 CAS 1028648-22-7 |
| BB-1h | 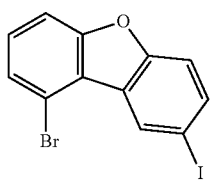 CAS 1822311-11-4 | 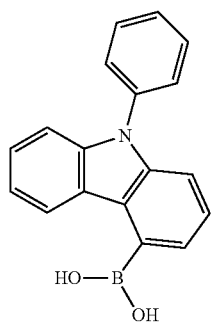 CAS 137055-65-9 |

| BB-1i | 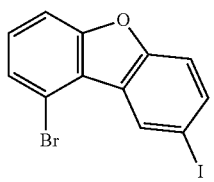  CAS 1822311-11-4 | 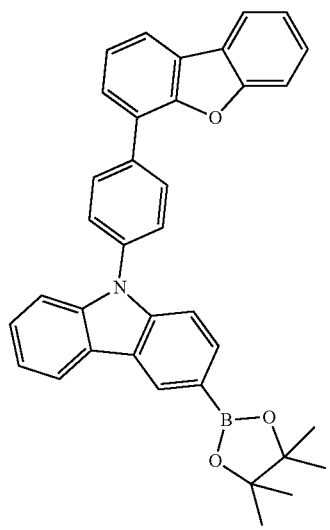  CAS 2260995-43-3 |
| --- | --- | --- |
| BB-1j | 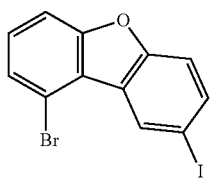  CAS 1822311-11-4 | 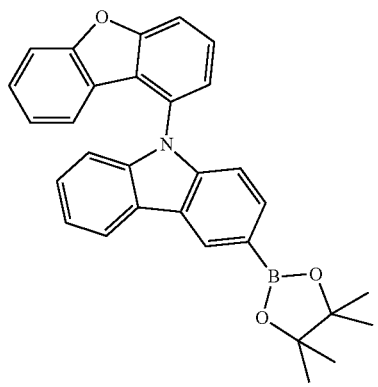  CAS 1427160-10-8 |
| Ex. | Product |
| --- | --- |
| BB-1b | 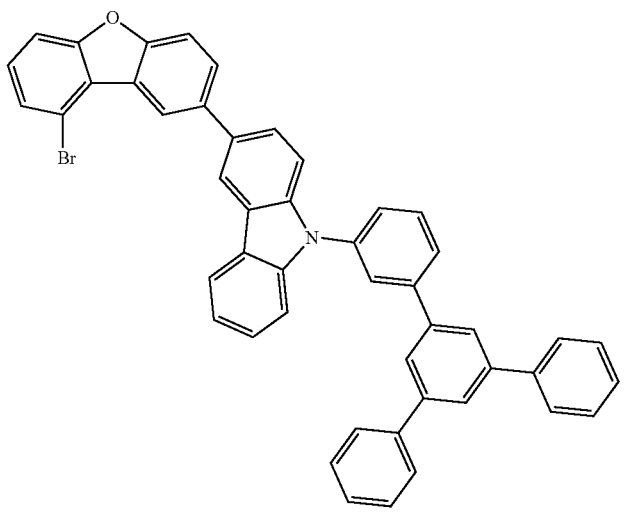 [SMILES: Brc1cccc2oc3ccc(-c4ccc5c(c4)c4ccccc4n5-c4cccc(-c5cc(-c6ccccc6)cc(-c6ccccc6)c5)c4)cc3c12] |

-continued
BB-1c
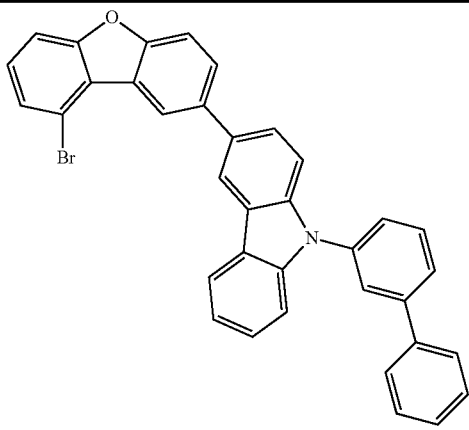
BB-1d
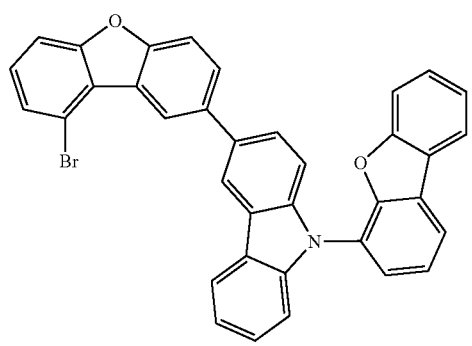 [SMILES: Brc1cccc2oc3ccc(-c4ccc5c(c4)c4ccccc4n5-c4cccc5c4oc4ccccc45)cc3c12]
BB-1e
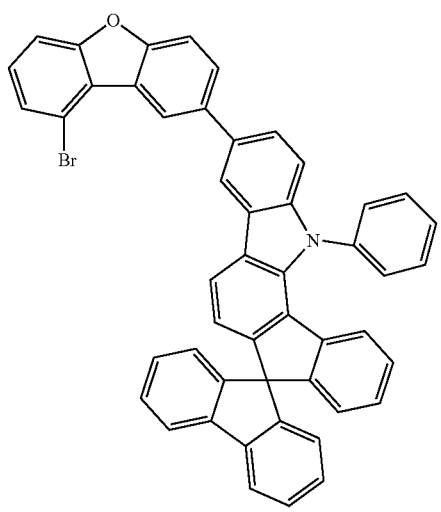 [SMILES: Brc1cccc2oc3ccc(-c4ccc5c(c4)c4ccc6c(c4n5-c4ccccc4)-c4ccccc4C64c5ccccc5-c5ccccc54)cc3c12]
BB-1f
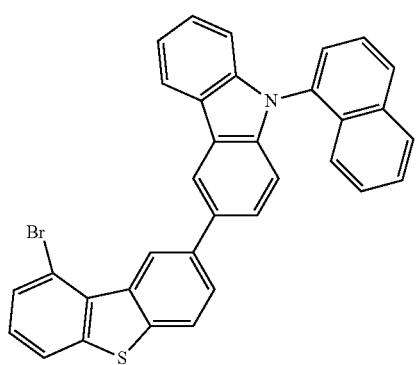 [SMILES: Brc1cccc2sc3ccc(-c4ccc5c(c4)c4ccccc4n5-c4cccc5ccccc45)cc3c12]

-continued
BB-1g
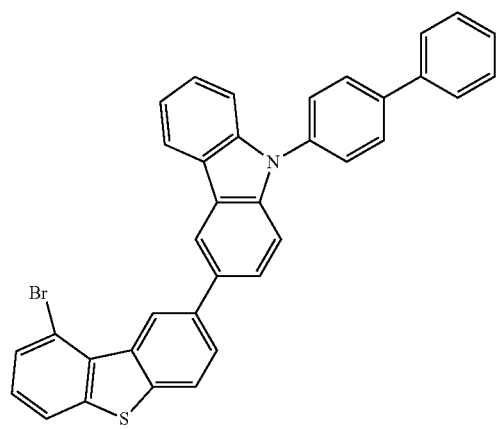 [SMILES: Brc1cccc2sc3ccc(-c4ccc5c(c4)c4ccccc4n5-c4ccc(-c5ccccc5)cc4)cc3c12]
BB-1h
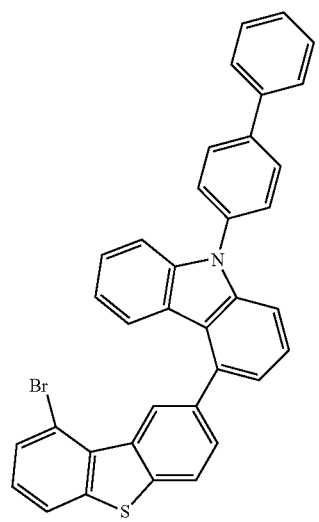 [SMILES: Brc1cccc2sc3ccc(-c4cccc5c4c4ccccc4n5-c4ccc(-c5ccccc5)cc4)cc3c12]
BB-1i
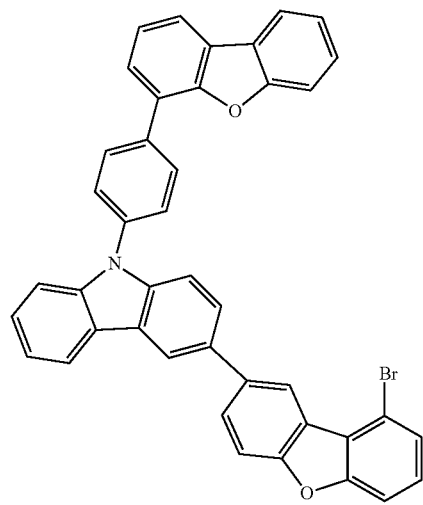 [SMILES: Brc1cccc2oc3ccc(-c4ccc5c(c4)c4ccccc4n5-c4ccc(-c5cccc6c5oc5ccccc56)cc4)cc3c12]

| | -continued |
|---|---|
| BB-1j | 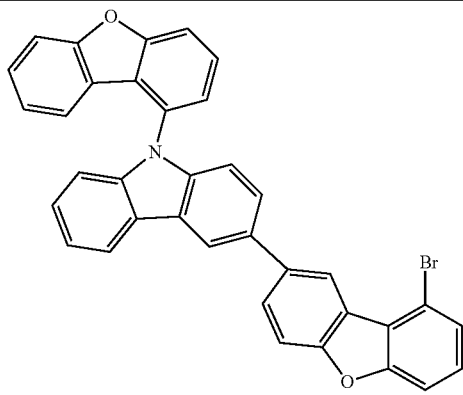 |

Stage 2: BB-2a

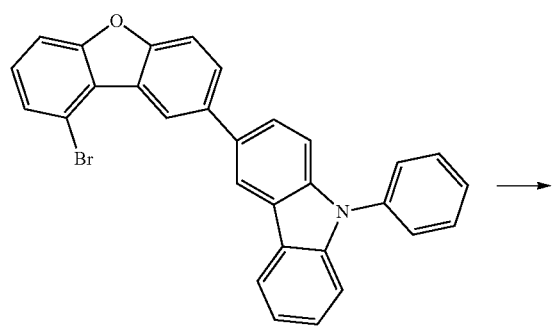

→

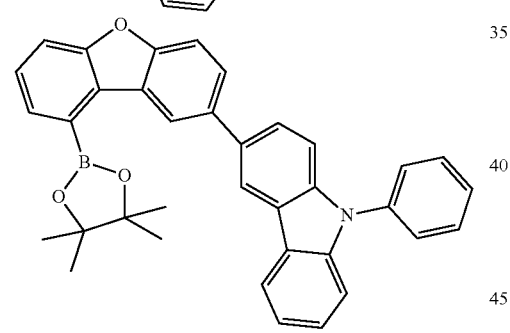

86 g (176 mmol) of 3-(9-bromodibenzofuran-2-yl)-9-phenyl-9H-carbazole, 82.1 g (320 mmol) of 4,4,5,5,4',4',5',5'-octamethyl-[2,2']bi[[1,3,2]dioxaborolanyl], 52.4 g (530 mmol) of potassium acetate and 2.8 g (12 mmol) of palladium acetate are mixed in 1 l of DMF and stirred at 100° C. After 24 h, the reaction mixture is left to cool to room temperature and the mixture is concentrated to one third under reduced pressure. Water is added and the precipitated solids are filtered off, washed with water, ethanol and heptane, and purified further by filtration through silica with THF as eluent. The product is obtained by removing the solvents under reduced pressure. Yield: 58.2 g (109 mmol; 62%).

The following compounds can be synthesized analogously:

| Ex. | Reactant | Product |
|---|---|---|
| BB-2b | 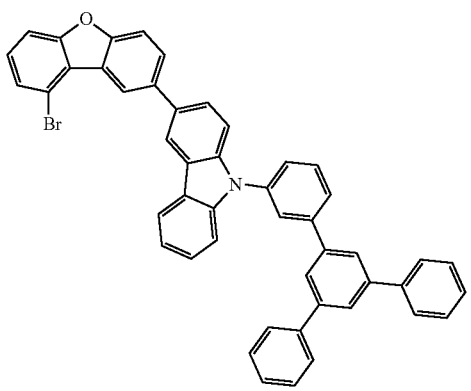 [SMILES: Brc1cccc2oc3ccc(-c4ccc5c(c4)c4ccccc4n5-c4cccc(-c5cc(-c6ccccc6)cc(-c6ccccc6)c5)c4)cc3c12] | 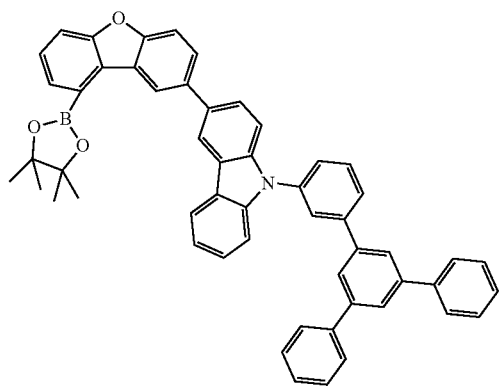 [SMILES: CC1(C)OB(c2cccc3oc4ccc(-c5ccc6c(c5)c5ccccc5n6-c5cccc(-c6cc(-c7ccccc7)cc(-c7ccccc7)c6)c5)cc4c23)OC1(C)C] |

-continued
| Ex. | Reactant | Product |
|---|---|---|
| BB-2c | 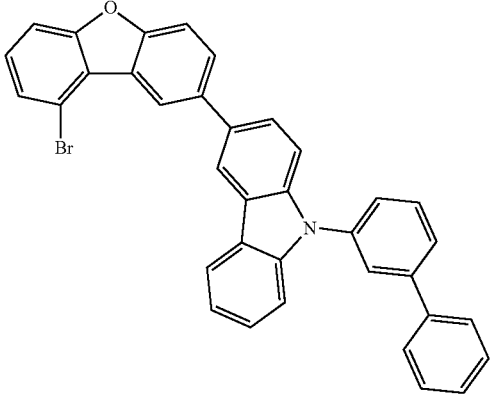 [SMILES: Brc1cccc2oc3ccc(-c4ccc5c(c4)c4ccccc4n5-c4cccc(-c5ccccc5)c4)cc3c12] | 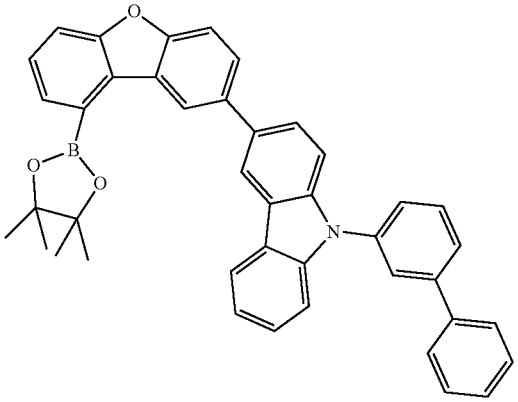 [SMILES: CC1(C)OB(c2cccc3oc4ccc(-c5ccc6c(c5)c5ccccc5n6-c5cccc(-c6ccccc6)c5)cc4c23)OC1(C)C] |
| BB-2d | 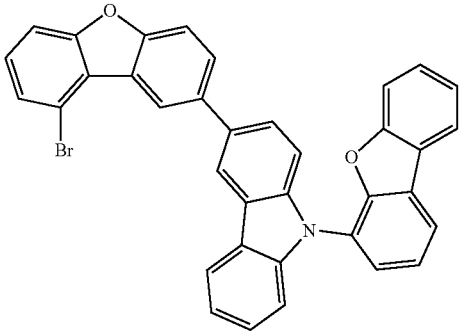 [SMILES: Brc1cccc2oc3ccc(-c4ccc5c(c4)c4ccccc4n5-c4cccc5c4oc4ccccc45)cc3c12] | 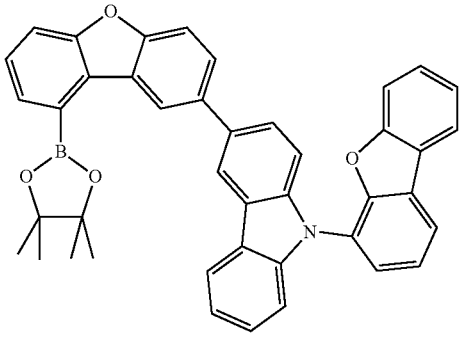 [SMILES: CC1(C)OB(c2cccc3oc4ccc(-c5ccc6c(c5)c5ccccc5n6-c5cccc6c5oc5ccccc56)cc4c23)OC1(C)C] |
| BB-2e | 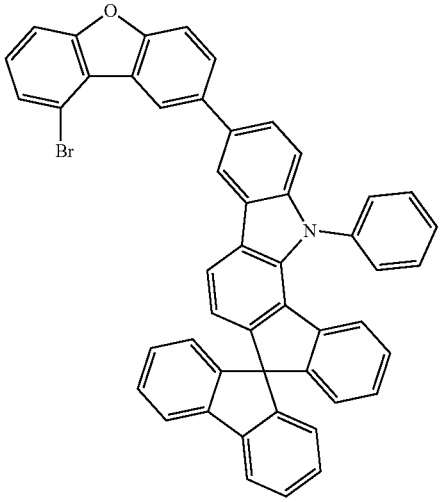 [SMILES: Brc1cccc2oc3ccc(-c4ccc5c(c4)c4ccc6c(c4n5-c4ccccc4)-c4ccccc4C64c5ccccc5-c5ccccc54)cc3c12] | 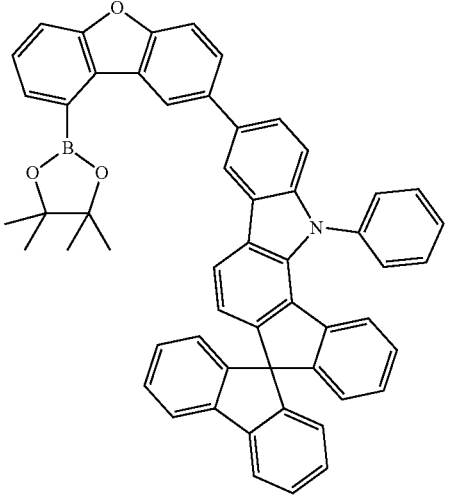 [SMILES: CC1(C)OB(c2cccc3oc4ccc(-c5ccc6c(c5)c5ccc7c(c5n6-c5ccccc5)-c5ccccc5C75c6ccccc6-c6ccccc65)cc4c23)OC1(C)C] |

-continued

| Ex. | Reactant | Product |
| --- | --- | --- |
| BB-2f | | |
| BB-2g | | |
| BB-2h | | |

| Ex. | Reactant | Product |
|---|---|---|
| BB-2i | | |
| BB-2j | | |

Stage 3: BB-3a

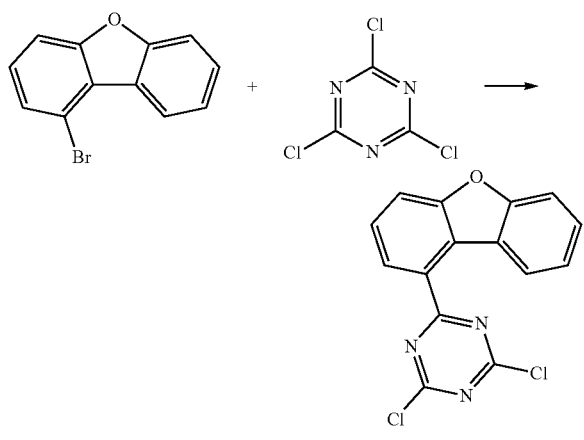

21.1 g (85.4 mmol) of 1-bromodibenzofuran in 100 ml of THF is added dropwise to 2.27 g (93.5 mmol) of magnesium (with addition of iodine to start the Grignard reaction), and the mixture is heated under reflux for 2 h. 350 ml of THF is added, and the reaction mixture is left to come to room temperature. The Grignard reagent is added dropwise to 15 g (81 mmol) of 2,4,6-trichloro[1,3,5]triazine, dissolved in 150 ml of THF, at −10° C. The mixture is left to stir at room temperature overnight. Then the mixture is cooled to 0° C., and 8 ml of hydrochloric acid (1 M) is added dropwise. The mixture is stirred for 1 h, then 400 ml of water is added. The organic phase is removed and washed with water. The aqueous phase is extracted with ethyl acetate. The organic phases are combined and concentrated under reduced pressure. The crude product is purified by flash chromatography (heptane/dichloromethane 10:1). Yield: 24.0 g (75.9 mmol; 89%).

Stage 4 (Symmetric): Compound 1

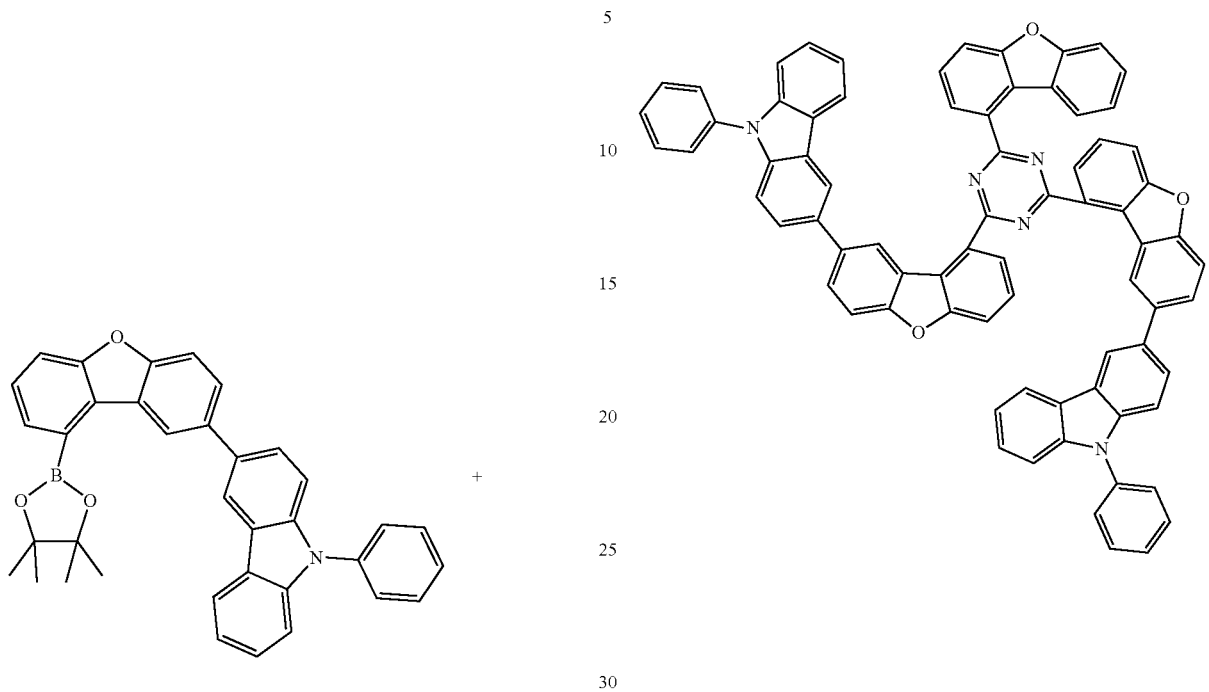

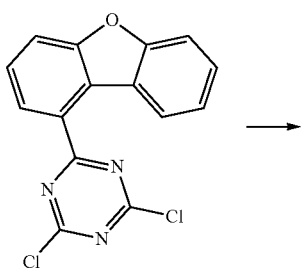

24 g (75.9 mmol) of 2,4-dichloro-6-dibenzofuran-1-yl-[1,3,5]triazine, 80.3 g (150 mmol) of 9-phenyl-3-[9-(4,4,5,5-tetramethyl-[1,3,2]dioxaborolan-2-yl)-dibenzofuran-2-yl]-9H-carbazole, 2.2 g (1.9 mmol) of tetrakis(triphenylphosphine)palladium(0) and 15.7 g (113.9 mmol) of potassium carbonate are mixed in 500 ml of water/THF (1:3) and stirred at 70° C. overnight. Subsequently, the reaction mixture is allowed to come to room temperature, ethyl acetate is added and the phases are separated. The organic phase is washed with water, and the aqueous phase is extracted with ethyl acetate. The combined organic phases are concentrated under reduced pressure and purified by flash chromatography (heptane/THF 10:1). The product is purified by recrystallization from heptane/toluene. Further purification is effected by sublimation (430° C., $10^{-4}$ mbar). Yield: 22.6 g (21.28 mmol; 28%).

The following compounds can be synthesized analogously:

| Ex. | Reactant 1 | Reactant 2 | Product |
|---|---|---|---|
| 2 | BB-2b | BB-3a | 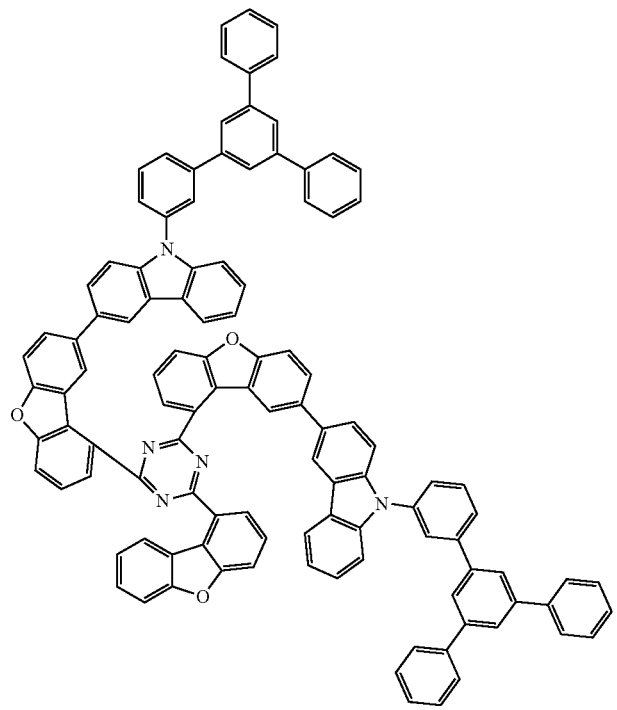 [SMILES: c1ccc(-c2cc(-c3ccccc3)cc(-c3cccc(-n4c5ccccc5c5cc(-c6ccc7oc8cccc(-c9nc(-c%10cccc%11oc%12ccccc%12c%10%11)nc(-c%10cccc%11oc%12ccc(-c%13ccc%14c(c%13)c%13ccccc%13n%14-c%13cccc(-c%14cc(-c%15ccccc%15)cc(-c%15ccccc%15)c%14)c%13)cc%12c%10%11)n9)c8c7c6)ccc54)c3)c2)cc1] |
| 3 | BB-2c | BB-3a | 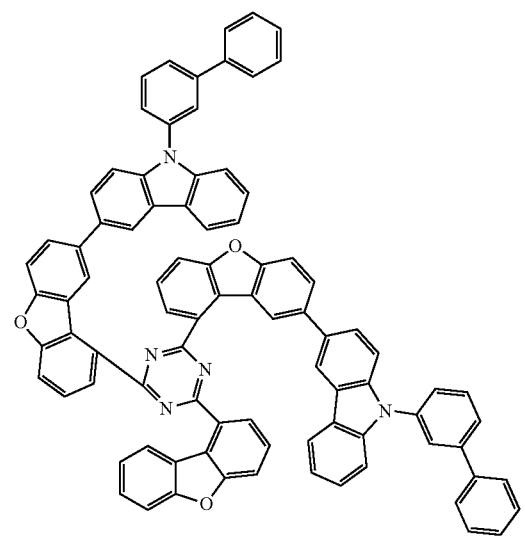 [SMILES: c1ccc(-c2cccc(-n3c4ccccc4c4cc(-c5ccc6oc7cccc(-c8nc(-c9cccc%10oc%11ccccc%11c9%10)nc(-c9cccc%10oc%11ccc(-c%12ccc%13c(c%12)c%12ccccc%12n%13-c%12cccc(-c%13ccccc%13)c%12)cc%11c9%10)n8)c7c6c5)ccc43)c2)cc1] |

| Ex. | Reactant 1 | Reactant 2 | Product |
|---|---|---|---|
| 4 | BB-2d | BB-3a | 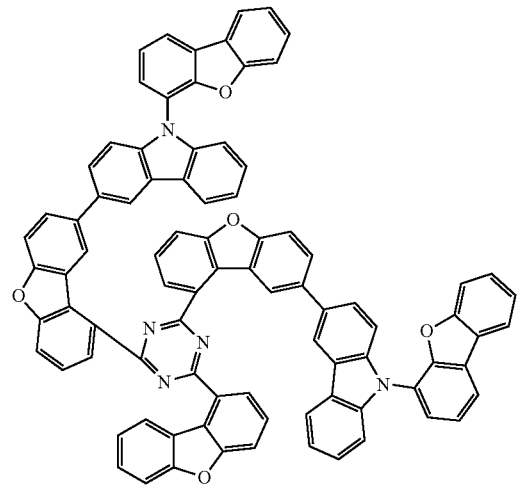 [SMILES: c1ccc2c(c1)oc1c(-n3c4ccccc4c4cc(-c5ccc6oc7cccc(-c8nc(-c9cccc%10oc%11ccccc%11c9%10)nc(-c9cccc%10oc%11ccc(-c%12ccc%13c(c%12)c%12ccccc%12n%13-c%12cccc%13c%12oc%12ccccc%12%13)cc%11c9%10)n8)c7c6c5)ccc43)cccc12] |
| 5 | BB-2e | BB-3a | 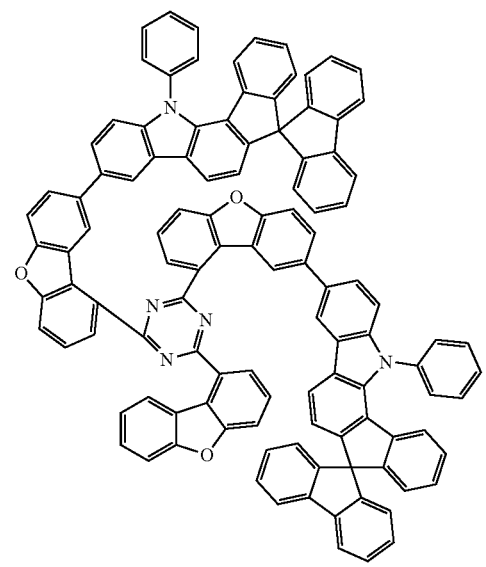 [SMILES: c1ccc(-n2c3ccc(-c4ccc5oc6cccc(-c7nc(-c8cccc9oc%10ccccc%10c89)nc(-c8cccc9oc%10ccc(-c%11ccc%12c(c%11)c%11ccc%13c(c%11n%12-c%11ccccc%11)-c%11ccccc%11C%13%11c%12ccccc%12-c%12ccccc%12%11)cc%10c89)n7)c6c5c4)cc3c3ccc4c(c32)-c2ccccc2C42c3ccccc3-c3ccccc32)cc1] |
| 6 | BB-2a | 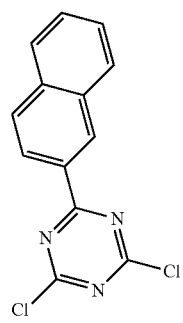<br>CAS 112719-97-8 | 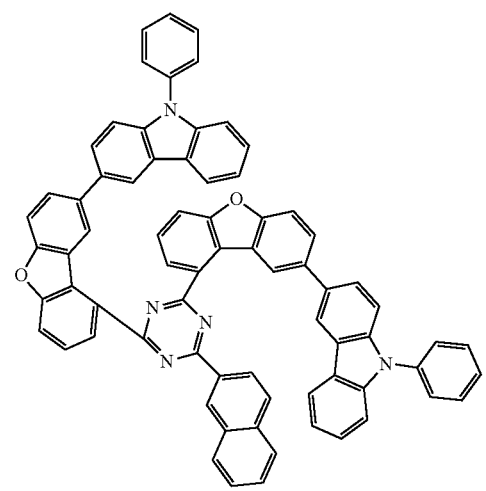 [SMILES: c1ccc(-n2c3ccccc3c3cc(-c4ccc5oc6cccc(-c7nc(-c8ccc9ccccc9c8)nc(-c8cccc9oc%10ccc(-c%11ccc%12c(c%11)c%11ccccc%11n%12-c%11ccccc%11)cc%10c89)n7)c6c5c4)ccc32)cc1] |

| Ex. | Reactant 1 | Reactant 2 | Product |
|---|---|---|---|
| 7 | BB-2b | 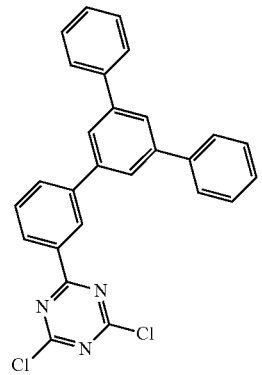 CAS 1845707-19-8 | 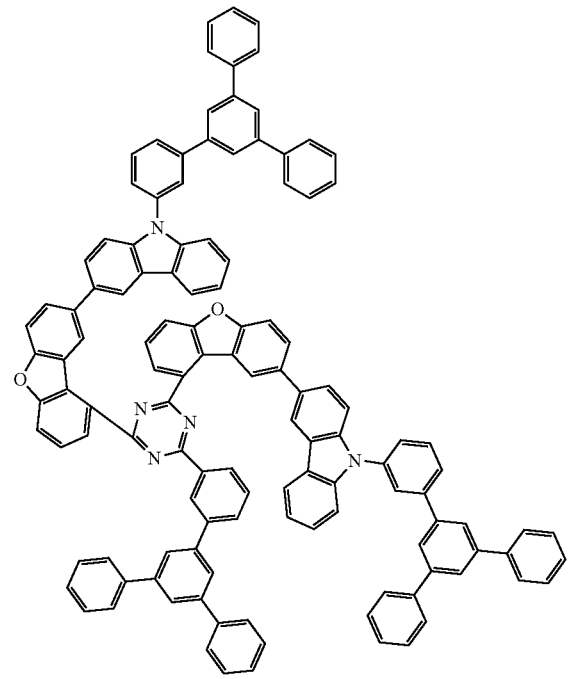 [SMILES: c1ccc(-c2cc(-c3ccccc3)cc(-c3cccc(-c4nc(-c5cccc6oc7ccc(-c8ccc9c(c8)c8ccccc8n9-c8cccc(-c9cc(-c%10ccccc%10)cc(-c%10ccccc%10)c9)c8)cc7c56)nc(-c5cccc6oc7ccc(-c8ccc9c(c8)c8ccccc8n9-c8cccc(-c9cc(-c%10ccccc%10)cc(-c%10ccccc%10)c9)c8)cc7c56)n4)c3)c2)cc1] |
| 8 | BB-2c | 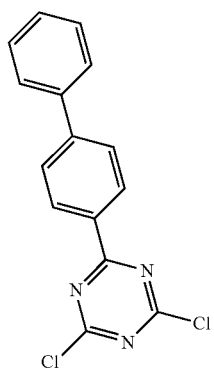 CAS 10202-45-6 | 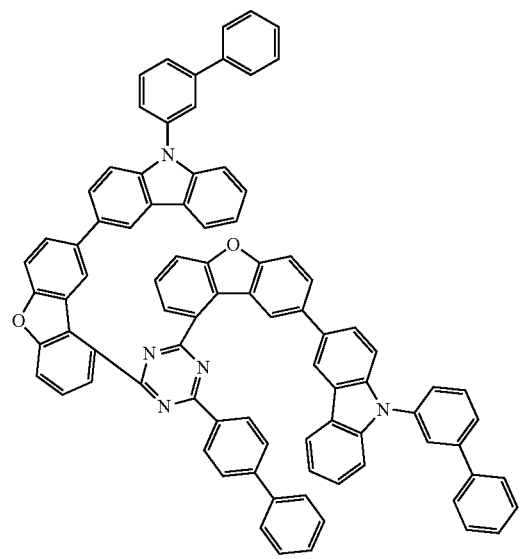 [SMILES: c1ccc(-c2ccc(-c3nc(-c4cccc5oc6ccc(-c7ccc8c(c7)c7ccccc7n8-c7cccc(-c8ccccc8)c7)cc6c45)nc(-c4cccc5oc6ccc(-c7ccc8c(c7)c7ccccc7n8-c7cccc(-c8ccccc8)c7)cc6c45)n3)cc2)cc1] |

-continued
| Ex. | Reactant 1 | Reactant 2 | Product |
|---|---|---|---|
| 9 | BB-2b | 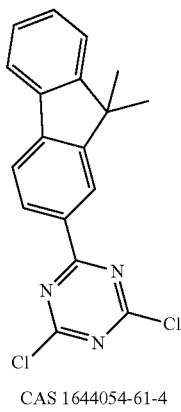 [SMILES: CC1(C)c2ccccc2-c2ccc(-c3nc(Cl)nc(Cl)n3)cc21]
CAS 1644054-61-4 | 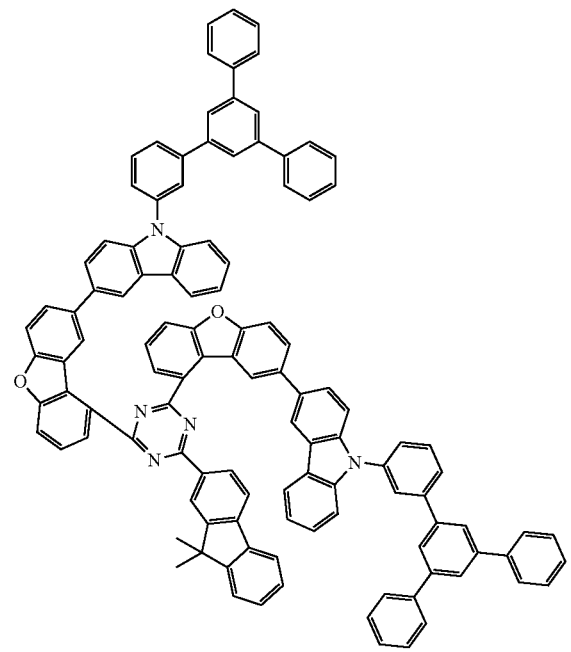 [SMILES: CC1(C)c2ccccc2-c2ccc(-c3nc(-c4cccc5oc6ccc(-c7ccc8c(c7)c7ccccc7n8-c7cccc(-c8cc(-c9ccccc9)cc(-c9ccccc9)c8)c7)cc6c45)nc(-c4cccc5oc6ccc(-c7ccc8c(c7)c7ccccc7n8-c7cccc(-c8cc(-c9ccccc9)cc(-c9ccccc9)c8)c7)cc6c45)n3)cc21] |
| 10 | BB-2a | 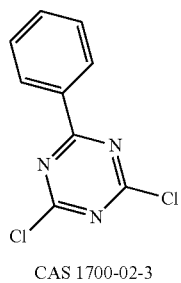 [SMILES: Clc1nc(Cl)nc(-c2ccccc2)n1]
CAS 1700-02-3 | 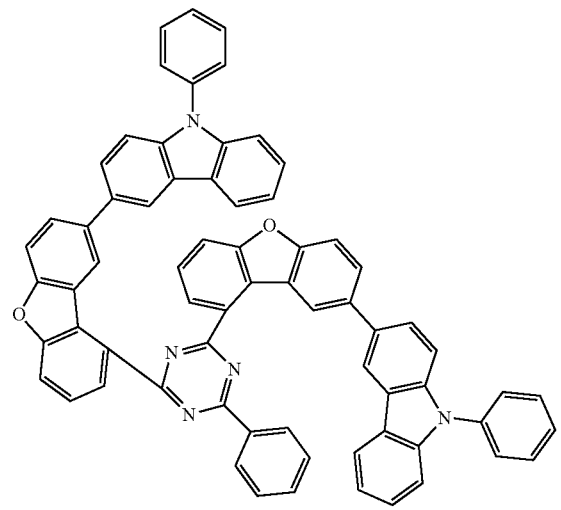 [SMILES: c1ccc(-c2nc(-c3cccc4oc5ccc(-c6ccc7c(c6)c6ccccc6n7-c6ccccc6)cc5c34)nc(-c3cccc4oc5ccc(-c6ccc7c(c6)c6ccccc6n7-c6ccccc6)cc5c34)n2)cc1] |

| Ex. | Reactant 1 | Reactant 2 | Product |
|---|---|---|---|
| 11 | BB-2f | CAS 2102042-41-9 | |
| 12 | BB-2g | | |
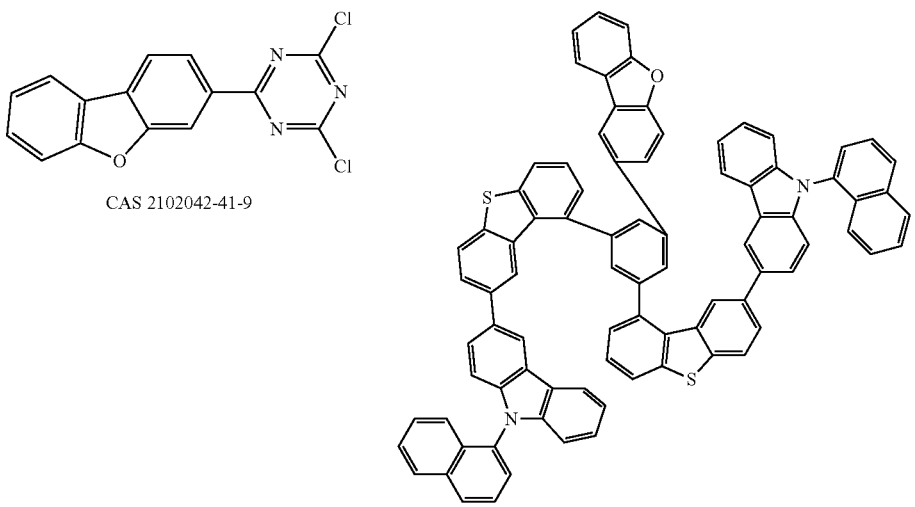
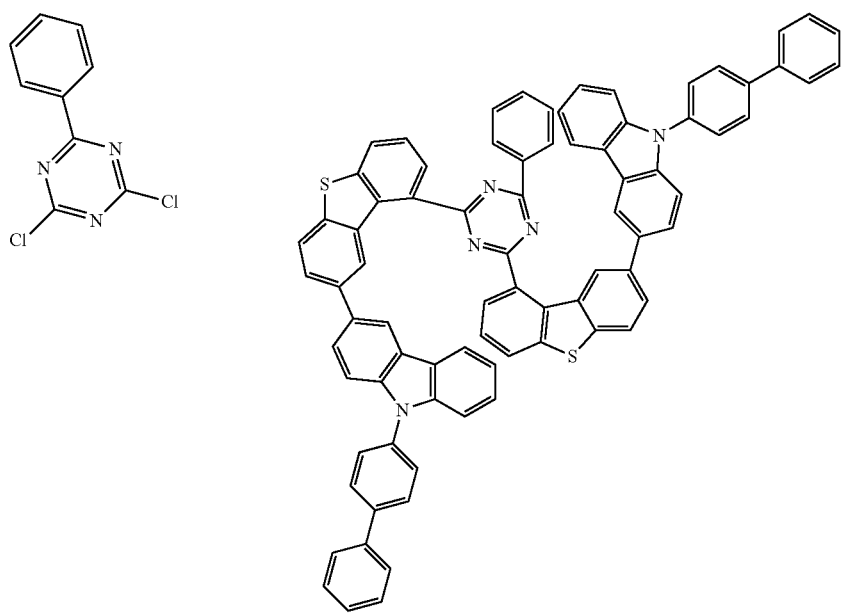

-continued
| Ex. | Reactant 1 | Reactant 2 | Product |
|---|---|---|---|
| 13 | BB-2h | 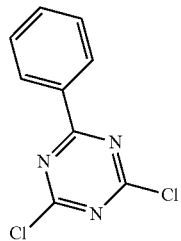 [SMILES: Clc1nc(Cl)nc(-c2ccccc2)n1] | 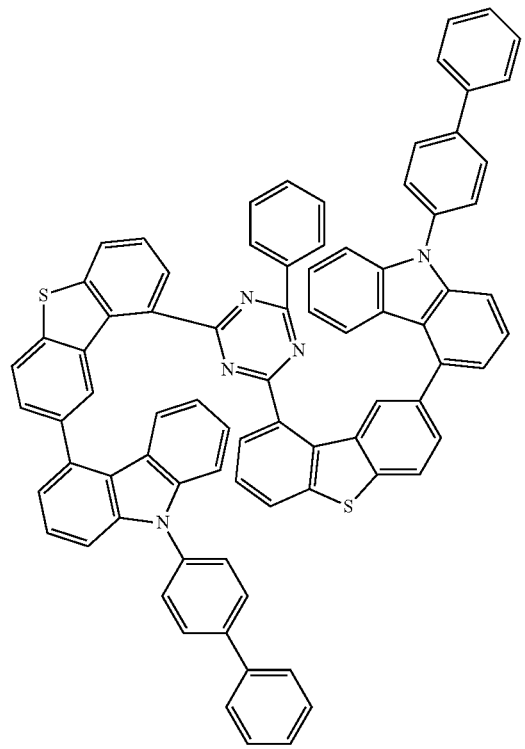 [SMILES: c1ccc(-c2ccc(-n3c4ccccc4c4c(-c5ccc6sc7cccc(-c8nc(-c9ccccc9)nc(-c9cccc%10sc%11ccc(-c%12cccc%13c%12c%12ccccc%12n%13-c%12ccc(-c%13ccccc%13)cc%12)cc%11c9%10)n8)c7c6c5)cccc43)cc2)cc1] |
| 14 | BB-2i | BB-3a | 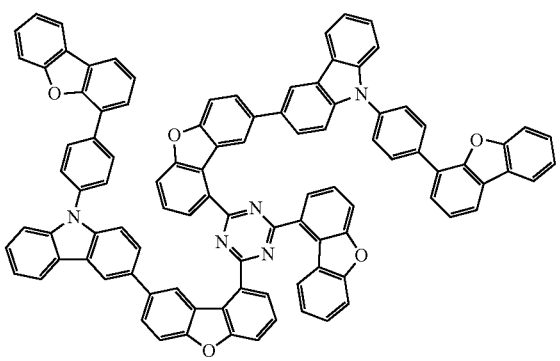 [SMILES: c1ccc2c(c1)oc1c(-c3ccc(-n4c5ccccc5c5cc(-c6ccc7oc8cccc(-c9nc(-c%10cccc%11oc%12ccccc%12c%10%11)nc(-c%10cccc%11oc%12ccc(-c%13ccc%14c(c%13)c%13ccccc%13n%14-c%13ccc(-c%14cccc%15c%14oc%14ccccc%14%15)cc%13)cc%12c%10%11)n9)c8c7c6)ccc54)cc3)cccc12] |
| 15 | BB-2j | BB-3a | 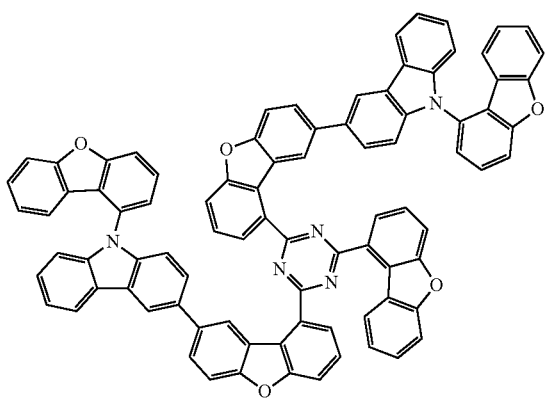 [SMILES: c1ccc2c(c1)oc1cccc(-c3nc(-c4cccc5oc6ccc(-c7ccc8c(c7)c7ccccc7n8-c7cccc8oc9ccccc9c78)cc6c45)nc(-c4cccc5oc6ccc(-c7ccc8c(c7)c7ccccc7n8-c7cccc8oc9ccccc9c78)cc6c45)n3)c12] |

Stage 5 (Asymmetric): BB-4a

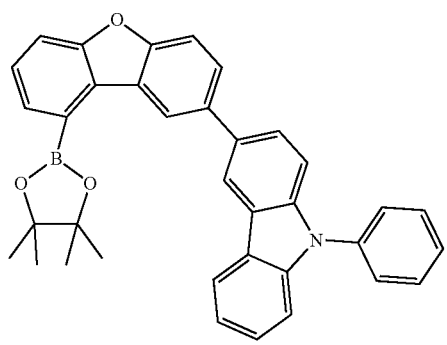

+

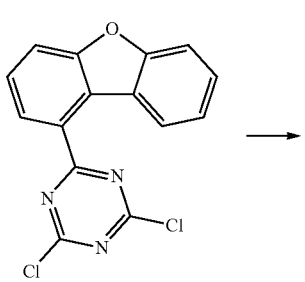

→

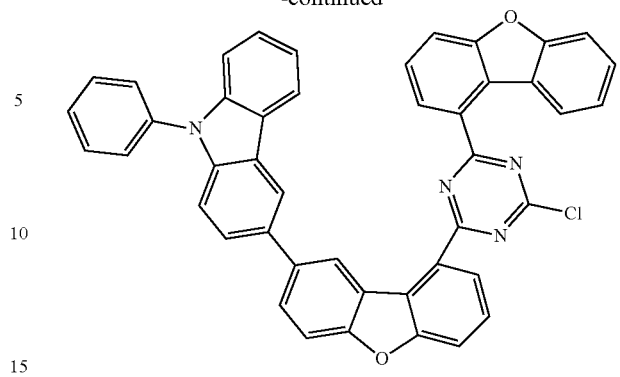

24 g (75.9 mmol) of 2,4-dichloro-6-dibenzofuran-1-yl-[1,3,5]triazine, 36.6 g (68.3 mmol) of 9-phenyl-3-[9-(4,4,5,5-tetramethyl-[1,3,2]dioxaborolan-2-yl)-dibenzofuran-2-yl]-9H-carbazole, 2.2 g (1.9 mmol) of tetrakis(triphenylphosphine)palladium(0) and 15.7 g (113.9 mmol) of potassium carbonate are mixed in 500 ml of water/THF (1:3) and stirred at 70° C. overnight. The mixture is allowed to come to room temperature, ethyl acetate is added and the phases are separated. The organic phase is washed with water, and the aqueous phase is extracted with ethyl acetate. The combined organic phases are concentrated under reduced pressure and purified by flash chromatography (heptane/THF 10:1). Yield: 30 g (43.5 mmol; 58%).

The following compounds can be synthesized analogously:

| Ex. | Reactant 1 | Reactant 2 | Product |
|---|---|---|---|
| BB-4b | BB-2a | (structure) CAS 112719-97-8 | (structure) |

-continued
| Ex. | Reactant 1 | Reactant 2 | Product |
|---|---|---|---|
| BB-4c | BB-2a | 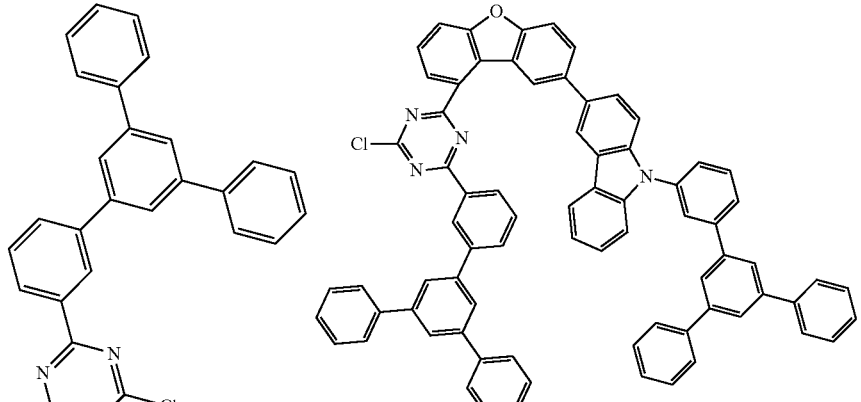 CAS 1845707-19-8 | 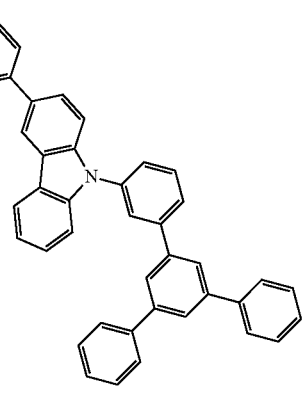 |
| BB-4d | BB-2a | 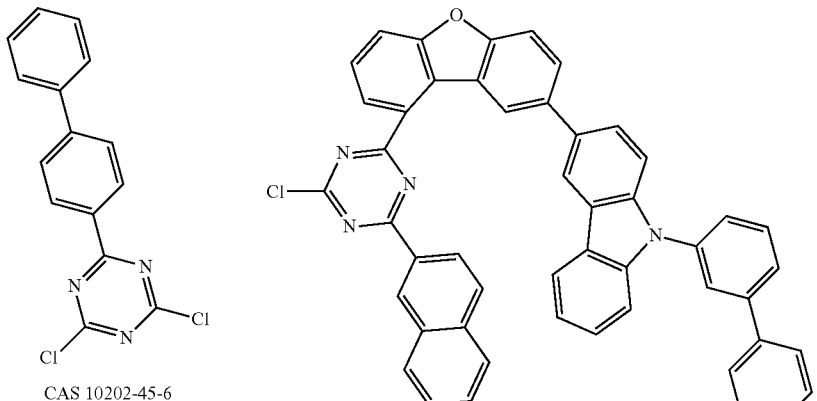 CAS 10202-45-6 | 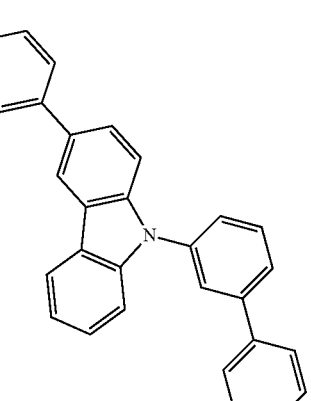 |
Stage 6 (Asymmetric): Compound 1.1
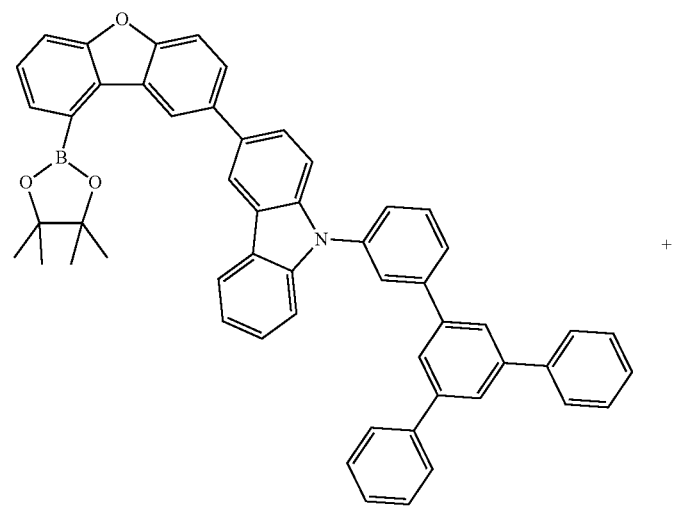 +

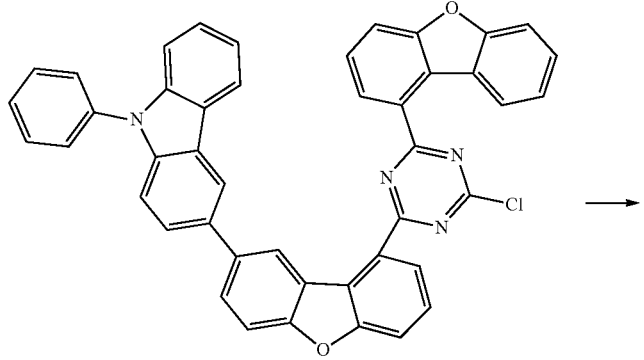

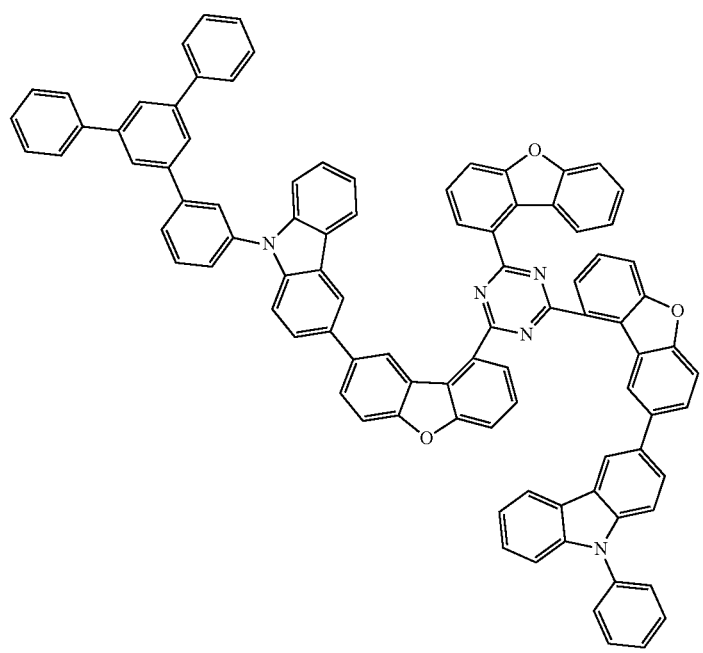

29 g (42.1 mmol) of 3-[9-(4-chloro-6-dibenzofuran-1-yl-[1,3,5]triazin-2-yl)-dibenzofuran-2-yl]-9-phenyl-9H-carbazole, 33.6 g (44 mmol) of BB-2b, 1.2 g (1.1 mmol) of tetrakis(triphenylphosphine)palladium(0) and 8.7 g (63.1 mmol) of potassium carbonate are mixed in 500 ml of water/THF (1:3) and stirred at 70° C. overnight. The reaction mixture is allowed to come to room temperature, ethyl acetate is added and the phases are separated. The organic phase is washed with water, and the aqueous phase is extracted with ethyl acetate. The combined organic phases are concentrated under reduced pressure. The product is purified by flash chromatography (heptane/THF 10:1) and then purified by recrystallization (heptane/toluene). Yield: 20.6 g (16.0 mmol; 38%).

In an analogous manner, it is possible to synthesize the following compounds:

| Ex. | Reactant 1 | Reactant 2 | Product |
|---|---|---|---|
| 1.2 | BB-4b | BB-2b | 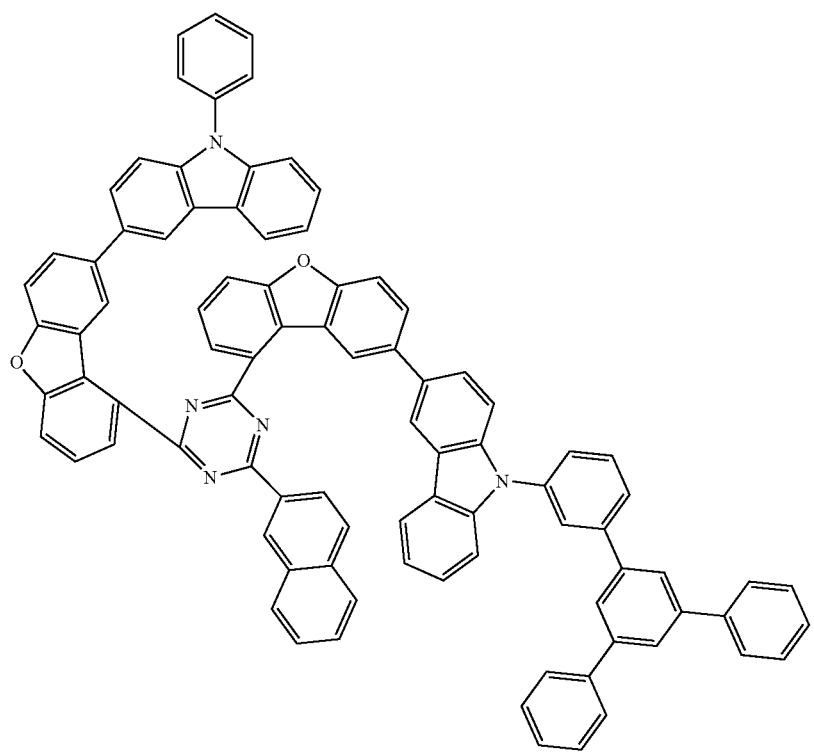 [SMILES: c1ccc(-c2cc(-c3ccccc3)cc(-c3cccc(-n4c5ccccc5c5cc(-c6ccc7oc8cccc(-c9nc(-c%10ccc%11ccccc%11c%10)nc(-c%10cccc%11oc%12ccc(-c%13ccc%14c(c%13)c%13ccccc%13n%14-c%13ccccc%13)cc%12c%10%11)n9)c8c7c6)ccc54)c3)c2)cc1] |
| 1.3 | BB-4c | BB-2c | 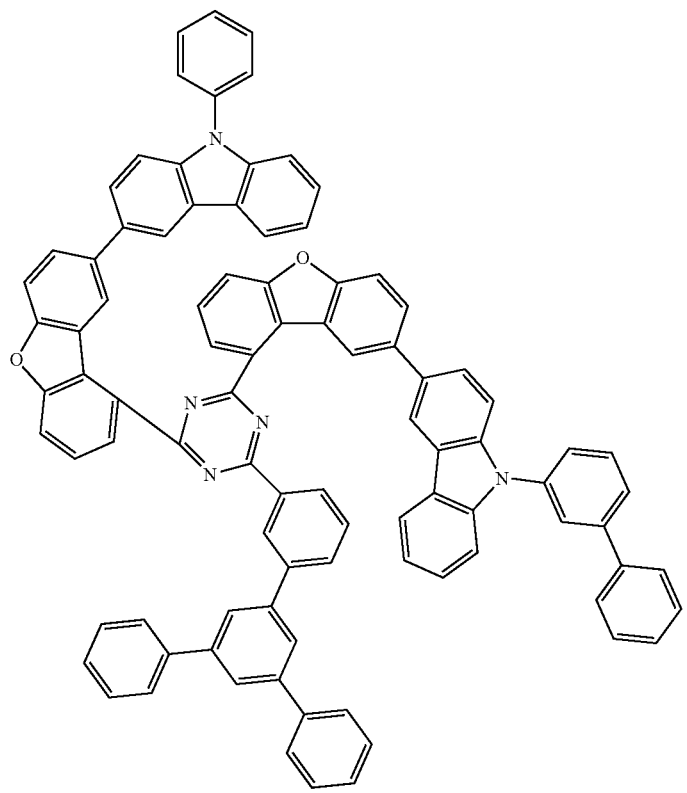 [SMILES: c1ccc(-c2cc(-c3ccccc3)cc(-c3cccc(-c4nc(-c5cccc6oc7ccc(-c8ccc9c(c8)c8ccccc8n9-c8ccccc8)cc7c56)nc(-c5cccc6oc7ccc(-c8ccc9c(c8)c8ccccc8n9-c8cccc(-c9ccccc9)c8)cc7c56)n4)c3)c2)cc1] |

-continued
| Ex. | Reactant 1 | Reactant 2 | Product |
|---|---|---|---|
| 1.4 | BB-4d | BB-2d | 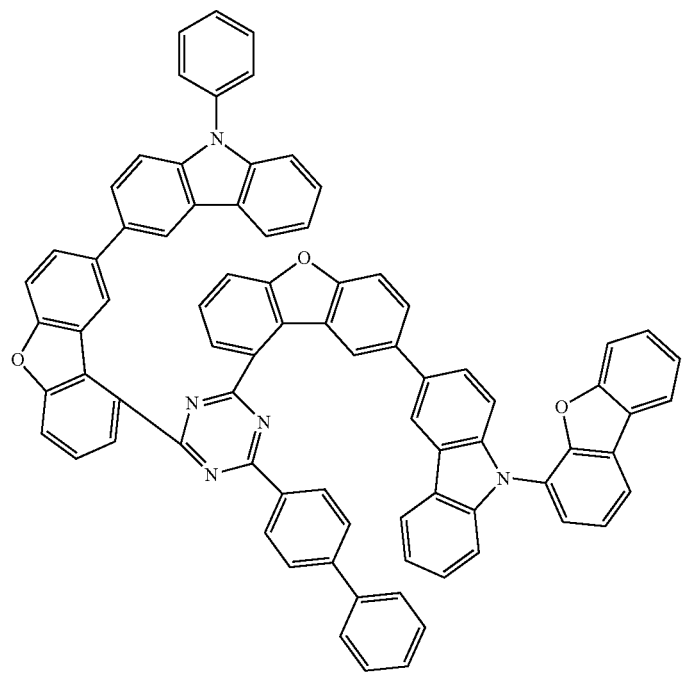 [SMILES: c1ccc(-c2ccc(-c3nc(-c4cccc5oc6ccc(-c7ccc8c(c7)c7ccccc7n8-c7ccccc7)cc6c45)nc(-c4cccc5oc6ccc(-c7ccc8c(c7)c7ccccc7n8-c7cccc8c7oc7ccccc78)cc6c45)n3)cc2)cc1] |
| 1.5 | BB-4a | BB-2e | 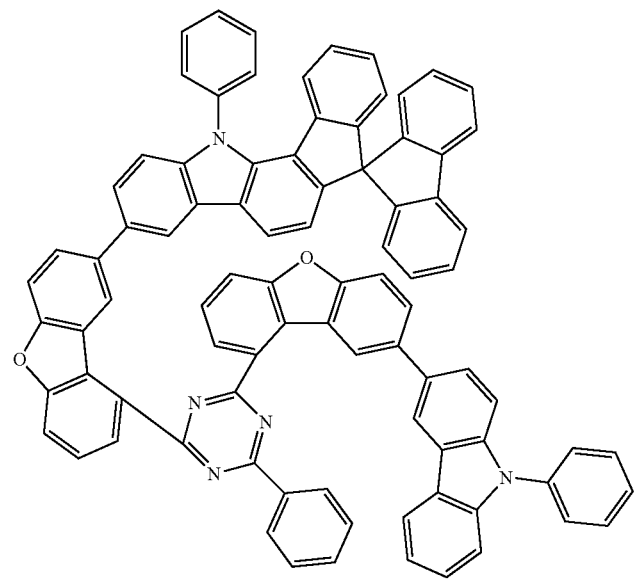 [SMILES: c1ccc(-c2nc(-c3cccc4oc5ccc(-c6ccc7c(c6)c6ccccc6n7-c6ccccc6)cc5c34)nc(-c3cccc4oc5ccc(-c6ccc7c(c6)c6ccc8c(c6n7-c6ccccc6)-c6ccccc6C86c7ccccc7-c7ccccc76)cc5c34)n2)cc1] |

| Ex. | Reactant 1 | Reactant 2 | Product |
|---|---|---|---|
| 1.6 | BB-4a | BB-2b | 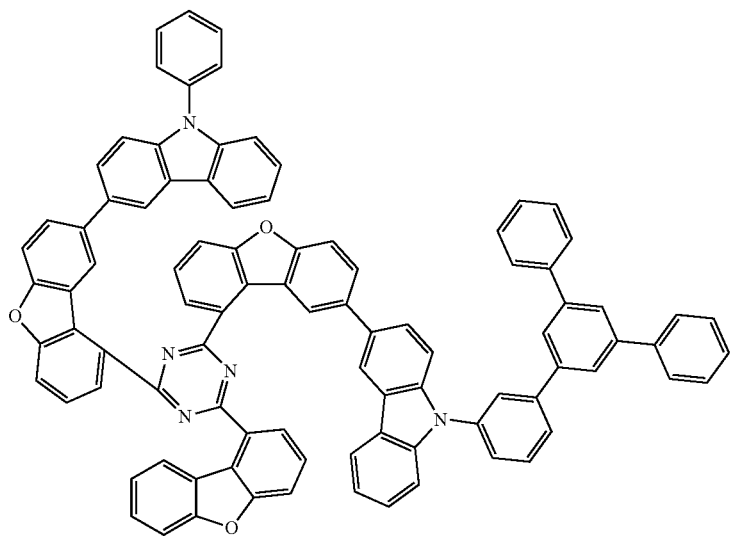 [SMILES: c1ccc(-c2cc(-c3ccccc3)cc(-c3cccc(-n4c5ccccc5c5cc(-c6ccc7oc8cccc(-c9nc(-c%10cccc%11oc%12ccccc%12c%10%11)nc(-c%10cccc%11oc%12ccc(-c%13ccc%14c(c%13)c%13ccccc%13n%14-c%13ccccc%13)cc%12c%10%11)n9)c8c7c6)ccc54)c3)c2)cc1] |
| 1.7 | BB-4a | BB-2c | 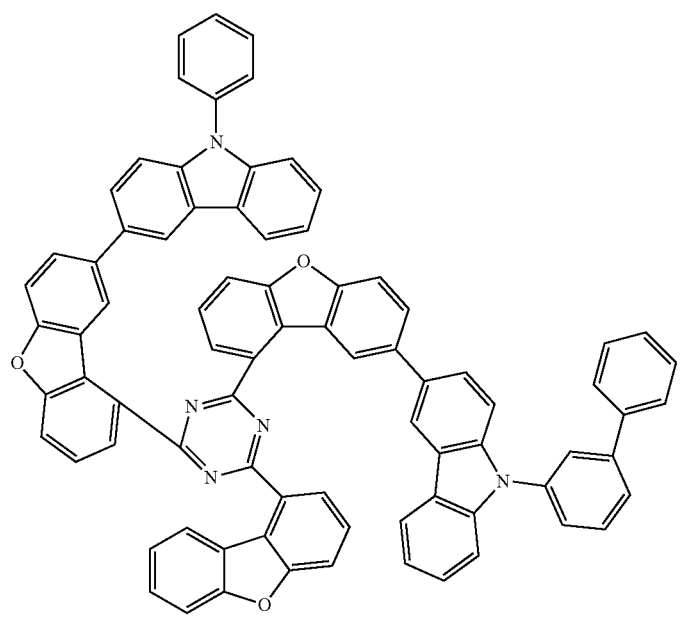 [SMILES: c1ccc(-c2cccc(-n3c4ccccc4c4cc(-c5ccc6oc7cccc(-c8nc(-c9cccc%10oc%11ccccc%11c9%10)nc(-c9cccc%10oc%11ccc(-c%12ccc%13c(c%12)c%12ccccc%12n%13-c%12ccccc%12)cc%11c9%10)n8)c7c6c5)ccc43)c2)cc1] |

Device Examples Processed from Solution: Production of the OLEDs

There are many descriptions of the production of vapour-deposited OLEDs in the literature, for example in WO 2004/058911. The production of solution-based OLEDs is detailed, for example, in WO 2004/037887 and WO 2010/097155. The examples that follow combine the two production processes, such that layers up to and including the emission layer are processed from solution and the subsequent layers (hole blocker layer/electron transport layer) are applied by vapour deposition under reduced pressure. For this purpose, the previously described general methods are matched to the circumstances described here (layer thickness variation, materials) and combined as follows.

The construction of the OLEDs used is as follows:
substrate,
ITO (50 nm),
buffer (20 nm),
hole transport layer (HTL, 20 nm),
emission layer (EML, 50 nm),
electron transport layer (ETL, 20 nm),
electron injection layer (EIL, 3 nm),
Al cathode (100 nm).

Substrates used are glass plaques coated with structured ITO (indium tin oxide) of thickness 50 nm. For better processing, they are coated with the buffer PEDOT:PSS (poly(3,4-ethylenedioxy-2,5-thiophene): polystyrenesulfonate) from Heraeus Precious Metals GmbH & Co. KG. Spin-coating is effected under air from water. The layer is subsequently baked at 180° C. for 10 minutes. The hole transport layer and the emission layer are applied to the glass plaques thus coated. The hole transport layer is the polymer of the structure shown in table 1, which can be synthesized according to WO 2010/097155. The polymer is dissolved in toluene, such that the solution typically has a solids content of about 5 g/l when, as is the case here, the layer thickness of 20 nm typical of a device is to be achieved by means of spin-coating. The layers are spun on in an inert gas atmosphere, nitrogen in the present case, and baked at 220° C. for 30 min.

The emission layer is always composed of at least one matrix material (host material) and an emitting dopant (emitter). Details given in such a form as H1 (92%):D1 (8%) mean here that the material H1 is present in the emission layer in a proportion by weight of 92% and the dopant D1 in a proportion by weight of 8%. The mixture for the emission layer is dissolved in toluene. The typical solids content of such solutions is about 14 g/l when, as here, the layer thickness of 50 nm which is typical of a device is to be achieved by means of spin-coating. The layers are spun on in an inert gas atmosphere, nitrogen in the present case, and baked for 10 minutes. The materials used are shown in table 1. The respective composition of the emission layer, the EML layer thickness and the baking temperature thereof are shown in table 2.

The materials for the electron transport layer and for the cathode are applied by thermal vapour deposition in a vacuum chamber. The electron transport layer, for example, may consist of more than one material, the materials being added to one another by co-evaporation in a particular proportion by volume. Details given in such a form as ETM:EIM (50%:50%) mean here that the ETM and EIM materials are present in the layer in a proportion by volume of 50% each. In the present case, the electron transport layer consists of the material ETM with a layer thickness of 20 nm. The electron injection layer is formed from 3 nm of the EIM material. Both materials are depicted in table 1. The concluding layer is a cathode layer of aluminium having a layer thickness of 100 nm.

The OLEDs are characterized in a standard manner. For this purpose, the electroluminescence spectra are recorded, and the current efficiency (measured in cd/A) and the external quantum efficiency (EQE, measured in percent) are calculated as a function of luminance, assuming Lambertian emission characteristics, from current-voltage-luminance characteristics (IUL characteristics), and finally the lifetime of the components is determined. The electroluminescence spectra are recorded at a luminance of 1000 cd/m², and the CIE 1931 x and y colour coordinates are calculated therefrom. The parameter EQE @ 1000 cd/m² refers to the external quantum efficiency at an operating luminance of 1000 cd/m². The lifetime LT95 @ 4000 cd/m² is the time that passes until the starting brightness of 4000 cd/m² has fallen by 5% to 3800 cd/m². The data for the various OLEDs are collated in table 3.

TABLE 1

Structures of the materials used

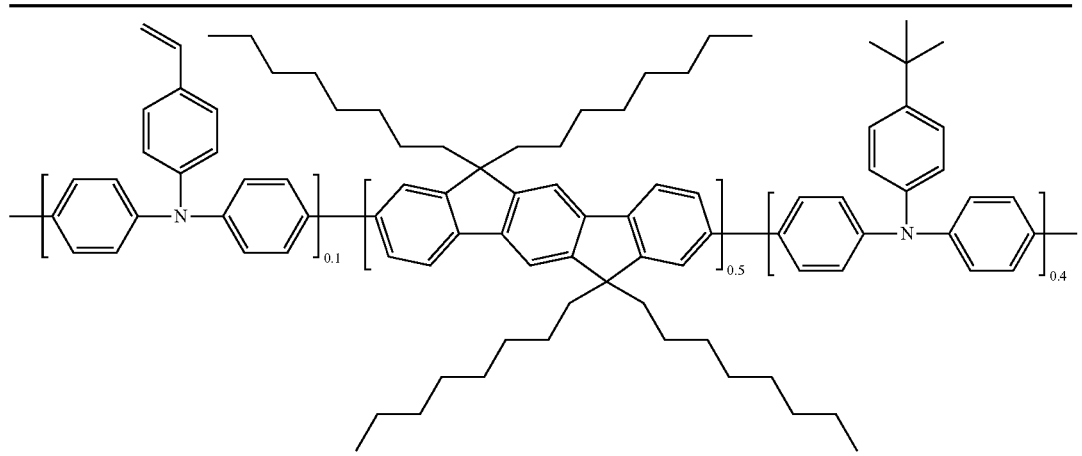

HTL-A

TABLE 1-continued
Structures of the materials used
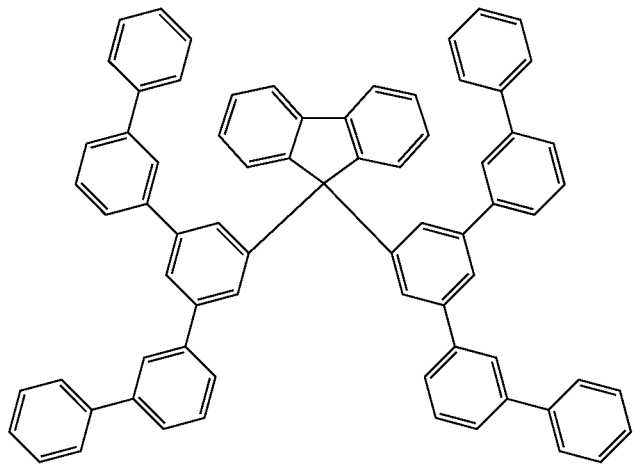 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1]
Host 2
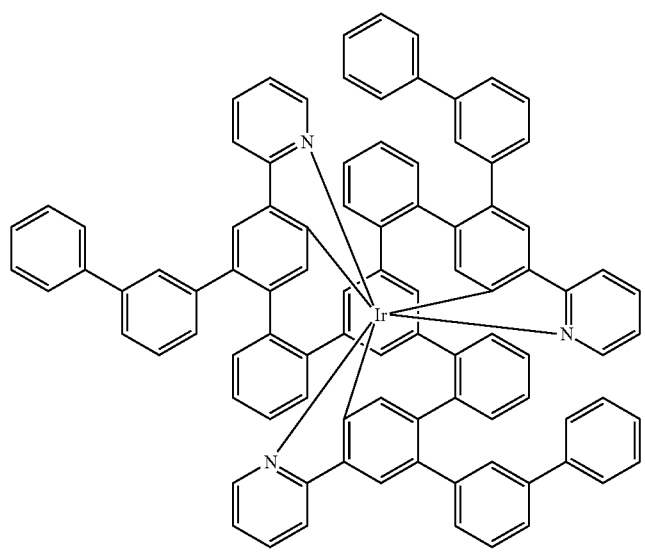
TEG TABLE 1-continued
Structures of the materials used
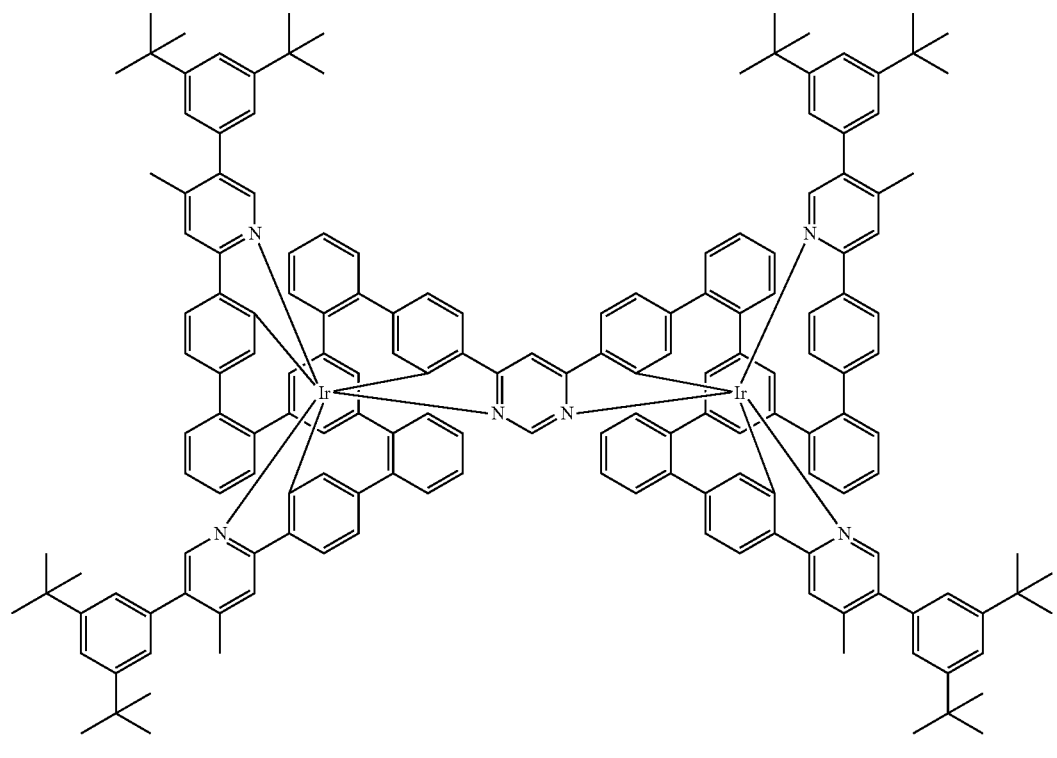
TER
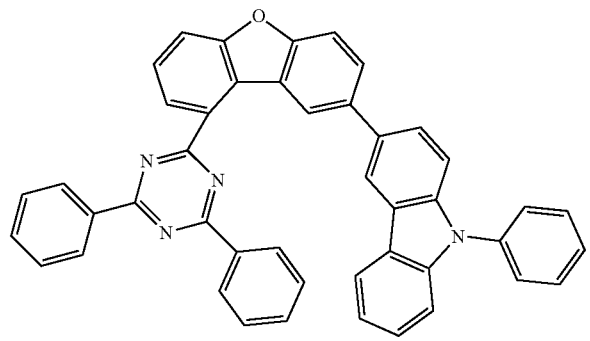 [SMILES: c1ccc(-c2nc(-c3ccccc3)nc(-c3cccc4oc5ccc(-c6ccc7c(c6)c6ccccc6n7-c6ccccc6)cc5c34)n2)cc1]
SdT1
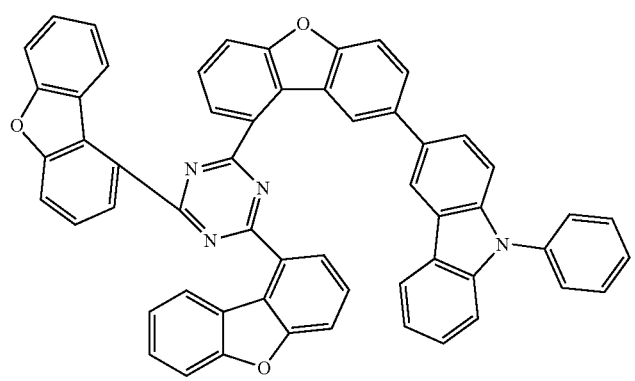 [SMILES: c1ccc(-n2c3ccccc3c3cc(-c4ccc5oc6cccc(-c7nc(-c8cccc9oc%10ccccc%10c89)nc(-c8cccc9oc%10ccccc%10c89)n7)c6c5c4)ccc32)cc1]
SdT2

TABLE 1-continued
Structures of the materials used
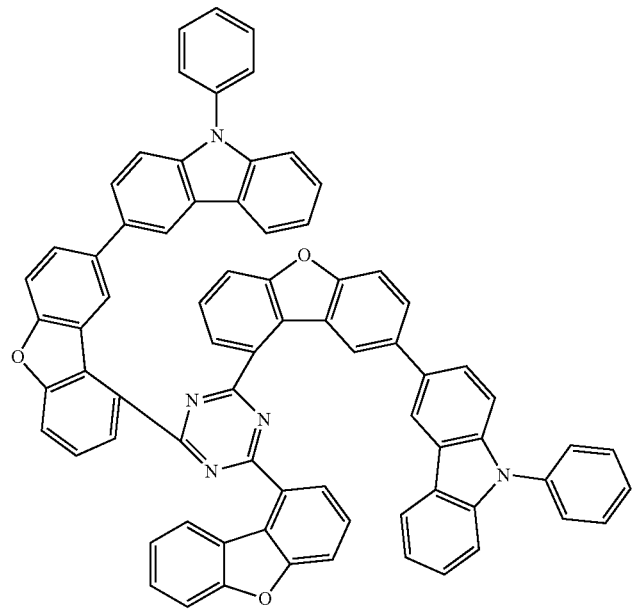 [SMILES: c1ccc(-n2c3ccccc3c3cc(-c4ccc5oc6cccc(-c7nc(-c8cccc9oc%10ccccc%10c89)nc(-c8cccc9oc%10ccc(-c%11ccc%12c(c%11)c%11ccccc%11n%12-c%11ccccc%11)cc%10c89)n7)c6c5c4)ccc32)cc1]
EG1
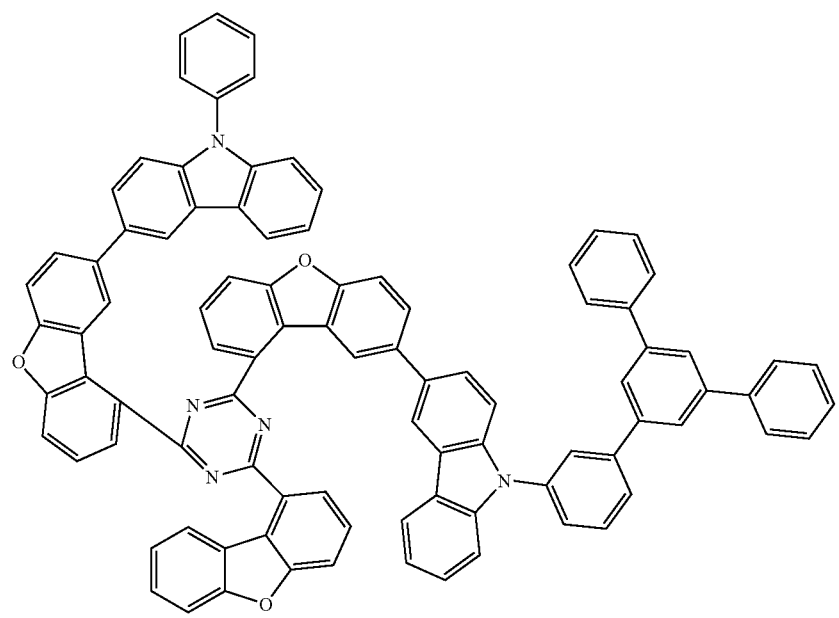 [SMILES: c1ccc(-c2cc(-c3ccccc3)cc(-c3cccc(-n4c5ccccc5c5cc(-c6ccc7oc8cccc(-c9nc(-c%10cccc%11oc%12ccccc%12c%10%11)nc(-c%10cccc%11oc%12ccc(-c%13ccc%14c(c%13)c%13ccccc%13n%14-c%13ccccc%13)cc%12c%10%11)n9)c8c7c6)ccc54)c3)c2)cc1]
EG2

TABLE 1-continued
Structures of the materials used
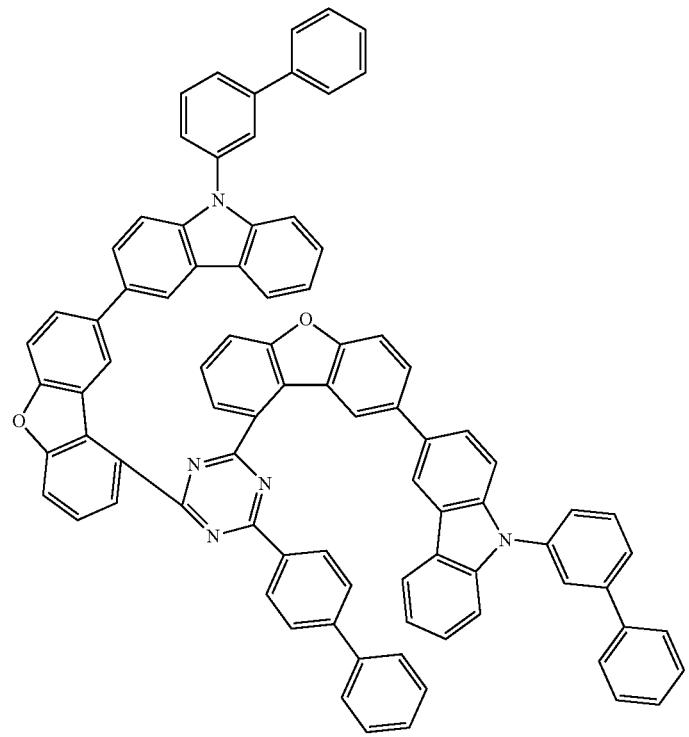 [SMILES: c1ccc(-c2ccc(-c3nc(-c4cccc5oc6ccc(-c7ccc8c(c7)c7ccccc7n8-c7cccc(-c8ccccc8)c7)cc6c45)nc(-c4cccc5oc6ccc(-c7ccc8c(c7)c7ccccc7n8-c7cccc(-c8ccccc8)c7)cc6c45)n3)cc2)cc1]
EG3
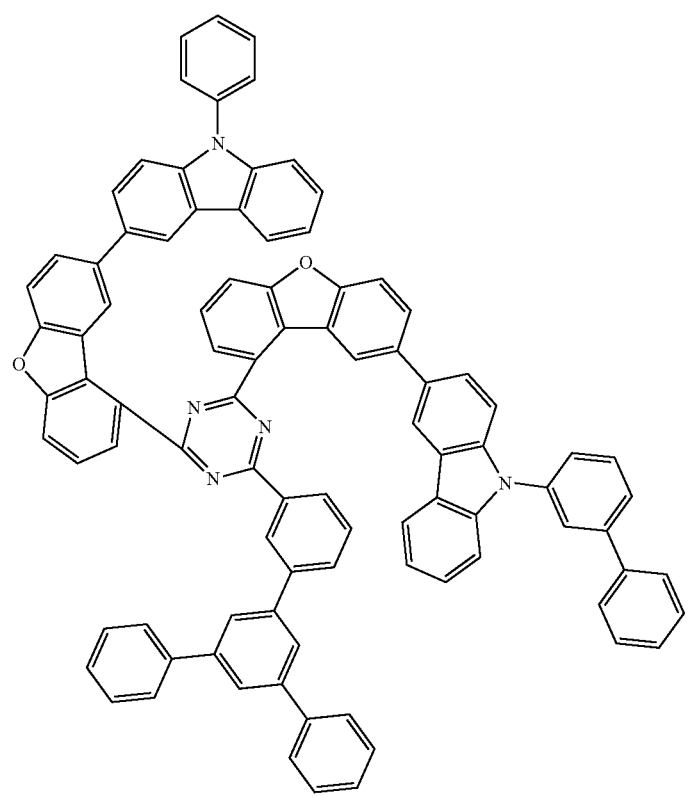 [SMILES: c1ccc(-c2cc(-c3ccccc3)cc(-c3cccc(-c4nc(-c5cccc6oc7ccc(-c8ccc9c(c8)c8ccccc8n9-c8ccccc8)cc7c56)nc(-c5cccc6oc7ccc(-c8ccc9c(c8)c8ccccc8n9-c8cccc(-c9ccccc9)c8)cc7c56)n4)c3)c2)cc1]
EG4

TABLE 1-continued
Structures of the materials used
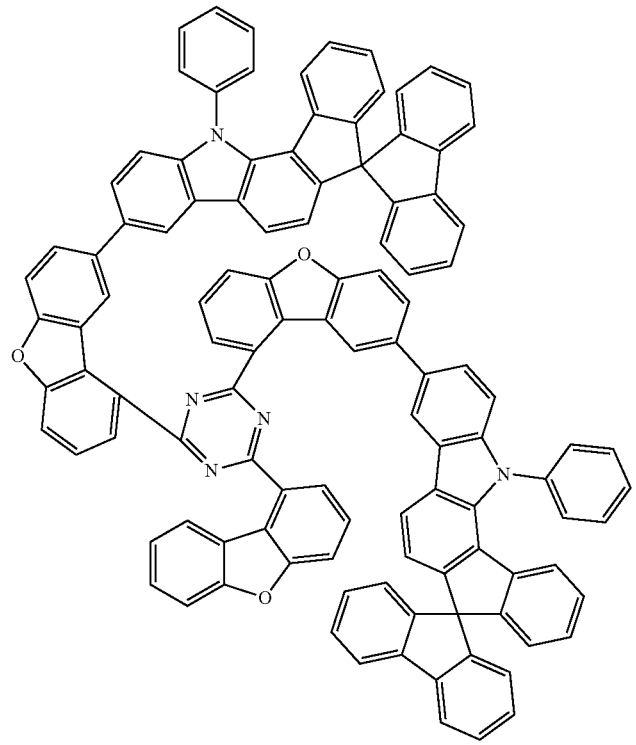 [SMILES: c1ccc(-n2c3ccc(-c4ccc5oc6cccc(-c7nc(-c8cccc9oc%10ccccc%10c89)nc(-c8cccc9oc%10ccc(-c%11ccc%12c(c%11)c%11ccc%13c(c%11n%12-c%11ccccc%11)-c%11ccccc%11C%13%11c%12ccccc%12-c%12ccccc%12%11)cc%10c89)n7)c6c5c4)cc3c3ccc4c(c32)-c2ccccc2C42c3ccccc3-c3ccccc32)cc1]
EG5
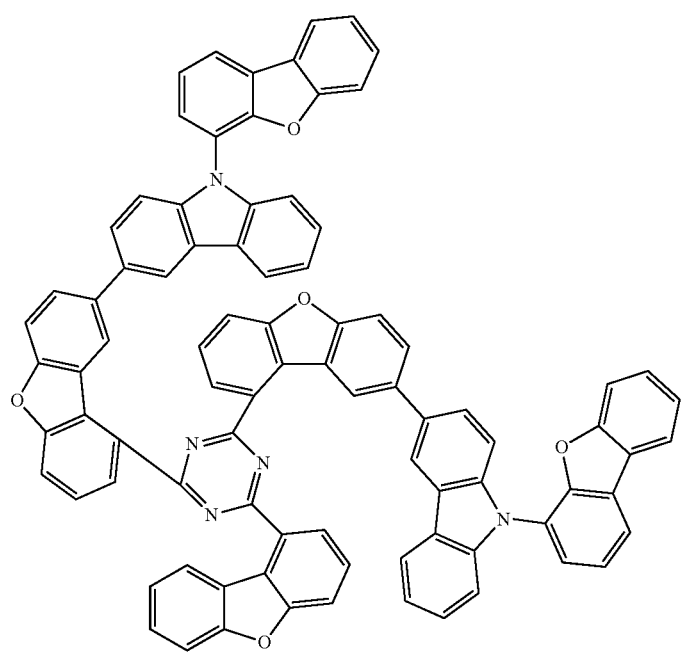 [SMILES: c1ccc2c(c1)oc1c(-n3c4ccccc4c4cc(-c5ccc6oc7cccc(-c8nc(-c9cccc%10oc%11ccccc%11c9%10)nc(-c9cccc%10oc%11ccc(-c%12ccc%13c(c%12)c%12ccccc%12n%13-c%12cccc%13c%12oc%12ccccc%12%13)cc%11c9%10)n8)c7c6c5)ccc43)cccc12]
EG6

TABLE 1-continued
Structures of the materials used
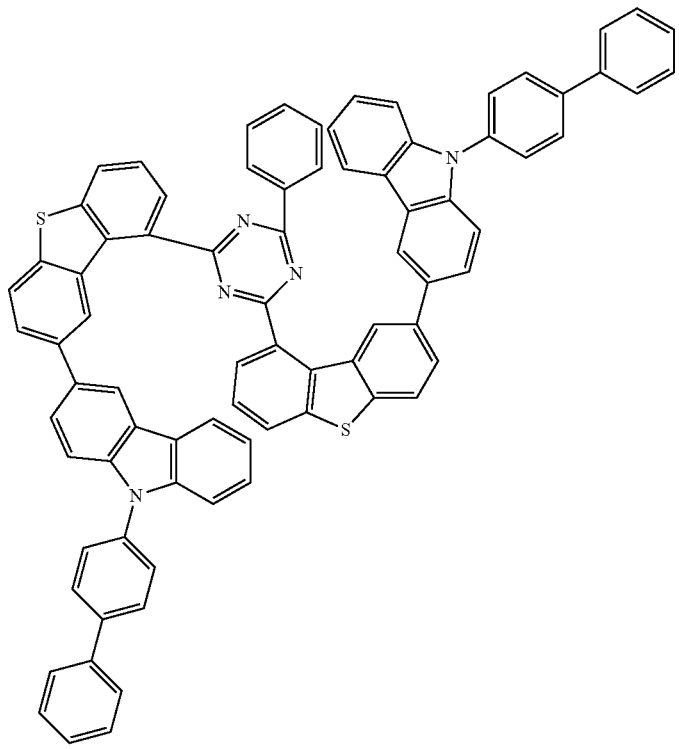 [SMILES: c1ccc(-c2ccc(-n3c4ccccc4c4cc(-c5ccc6sc7cccc(-c8nc(-c9ccccc9)nc(-c9cccc%10sc%11ccc(-c%12ccc%13c(c%12)c%12ccccc%12n%13-c%12ccc(-c%13ccccc%13)cc%12)cc%11c9%10)n8)c7c6c5)ccc43)cc2)cc1]
EG7
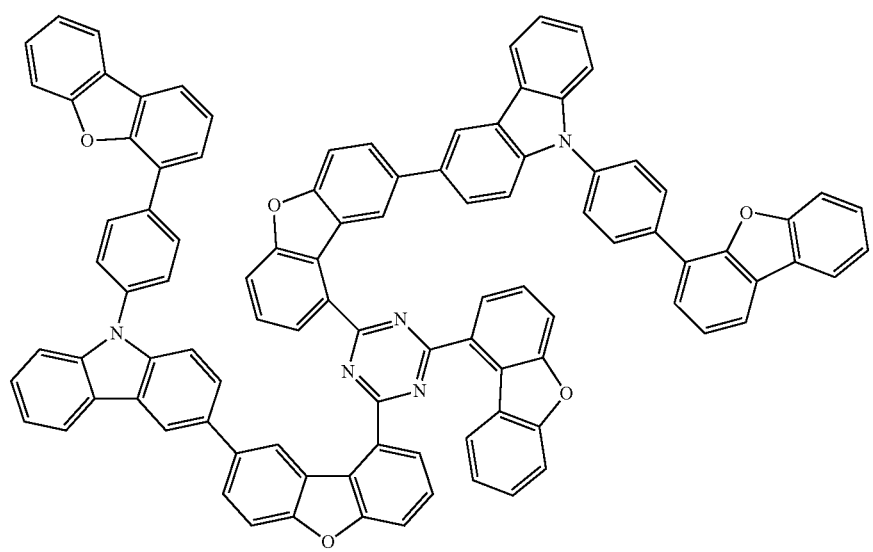 [SMILES: c1ccc2c(c1)oc1c(-c3ccc(-n4c5ccccc5c5cc(-c6ccc7oc8cccc(-c9nc(-c%10cccc%11oc%12ccccc%12c%10%11)nc(-c%10cccc%11oc%12ccc(-c%13ccc%14c(c%13)c%13ccccc%13n%14-c%13ccc(-c%14cccc%15c%14oc%14ccccc%14%15)cc%13)cc%12c%10%11)n9)c8c7c6)ccc54)cc3)cccc12]
EG8

TABLE 1-continued
Structures of the materials used
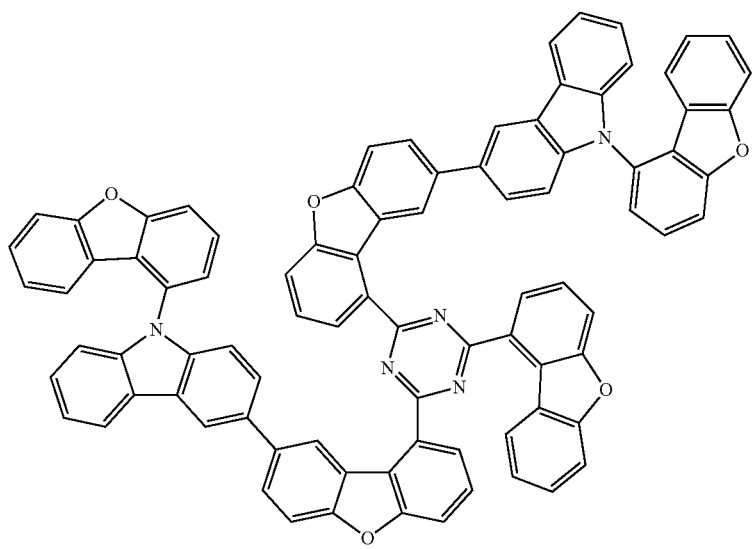 [SMILES: c1ccc2c(c1)oc1cccc(-c3nc(-c4cccc5oc6ccc(-c7ccc8c(c7)c7ccccc7n8-c7cccc8oc9ccccc9c78)cc6c45)nc(-c4cccc5oc6ccc(-c7ccc8c(c7)c7ccccc7n8-c7cccc8oc9ccccc9c78)cc6c45)n3)c12]
EG9
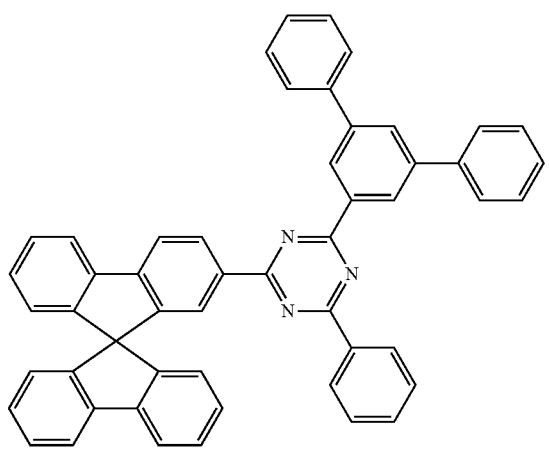 [SMILES: c1ccc(-c2cc(-c3ccccc3)cc(-c3nc(-c4ccccc4)nc(-c4ccc5c(c4)C4(c6ccccc6-c6ccccc64)c4ccccc4-5)n3)c2)cc1]
ETM
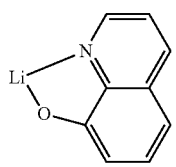
EIM
TABLE 2
Detailed device construction of the solution-processed OLEDs
| Ex. | HIL thickness [nm] | HTL thickness [nm] | EML thickness [nm] | EML baking temperature [° C.] | ETL thickness [nm] | EIL thickness [nm] |
|---|---|---|---|---|---|---|
| C1 | PEDOT:PSS 80 nm | HTL-A 20 nm | SdT1:Host2:TEG:TER (40%:35%:17%:8%) 50 nm | 140 | ETM 20 nm | EIM 3 nm |

TABLE 2-continued

Detailed device construction of the solution-processed OLEDs

| Ex. | HIL thickness [nm] | HTL thickness [nm] | EML thickness [nm] | EML baking temperature [° C.] | ETL thickness [nm] | EIL thickness [nm] |
|---|---|---|---|---|---|---|
| C2 | PEDOT:PSS 80 nm | HTL-A 20 nm | SdT2:Host2:TEG:TER (40%:35%:17%:8%) 50 nm | 160 | ETM 20 nm | EIM 3 nm |
| I3 | PEDOT:PSS 80 nm | HTL-A 20 nm | EG1:Host2:TEG:TER (40%:35%:17%:8%) 50 nm | 160 | ETM 20 nm | EIM 3 nm |
| I4 | PEDOT:PSS 80 nm | HTL-A 20 nm | EG2:Host2:TEG:TER (40%:35%:17%:8%) 50 nm | 160 | ETM 20 nm | EIM 3 nm |
| I5 | PEDOT:PSS 80 nm | HTL-A 20 nm | EG3:Host2:TEG:TER (40%:35%:17%:8%) 50 nm | 160 | ETM 20 nm | EIM 3 nm |
| I6 | PEDOT:PSS 80 nm | HTL-A 20 nm | EG4:Host2:TEG:TER (40%:35%:17%:8%) 50 nm | 160 | ETM 20 nm | EIM 3 nm |
| I7 | PEDOT:PSS 80 nm | HTL-A 20 nm | EG5:Host2:TEG:TER (40%:35%:17%:8%) 50 nm | 160 | ETM 20 nm | EIM 3 nm |
| I8 | PEDOT:PSS 80 nm | HTL-A 20 nm | EG6:Host2:TEG:TER (40%:35%:17%:8%) 50 nm | 160 | ETM 20 nm | EIM 3 nm |
| I9 | PEDOT:PSS 80 nm | HTL-A 20 nm | EG7:Host2:TEG:TER (40%:35%:17%:8%) 50 nm | 160 | ETM 20 nm | EIM 3 nm |
| I10 | PEDOT:PSS 80 nm | HTL-A 20 nm | EG8:Host2:TEG:TER (40%:35%:17%:8%) 50 nm | 160 | ETM 20 nm | EIM 3 nm |
| I11 | PEDOT:PSS 80 nm | HTL-A 20 nm | EG9:Host2:TEG:TER (40%:35%:17%:8%) 50 nm | 160 | ETM 20 nm | EIM 3 nm |

TABLE 3

Data of the solution-processed OLEDs

| Ex. | CIE x/y @1000 cd/m$^2$ | EQE @1000 cd/m$^2$ (%) | LT95 @4000 cd/m$^2$ (hrs) |
|---|---|---|---|
| C1 | 0.67  0.33 | 12.3 | 75 |
| C2 | 0.67  0.33 | 12.8 | 70 |
| I3 | 0.67  0.33 | 13.4 | 180 |
| I4 | 0.67  0.33 | 13.1 | 200 |
| I5 | 0.67  0.33 | 13.3 | 170 |
| I6 | 0.67  0.33 | 13.2 | 190 |
| I7 | 0.67  0.33 | 13.3 | 220 |
| I8 | 0.67  0.33 | 13.4 | 180 |
| I9 | 0.67  0.33 | 13.0 | 140 |
| I10 | 0.67  0.33 | 13.5 | 190 |
| I11 | 0.67  0.33 | 13.2 | 210 |

The results in table 3 show that it is possible to achieve not only a slight improvement in external quantum efficiency but also a distinct improvement in lifetime. The structures found are thus suitable as host for processing from solution and lead to excellent performance data.

The invention claimed is:
1. A compound of formula (1)

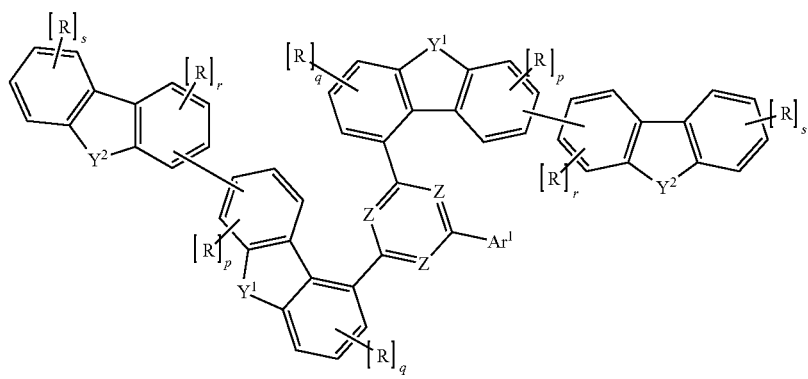

Formula (1)

where the symbols and indices used are as follows:
- $Y^1$ is the same or different at each instance and is O or S;
- $Y^2$ is the same or different at each instance and is $NAr^2$, O, S or $CR_2$;
- Z is the same or different at each instance and is CR or N, with the proviso that at least two Z are N;
- $Ar^1$, $Ar^2$ is the same or different at each instance and is an aromatic or heteroaromatic ring system which has 5 to 40 aromatic ring atoms and may be substituted by one or more R radicals;
- R is the same or different at each instance and is H, D, F, Cl, Br, I, $N(Ar')_2$, $N(R^1)_2$, $OAr'$, $SAr'$, CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may in each case be substituted by one or more $R^1$ radicals, where one or more nonadjacent $CH_2$ groups may be replaced by $Si(R^1)_2$, C=O, $NR^1$, O, S or $CONR^1$, or an aromatic or heteroaromatic ring system which has 5 to 60 aromatic ring atoms, preferably 5 to 40 aromatic ring atoms, and may be substituted in each case by one or more $R^1$ radicals; at the same time, two R radicals together may also form a ring system;
- Ar' is the same or different at each instance and is an aromatic or heteroaromatic ring system which has 5 to 40 aromatic ring atoms and may be substituted by one or more $R^1$ radicals; at the same time, two Ar' radicals bonded to the same nitrogen atom may also be bridged to one another by a single bond or a bridge selected from $N(R^1)$, $C(R^1)_2$, O and S;
- $R^1$ is the same or different at each instance and is H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 carbon atoms or an alkenyl or alkynyl group having 2 to 20 carbon atoms or a branched or cyclic alkyl group having 3 to 20 carbon atoms, where the alkyl, alkenyl or alkynyl group may each be substituted by one or more $R^2$ radicals, where one or more nonadjacent $CH_2$ groups may be replaced by $Si(R^2)_2$, C=O, $NR^2$, O, S or $CONR^2$ and where one or more hydrogen atoms in the alkyl, alkenyl or alkynyl group may be replaced by D, F, Cl, Br, I or CN, or an aromatic or heteroaromatic ring system which has 5 to 40 aromatic ring atoms and may be substituted in each case by one or more $R^2$ radicals; at the same time, two or more $R^1$ radicals together may form an aliphatic ring system;
- $R^2$ is the same or different at each instance and is H, D, F, CN or an aliphatic, aromatic or heteroaromatic organic radical having 1 to 20 carbon atoms, in which one or more hydrogen atoms may also be replaced by F;
- p, q, r is the same or different at each instance and is 0, 1, 2 or 3;
- s is the same or different at each instance and is 0, 1, 2, 3 or 4.

2. The compound according to claim 1, wherein the compound is of formula (2)

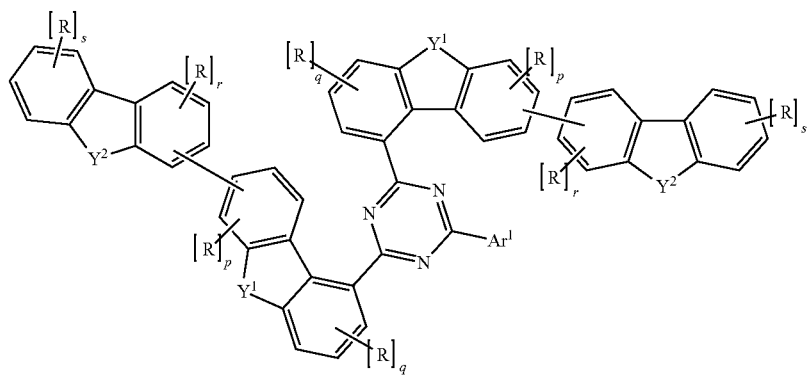

Formula (2)

where the symbols and indices have the definitions given in claim 1.

3. The compound according to claim 1, wherein the compound is of formula (3)

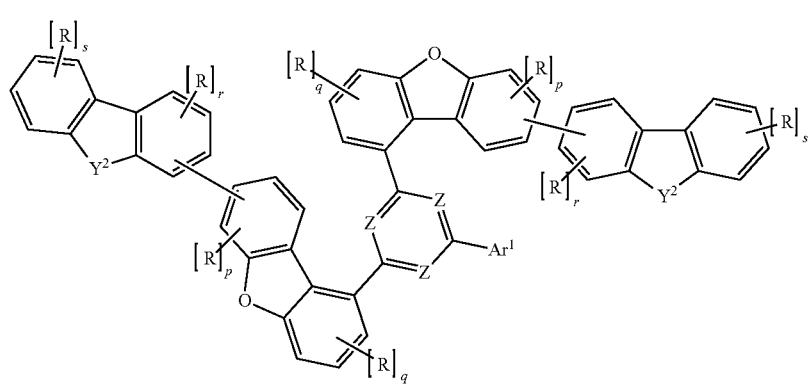

Formula (3)

where the symbols and indices have the definitions given in claim 1.

4. The compound according to claim 1, wherein the compound is of formula (4)

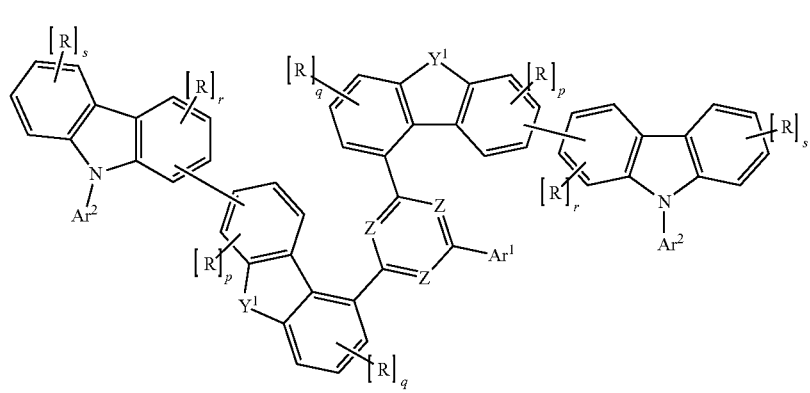

Formula (4)

where the symbols and indices have the definitions given in claim 1.

5. The compound according to claim 1, wherein $Y^2$ is $NAr^2$ and a carbazole group having at least two adjacent R radicals that form a ring system with one another, so as to form a structure of one of the formulae (CARB-1) to (CARB-6)

(CARB-1)

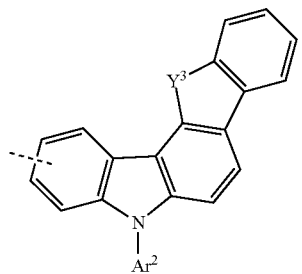

-continued (CARB-2)

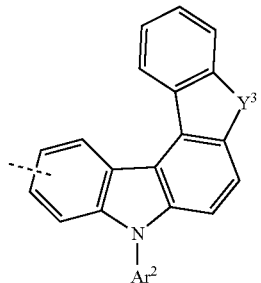

(CARB-3)

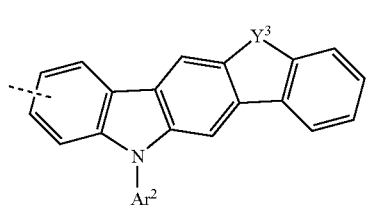

-continued (CARB-4)

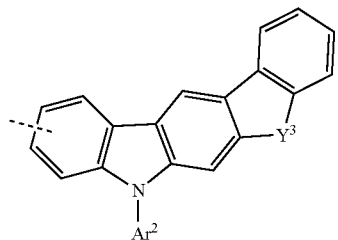

(CARB-5)

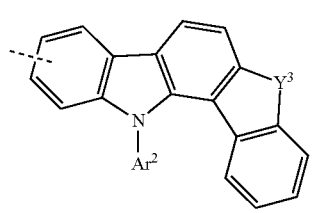

(CARB-6)

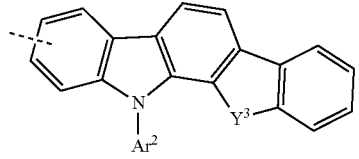

where Ar² and R¹ have the definitions given in claim 1, the structures may be substituted by one or more R radicals on the carbazole and by one or more R¹ radicals on the fused-on structure, Y³ is C(R¹)₂, NR¹, O or S, and the structures are joined to the dibenzofuran or dibenzothiophene via the dotted bond.

6. The compound according to claim 1, wherein the compound is of formula (5)

Formula (5)

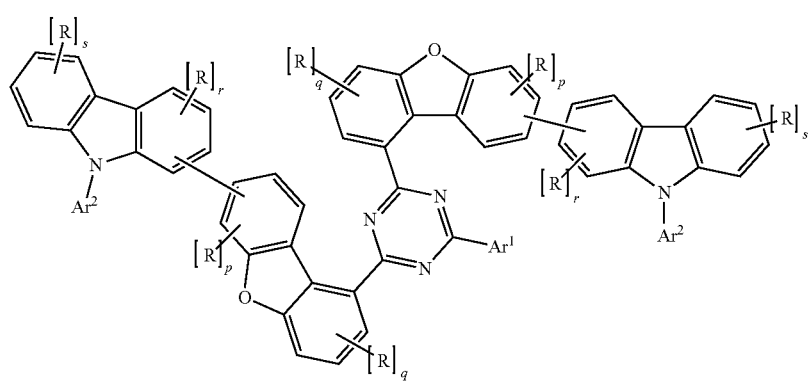

where the symbols and indices have the definitions given in claim 1.

7. The compound according to claim 1, wherein the compound is of one of the formulae (1a) to (5a)

Formula (1a)

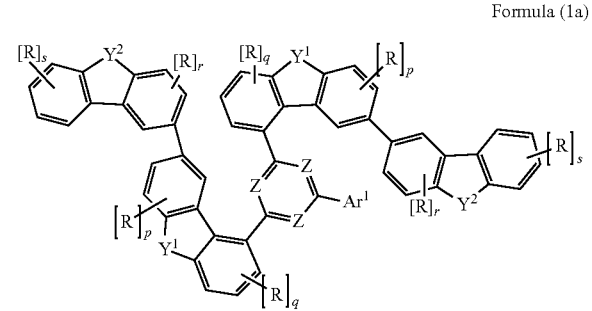

Formula (2a)

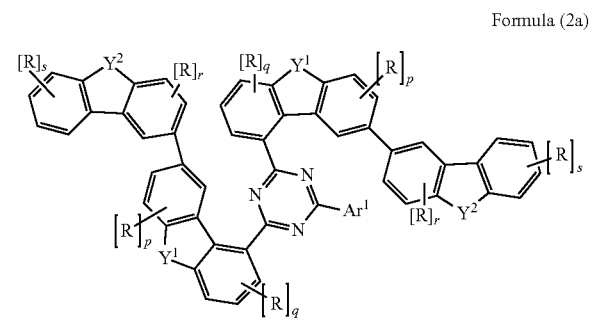

Formula (3a)

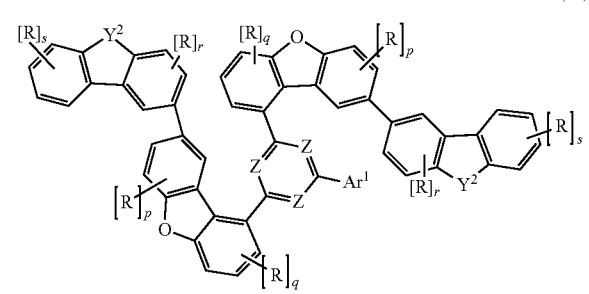

-continued

Formula (4a)

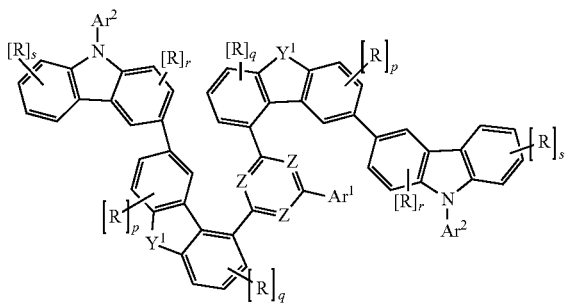

Formula (5a)

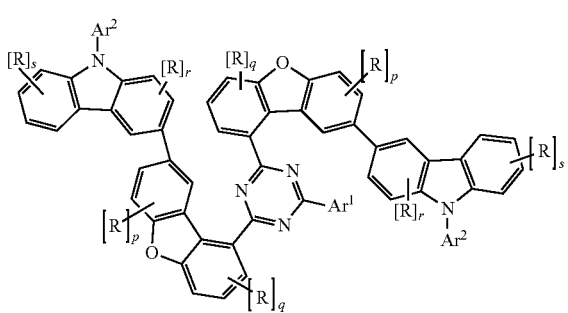

where the symbols and indices have the definitions given in claim 1.

8. The compound according to claim 1, wherein the compound is of formula (6a)

Formula (6a)

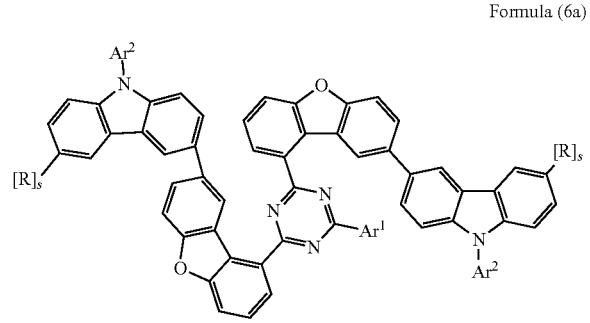

where the symbols have the definitions given in claim 1 and s is the same or different at each instance and is 0 or 1.

9. The compound according to claim 1, wherein $Ar^1$ and $Ar^2$ are the same or different at each instance and are selected from the group consisting of phenyl, biphenyl, terphenyl, quaterphenyl, fluorene, spirobifluorene, naphthalene, indole, benzofuran, benzothiophene, carbazole, dibenzofuran, dibenzothiophene, indenocarbazole, indolocarbazole, phenanthrene, triphenylene or a combination of two or three of these groups, each of which may be substituted by one or more R radicals.

10. A process for preparing a compound according to claim 1 by reacting an $Ar^1$-functionalized dichloropyrimidine or -triazine with a 1-dibenzofuranboronic acid or ester thereof or a 1-dibenzothiopheneboronic acid or ester thereof in a Suzuki coupling.

11. A formulation comprising at least one compound according to claim 1 and at least one further compound and/or a solvent.

12. A method comprising incorporating the compound according to claim 1, in an electronic device.

13. An electronic device comprising at least one compound according claim 1.

14. The electronic device according to claim 13 which is an organic electroluminescent device, wherein the compound is used in an emitting layer as matrix material for phosphorescent emitters or for emitters that exhibit TADF (thermally activated delayed fluorescence) and/or in an electron transport layer and/or in a hole blocker layer.

15. The electronic device according to claim 14, wherein the compound is used in an emitting layer as matrix material for a phosphorescent emitter, wherein the compound is used in combination with one or more further matrix materials selected from the group consisting of aromatic ketones, aromatic phosphine oxides, aromatic sulfoxides, aromatic sulfones, triarylamines, carbazole derivatives, indolocarbazole derivatives, indenocarbazole derivatives, azacarbazole derivatives, bipolar matrix materials, azaboroles, boronic esters, triazine derivatives, zinc complexes, diazasilole or tetraazasilole derivatives, diazaphosphole derivatives, bridged carbazole derivatives, triphenylene derivatives, dibenzofuran derivatives, dibenzothiophene derivatives, wide bandgap materials and/or phosphorescent compounds having shorter-wave emission than the emitter.

* * * * *